United States Patent
Bradley et al.

(10) Patent No.: US 7,405,210 B2
(45) Date of Patent: Jul. 29, 2008

(54) PYRROLOPYRIDINE-2-CARBOXYLIC ACID AMIDE INHIBITORS OF GLYCOGEN PHOSPHORYLASE

(75) Inventors: Stuart Edward Bradley, Oxford (GB); Thomas Martin Krulle, Oxford (GB); Peter John Murray, Oxford (GB); Martin James Procter, Oxford (GB); Robert John Rowley, Oxford (GB); Colin Peter Sambrook Smith, Oxford (GB); Gerard Hugh Thomas, Oxford (GB)

(73) Assignee: OSI Pharmaceuticals, Inc., Melville, NY (US)

( * ) Notice: Subject to any disclaimer, the term of this patent is extended or adjusted under 35 U.S.C. 154(b) by 0 days.

(21) Appl. No.: 10/851,902

(22) Filed: May 20, 2004

(65) Prior Publication Data

US 2005/0261272 A1 Nov. 24, 2005
US 2007/0244090 A9 Oct. 18, 2007

Related U.S. Application Data

(60) Provisional application No. 60/472,375, filed on May 21, 2003, provisional application No. 60/551,256, filed on Mar. 8, 2004.

(51) Int. Cl.
C07D 471/02 (2006.01)
A61K 31/44 (2006.01)
(52) U.S. Cl. ............................... 514/231.5; 514/252.13; 514/300; 544/111; 544/362; 546/113
(58) Field of Classification Search ................. 546/113, 546/18; 544/224, 111, 362; 514/231.5, 300, 514/252.13
See application file for complete search history.

(56) References Cited

U.S. PATENT DOCUMENTS

| | | | |
|---|---|---|---|
| 4,931,429 A | 6/1990 | Hanson et al. | 514/19 |
| 5,346,907 A | 9/1994 | Kerwin, Jr. et al. | 514/312 |
| 5,618,792 A | 4/1997 | Gyorkos et al. | 514/18 |
| 5,618,825 A | 4/1997 | Baldwin et al. | 514/317 |
| 5,672,582 A | 9/1997 | Veber et al. | 514/19 |
| 5,710,153 A | 1/1998 | Ohmoto et al. | 514/236.2 |
| 5,756,810 A | 5/1998 | Baldwin et al. | 560/20 |
| 5,821,241 A | 10/1998 | Claremon et al. | 514/221 |
| 5,869,455 A | 2/1999 | Gyorkos et al. | 514/18 |
| 5,885,967 A | 3/1999 | Schacht et al. | 514/19 |
| 5,952,322 A | 9/1999 | Hoover et al. | 514/210 |
| 6,001,811 A | 12/1999 | Gyorkos et al. | 514/18 |
| 6,034,067 A | 3/2000 | Grootenhuis et al. | 514/18 |
| 6,037,325 A | 3/2000 | Gyorkos et al. | 514/18 |
| 6,090,787 A | 7/2000 | Schacht et al. | 514/19 |
| 6,107,309 A | 8/2000 | Bhatnagar et al. | 514/316 |
| 6,107,329 A | 8/2000 | Hoover et al. | 514/415 |
| 6,124,277 A | 9/2000 | Schacht et al. | 514/183 |
| 6,150,387 A | 11/2000 | Bohme et al. | 514/365 |
| 6,174,887 B1 | 1/2001 | Haruta et al. | 514/252.12 |
| 6,277,877 B1 | 8/2001 | Hoover et al. | 514/415 |
| 6,297,269 B1 * | 10/2001 | Hulin et al. | 514/414 |
| 6,399,601 B1 | 6/2002 | Du Bois | 514/233.8 |
| 6,410,684 B1 | 6/2002 | Adang | 530/331 |
| 6,420,561 B1 | 7/2002 | Haruta et al. | 544/399 |
| 6,432,921 B2 | 8/2002 | Adang et al. | 514/18 |
| 6,455,529 B1 | 9/2002 | Gante et al. | 514/253.1 |
| 2003/0004162 A1 | 1/2003 | Treadway | 514/228.2 |

FOREIGN PATENT DOCUMENTS

| | | |
|---|---|---|
| EP | 0254545 | 1/1988 |
| EP | 0 321 192 A | 6/1989 |
| EP | 0345990 | 12/1989 |
| EP | 0 712 844 | 5/1996 |
| EP | 0810221 | 12/1997 |
| EP | 0 846 464 | 6/1998 |
| EP | 0846464 | 6/1998 |
| EP | 1101759 | 5/2001 |
| EP | 0832066 | 9/2001 |
| EP | 1136071 | 9/2001 |
| EP | 0832065 | 10/2001 |
| EP | 1179341 | 2/2002 |
| EP | 1201239 | 5/2002 |
| EP | 0978276 | 9/2002 |
| GB | 2292149 | 2/1996 |
| WO | WO96/36595 | 11/1996 |
| WO | WO96/39384 | 12/1996 |
| WO | WO97/17985 | 5/1997 |

(Continued)

OTHER PUBLICATIONS

Benjamin Frydman, Santiago J. Reil, Juan Boned, & Henry Rapoport, Synthesis of Substituted 4- and 6-Azaindoles, J. Org. Chem. 33:10 3762-3766 (1968).*

(Continued)

*Primary Examiner*—Zinna N. Davis
(74) *Attorney, Agent, or Firm*—Michael Rafa; Lex Stewart; Frank Forman

(57) ABSTRACT

Compounds represented by Formula (I):

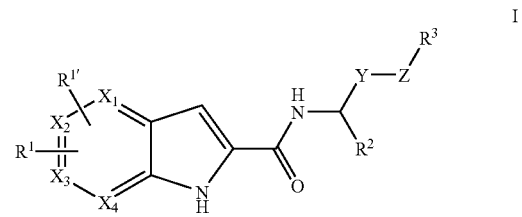

or pharmaceutically acceptable salts thereof, are inhibitors of glycogen phosphorylase and are useful in the prophylactic or therapeutic treatment of diabetes, hyperglycemia, hypercholesterolemia, hyperinsulinemia, hyperlipidemia, hypertension, atherosclerosis or tissue ischemia e.g. myocardial ischemia, and as cardioprotectants.

20 Claims, No Drawings

FOREIGN PATENT DOCUMENTS

| | | |
|---|---|---|
| WO | WO97/28798 | 8/1997 |
| WO | WO97/31016 | 8/1997 |
| WO | WO98/25617 | 6/1998 |
| WO | WO 00/43384 | 7/2000 |
| WO | WO 00/44753 | 8/2000 |
| WO | WO 00/69815 | 11/2000 |
| WO | WO 00/76970 | 12/2000 |
| WO | WO 01/02424 | 1/2001 |
| WO | WO 01/32622 | 5/2001 |
| WO | WO 01/55146 | 8/2001 |
| WO | WO 01/62775 | 8/2001 |
| WO | WO 01/68055 | 9/2001 |
| WO | WO 01/94310 | 12/2001 |
| WO | WO 01/96346 | 12/2001 |
| WO | WO 02/16314 | 2/2002 |
| WO | WO 02/20475 | 3/2002 |
| WO | WO 02/20530 | 3/2002 |
| WO | WO 02/26697 | 4/2002 |
| WO | WO 02/40469 | 5/2002 |
| WO | WO 02/46159 | 6/2002 |
| WO | WO03042178 * | 11/2002 |
| WO | WO 03/064423 | 8/2003 |
| WO | WO 2004/039807 A | 5/2004 |

OTHER PUBLICATIONS

George A. Patani & Edmond J. LaVoie, Bioisosterism: A Rational Approach in Drug Design, Chem. Rev. 96:3147-3176 (1996).*
Ross et al., *American Journal of Physiology. Heart and Circulatory Physiology*, Mar. 2004, 286(3), H1177-84.
R. Kurukulasuriya, J.T. Link, et al., *Current Medicinal Chem.*, 10:99-121(2003).
R. Kurukulasuriya, J.T. Link, et al., *Current Medicinal Chem.*, 10:123-153(2003).
S.P. Hiremath et al., *Acta Ciencia Indica, XVIII*:397(1992).
Kermack, et al., *J. Chem, Soc.*, 1921, 119, 1602.
Cannon et al., *J. Med. Chem.*, 1981, 24, 238.
Chen et al, J. Org. Chem. 1997, 62, 2676.
Sy, W., *Synth. Commun.*, 1992, 22, 3215.
Spivey et al., *J. Org. Chem.*, 1999, 64, 9430.
Hands et al., *Synthesis*, 1996, 7, 877.
A. Fässler et al., (*Tetrahedron Lett.*, 1998, 39, 4925.
Johnson et.al., *J. Med. Chem.*, 1986, 29, 2100-2104.
Wermuth, et al. "The Practise of Medicinal Chemistry" Practice of Medicinal Chemistry 1996 pp. 203-237 Chapter IIC and IID.

* cited by examiner

PYRROLOPYRIDINE-2-CARBOXYLIC ACID AMIDE INHIBITORS OF GLYCOGEN PHOSPHORYLASE

This application claims the benefit of U.S. Provisional Patent Application No. 60/472,375 filed May 21, 2003 and U.S. Provisional Patent Application No. 60/551,256 filed Mar. 08, 2004.

BACKGROUND OF THE INVENTION

The present invention is directed to pyrrolopyridine-2-carboxylic acid amides. In particular, the present invention is directed to pyrrolopyridine-2-carboxylic acid amides that are inhibitors of glycogen phosphorylase.

Insulin dependent Type I diabetes and non-insulin dependent Type II diabetes continue to present treatment difficulties even though clinically accepted regimens that include diet, exercise, hypoglycemic agents, and insulin are available. Treatment is patient dependent—therefore there is a continuing need for novel hypoglycemic agents, particularly ones that may be better tolerated with fewer adverse effects.

The liver and certain other organs produce glucose—thereby raising the blood sugar level—by breaking down glycogen or by synthesizing glucose from small molecule precursors. The breakdown of glycogen is catalyzed by glycogen phosphorylase enzyme. Accordingly, inhibiting glycogen phosphorylase ("GP") may lower the elevated blood sugar level in diabetic patients.

Similarly, hypertension and its associated pathologies such as, for example, atherosclerosis, lipidemia, hyperlipidemia and hypercholesterolemia have been associated with elevated insulin levels (hyperinsulinemia), which can lead to abnormal blood sugar levels. Furthermore, myocardial ischemia can result. Such maladies may be treated with hypoglycemic agents, including compounds that inhibit glycogen phosphorylase. The cardioprotective effects of glycogen phosphorylase inhibitors, for example following reperfusion injury, has also been described (see, for example, Ross et al., *American Journal of Physiology. Heart and Circulatory Physiology*, March 2004, 286(3), H1177–84). Accordingly, it is accepted that compounds that inhibit glycogen phosphorylase (see, for example, U.S. Pat. No. 6,297,269) are useful in the treatment of diabetes, hyperglycemia, hypercholesterolemia, hyperinsulinemia, hyperlipidemia, atherosclerosis or myocardial ischemia. Nevertheless, it would be desirable to obtain other novel compounds that inhibit glycogen phosphorylase.

R. Kurukulasuriya, J. T. Link, et al., *Current Medicinal Chem.*, 10:99–121 (2003) describes "Prospects for Pharmacologic Inhibition of Hepatic Glucose Production." R. Kurukulasuriya, J. T. Link, et al., *Current Medicinal Chem.*, 10:123–153 (2003) describes "Potential Drug Targets and Progress Towards Pharmacologic Inhibition of Hepatic Glucose Production."

U.S. Pat. No. 6,297,269 and European Patent Application No. EP 0832066 describe substituted N-(indole-2-carbonyl) amides and derivatives as glycogen phosphorylase inhibitors. U.S. Pat. Nos. 6,107,329 and 6,277,877 describe substituted N-(indole-2-carbonyl)glycinamides and derivatives as glycogen phosphorylase inhibitors. U.S. Pat. No. 6,399,601 describes bicyclic pyrrolyl amides as glycogen phosphorylase inhibitors. European Patent Application Nos. EP 0978276 and EP 1136071 describe inhibitors of human glycogen phosphorylase and their use. International Patent Publication No. WO 01/68055 describes glycogen phosphorylase inhibitors. U.S. Pat. No. 5,952,322 describes a method of reducing non-cardiac ischemial tissue damage using glycogen phosphorylase inhibitors.

International Patent Publication No. WO 01/55146 describes arylamidines. International Patent Publication No. WO 01/62775 describes antiarrhythmic peptides. International Patent Publication No. WO 01/96346 describes tricyclic compounds. International Patent Publication No. WO 02/16314 describes substituted polyamine compounds. International Patent Publication No. WO 02/20475 describes serine protease activity inhibitors. International Patent Publication No. WO 02/40469 describes bombesin receptor antagonists. International Patent Publication No. WO 02/46159 describes guanidine and amidine derivatives. International Patent Publication No. WO 00/69815 describes ureido-substituted cyclic amine derivatives.

International Patent Publication No. WO 00/43384 describes aromatic heterocyclic compounds. International Patent Publication Nos. WO 02/26697 and WO 00/76970 describe aromatic derivatives. International Patent Publication No. WO 01/32622 describes indoles. European Patent Application No. EP 1101759 describes phenylazole compounds. European Patent Application No. EP 1179341 describes cyclic amino compounds. U.S. Pat. No. 6,037,325 describes substituted heterocyclic compounds. U.S. Pat. No. 5,672,582 describes 4-substituted cyclohexylamine derivatives. European Patent Application No. EP 1201239 describes cyclic amine CCR3 antagonists. International Patent Publication No. WO 98/25617 describes substituted aryl piperazines. U.S. Pat. No. 5,756,810 describes preparing 3-nitrobenzoate compounds.

U.S. Pat. No. 5,710,153 describes tetrazole compounds. U.S. Pat. Nos. 6,174,887 and 6,420,561 describe amide compounds. S. P. Hiremath et al., *Acta Ciencia Indica*, XVIII:397 (1992) describes the synthesis and biological activities of indolylthiosemicarbazides and semicarbazides. International Patent Publication No. WO 96/36595 describes 3,4-disubstituted phenylsulfonamides. U.S. Pat. No. 5,618,825 describes combinatorial sulfonamide libraries. European Patent Application No. EP 0810221 describes oxygen-containing heterocyclic derivatives. European Patent Application No. EP 0345990 describes polypeptide compounds. European Patent Application No. EP 0254545 describes diamine compounds.

International Patent Publication No. WO 97/31016 describes inhibitors of SH2-mediated processes. U.S. Pat. No. 6,034,067 describes serine protease inhibitors. International Patent Publication No. WO 97/17985 and U.S. Pat. No. 6,107,309 describe hemoregulatory compounds. U.S. Pat. No. 6,432,921 describes thrombin inhibitors. U.K. Patent Application No. GB 2292149 describes peptide inhibitors of pro-interleukin-1β converting enzyme. U.S. Pat. No. 5,821,241 describes fibrinogen receptor antagonists.

International Patent Publication No. WO 01/02424 describes peptide boronic acid compounds. U.S. Pat. Nos. 6,001,811, 5,869,455 and 5,618,792 describe oxadiazole, thiadiazole and triazole peptoids. U.S. Pat. Nos. 5,885,967, 6,090,787 and 6,124,277 describe thrombin inhibiting peptide derivatives. U.S. Pat. No. 6,455,529 describes adhesion receptor antagonists. U.S. Pat. No. 6,410,684 describes serine protease inhibitors.

International Patent Publication No. WO 01/94310 describes bis-heterocyclic alkaloids. U.S. Patent Publication No. 20030004162A1, European Patent Application No. EP 0846464, and International Publication No. WO 96/39384 describe glycogen phosphorylase inhibitors. International Patent Publication No. WO 97/28798 describes pyrrolidine derivatives. U.S. Pat. No. 5,346,907 describes amino acid analogs.

SUMMARY OF THE INVENTION

Compounds represented by Formula (I):

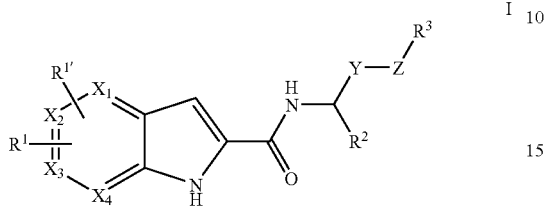

or stereoisomers or pharmaceutically acceptable salts thereof, are inhibitors of glycogen phosphorylase and are useful in the prophylactic or therapeutic treatment of diabetes, hyperglycemia, hypercholesterolemia, hyperinsulinemia, hyperlipidemia, hypertension, atherosclerosis or tissue ischemia e.g. myocardial ischemia, and as cardioprotectants.

DETAILED DESCRIPTION OF THE INVENTION

The present invention is directed to a compound of Formula (I):

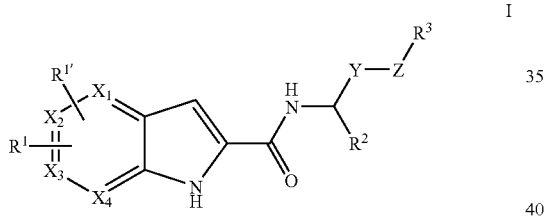

or a stereoisomer, or a pharmaceutically acceptable salt thereof, wherein:
one of $X_1$, $X_2$, $X_3$ and $X_4$ must be N and the others must be C;
$R^1$ and $R^{1'}$ are each independently, halogen, hydroxy, cyano, $C_{0-4}$alkyl, $C_{1-4}$alkoxy, fluoromethyl, difluoromethyl, trifluoromethyl, ethenyl, or ethynyl;
$R^2$ is $C_{0-4}$alkyl, $COOR^6$, $COR^6$, $C_{1-4}$alkoxy$C_{1-4}$alkyl-, hydroxy$C_{1-4}$alkyl-, cycloalkyl$C_{0-4}$alkyl-, aryl$C_{0-4}$alkyl-, hetaryl$C_{0-4}$alkyl-, wherein any of the aryl or hetaryl rings are optionally substituted with 1–2 independent halogen, cyano, $C_{1-4}$alkyl, $C_{1-4}$alkoxy, —N($C_{0-4}$alkyl)($C_{0-4}$alkyl), —SO$_2$C$_{1-4}$alkyl, —SO$_2$N($C_{0-4}$alkyl)($C_{0-4}$alkyl), hydroxy, fluoromethyl, difluoromethyl, or trifluoromethyl substituents;
Y is $C_{0-2}$alkyl or —CH(OH)—;
Z is CH$_2$, —C(O)—, —O—, >N($C_{0-4}$alkyl), >N($C_{3-6}$cycloalkyl), or absent; but when Y is —CH(OH)—, Z or $R^3$ must be bonded to Y through a carbon-carbon bond;
$R^3$ is hydrogen, —COOC$_{0-4}$alkyl, $C_{1-4}$alkoxy, $C_{1-4}$alkyl, aryl$C_{1-4}$alkylthio-, —$C_{0-4}$alkylaryl, —$C_{0-4}$alkylhetaryl, —$C_{0-4}$alkylcycloalkyl or —$C_{0-4}$alkylheterocyclyl, wherein any of the rings is optionally substituted with 1–3 independent halogen, cyano, $C_{1-4}$alkyl, fluoromethyl, difluoromethyl, trifluoromethyl, —$C_{0-4}$alkylNHC(O)O($C_{1-4}$alkyl), —$C_{0-4}$alkylNR$^7$R$^8$, —C(O)R$^9$, $C_{1-4}$alkoxyC$_{0-4}$alkyl-, —COOC$_{0-4}$alkyl, —$C_{0-4}$alkylNHC(O)R$^9$, —$C_{0-4}$alkylC(O)N(R$^{10}$)$_2$, —$C_{1-4}$alkoxyC$_{1-4}$alkoxy, hydroxyC$_{0-4}$alkyl-, —NHSO$_2$R$^{10}$, —SO$_2$(C$_{1-4}$alkyl), —SO$_2$NR$^{11}$R$^{12}$, 5- to 6-membered heterocyclyl, phenylC$_{0-2}$alkoxy, or phenylC$_{0-2}$alkyl substituents, wherein phenyl is optionally substituted with 1–2 independent halogen, cyano, $C_{1-4}$alkyl, $C_{1-4}$alkoxy, —N(C$_{0-4}$alkyl)(C$_{0-4}$alkyl), —SO$_2$C$_{1-4}$alkyl, —SO$_2$N(C$_{0-4}$alkyl)(C$_{0-4}$alkyl), hydroxy, fluoromethyl, difluoromethyl or trifluoromethyl substituents, or two bonds on a ring carbon of the heterocyclyl group optionally can form an oxo (=O) substituent;
or $R^3$ is —NR$^4$(—C$_{0-4}$alkylR$^5$);
$R^4$ is $C_{0-3}$alkyl, —C$_{2-3}$alkyl-NR$^7$R$^8$, C$_{3-6}$cycloalkyl optionally substituted by hydroxyC$_{0-4}$alkyl- further optionally substituted by hydroxy, $C_{1-2}$alkoxyC$_{2-4}$alkyl-, or $C_{1-2}$alkyl-S(O)$_n$—C$_{2-3}$alkyl-;
n is 0, 1, or 2;
$R^5$ is hydrogen, hydroxyC$_{2-3}$alkyl-, $C_{1-2}$alkoxyC$_{0-4}$alkyl-, or aryl, hetaryl, or heterocyclyl;
wherein a heterocyclic nitrogen-containing $R^5$ ring optionally is mono-substituted on the ring nitrogen with $C_{1-4}$alkyl, benzyl, benzoyl, $C_{1-4}$alkyl-C(O)—, —SO$_2$C$_{1-4}$alkyl, —SO$_2$N(C$_{0-4}$alkyl)(C$_{0-4}$alkyl), $C_{1-4}$alkoxycarbonyl or aryl(C$_{1-4}$alkoxy)carbonyl; and wherein the $R^5$ rings are optionally mono-substituted on a ring carbon with halogen, cyano, $C_{1-4}$alkyl-C(O)—, $C_{1-4}$alkyl-SO$_2$—, $C_{1-4}$alkyl, $C_{1-4}$alkoxy, hydroxy, —N(C$_{0-4}$alkyl)(C$_{0-4}$alkyl), hydroxyC$_{0-4}$alkyl-, or $C_{0-4}$alkylcarbamoyl-, provided that no quaternised nitrogen is included; or two bonds on a ring carbon of the heterocyclyl group optionally can form an oxo (=O) substituent;
$R^6$ is $C_{1-4}$alkyl, aryl, or hetaryl;
$R^7$ and $R^8$ are independently $C_{0-4}$alkyl, $C_{3-6}$cycloalkyl, or CO($C_{1-4}$alkyl);
$R^9$ is $C_{1-4}$alkyl, or $C_{3-6}$cycloalkyl;
$R^{10}$ is $C_{0-4}$alkyl, or $C_{3-6}$cycloalkyl;
$R^{11}$ and $R^{12}$ are independently $C_{0-4}$alkyl or together with the nitrogen to which they are attached may form a 4- to 6-membered heterocycle; and
wherein there are no nitrogen-oxygen, nitrogen-nitrogen or nitrogen-halogen bonds in linking the three components —Y—Z—R$^3$ to each other.

The molecular weight of the compounds of Formula (I) is preferably less than 800, more preferably less than 600.

In the first aspect, the present invention is directed to a compound represented by Formula (I), or a stereoisomer, or a pharmaceutically acceptable salt thereof, wherein $X_1$ is N, and the other variables are as defined above for Formula (I).

In an embodiment of the first aspect, the present invention is directed to a compound represented by Formula (I), or a stereoisomer, or a pharmaceutically acceptable salt thereof, wherein $X_1$ is N, Y is $C_{0-2}$alkyl, and Z is —C(O)—, and the other variables are as defined above for Formula (I).

In another embodiment of the first aspect, the present invention is directed to a compound represented by Formula (I), or a stereoisomer, or a pharmaceutically acceptable salt thereof, wherein $X_1$ is N, Y is $C_{0-2}$alkyl, and Z is —O—, and the other variables are as defined above for Formula (I).

In yet another embodiment of the first aspect, the present invention is directed to a compound represented by Formula (I), or a stereoisomer, or a pharmaceutically acceptable salt thereof, wherein $X_1$ is N, Y is $C_{0-2}$alkyl, and Z is >N($C_{0-4}$alkyl), and the other variables are as defined above for Formula (I).

In a second aspect, the present invention is directed to a compound represented by Formula (I), or a stereoisomer, or a pharmaceutically acceptable salt thereof, wherein $X_2$ is N, and the other variables are as defined above for Formula (I).

In an embodiment of the second aspect, the present invention is directed to a compound represented by Formula (I), or a stereoisomer, or a pharmaceutically acceptable salt thereof, wherein $X_2$ is N, Y is $C_{0-2}$alkyl, and Z is —C(O)—, and the other variables are as defined above for Formula (I).

In a third aspect, the present invention is directed to a compound represented by Formula (I), or a stereoisomer, or a pharmaceutically acceptable salt thereof, wherein $X_3$ is N, and the other variables are as defined above for Formula (I).

In an embodiment of the third aspect, the present invention is directed to a compound represented by Formula (I), or a stereoisomer, or a pharmaceutically acceptable salt thereof, wherein $X_3$ is N, Y is $C_{0-2}$alkyl, and Z is —C(O)—, and the other variables are as defined above for Formula (I).

In another embodiment of the third aspect, the present invention is directed to a compound represented by Formula (I), or a stereoisomer, or a pharmaceutically acceptable salt thereof, wherein $X_3$ is N, Y is —CH(OH)—, and Z is —C(O)—, and the other variables are as defined above for Formula (I).

In yet another embodiment of the third aspect, the present invention is directed to a compound represented by Formula (I), or a stereoisomer, or a pharmaceutically acceptable salt thereof, wherein $X_3$ is N, Y is $C_{0-2}$alkyl, and Z is —O—, and the other variables are as defined above for Formula (I).

In still another embodiment of the third aspect, the present invention is directed to a compound represented by Formula (I), or a stereoisomer, or a pharmaceutically acceptable salt thereof, wherein $X_3$ is N, Y is $C_{0-2}$alkyl, and Z is absent, and the other variables are as defined above for Formula (I).

In yet still another embodiment of the third aspect, the present invention is directed to a compound represented by Formula (I), or a stereoisomer, or a pharmaceutically acceptable salt thereof, wherein $X_3$ is N, Y is $C_{0-2}$alkyl, and Z is >N($C_{0-4}$alkyl), and the other variables are as defined above for Formula (I).

In a fourth aspect, the present invention is directed to a compound represented by Formula (I), or a stereoisomer, or a pharmaceutically acceptable salt thereof, wherein $X_4$ is N, and the other variables are as defined above for Formula (I).

In an embodiment of the fourth aspect, the present invention is directed to a compound represented by Formula (I), or a stereoisomer, or a pharmaceutically acceptable salt thereof, wherein $X_4$ is N, Y is —CH(OH)—, and Z is —C(O)—, and the other variables are as defined above for Formula (I).

When Y is a direct bond then Z is preferably other than —O—, >N($C_{0-4}$alkyl) or >N($C_{3-6}$cycloalkyl).

Preferably $X_3$ is N.

Preferably $R^1$ and $R^{1'}$ are each independently, halogen, cyano, hydrogen, methyl, methoxy, or ethynyl. More preferably $R^1$ and $R^{1'}$ are each independently, halogen, cyano, or hydrogen.

Preferably at least one of $R^1$ and $R^{1'}$ is hydrogen. More preferably one of $R^1$ and $R^{1'}$ is hydrogen.

A preferred group of compounds are those where $X_3$ is N, one of $R^1$ and $R^{1'}$ is hydrogen and the other is a 5-halo or 5-cyano group.

Preferably Y is $C_{0-2}$alkyl, more preferably Y is a direct bond.

Preferably Z is —C(O)—.

A preferred group of compounds are those wherein $X_3$ is N;

Y is $C_{0-2}$alkyl; and

Z is —C(O)—.

Preferably $R^2$ is $C_{0-4}$alkyl or aryl$C_{0-4}$alkyl-, wherein the aryl ring is optionally substituted with 1–2 independent halogen, cyano, $C_{1-4}$alkyl, $C_{1-4}$alkoxy, —N($C_{0-4}$alkyl)($C_{0-4}$alkyl), —SO$_2$C$_{1-4}$alkyl, —SO$_2$N($C_{0-4}$alkyl)($C_{0-4}$alkyl), hydroxy, fluoromethyl, difluoromethyl, or trifluoromethyl substituents. More preferably $R^2$ is benzyl optionally substituted with 1–2 halogen substituents. A particular $R^2$ substituent which may be mentioned is —(S)-(4-fluorobenzyl).

Preferably $R^3$ is —$C_{0-4}$alkylheterocyclyl optionally substituted with 1–3 independent halogen, cyano, $C_{1-4}$alkyl, fluoromethyl, difluoromethyl, trifluoromethyl, —$C_{0-4}$alkylNHC(O)O($C_{1-4}$alkyl), —$C_{0-4}$alkylNR$^7$R$^8$, —C(O)R$^9$, $C_{1-4}$alkoxy$C_{0-4}$alkyl-, —COOC$_{0-4}$alkyl, —$C_{0-4}$alkylNHC(O)R$^9$, —$C_{0-4}$alkylC(O)N(R$^{10}$)$_2$, —$C_{1-4}$alkoxy$C_{1-4}$alkoxy, hydroxy$C_{0-4}$alkyl-, —NHSO$_2$R$^{10}$, —SO$_2$($C_{1-4}$alkyl), —SO$_2$NR$^{11}$R$^{12}$, 5- to 6-membered heterocyclyl, phenyl$C_{0-2}$alkoxy, or phenyl$C_{0-2}$alkyl substituents, wherein phenyl is optionally substituted with 1–2 independent halogen, cyano, $C_{1-4}$alkyl, $C_{1-4}$alkoxy, —N($C_{0-4}$alkyl)($C_{0-4}$alkyl), —SO$_2$C$_{1-4}$alkyl, —SO$_2$N($C_{0-4}$alkyl)($C_{0-4}$alkyl), hydroxy, fluoromethyl, difluoromethyl, or trifluoromethyl substituents, or two bonds on a ring carbon of the heterocyclyl group optionally can form an oxo (=O) substituent; or $R^3$ is —NR$^4$(—$C_{0-4}$alkylR$^5$).

More preferably $R^3$ is a nitrogen containing heterocyclyl group, especially a 4–8-membered nitrogen containing heterocyclyl group, linked to Z via a ring nitrogen atom, optionally substituted with 1–3 independent halogen, cyano, $C_{1-4}$alkyl, fluoromethyl, difluoromethyl, trifluoromethyl, —$C_{0-4}$alkylNHC(O)O($C_{1-4}$alkyl), —$C_{0-4}$alkylNR$^7$R$^8$, —C(O)R$^9$, $C_{1-4}$alkoxy$C_{0-4}$alkyl-, —COOC$_{0-4}$alkyl, —$C_{0-4}$alkylNHC(O)R$^9$, —$C_{0-4}$alkylC(O)N(R$^{10}$)$_2$, —$C_{1-4}$alkoxy$C_{1-4}$alkoxy, hydroxy$C_{0-4}$alkyl-, —NHSO$_2$R$^{10}$, —SO$_2$($C_{1-4}$alkyl), —SO$_2$NR$^{11}$R$^{12}$, 5- to 6-membered heterocyclyl, phenyl$C_{0-2}$alkoxy, or phenyl$C_{0-2}$alkyl substituents, wherein phenyl is optionally substituted with 1–2 independent halogen, cyano, $C_{1-4}$alkyl, $C_{1-4}$alkoxy, —N($C_{0-4}$alkyl)($C_{0-4}$alkyl), —SO$_2$C$_{1-4}$alkyl, —SO$_2$N($C_{0-4}$alkyl)($C_{0-4}$alkyl), hydroxy, fluoromethyl, difluoromethyl, or trifluoromethyl substituents, or two bonds on a ring carbon of the heterocyclyl group optionally can form an oxo (=O) substituent; or $R^3$ is —NR$^4$(—$C_{0-4}$alkylR$^5$).

Examples of nitrogen containing heterocyclyl groups which $R^3$ may represent include azetidin-1-yl, pyrrolidin-1-yl, piperidin-1-yl, 1,4-diazapan-1-yl, piperazin-1-yl, morpholin-4-yl, thiomorpholin-4-yl, 1,1-dioxo-thiomorpholin-4-yl, or thiazolidin-3-yl; which groups may be optionally substituted as described above Preferred substituent groups for $R^3$ include —$C_{1-4}$alkoxy, hydroxy and oxo.

Even more preferably $R^3$ is pyrrolidin-1-yl or piperidin-1-yl optionally substituted with hydroxyl, e.g. 4-hydroxypiperidin-1-yl and 3-(S)-hydroxypyrrolidin-1-yl.

Specific compounds of the invention which may be mentioned are those included in the examples, in particular 5-chloro-1H-pyrrolo[2,3-c]pyridine-2-carboxylic acid [1-(S)-(4-fluorobenzyl)-2-(4-hydroxypiperidin-1-yl)-2-oxoethyl]amide and 5-chloro-1H-pyrrolo[2,3-c]pyridine-2-carboxylic acid [1-(S)-(4-fluorobenzyl)-2-(3-(S)-hydroxypyrrolidin-1-yl)-2-oxoethyl]amide.

A particular group of compounds which may be mentioned are those represented by Formula (IA):

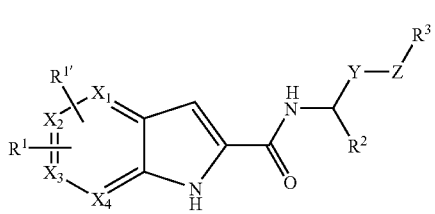

or a stereoisomer, or a pharmaceutically acceptable salt thereof, wherein:
one of $X_1$, $X_2$, $X_3$ and $X_4$ must be N and the others must be C;
$R^1$ and $R^{1'}$ are each independently, halogen, hydroxy, cyano, $C_{0-4}$alkyl, $C_{1-4}$alkoxy, fluoromethyl, difluoromethyl, trifluoromethyl, ethenyl, or ethynyl;
$R^2$ is $C_{0-4}$alkyl, aryl$C_{0-4}$alkyl-, hetaryl$C_{0-4}$alkyl-, wherein any of the aryl or hetaryl rings are optionally substituted with 1–2 independent halogen, cyano, $C_{1-4}$alkyl, $C_{1-4}$alkoxy, —N($C_{0-4}$alkyl)($C_{0-4}$alkyl), —SO$_2$C$_{1-4}$alkyl, —SO$_2$N(CO$_{0-4}$alkyl)($C_{0-4}$alkyl), hydroxy, fluoromethyl, difluoromethyl, or trifluoromethyl substituents;
Y is $C_{0-2}$alkyl or —CH(OH)—;
Z is CH$_2$, —C(O)—, —O—, >N($C_{0-4}$alkyl), >N($C_{3-6}$cycloalkyl), or absent; but when Y is —CH(OH)—, Z or $R^3$ must be bonded to Y through a carbon-carbon bond;
$R^3$ is hydrogen, —COOC$_{0-4}$alkyl, $C_{1-4}$alkoxy, aryl$C_{1-4}$alkylthio-, —$C_{0-4}$alkylaryl, —$C_{0-4}$alkylhetaryl, or —$C_{0-4}$alkylheterocyclyl, wherein any of the rings is optionally substituted with 1–3 independent halogen, cyano, $C_{1-4}$alkyl, fluoromethyl, difluoromethyl, trifluoromethyl, —$C_{0-4}$alkylN($C_{0-4}$alkyl)($C_{0-4}$alkyl), —C(O)($C_{0-4}$alkyl), $C_{1-4}$alkoxy$C_{0-4}$alkyl-, —COOC$_{0-4}$alkyl, $C_{0-4}$alkylcarbamoyl-, —$C_{1-4}$alkoxymethoxy, hydroxy$C_{0-4}$alkyl-, —SO$_2$($C_{1-4}$alkyl), or phenyl$C_{0-2}$alkyl substituents, or two bonds on a ring carbon of the heterocyclyl group optionally can form an oxo (=O) substituent;
or $R^3$ is —NR$^4$(—$C_{0-4}$alkylR$^5$);
$R^4$ is $C_{0-3}$alkyl, —$C_{2-3}$alkyl-N($C_{1-3}$alkyl)($C_{1-3}$alkyl), $C_{3-6}$cycloalkyl, hydroxy$C_{2-3}$alkyl-, $C_{1-2}$alkoxy$C_{2-4}$alkyl-, or $C_{1-2}$alkyl-S(O)$_n$—$C_{2-3}$alkyl-;
n is 0, 1, or 2;
$R^5$ is hydrogen, hydroxy$C_{2-3}$alkyl-, $C_{1-2}$alkoxy$C_{2-4}$alkyl, or an aryl, hetaryl, or heterocyclyl;
wherein a heterocyclic nitrogen-containing $R^5$ ring optionally is mono-substituted on the ring nitrogen with $C_{1-4}$alkyl, benzyl, benzoyl, $C_{1-4}$alkyl-C(O)—, —SO$_2$C$_{1-4}$alkyl, —SO$_2$N($C_{0-4}$alkyl)($C_{0-4}$alkyl), $C_{1-4}$alkoxycarbonyl or aryl($C_{1-4}$alkoxy)carbonyl; and wherein the $R^5$ rings are optionally mono-substituted on a ring carbon with halogen, cyano, $C_{1-4}$alkyl-C(O)—, $C_{1-4}$alkyl-SO$_2$—, $C_{1-4}$alkyl, $C_{1-4}$alkoxy, —N($C_{0-4}$alkyl)($C_{0-4}$alkyl), hydroxy$C_{0-4}$alkyl-, or $C_{0-4}$alkylcarbamoyl-, provided that no quaternised nitrogen is included; and
wherein there are no nitrogen-oxygen, nitrogen-nitrogen or nitrogen-halogen bonds in linking the three components —Y—Z—R$^3$ to each other.

While the preferred groups for each variable have generally been listed above separately for each variable, preferred compounds of this invention include those in which several or each variable in Formula (I) is selected from the preferred, more preferred, most preferred, especially or particularly listed groups for each variable. Therefore, this invention is intended to include all combinations of preferred, more preferred, most preferred, especially and particularly listed groups.

As used herein, unless stated otherwise, "alkyl" as well as other groups having the prefix "alk" such as, for example, alkoxy, alkanyl, alkenyl, alkynyl, and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains having at least one unsaturated carbon-carbon bond.

As used herein, for example, "$C_{0-4}$alkyl" is used to mean an alkyl having 0–4 carbons—that is, 0, 1, 2, 3, or 4 carbons in a straight or branched configuration. An alkyl having no carbon is hydrogen when the alkyl is a terminal group. An alkyl having no carbon is a direct bond when the alkyl is a bridging (connecting) group.

The terms "cycloalkyl" and "carbocyclic ring" mean carbocycles containing no heteroatoms, and include mono-, bi-, and tricyclic saturated carbocycles, as well as fused and bridged systems. Such fused ring systems can include one ring that is partially or fully unsaturated, such as a benzene ring, to form fused ring systems, such as benzofused carbocycles. Cycloalkyl includes such fused ring systems as spirofused ring systems. Examples of cycloalkyl and carbocyclic rings include $C_{3-10}$cycloalkyl groups, particularly $C_{3-8}$cycloalkyl groups, such as cyclopropyl, cyclobutyl, cyclopentyl, cyclohexyl, and decahydronaphthalene, adamantane, indanyl, 1,2,3,4-tetrahydronaphthalene and the like.

The term "halogen" includes fluorine, chlorine, bromine, and iodine atoms.

The term "carbamoyl" unless specifically described otherwise means —C(O)—NH— or —NH—C(O)—.

The term "aryl" is well known to chemists. The preferred aryl groups are phenyl and naphthyl, more preferably phenyl.

The term "hetaryl" is well known to chemists. The term includes 5- or 6-membered heteroaryl rings containing 1–4 heteroatoms chosen from oxygen, sulfur, and nitrogen in which oxygen and sulfur are not next to each other. Examples of such heteroaryl rings are furyl, thienyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridyl, pyridazinyl, pyrimidinyl, pyrazinyl, and triazinyl. The term "hetaryl" includes hetaryl rings with fused carbocyclic ring systems that are partially or fully unsaturated, such as a benzene ring, to form a benzofused hetaryl. For example, benzimidazole, benzoxazole, benzothiazole, benzofuran, quinoline, isoquinoline, quinoxaline, and the like.

Unless otherwise stated, the terms "heterocyclic ring", "heterocyclyl" and "heterocycle" are equivalent, and include 4–10-membered, e.g. 4–8-membered, saturated or partially saturated rings containing one or two heteroatoms chosen from oxygen, sulfur, and nitrogen. The sulfur and oxygen heteroatoms are not directly attached to one another. Any nitrogen heteroatoms in the ring may optionally be substituted with $C_{1-4}$alkyl. Examples of heterocyclic rings include azetidine, oxetane, tetrahydrofuran, tetrahydropyran, oxepane, oxocane, thietane, thiazolidine, oxazolidine, oxazetidine, pyrazolidine, isoxazolidine, isothiazolidine, tetrahydrothiophene, tetrahydrothiopyran, thiepane, thiocane, azetidine, pyrrolidine, piperidine, N-methylpiperidine, azepane, 1,4-diazapane, azocane, [1,3]dioxane, oxazolidine, piperazine, homopiperazine, morpholine, thiomorpholine, 1,2,3,6-tetrahydropyridine and the like. Other examples of heterocyclic rings include the oxidized forms of the sulfur-containing rings. Thus, tetrahydrothiophene-1,1-oxide, tetrahydrothiophene-1,1-dioxide, thiomorpholine-1-oxide, thiomorpholine-1,1-dioxide, tetrahydrothiopyran-1-oxide, tetrahydrothiopyran-1,1-dioxide, thiazolidine-1-oxide, and thiazolidine-1,1-dioxide are also considered to be heterocyclic rings. The term "heterocyclic" also includes fused ring systems and can include a carbocyclic ring that is partially or fully unsaturated, such as a benzene ring, to form benzofused heterocycles. For example, 3,4-dihydro-1,4-benzodioxine, tetrahydroquinoline, tetrahydroisoquinoline and the like.

Compounds described herein may contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula (I) is shown without a definitive stereochemistry at certain positions. The present invention includes all stereoisomers of Formula (I) and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

When a tautomer of the compound of Formula (I) exists, the present invention includes any possible tautomers and pharmaceutically acceptable salts thereof, and mixtures thereof, except where specifically drawn or stated otherwise.

When the compound of Formula (I) and pharmaceutically acceptable salts thereof exist in the form of solvates or polymorphic forms, the present invention includes any possible solvates and polymorphic forms. A type of a solvent that forms the solvate is not particularly limited so long as the solvent is pharmacologically acceptable. For example, water, ethanol, propanol, acetone or the like can be used.

The invention also encompasses a pharmaceutical composition that is comprised of a compound of Formula (I), or a pharmaceutically acceptable salt thereof, in combination with a pharmaceutically acceptable carrier.

Preferably the composition is comprised of a pharmaceutically acceptable carrier and a non-toxic therapeutically effective amount of a compound of Formula (I), or a pharmaceutically acceptable salt thereof.

Moreover, within this preferred embodiment, the invention encompasses a pharmaceutical composition for the treatment of disease by inhibiting glycogen phosphorylase, resulting in the prophylactic or therapeutic treatment of diabetes, hyperglycemia, hypercholesterolemia, hyperinsulinemia, hyperlipidemia, hypertension, atherosclerosis or tissue ischemia e.g. myocardial ischemia comprising a pharmaceutically acceptable carrier and a non-toxic therapeutically effective amount of compound of Formula (I), or a pharmaceutically acceptable salt thereof.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include arginine, betaine, caffeine, choline, N'N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

Since the compounds of Formula (I) are intended for pharmaceutical use they are preferably provided in substantially pure form, for example at least 60% pure, more suitably at least 75% pure especially at least 98% pure (% are on a weight for weight basis).

The pharmaceutical compositions of the present invention comprise a compound represented by Formula (I), or a pharmaceutically acceptable salt thereof, as an active ingredient, a pharmaceutically acceptable carrier and optionally other therapeutic ingredients or adjuvants. The compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The compositions are preferably suitable for oral administration The pharmaceutical compositions may be conveniently presented in unit dosage form and prepared by any of the methods well known in the art of pharmacy.

In practice, the compounds of Formula (I), or pharmaceutically acceptable salts thereof, can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous). Thus, the pharmaceutical compositions of the present invention can be presented as discrete units suitable for oral administration such as capsules, sachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compounds of Formula (I), or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound of Formula (I) or a pharmaceutically acceptable salt thereof. The compounds of Formula (I), or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each sachet or capsule preferably contains from about 0.05 mg to about 5 g of the active ingredient.

For example, a formulation intended for oral administration to humans may contain from about 0.5 mg to about 5 g of active agent, compounded with an appropriate and convenient amount of carrier material, which may vary from about 5 to about 95% of the total composition. Unit dosage forms will generally contain from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound of Formula (I), or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of Formula (I), or a pharmaceutically acceptable salt thereof, may also be prepared in powder or liquid concentrate form.

Generally, dosage levels on the order of 0.01 mg/kg to about 150 mg/kg of body weight per day are useful in the treatment of the above-indicated conditions, or alternatively about 0.5 mg to about 7 g per patient per day. For example, diabetes and hyperglycemia may be effectively treated by the administration of from about 0.01 to 50 mg of the compound per kilogram of body weight per day, or alternatively about 0.5 mg to about 3.5 g per patient per day. Similarly, hypercholesterolemia, hyperinsulinemia, hyperlipidemia, hypertension, atherosclerosis or tissue ischemia e.g. myocardial ischemia may be effectively treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

The compounds of Formula (I) and pharmaceutically acceptable salts thereof, may be used in the treatment of diseases or conditions in which glycogen phosphorylase plays a role.

Thus the invention also provides a method for the treatment of a disease or condition in which glycogen phosphorylase plays a role comprising a step of administering to a subject in need thereof an effective amount of a compound of Formula (I), or a pharmaceutically acceptable salt thereof.

Diseases or conditions in which glycogen phosphorylase plays a role include diabetes (including Type I and Type II, impaired glucose tolerance, insulin resistance and diabetic complications such as neuropathy, nephropathy, retinopathy and cataracts), hyperglycemia, hypercholesterolemia, hyperinsulinemia, hyperlipidemia, hypertension, atherosclerosis, tissue ischemia e.g. myocardial ischemia.

The invention also provides a method for the treatment of hyperglycemia or diabetes comprising a step of administering to a subject in need thereof an effective amount of a compound of Formula (I), or a pharmaceutically acceptable salt thereof.

The invention also provides a method for the prevention of diabetes in a human demonstrating pre-diabetic hyperglycemia or impaired glucose tolerance comprising a step of administering to a subject in need thereof an effective prophylactic amount of a compound of Formula (I), or a pharmaceutically acceptable salt thereof.

The invention also provides a method for the treatment of hypercholesterolemia, hyperinsulinemia, hyperlipidemia, hypertension, atherosclerosis or tissue ischemia comprising a step of administering to a patient in need thereof an effective amount of a compound of Formula (I), or a pharmaceutically acceptable salt thereof.

The invention also provides a method of cardioprotection e.g. following reperfusion injury, comprising a step of administering to a subject in need thereof an effective amount of a compound of Formula (I), or a pharmaceutically acceptable salt thereof.

The invention also provides the use of a compound of Formula (I), or a pharmaceutically acceptable salt thereof, in the treatment of a condition as defined above.

The invention also provides the use of a compound of Formula (I), or a pharmaceutically acceptable salt thereof, in the manufacture of a medicament for the treatment of a condition as defined above.

In the methods of the invention the term "treatment" includes both therapeutic and prophylactic treatment.

The compounds of Formula (I), or pharmaceutically acceptable salts thereof, may be administered alone or in combination with one or more other therapeutically active compounds. The other therapeutically active compounds may be for the treatment of the same disease or condition as the compounds of Formula (I) or a different disease or condition. The therapeutically active compounds may be administered simultaneously, sequentially or separately.

The compounds of Formula (I) may be administered with other active compounds for the treatment of diabetes, for example insulin and insulin analogs, sulfonyl ureas and analogs, biguanides, α2 agonists, fatty acid oxidation inhibitors, α-glucosidase inhibitors, β-agonists, phosphodiesterase inhibitors, lipid lowering agents, antiobesity agents, amylin antagonists, lipoxygenase inhibitors, somostatin analogs, glucokinase activators, glucagon antagonists, insulin signalling agonists, PTP1B inhibitors, gluconeogenesis inhibitors, antilypolitic agents, GSK inhibitors, galanin receptor agonists, anorectic agents, CCK receptor agonists, leptin, CRF antagonists or CRF binding proteins.

The compounds of Formula (I) may also be administered in combination with thyromimetic compounds, aldose reductase inhibitors, glucocorticoid receptor antagonists, NHE-1 inhibitors or sorbitol dehydrogenase inhibitors.

The compounds of Formula (I) may exhibit advantageous properties compared to known glycogen phosphorylase inhibitors, for example, the compounds may exhibit improved solubility thus improving absorption properties and bioavailability. Furthermore the compounds of Formula (I) may exhibit further advantageous properties such as reduced inhibition of cytochrome P450 enzymes, meaning that they are less likely to cause adverse drug-drug interactions than known glycogen phosphorylase inhibitors.

All publications, including, but not limited to, patents and patent application cited in this specification, are herein incorporated by reference as if each individual publication were specifically and individually indicated to be incorporated by reference herein as fully set forth.

In accordance with this invention, the compounds of Formula (I) can be prepared as outlined in Scheme 1 below wherein $R^1$, $R^{1'}$, $R^2$, $R^3$, $X_1$, $X_2$, $X_3$, $X_4$, Y and Z are as defined above for Formula (I):

Scheme 1

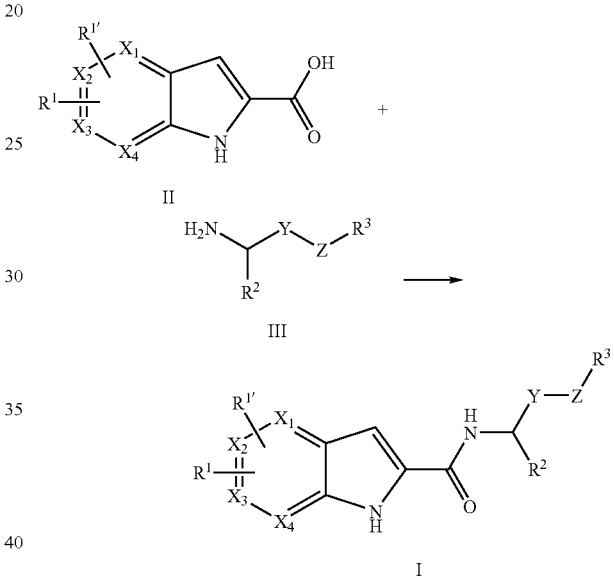

According to Scheme 1, the compounds of Formula (I) may be prepared by coupling the appropriate pyrrolopyridine-2-carboxylic acid of Formula (II), or a protected or activated derivative thereof, with the appropriate amine of Formula (III). Compounds of Formula (II) can be obtained by the syntheses described in Schemes 3 and 5 below. Compounds of Formula (III) are generally commercially available or can be obtained by the syntheses described in Schemes 8 and 9 below.

Typically, the compound of Formula (II), or a protected or activated derivative thereof, is combined with a compound of Formula (III) in the presence of a suitable coupling agent. Examples of suitable coupling reagents are 1-(3-dimethylaminopropyl)-3-ethylcarbodiimide hydrochloride/hydroxybenzotriazole (EDCI/HOBt), 1,1-carbonyldiimidazole (CDI), dicyclohexylcarbodiimide/hydroxybenzotriazole (DCC/HOBt), O-(1H-benzotriazol-1-yl)-N,N,N',N'-tetramethyluronium tetrafluoroborate (R. Knorr et al., *Tetrahedron Lett.*, 1989, 30, 1927–1930) and polymer supported carbodiimide-1-hydroxybenzotriazole (for representative procedures, see for example, Argonaut Technical Note 501 available from Argonaut Technologies, Inc., Foster City, Calif.). The couplings are performed in an inert solvent, preferably an aprotic solvent at a temperature of about 0° C. to about 45° C.

for about 1 to 72 h in the presence of a tertiary amine base such as diisopropylethylamine (DIPEA) or triethylamine. Exemplary solvents include acetonitrile, chloroform, dichloromethane, N,N-dimethylformamide (DMF) or mixtures thereof. Use of these coupling agents and appropriate selection of solvents and temperatures are known to those skilled in the art or can be readily determined from the literature. These and other exemplary conditions useful for coupling carboxylic acids are described in Houben-Weyl, Vol XV, part II, E. Wunsch, Ed., G. Thieme Verlag, 1974, Stuttgart, and M. Bodansky, Principles of Peptide Synthesis, Springer-Verlag, Berlin, 1984 and The Peptides, Analysis, Synthesis and Biology (Ed., E. Gross and J. Meienhofer), Vols 1–5, Academic Press NY 1979–1983.

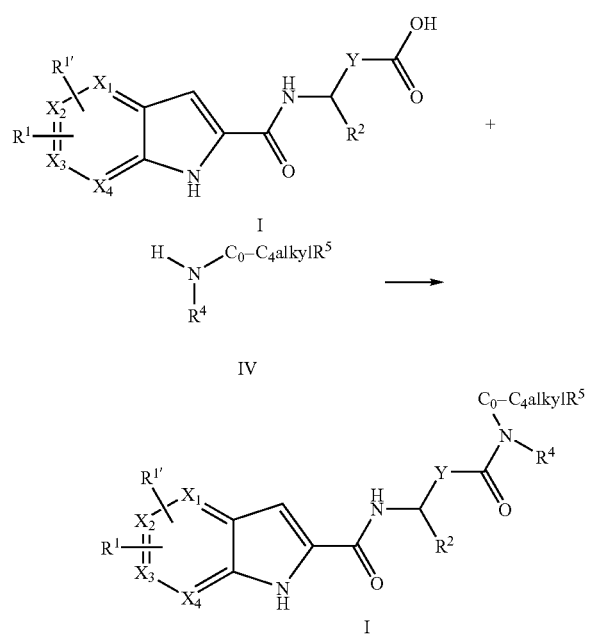

In a second process, the compounds of Formula (I) (wherein Z is C=O and $R^3$ is —$NR^4$(—$C_{0-4}$alkyl$R^5$)) may be prepared according to Scheme 2 by coupling the appropriate carboxylic acid of Formula (I), or a protected or activated derivative thereof, (wherein Z is absent and $R^3$ is —$CO_2H$) with the appropriate amine of Formula (IV). Examples of suitable coupling agents and conditions are as described above. Compounds of Formula (IV) are commercially available or are readily prepared by known techniques.

Compounds of Formula (II) can be prepared as illustrated in Scheme 3.

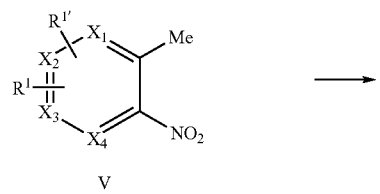

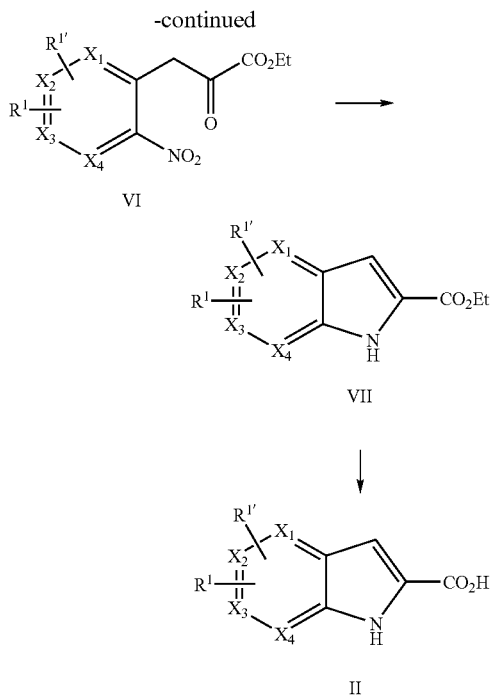

Compounds of Formula (VI) may be prepared by condensation of ortho methyl nitro compounds of Formula (V) with an oxalate ester in a solvent such as diethyl ether in the presence of a base such as potassium ethoxide or DBU. Compounds of Formula (VII) are prepared from compounds of Formula (VI) under reducing conditions, such as iron powder and ammonium chloride, or by hydrogenation in ethanol using palladium catalysis. Compounds of Formula (VII) undergo ester hydrolysis using aqueous alkali to give pyrrolopyridine-2-carboxylic acids of Formula (II). Further information on the conversion of compounds of Formula (V) to compounds of Formula (II) are described in the literature (Kerrnack, et al., *J. Chem, Soc.*, 1921, 119, 1602; Cannon et al., *J. Med. Chem.*, 1981, 24, 238; Julian et al., in Heterocyclic Compounds, Vol 3 (Wiley, New York, N.Y., 1962, R. C. Elderfield, Ed.) p 18.

Alternatively, the compound of Formula (VII) wherein $X_2$ is nitrogen can be prepared as illustrated in Scheme 4.

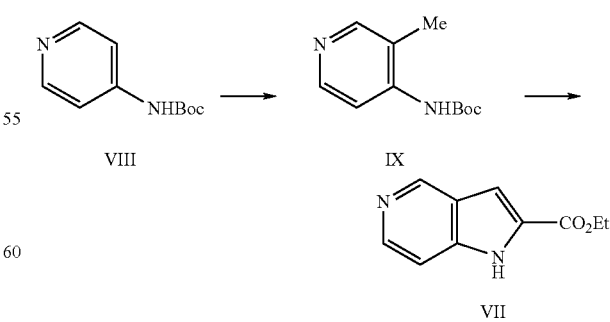

Deprotonation of compounds of Formula (VIII) with an organolithium such as n-butyllithium in a suitable solvent such as THF, followed by quenching with methyl iodide gives compounds of Formula (IX). Such compounds can undergo further deprotonation with tert-butyllithium, in a suitable solvent such as THF, followed by quenching with diethyl oxalate and subsequent heating of the intermediate under reflux in hydrochloric acid, to give compounds of Formula (VII).

Compounds of Formula (II) may also be prepared according to Scheme 5 by Heck coupling of an ortho-iodo aminopyridine (XIV) followed by cyclisation at a temperature of between 100 to 150° C. in the presence of catalyst such as palladium acetate and a base such as DABCO in a solvent such as DMF (See Chen et al, J. Org. Chem. 1997, 62, 2676). The ortho-iodo aminopyridines (XIV) can be made by direct iodination of the appropriate aminopyridine (XIII) using iodine in the presence of silver sulfate in a solvent such as ethanol at ambient temperature (see Sy, W., *Synth. Commun.*, 1992, 22, 3215).

Scheme 5

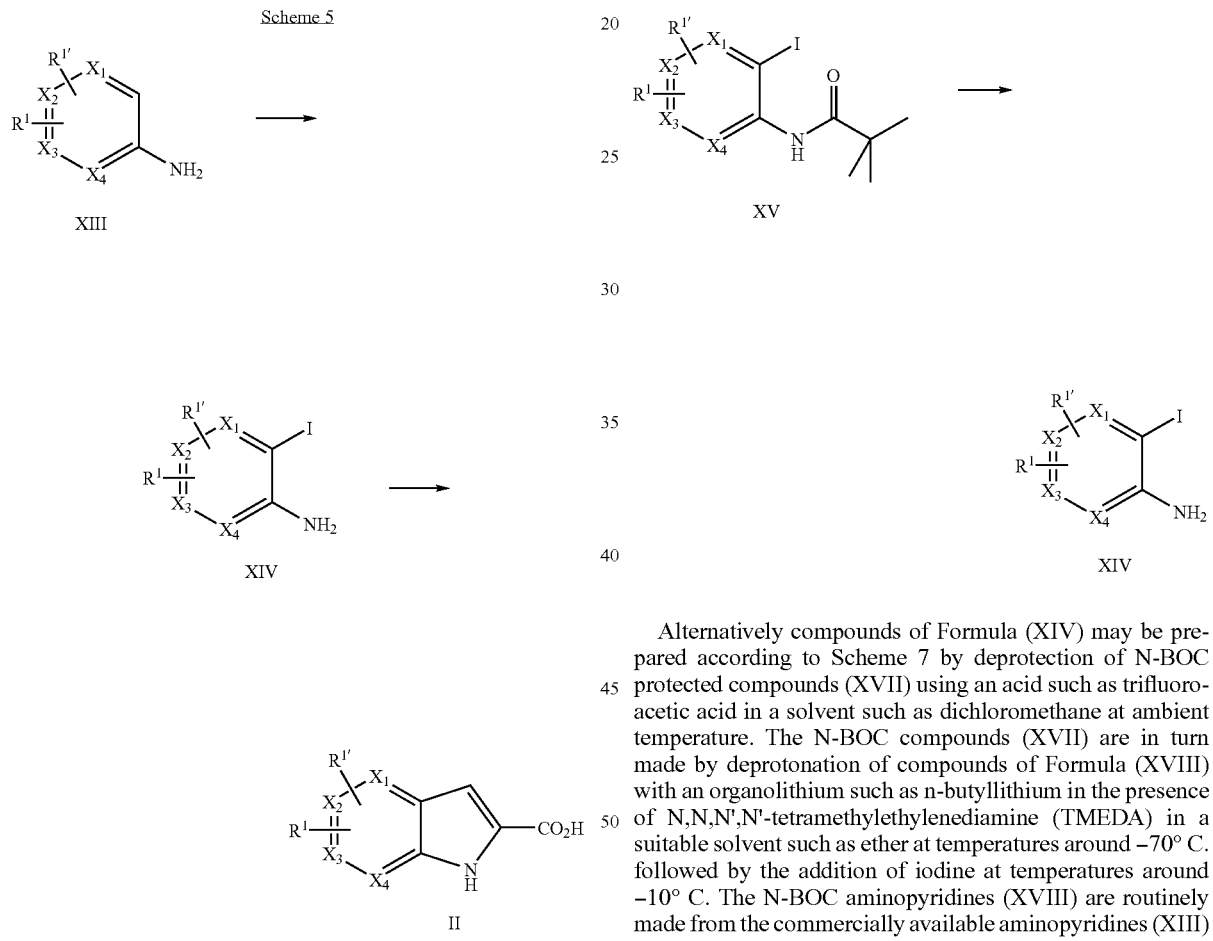

Alternatively compounds of Formula (XIV) may be prepared according to Scheme 6 by deprotection of N-pivaloyl compounds (XV) by heating under reflux using hydrochloric acid. The N-pivaloyl compounds (XV) are in turn made by deprotonation of compounds of Formula (XVI) with an organolithium such as tert-butyllithium in a suitable solvent such as THF, followed by quenching with iodine at a low temperature. Compounds of formula (XVI) may be made by protection of commercially available aminopyridines (XIII) with trimethylacetyl chloride and a base such as triethylamine in a solvent such as dichloromethane.

Scheme 6

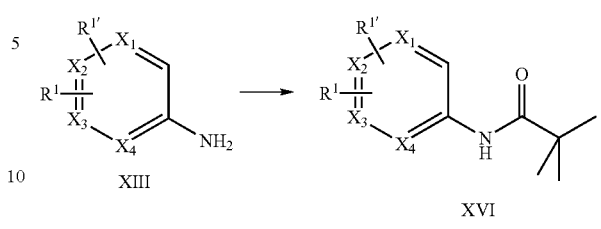

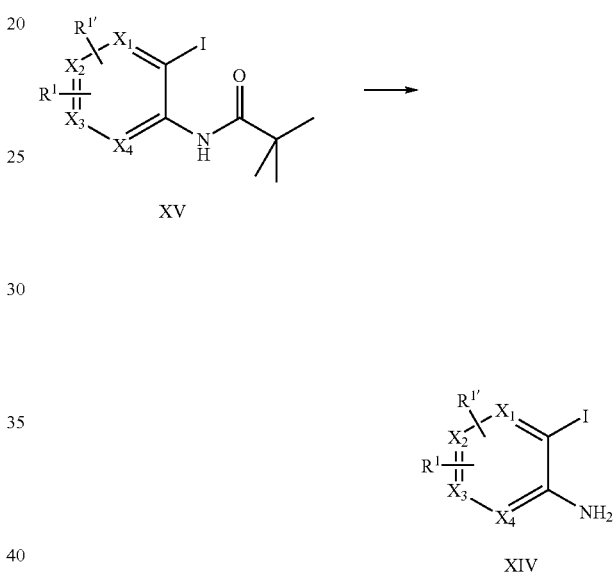

Alternatively compounds of Formula (XIV) may be prepared according to Scheme 7 by deprotection of N-BOC protected compounds (XVII) using an acid such as trifluoroacetic acid in a solvent such as dichloromethane at ambient temperature. The N-BOC compounds (XVII) are in turn made by deprotonation of compounds of Formula (XVIII) with an organolithium such as n-butyllithium in the presence of N,N,N',N'-tetramethylethylenediamine (TMEDA) in a suitable solvent such as ether at temperatures around –70° C. followed by the addition of iodine at temperatures around –10° C. The N-BOC aminopyridines (XVIII) are routinely made from the commercially available aminopyridines (XIII) using di-tert-butyldicarbonate by heating in a solvent such as 1,4-dioxane.

Scheme 7

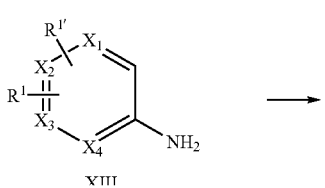

-continued

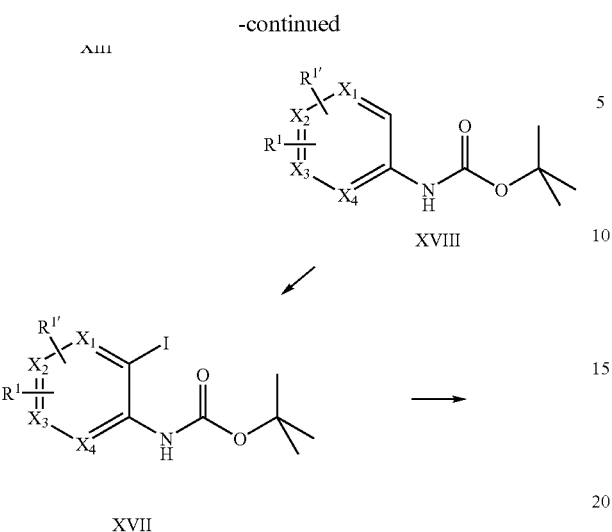

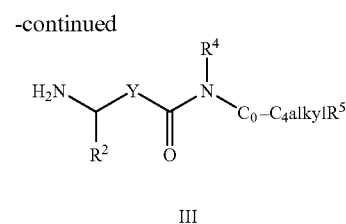

Compounds of Formula (III) may be prepared from compounds of Formula (XI) by removal of the protecting group, where PG=Boc, under acidic conditions using for example trifluoroacetic acid in dichloromethane at temperatures of around 25° C.

Compounds of Formula (III) wherein $R^2$ is H, Y is $C_0$ alkyl, Z is —C(O)— and $R^3$ is —$C_0$alkylaryl or —$C_0$alkylhetaryl can be prepared according to Scheme 9.

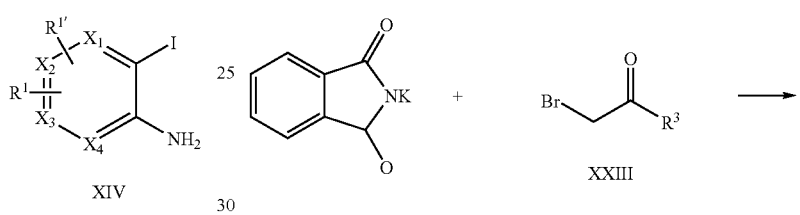

Protected or activated derivatives of the compounds of Formula (II) may be prepared by methods known to those skilled in the art.

Compounds of Formula (III) can be prepared as illustrated in Scheme 8.

Compounds of Formula (X) are generally commercially available or are readily prepared by known techniques. PG represents a protecting group such as, for example, tert-butyloxycarbonyl (Boc). Compounds of Formula (XI) are made from carboxylic acids of Formula (X) using standard coupling conditions as described above for Scheme 1.

Compounds of Formula (III) can be prepared as illustrated in Scheme 8.

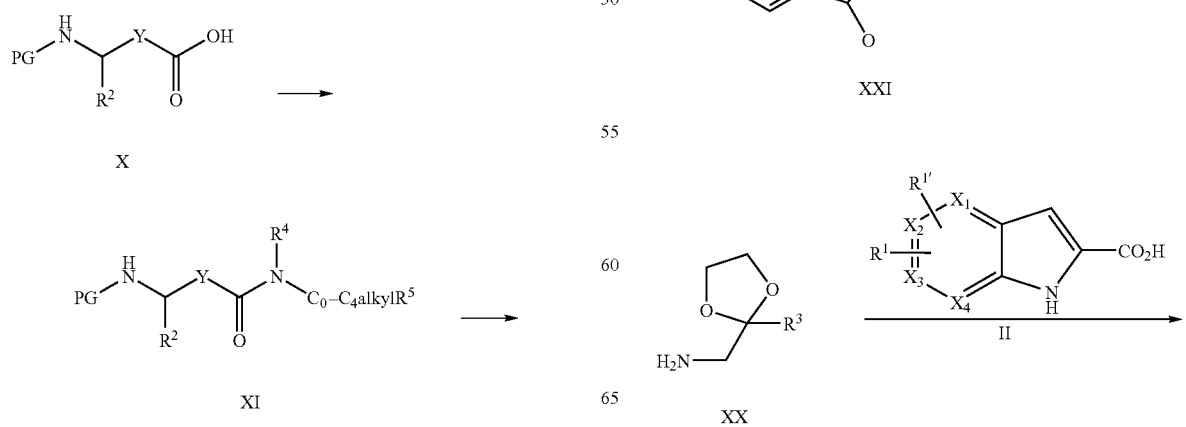

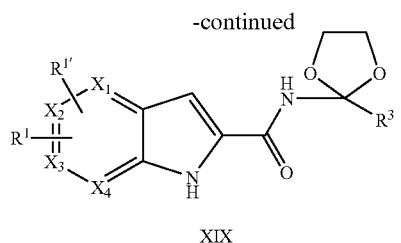

XIX

Compounds of Formula (XXIII) are reacted with potassium phthalimide in a solvent such as DMF to give compounds of Formula (XXII) which can then be reacted with ethylene glycol in the presence of a catalytic amount of acid such as p-toluene sulfonic acid in a solvent such as toluene whilst removing water to give compounds of Formula (XXI). The phthalimide protecting group can then be removed using hydrazine hydrate by heating as a neat solution or by heating in a solvent such as ethanol to give compounds of Formula (XX). These amines are then coupled with compounds of Formula (II) under standard coupling conditions as described in Scheme 1, and then the ketal group is removed in the presence of acid such as hydrochloric acid in a solvent such as acetone at reflux temperature to give the compounds of Formula (I).

Scheme 10

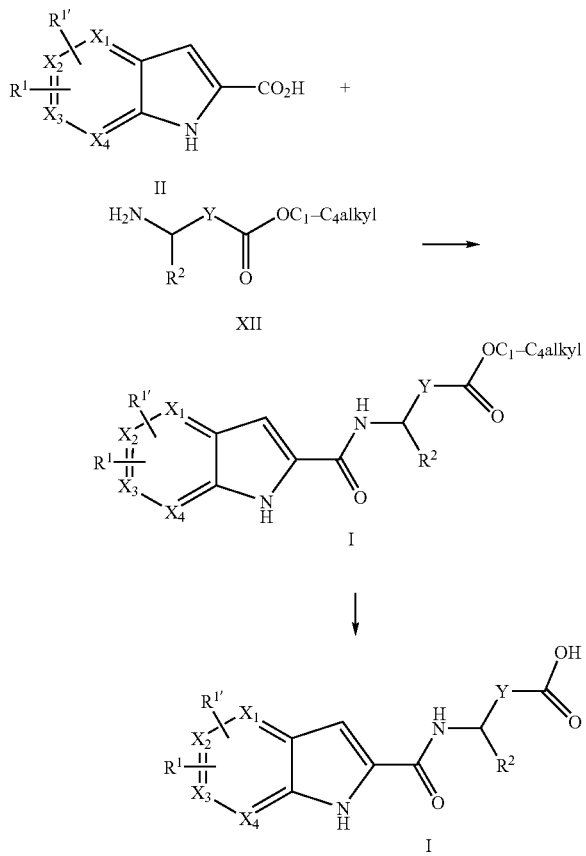

Compounds of Formula (I) (wherein Z is C=O and $R^3$ is $C_{1-4}$alkoxy) may be prepared as illustrated in Scheme 10 by combination of compounds of Formula (II) and compounds of Formula (XII) under standard coupling conditions as described for Scheme 1. Compounds of Formula (XII) are generally commercially available or are readily prepared by known techniques Compounds of Formula (I) (wherein Z is absent and $R^3$ is —$CO_2H$) may be prepared by ester hydrolysis of compounds of Formula (I) (where Z is C=O and $R^3$ is a $C_{1-4}$alkoxy group) using aqueous alkali typically at a temperature of around 25° C. for 30 min to 20 h.

The compounds of Formula (I) may be prepared singly or as compound libraries comprising at least 2, for example 5 to 1,000 compounds and more preferably 10 to 100 compounds of Formula (I). Compound libraries may be prepared by a combinatorial "split and mix" approach or by multiple parallel synthesis using either solution or solid phase chemistry, using procedures known to those skilled in the art.

During the synthesis of the compounds of Formula (I), labile functional groups in the intermediate compounds, e.g. hydroxy, carboxy and amino groups, may be protected. The compounds of Formula (II) may be protected in the 1-position e.g. with an arylmethyl, acyl, alkoxycarbonyl, sulfonyl or silyl group. The protecting groups may be removed at any stage in the synthesis of the compounds of Formula (I) or may be present on the final compound of Formula (I). A comprehensive discussion of the ways in which various labile functional groups may be protected and methods for cleaving the resulting protected derivatives is given in for example, Protective Groups in Organic Chemistry, T. W. Greene and P. G. M. Wuts, (1991) Wiley-Interscience, New York, $2^{nd}$ edition.

Any novel intermediates as defined above are also included within the scope of the invention.

The invention also provides a compound of Formula (IIA):

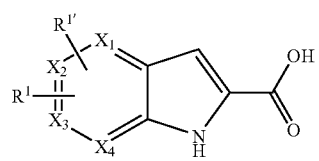

IIA or a $C_{1-4}$alkyl ester or protected derivative thereof, wherein:
one of $X_1, X_2, X_3$ and $X_4$ must be N and the others must be C;
$R^1$ and $R^{1'}$ are each independently, halogen, hydroxyl, cyano, $C_{0-4}$alkyl, $C_{1-4}$alkoxy, fluoromethyl, difluoromethyl, trifluoromethyl, ethenyl, or ethynyl or absent;
provided that when $X_1$, $X_3$ or $X_4$ is N, then $R^1$ and $R^{1'}$ are not both hydrogen.

Preferred compounds of formula (IIA) include those where $X_3$ is N.

Preferably one of $R^1$ and $R^{1'}$ is hydrogen and the other is halo or cyano, in particular, when $X_1$, $X_3$ or $X_4$ is N, 5-halo e.g. 5-chloro, or 5-cyano.

Specific compounds of Formula (IIA) include:
5-Chloro-1H-pyrrolo[3,2-b]pyridine-2-carboxylic acid;
5-Bromo-1H-pyrrolo[3,2-b]pyridine-2-carboxylic acid;
5-Cyano-1H-pyrrolo[3,2-b]pyridine-2-carboxylic acid;
5-Methoxy-1H-pyrrolo[3,2-b]pyridine-2-carboxylic acid;
1H-Pyrrolo[3,2-c]pyridine-2-carboxylic acid;
6-Chloro-1H-pyrrolo[3,2-c]pyridine-2-carboxylic acid;
6-Cyano-1H-pyrrolo[3,2-c]pyridine-2-carboxylic acid;
5-Chloro-1H-pyrrolo[2,3-c]pyridine-2-carboxylic acid;
5-Bromo-1H-pyrrolo[2,3-c]pyridine-2-carboxylic acid;

5-Ethynyl-1H-pyrrolo[2,3-c]pyridine-2-carboxylic acid;
5-Cyano-1H-pyrrolo[2,3-c]pyridine-2-carboxylic acid;
5-Methyl-1H-pyrrolo[2,3-c]pyridine-2-carboxylic acid;
5-Chloro-1H-pyrrolo[2,3-b]pyridine-2-carboxylic acid;
6-Chloro-1H-pyrrolo[2,3-b]pyridine-2-carboxylic acid; and
6-Cyano-1H-pyrrolo[2,3-b]pyridine-2-carboxylic acid.

The invention also provides a compound of formula (XIX):

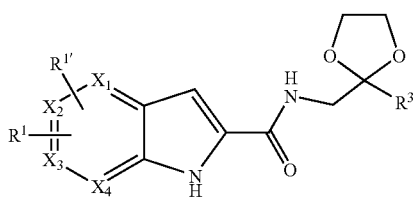

XIX wherein $R^1$, $R^{1'}$, $X_1$, $X_2$, $X_3$, and $X_4$ are as defined above for Formula (I) and $R^3$ is $—C_0$alkylaryl or $—C_0$alkylhetaryl.

The invention also provides the novel compound 4(S)-(4-fluorobenzyl)oxazolidine-2,5-dione, which may be prepared as described in the Experimental section below.

EXPERIMENTAL

Materials & Methods

Column chromatography was carried out on $SiO_2$ (40–63 mesh). LCMS data were obtained using a Waters Symmetry 3.5μ $C_{18}$ column (2.1×30.0 mm, flow rate=0.8 mL/min) eluting with a (5% MeCN in $H_2O$)—MeCN solution containing 0.1% $HCO_2H$ over 6 min and UV detection at 220 nm. Gradient information: 0.0–1.2 min: 100% (5% MeCN in $H_2O$); 1.2–3.8 min: ramp up to 10% (5% MeCN in $H_2O$)—90% MeCN; 3.8–4.4 min: hold at 10% (5% MeCN in $H_2O$)–90% MeCN; 4.4–5.5 min: ramp up to 100% MeCN; 5.5–6.0 min: return to 100% (5% MeCN in $H_2O$). The mass spectra were obtained employing an electrospray ionisation source in the positive ($ES^+$) ion mode. NMR spectra were acquired at 27° C. on a Varian Mercury 400 spectrometer operating at 400 MHz or on a Bruker AMX2 500 spectrometer operating at 500 MHz. Mass directed purification was performed on a Micromass Platform LC with cone voltage 30 v, employing an electrospray ionisation source in the positive ($ES^+$) ion mode, Waters 996 Photodiode Array Detector (210–390 nm), Xterra Prep MS, $C_{18}$, 5μ 19×50 mm columns, and a mobile Phase of MeCN+0.1% Formic Acid/ $H_2O$+5% MeCN+0.1% Formic Acid Abbreviations and acronyms: BOC: tert-butyloxycarbonyl; DABCO: bicyclo(2,2,2)-1,4-diazaoctane; DBU: 1,8-Diazabicyclo[5.4.0]undec-7-ene; DCM: Dichloromethane; DIPEA: N,N-Diisopropylethylamine; DMAP: 4-(N,N-dimethylamino)pyridine; DMF: N,N-Dimethylformamide; DMSO: Dimethylsulfoxide; DMTMM: 4-(4,6-dimethoxy[1.3.5]triazin-2-yl)-4-methylmorpholinium chloride hydrate; EDCI: 1-(3-Dimethylaminopropyl)-3-ethylcarbodiimide hydrochloride; GP: Glycogen Phosphorylase; HATU: O-(7-Azabenzotriazol-1-yl)-N,N,N',N'-tetramethyluronium hexafluorophosphate; HOBt: 1-Hydroxybenzotriazole; MDP: Mass directed purification; $MgSO_4$: Magnesium sulfate; PS: Polymer supported; rt: room temperature; RT: Retention time; THF: Tetrahydrofuran, TBTU: O-(benzotriazol-1-yl) N,N,N',N'-tetramethyluronium tetrafluoroborate Preparation 1: 6-Methyl-5-nitropyridin-2-ylamine

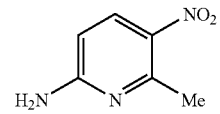

The title compound was prepared according to the method of Parker and Shive (J. Am. Chem. Soc., 1947, 69, 63) as a brown powder. $δ_H$ ($d_6$ DMSO): 2.6 (3H, s), 6.37 (1H, d, 9.13 Hz), 7.31 (2H, s), 8.08 (1H, d, 9.13 Hz); m/z ($ES^+$)=154.06 $[M+H]^+$; RT=0.57 min.

Preparation 2: 6-Methyl-5-nitro-1H-pyridin-2-one

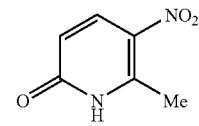

The title compound was prepared according to the method of Baumgarten and Su (J. Am. Chem. Soc, 1952, 74, 3828) as a brown powder. $δ_H$ ($d_6$ DMSO): 2.62 (3H, s), 6.28 (1H, d, 9.94 Hz), 8.10 (1H, d, 9.94 Hz).

Preparation 3: 2-Chloro-6-methyl-5-nitropyridine

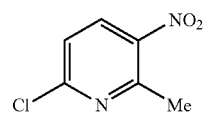

A suspension of 6-methyl-5-nitro-1H-pyridin-2-one (Preparation 2, 3.53 g, 22.9 mmol) in phosphorous oxychloride (20 mL) was heated to 115° C. (oil bath temperature) for 3 h then allowed to cool to rt. The phosphorous oxychloride was removed in vacuo and the residue poured into iced water (100 mL). The mixture was quenched by addition of saturated sodium bicarbonate solution, then the aqueous mixture was extracted with ethyl acetate (3×100 mL). The combined organics were washed with brine, dried ($MgSO_4$), filtered and concentrated in vacuo to furnish the title compound as a brown solid. $δ_H$ ($CDCl_3$): 2.86 (3H, s), 7.36 (1H, d, 8.59 Hz), 8.27 (1H, d, 8.32 Hz).

Preparation 4:
3-(2-Chloro-5-nitropyridin-6-yl)-2-oxopropionic acid ethyl ester

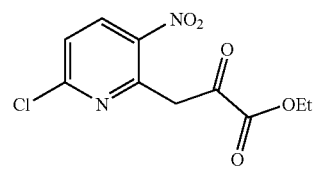

To a solution of potassium ethoxide (134 mg, 1.59 mmol) in diethyl ether (5 mL) and ethanol (1 mL) was added diethyl oxalate (218 μL, 1.59 mmol) in one portion and the resulting solution was stirred for 30 min at rt. 2-Chloro-6-methyl-5-nitropyridine (Preparation 3, 250 mg, 1.45 mmol) was added as a suspension in diethyl ether (2 mL, anhydrous) and stirring was continued for 17 h at rt. The mixture was filtered on a sinter, washing with cold diethyl ether. The collected precipitate was dissolved in glacial acetic acid then evaporated to dryness in vacuo to give the title compound as a brown powder. δ$_H$ (CDCl$_3$): 1.40 (3H, t, 7.27 Hz), 4.38 (2H, q, 7.25 Hz), 7.33 (1H, d, 8.59 Hz), 7.37 (1H, s), 8.40 (1H, d, 8.86 Hz).

Preparation 5:
5-Chloro-1H-pyrrolo[3,2-b]pyridine-2-carboxylic acid ethyl ester

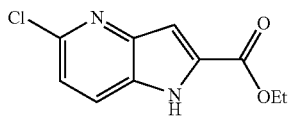

To a solution of 3-(2-chloro-5-nitropyridin-6-yl)-2-oxo-propionic acid ethyl ester (Preparation 4, 1.53 g, 5.6 mmol) in THF (65 mL) and ethanol (30 mL) was added saturated aqueous ammonium chloride solution (30 mL) and the suspension was vigorously stirred at rt. Iron powder (1.95 g, 34.8 mmol) was added portionwise and the mixture was heated under reflux for 2 h then allowed to cool prior to filtration through a celite plug, and washed through with warm THF. The mixture was concentrated under reduced pressure to give an aqueous suspension, which was filtered through a sinter, washing with water. The wet solid was washed with methanol and dried. The residue was adsorbed onto silica gel and purified via flash chromatography eluting with ethyl acetate/hexane (1:19) to give the title compound as a white solid. δ$_H$ (CD$_3$OD): 1.42 (3H, t, 7.03 Hz), 4.42 (2H, q, 7.32 Hz), 7.15 (1H, s), 7.30 (1H, d, 8.79 Hz), 7.89 (1H, d, 8.35 Hz); m/z (ES$^+$)=225.03 [M+H]$^+$; RT=3.32 min.

Preparation 6:
5-Chloro-1H-pyrrolo[3,2-b]pyridine-2-carboxylic acid

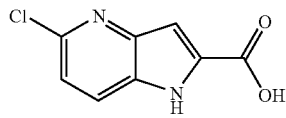

To a stirred solution of 5-chloro-1H-pyrrolo[3,2-b]pyridine-2-carboxylic acid ethyl ester (Preparation 5, 151 mg, 0.67 mmol) in ethanol (10 mL) was added sodium hydroxide (0.35 mL, 2M) and the stirred solution was heated at 70° C. for 2 h. The reaction mixture was then allowed to cool to rt and left to stand for 16 h. The pH was adjusted to 4 by addition of glacial acetic acid, the solvents removed in vacuo to give a white solid, which was suspended in dichloromethane and filtered through a sinter, washing with additional dichloromethane. The filter cake was washed with ethyl acetate (3×30 mL) and dried to give the title compound as a white solid. δ$_H$ (CD$_3$OD): 6.97 (1H, s), 7.17 (1H, d, 8.35 Hz), 7.83 (1H, d, 8.35 Hz); m/z (ES$^+$)=197 [M+H]$^+$; RT=2.82 min.

Preparation 7:
N-tert-Butyloxycarbonyl-(S)-phenylalanine dimethylamide

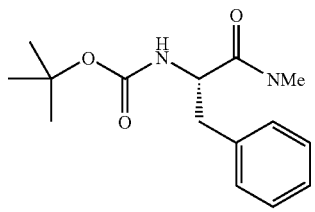

A solution of dimethylamine hydrochloride (1.45 g, 17.8 mmol) in DMF (46 mL) was cooled to −10° C. and triethylamine (2.7 mL, 19.4 mmol) was added. N-Boc-L-phenylalanine (4.59 g, 17.3 mmol, Aldrich) and HOBt (3.49 g, 26 mmol) were then added and the reaction stirred for 5 min before addition of EDCI (3.33 g, 17.4 mmol). The reaction mixture was left to stir for 16 h then diluted with ethyl acetate (400 mL), washed sequentially with aqueous sodium hydroxide solution (2M, 2×100 mL), hydrochloric acid (2N, 2×100 mL), brine (250 mL) and then dried (MgSO$_4$). Evaporation in vacuo gave the title compound as a pale yellow oil. δ$_H$ (CDCl$_3$): 1.41 (9H, s), 2.61, 2.85 (6H, 2s), 2.91–2.99 (2H, m), 4.83 (1H, m), 5.40 (1H, br d), 7.18–7.29 (5H, m).

Preparation 8:
2-(S)-Amino-N,N-dimethyl-3-phenylpropionamide hydrochloride

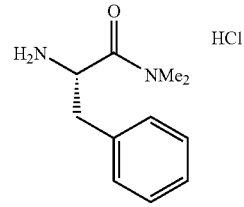

To a solution of N-tert-butyloxycarbonyl-(S)-phenylalanine dimethylamide (Preparation 7, 24.8 g, 84 mmol) in methanol (50 mL) was added a solution of hydrochloric acid (4N, in dioxane, 40 mL) and the mixture stirred at rt for 3 h. The resulting solution was concentrated in vacuo then dissolved in water (300 mL). The aqueous solution was washed with ethyl acetate (3×100 mL) and concentrated again. Successive recrystallisations with methanol (200 mL) and a mixture of methanol and toluene (1:1, 200 mL) gave the title compound as colourless crystals. δ$_H$ (D$_2$O) 2.75, 2.90 (6H, 2×s), 3.18 (2H, m), 4.72 (1H, t), 7.28–7.45 (5H, m).

Preparation 9: Pyridin-4-ylcarbamic acid tert-butyl ester

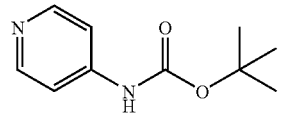

Pyridin-4-ylcarbamic acid tert-butyl ester was prepared according to the method of Spivey et al., (*J. Org. Chem.,* 1999, 64, 9430) to give the title compound as a white crystalline solid. $\delta_H$ (CDCl$_3$): 1.52 (9H, s), 7.08 (1H, br s), 7.32 (2H, d), 8.43 (2H, d).

Preparation 10: (3-Methylpyridin-4-yl)carbamic acid tert-butyl ester

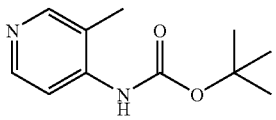

(3-Methylpyridin-4-yl)carbamic acid tert-butyl ester was prepared according to the method of Hands et al., (*Synthesis,* 1996, 7, 877) to give the title compound as a pale yellow solid. $\delta_H$ (CDCl$_3$): 1.55 (9H, s), 2.22 (3H, s), 6.52 (1H, s), 7.97 (1H, d), 8.27 (1H, s), 8.36 (1H, d).

Preparation 11:
1H-Pyrrolo[3,2-c]pyridine-2-carboxylic acid ethyl ester

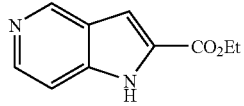

A solution of (3-methylpyridin-4-yl)carbamic acid tert-butyl ester (Preparation 10, 1.0 g, 4.8 mmol) in anhydrous THF (10 mL) was cooled to −40° C. and tert-butyl lithium (5.9 mL, 10.1 mmol) added dropwise. The temperature was maintained at −40° C. for 1 h and then a solution of diethyl oxalate (0.72 mL, 5.3 mmol) in THF (20 mL) was added to the mixture. The reaction was warmed to 0° C., maintained at this temperature for 2 h, warmed to rt and stirred for 16 h. Hydrochloric acid (2N, 40 mL) was added and the reaction heated under reflux for 90 min, concentrated in vacuo and adjusted to pH 8 with saturated aqueous sodium hydrogen carbonate solution. The mixture was extracted with ethyl acetate (3×100 mL) and the organic solution dried (MgSO$_4$) and concentrated in vacuo to give the title compound. $\delta_H$ (d$_6$ DMSO): 1.33 (3H, t), 4.35 (2H, q), 7.27 (1H, s), 7.38 (1H, d), 8.25 (1H, d), 8.95 (1H, s); m/z (ES$^+$)=191 [M+H]$^+$.

Preparation 12:
1H-Pyrrolo[3,2-c]pyridine-2-carboxylic acid

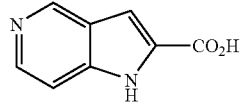

Aqueous sodium hydroxide solution (2.4 mL, 2M, 4.8 mmol) was added to a solution of 1H-pyrrolo[3,2-c]pyridine-2-carboxylic acid ethyl ester (Preparation 11, 0.76 g, 4.0 mmol) in ethanol (40 mL) and the mixture heated under reflux for 2 h before being cooled and concentrated in vacuo. The residue was dissolved in a minimum amount of water, glacial acetic acid (1 mL) was added and the solution cooled in a refrigerator for 3 days. The resultant precipitate was collected by filtration washed with ether and dried in vacuo to give the title compound as a cream coloured solid. $\delta_H$ (D$_2$O): 7.05 (1H, s), 7.63 (1H, d), 8.08 (1H, d), 8.94 (1H, s).

Preparation 13:
3-(3-Nitropyridin-4-yl)-2-oxopropionic acid ethyl ester

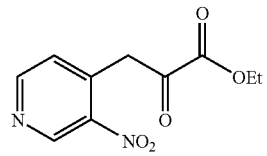

To a solution of potassium ethoxide (3.1 g, 36.2 mmol) in diethyl ether (70 mL) and ethanol (10 mL) under an argon atmosphere was added diethyl oxalate (4.9 mL, 36.2 mmol) and the reaction stirred at rt for 30 min. A solution of 4-methyl-3-nitropyridine (5.0 g, 36.2 mmol) in diethyl ether (20 mL) was added resulting in the immediate formation of a dark red precipitate. The reaction mixture was stirred at rt for 72 h, then cooled to 0° C. and filtered. The solid was dissolved in water (500 mL) acidified to pH 4 with acetic acid and the precipitate collected and dried to give the title compound as a red solid. $\delta_H$ (d$_6$ DMSO): 1.27 (3H, t), 4.25 (2H, q), 6.74 (1H, s), 8.34 (1H, d), 8.43 (1H, d), 8.98 (1H, s); m/z (ES$^+$)=239 [M+H]$^+$.

Preparation 14:
1H-Pyrrolo[2,3-c]pyridine-2-carboxylic acid ethyl ester

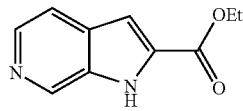

To a solution of 3-(3-nitropyridin-4-yl)-2-oxopropionic acid ethyl ester (Preparation 13, 500 mg, 2.1 mmol) in ethanol (20 mL) and THF (10 mL) was added saturated ammonium chloride solution (10 mL) and iron powder (700 mg, 12.6 mmol). The reaction was heated under reflux for 1 h, then filtered through celite and washed through with hot ethyl acetate (3×30 mL). The combined organic fractions were washed with brine (20 mL), dried (MgSO$_4$) and concentrated in vacuo to give the title compound as a brown solid. $\delta_H$ (CD$_3$OD): 1.44 (3H, t), 4.43 (2H, q), 7.21 (1H, s), 7.69 (1H, d), 8.12 (1H, d), 8.80 (1H, s).

Preparation 15:
1H-Pyrrolo[2,3-c]pyridine-2-carboxylic acid

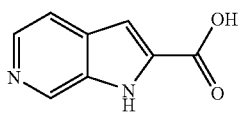

To a solution of 1H-pyrrolo[2,3-c]pyridine-2-carboxylic acid ethyl ester (Preparation 14, 310 mg, 1.6 mmol) in ethanol (20 mL) was added 2N sodium hydroxide solution (1 mL, 2.0 mmol) and the reaction mixture heated under reflux for 1.5 h then concentrated in vacuo. The residue was dissolved in water (10 mL) and acidified with acetic acid giving an immediate brown precipitate. The solid was filtered and dried to give the title compound as a beige solid. $\delta_H$ (D$_2$O): 7.11 (1H, s), 7.99 (1H, d), 8.05 (1H, d), 8.85 (1H, s); m/z (ES$^+$)=163 [M+H]$^+$.

Preparation 16:
3-(2-Chloro-5-nitropyridin-4-yl)-2-oxopropionic acid ethyl ester

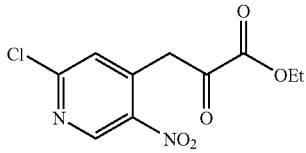

Route A: To a solution of potassium ethoxide (1.46 g, 17.4 mmol) in diethyl ether (80 mL) and ethanol (10 mL) under an argon atmosphere was added diethyl oxalate (2.4 mL, 17.4 mmol) and the mixture stirred at rt for 0.5 h. A solution of 2-chloro-4-methyl-5-nitropyridine (3.0 g, 17.4 mmol) in diethyl ether (20 mL) was added resulting in the formation of a dark green precipitate. The reaction was stirred at rt for 15 h, cooled to 0° C., filtered and washed with cold diethyl ether to give a dark green solid. The solid was dissolved in water (200 mL) and acidified to pH 4 with acetic acid to give an orange precipitate. The solid was collected by filtration and dried to give the title compound. m/z (ES$^+$)=273 [M+H]$^+$.

Route B: To a solution of 2-chloro-4-methyl-5-nitropyridine (1.0 g, 5.8 mmol) in diethyl oxalate (4.23 g, 29 mmol) under an argon atmosphere was added 1,8-diazabicyclo[5.4.0]undec-7-ene (0.95 mL, 6.4 mol). The mixture was stirred at rt for 1.5 h then diluted with t-butyl methyl ether (40 mL), water (30 mL) and acetic acid (1 ml). The organic layer was separated, washed with water, dried (MgSO$_4$) and evaporated to dryness. The resultant damp red solid residue was finally dried under high vacuum at 40–50° C. to give the title compound.

Preparation 17:
5-Chloro-1H-pyrrolo[2,3-c]pyridine-2-carboxylic acid ethyl ester

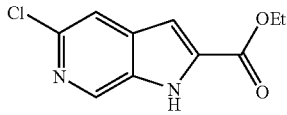

3-(2-Chloro-5-nitropyridin-4-yl)-2-oxopropionic acid ethyl ester (Preparation 16, 3.0 g, 11.0 mmol) was dissolved in ethanol (100 mL) and THF (50 mL). Iron powder (3.7 g, 66.0 mmol) and saturated ammonium chloride solution (50 mL) were added and the mixture heated under reflux for 2 h. The mixture was cooled, filtered through celite and washed several times with ethyl acetate. The organic layers were combined, washed with brine (100 mL), dried (MgSO$_4$) and concentrated in vacuo to give the title compound as a brown solid. $\delta_H$ (CD$_3$OD): 1.42 (3H, t), 4.44 (2H, q), 7.15 (1H, s), 7.70 (1H, s), 8.59 (1H, s); m/z (ES$^+$)=225 [M+H]$^+$.

Preparation 18:
5-Chloro-1H-pyrrolo[2,3-c]pyridine-2-carboxylic acid

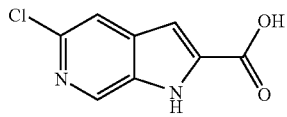

Route A: To a solution of 5-chloro-1H-pyrrolo[2,3-c]pyridine-2-carboxylic acid ethyl ester (Preparation 17, 1.78 g, 7.9 mmol) in ethanol (70 mL) was added sodium hydroxide solution (5.2 mL, 2M, 10.3 mmol) and the mixture heated under reflux for 2 h. The solvent was removed in vacuo and the solid dissolved in water (150 mL) and acidified to pH 4 with acetic acid to give the title compound as a brown solid that was isolated by filtration. $\delta_H$ (CD$_3$OD): 7.13 (1H, s), 7.68 (1H, s), 8.58 (1H, s); m/z (ES$^+$)=197 [M+H]$^+$.

Route B: A mixture of 6-chloro-4-iodopyridin-3-ylamine (Preparation 106, 0.33 g, 1.30 mmol), pyruvic acid (0.27 mL, 3.89 mmol), DABCO (0.44 g, 3.89 mmol) and palladium acetate (0.015 g, 0.07 mmol) in dry DMF was stirred vigorously and degassed with argon for 15 min. The reaction mixture was heated to 107° C. for 5 h. The reaction mixture was allowed to cool to rt and stirred for 16 h. The volatiles were removed under reduced pressure and the residue partitioned between ethyl acetate (100 mL) and water (50 mL). The layers were separated and the aqueous extracted with ethyl acetate (2×50 mL). The combined organics were extracted with aqueous NaOH (2M, 3×70 mL). The combined aqueous extracts were acidified to pH 4 by careful addition of glacial acetic acid, then extracted with ethyl acetate (3×60 mL). The combined organics were washed with brine (50 mL), dried (MgSO$_4$), filtered and concentrated in vacuo to give the title compound as a brown solid. RT=2.72 min, m/z (ES$^+$)=197 [M+H]$^+$

Preparation 19: [1-(S)-(4-Fluorobenzyl)-2-(4-hydroxypiperidin-1-yl)-2-oxoethyl]carbamic acid tert-butyl ester

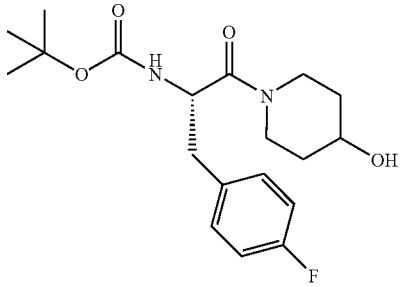

To a stirred solution of Boc-3-(4-fluorophenyl)-(S)-alanine (10.0 g, 35.3 mmol), 4-hydroxypiperidine hydrochloride (5.1 g, 37.1 mmol) and HOBt (7.2 g, 52.9 mmol) in DMF (100 mL), was added DIPEA (12.3 mL, 70.6 mmol) and after 5 min, EDCI (7.4 g, 38.8 mmol) and the reaction stirred at rt for 16 h. The solvent was removed in vacuo and the residue partitioned between water (150 mL) and ethyl acetate (2×150 mL). The combined organic fractions were washed with sodium hydroxide solution (2M, 50 mL), hydrochloric acid (2N, 50 mL), dried (MgSO$_4$) and concentrated in vacuo. The product was chromatographed on silica gel eluting with ethyl acetate to give the title compound as a white solid. m/z (ES$^+$)= 367 [M+H]$^+$; RT=3.28 min.

Preparation 20: 2-(S)-Amino-3-(4-fluorophenyl)-1-(4-hydroxypiperidin-1-yl)propan-1-one hydrochloride

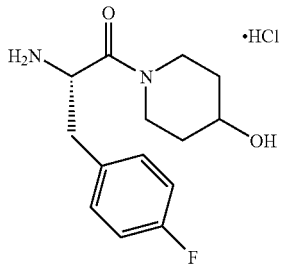

Route A: To a solution of [1 (S)-(4-fluorobenzyl)-2-(4-hydroxypiperidin-1-yl)-2-oxoethyl]carbamic acid tert-butyl ester (Preparation 19, 11.6 g, 31.7 mmol) in methanol (40 mL) was added hydrochloric acid in dioxane (24 mL, 4N, 95.0 mmol) and the reaction mixture stirred at rt for 6 h. The solvent was removed in vacuo and the residue was dissolved in water (100 mL) and extracted into ethyl acetate (2×50 mL). The aqueous phase was evaporated to dryness to give the title compound as a white solid. $\delta_H$ (D$_2$O): 0.52–0.63 (0.5H, m), 1.12–1.23 (0.5H, m), 1.26–1.38 (1H, m), 1.42–1.50 (0.5H, m), 1.59–1.69 (0.5H, m), 1.72–1.82 (1H, m), 2.61–2.71 (0.5H, m), 2.91–3.15 (4H, m), 3.33–3.47 (1H, m), 3.69–3.78 (1H, m), 3.88–3.96 (1H, m), 4.60–4.72 (1H, m), 7.02–7.11 (2H, m), 7.14–7.26 (2H, m).

Route B: To a solution of 4-hydroxypiperidine (40 mg, 0.4 mmol) in anhydrous THF (3 mL) under an argon atmosphere was added a solution of 4(S)-(4-fluorobenzyl)oxazolidine-2, 5-dione (Preparation 117, 100 mg, 0.48 mmol) in THF (2 mL) dropwise over 15 min. The resulting mixture was stirred for 40 h at rt before removal of the solvent in vacuo. The crude material was purified by column chromatography (SiO$_2$, 9:1 dichloromethane/methanol) to afford an oil. The free amine was dissolved in methanol (2 mL) and a solution of 4M HCl in dioxane (0.3 mL) was added and stirring was continued for 15 min. The solvent was removed in vacuo and the material partitioned between ethyl acetate (5 mL) and water (5 mL). The aqueous layer was concentrated in vacuo to give the title compound. $\delta_H$ (CD$_3$OD): 7.36–7.29 (2H, m), 7.17–7.10 (2H, m), 4.70 (1H, t), 4.09–4.00 (0.5H, m), 3.91–3.74 (1.5H, m), 3.64–3.56 (0.5H, m), 3.43–3.31 (1H, m), 3.26–3.07 (3H, m), 2.89–2.80 (0.5H, m), 1.87–1.69 (1.5H, m), 1.56–1.36 (2H, m), 1.09–0.99 (0.5H, m).

Preparation 21: (3S,2R)-3-Amino-2-hydroxy-4-phenylbutyric acid methyl ester

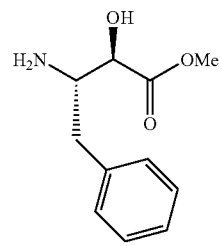

(3S,2R)-3-Amino-2-hydroxy-4-phenylbutyric acid methyl ester was synthesized according to the method of A. Fässler et al., (*Tetrahedron Lett.*, 1998, 39, 4925) in three steps from commercially available N-(tert-butyloxycarbonyl)-L-phenylalaninal. R$_f$ 0.29 (dichloromethane/methanol: 9/1); $\delta_H$ (CDCl$_3$): 2.04 (3H, m), 2.73 (1H, dd), 2.92 (1H, dd), 3.36 (1H, ddd), 3.79 (3H, s), 4.08 (1H, d), 7.22–7.33 (5H, m).

Preparation 21A: (3S,2S)-3-Amino-2-hydroxy-4-phenylbutyric acid methyl ester

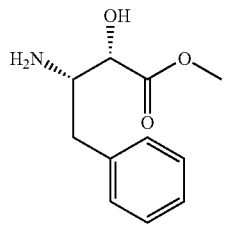

(3S,2S)-3-Amino-2-hydroxy-4-phenylbutyric acid methyl ester was obtained as a side product in Preparation 21. R$_f$ 0.19 (dichloromethane/methanol: 9/1); $\delta_H$ (CDCl$_3$): 2.10 (2H, br s), 2.61 (1H, dd), 2.84 (1H, dd), 3.38 (1H, m), 3.78 (3H, s), 4.14 (1H, br s).

Preparation 22: Cis-3,4-Dihydroxypyrrolidine-1-carboxylic acid benzyl ester

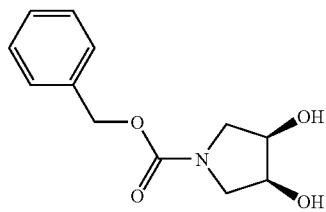

A solution of benzyl-2,5-dihydro-1H-pyrrole-1-carboxylate (10.0 g, 49.3 mmol) in THF (200 mL) was treated with osmium tetroxide solution (2.5% in tert-butanol, 5 mL) and N-methylmorpholine (6.90 g, 59.0 mmol) and the reaction mixture stirred at rt under argon for 72 h. Aqueous sodium thiosulfate solution (10%, 200 mL) was added and the mixture stirred for a further 1 h and then concentrated in vacuo. The resulting aqueous layer was extracted with ethyl acetate (3×200 mL) and the combined organic layers washed with aqueous sodium thiosulfate solution (10%, 300 mL) and hydrochloric acid (1N, 300 mL). The organic fraction was dried (MgSO$_4$) and concentrated in vacuo to give the title compound as an off-white solid.

$\delta_H$ (CDCl$_3$): 2.67 (2H, br s), 3.38–3.45 (2H, m), 3.63–3.67 (2H, m), 4.22–4.26 (2H, m), 5.12 (2H, s), 7.30–7.38 (5H, m); m/z (ES$^+$)=238 [M+H]$^+$.

Preparation 23: Cis-3,4-Dihydroxypyrrolidine

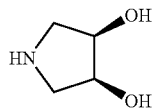

Palladium-on-carbon (144 mg, 10 wt %) was added to a solution of cis-3,4-dihydroxypyrrolidine-1-carboxylic acid benzyl ester (Preparation 22, 403 mg, 1.70 mmol) in ethanol (20 mL) and cyclohexene (2 mL) and the mixture stirred and heated under reflux for 6 h. After filtration through celite and repeated washing of the catalyst with methanol (CARE!), the filtrate and washings were combined and concentrated in vacuo to give the title compound as a colourless oil. $\delta_H$ (d$_4$ MeOH): 2.81 (2H, dd), 3.03 (2H, m), 4.07 (2H, m).

Preparation 24: 2-Bromo-4-methyl-5-nitropyridine

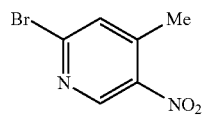

To a suspension of 2-hydroxy-4-methyl-5-nitropyridine (1 g, 6.5 mmol) in dichloroethane (10 mL) was added a solution of phosphorus oxybromide (2.8 g, 9.7 mmol) in dichloroethane (10 mL). The reaction mixture was heated under reflux for 4 h, then cooled to rt and quenched with water (40 mL). The layers were separated and the aqueous layer extracted into dichloromethane (2×3 mL). The combined organics were dried (MgSO$_4$), concentrated in vacuo and chromatographed on silica gel eluting with dichloromethane to give the title compound as a pale yellow solid. $\delta_H$ (CDCl$_3$): 2.63 (3H, s), 7.52 (1H, s), 8.96 (1H, s).

Preparation 25: 3-(2-Bromo-5-nitropyridin-4-yl)-2-oxopropionic acid ethyl ester

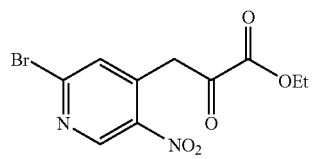

To a solution of potassium ethoxide (2.05 g, 24.3 mmol) in diethyl ether (70 mL) and ethanol (10 mL) under an argon atmosphere was added diethyl oxalate (3.3 mL, 24.3 mmol) and the reaction stirred at rt for 15 min. A solution of 2-bromo-4-methyl-5-nitropyridine (Preparation 24, 4.8 g, 22.1 mmol) in diethyl ether (20 mL) was added to the reaction mixture giving an immediate black precipitate. The reaction was allowed to stir at rt for 6 h, then cooled to 0° C. and filtered to give a black solid. The solid was dissolved in water (250 mL) and acidified to pH 4 with acetic acid resulting in formation of a red precipitate. The solid was collected and dried to give the title compound as a red solid. $\delta_H$ (d$_6$ DMSO): 1.16 (3H, t), 4.01 (2H, q), 6.55 (1H, s), 7.92 (1H, s), 8.96 (1H, s).

Preparation 26: 5-Bromo-1H-pyrrolo[2,3-c]pyridine-2-carboxylic acid ethyl ester

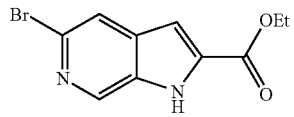

Route A: To a solution of 3-(2-bromo-5-nitropyridin-4-yl)-2-oxopropionic acid ethyl ester (Preparation 25, 3.38 g, 10.7 mmol) in THF (50 mL) and ethanol (100 mL) was added saturated ammonium chloride solution (50 mL) and iron powder (3.57 g, 64.0 mmol) and the reaction heated under reflux for 2 h. The reaction mixture was filtered through celite and washed several times with ethyl acetate. The solvent was removed in vacuo and the remainder partitioned between saturated sodium hydrogen carbonate solution (100 mL) and ethyl acetate (3×150 mL). The combined organic fractions were dried (MgSO$_4$) and concentrated in vacuo to give the title compound as a brown solid. $\delta_H$ (CD$_3$OD): 1.42 (3H, t), 4.43 (2H, q), 7.14 (1H, s), 7.85 (1H, s), 8.58 (1H, s); m/z (ES$^+$)=269 [M+H]$^+$.

Route B: To a solution of 2-bromo-4-methyl-5-nitropyridine (Preparation 24, 5.7 g, 26.3 mmol) in diethyl oxalate (17.9 mL) under argon was added 1,8-diazabicyclo[5,4,0]undec-7-ene (4.5 mL, 30.2 mmol) to give a dark red precipitate. Reaction mixture was stirred at rt for 4.5 h and concentrated in vacuo. Acetic acid (140 mL) was added to the residue under argon and heated to 60° C. Iron (2.94 g, 52.6 mmol) was added in small portions over a period of 1 h. The reaction mixture was heated at 80° C. for 4 h. The reaction mixture was cooled to rt and poured into water (300 mL) which gave a beige precipitate. The precipitate was isolated and washed with water. The solid obtained was dissolved in ethyl acetate (700 ml) and filtered. The filtrate was concentrated in vacuo to give the title compound. m/z (ES+)=269 [M+H]$^+$; RT=3.39 min.

Preparation 27:
5-Bromo-1H-pyrrolo[2,3-c]pyridine-2-carboxylic acid

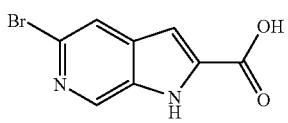

Sodium hydroxide solution (1.1 mL, 2M, 2.23 mmol) was added to a solution of 5-bromo-1H-pyrrolo[2,3-c]pyridine-2-carboxylic acid ethyl ester (Preparation 26, 500 mg, 1.86 mmol) in ethanol (20 mL), and the reaction mixture heated under reflux for 1.5 h and then concentrated in vacuo. The residue was dissolved in water (15 mL) and acidified with acetic acid resulting in formation of a brown precipitate. The solid was collected by filtration and dried to give the title compound as a brown solid. $\delta_H$ (d$_6$ DMSO): 7.08 (1H, s), 7.97 (1H, s), 8.60 (1H, s); m/z (ES$^+$)=241 [M+H]$^+$.

Preparation 28:
1H-Pyrrolo[2,3-b]pyridine-2-carboxylic acid

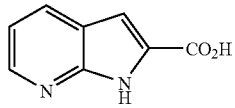

The title compound was prepared according to the method of Romero and Mitchell (WO 91/09849).

Preparation 29: 2-Methyl-3-nitropyridine

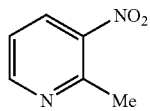

A mixture of 2-chloro-3-nitropyridine (1.00 g, 6.30 mmol), potassium carbonate (2.62 g, 18.90 mmol), tetrakis(triphenylphosphine)palladium (0.73 g, 0.63 mmol) and trimethyl boroxine (0.88 mL, 6.30 mmol) in 1,4-dioxane (2 mL) and water (8 mL) was heated to 110° C. (oil bath temperature) for 6 h and then stirred for 16 h at rt. The mixture was then filtered through a celite pad, washing through with THF. The filtrate was adsorbed onto silica gel in vacuo and purified via flash column chromatography eluting with ethyl acetate/hexanes (3:7) to give the title compound as a yellow solid. $\delta_H$ (CDCl$_3$): 2.86 (3H, s), 7.34 (1H, dd), 8.26 (1H, dd), 8.71 (1H, dd).

Preparation 30:
3-(3-Nitropyridin-2-yl)-2-oxopropionic acid ethyl ester

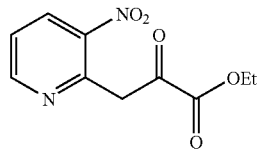

To a solution of potassium ethoxide (2.44 g, 27.7 mmol) in diethyl ether (90 mL) and ethanol (8 mL) was added diethyl oxalate (3.79 mL, 27.7 mmol) resulting in a yellow suspension. The reaction mixture was stirred for 5 min prior to the addition of 2-methyl-3-nitropyridine (Preparation 29, 3.40 g, 24.6 mmol) in one portion. The resulting red suspension was stirred at rt, under argon, for 20 h. The mixture was filtered, washed thoroughly with diethyl ether and dried. The red solid was dissolved in water and the mixture adjusted to pH 4 by addition of glacial acetic acid. The resulting precipitate was collected by filtration, dissolved in dichloromethane, washed with brine, dried (MgSO$_4$), and then filtered and concentrated in vacuo to give the title compound as an orange solid. $\delta_H$ (CDCl$_3$): 1.40 (3H, t), 4.39 (2H, q), 7.34 (1H, s), 7.36 (1H, dd), 8.43 (1H, dd), 8.66 (1H, dd).

Preparation 31:
1H-Pyrrolo[3,2-b]pyridine-2-carboxylic acid ethyl ester

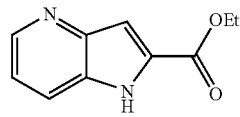

To a suspension of 3-(3-nitropyridin-2-yl)-2-oxopropionic acid ethyl ester (Preparation 30, 1.00 g, 4.20 mmol) in ethanol (30 mL, absolute) was added palladium (10% on activated carbon, 447 mg, 0.42 mmol) and the reaction mixture placed under an atmosphere of hydrogen at a pressure of 20–30psi for 12 h with vigorous stirring. The reaction mixture was filtered through celite, washing with ethyl acetate and the filtrate concentrated in vacuo to ca. 20 mL. Water (150 mL) was added and the mixture cooled to between 0° C. and 5° C. The precipitate that formed was collected by filtration and dried to give the title compound as a beige solid. $\delta_H$ (CDCl$_3$): 1.44 (3H, t), 4.45 (2H, q), 7.25 (1H, dd), 7.39 (1H, s), 7.75 (1H, dd), 8.57 (1H, dd), 8.98 (1H, s).

Preparation 32:
1H-Pyrrolo[3,2-b]pyridine-2-carboxylic acid

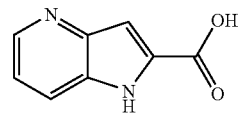

A suspension of 1H-pyrrolo[3,2-b]pyridine-2-carboxylic acid ethyl ester (Preparation 31, 0.34 g, 1.77 mmol) in aqueous sodium hydroxide solution (2M, 10 mL) was heated under reflux for 3 h and the resulting solution was allowed to cool to rt. The pH was adjusted to 4 by addition of glacial acetic acid. Excess acetic acid was removed in vacuo and the resulting suspension cooled to 0° C. and then left standing at rt for 16 h. The resulting beige precipitate was collected by filtration and dried to give the title compound as a beige solid. $\delta_H$ (d$_6$ DMSO): 7.12 (1H, s), 7.23 (1H, dd), 7.79 (1H, d), 8.42 (1H, dd).

Preparation 33: 6-Methoxy-2-methyl-3-nitropyridine

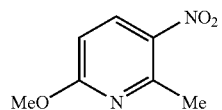

To a stirred suspension of 2-chloro-6-methoxy-3-nitropyridine (2.44 g, 12.9 mmol) in 10% v/v aqueous dioxane (25 mL) was added tetrakis(triphenyl phosphine) palladium (1.50 g, 1.3 mmol) and the mixture stirred for 15 min prior to the addition of trimethylboroxine (1.81 mL, 12.9 mmol) and potassium carbonate (5.36 g, 38.8 mmol). The reaction mixture was heated under reflux for 6 h then allowed to cool to rt over 16 h. Ethyl acetate (100 mL) was added and the mixture stirred vigorously for 1 h. The mixture was filtered through celite, washing through with ethyl acetate. The aqueous phase was separated and extracted with ethyl acetate (3×30 mL) and the combined organics were washed with brine (50 mL), dried (MgSO$_4$), filtered and adsorbed onto silica gel. Purification via flash column chromatography (SiO$_2$, ethyl acetate/isohexane, 1:20) gave the title compound as a pale yellow solid. $\delta_H$ (CDCl$_3$): 2.81 (3H, s), 4.01 (3H, s), 6.65 (1H, d), 8.26 (1H, d).

Preparation 34:
3-(6-Methoxy-3-nitropyridin-2-yl)-2-oxopropionic acid ethyl ester

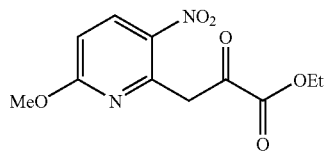

To a stirred suspension of potassium ethoxide (0.55 g, 6.55 mmol) in diethyl ether (20 mL, anhydrous) and ethanol (4 mL) was added diethyl oxalate (894 μL, 6.55 mmol) and the reaction mixture was stirred for 30 min prior to the addition of 6-methoxy-2-methyl-3-nitropyridine (Preparation 33, 1.0 g, 5.95 mmol) in diethyl ether (8 mL). The resulting red suspension was stirred at rt, under argon, for 20 h. The mixture was filtered, the solid washed thoroughly with diethyl ether then dried. The red solid was then taken up in hot water and the solution cooled to 0° C. The precipitate was filtered, washed with cold water, and dried to give the title compound as a beige solid. $\delta_H$ (CDCl$_3$): 1.40 (3H, t), 4.07 (3H, s), 4.39 (2H, q), 6.74 (1H, d), 7.57 (1H, s), 8.40 (1H, d), 13.82 (1H, s).

Preparation 35:
5-Methoxy-1H-pyrrolo[3,2-b]pyridine-2-carboxylic acid ethyl ester

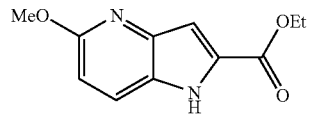

To a suspension of 3-(6-methoxy-3-nitropyridin-2-yl)-2-oxopropionic acid ethyl ester (Preparation 34, 276 mg, 1.03 mmol) in THF (12 mL) and ethanol (5 mL) was added saturated aqueous ammonium chloride solution (5 mL) and iron powder (346 mg, 6.18 mmol) in one portion. The reaction mixture was heated under reflux for 1 h then filtered whilst still hot through a celite plug, washing with hot ethyl acetate. The filtrate was cooled and washed with brine (20 mL), dried (MgSO$_4$), filtered and adsorbed onto silica gel in vacuo. Purification via flash column chromatography (SiO$_2$, ethyl acetate/hexanes, 1:9) gave the title compound as a beige solid. $\delta_H$ (CDCl$_3$): 1.40 (3H, t), 3.99 (3H, s), 4.41 (2H, q), 6.74 (1H, d), 7.20 (1H, m), 7.62 (1H, d), 9.27 (1H, s).

Preparation 36:
5-Methoxy-1H-pyrrolo[3,2-b]pyridine-2-carboxylic acid

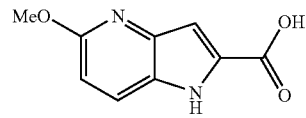

To a solution of 5-methoxy-1H-pyrrolo[3,2-b]pyridine-2-carboxylic acid ethyl ester (Preparation 35, 128 mg, 0.58 mmol) in ethanol (10 mL, absolute) was added aqueous sodium hydroxide (0.35 mL, 2M) and the mixture heated to 70° C. for 3 h then cooled to rt. The solution was adjusted to pH 4 by addition of glacial acetic acid and the solvents removed under reduced pressure. Ethyl acetate (20 mL) was added to the resulting oil and the mixture sonicated until a fine suspension formed. The mother liquor was decanted and the remaining solid was washed with ethyl acetate and dried in vacuo to give the title compound as a pale orange powder. $\delta_H$ (CD$_3$OD): 3.92 (3H, s), 6.63 (1H, d), 6.94 (1H, s), 7.72 (1H, d).

Preparation 37: 2-[2-(4-Methoxyphenyl)-2-oxoethyl]isoindole-1,3-dione

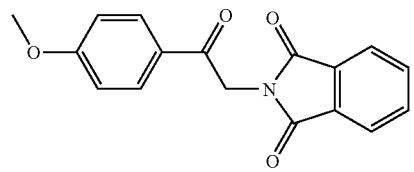

To a solution of 4-methoxyphenacyl bromide (5.78 g, 25.23 mmol) in DMF (20 mL) was added potassium phthalimide (5.00 g, 26.99 mmol) and the reaction stirred at rt for 18 h. The reaction mixture was partitioned between dichloromethane (200 mL) and water (100 mL). The layers were separated and the aqueous layer extracted with dichloromethane (3×50 mL). The combined organics were washed with sodium hydroxide (2M, 50 mL), water (50 mL) and brine (50 mL) and dried (MgSO$_4$). Filtration, then concentration in vacuo gave an off white solid. Trituration with diethyl ether followed by collection by filtration gave the title compound as a white solid. $\delta_H$ (CDCl$_3$): 3.86 (3H, s), 5.15 (2H, s), 7.09 (2H, d), 7.81–8.01 (4H, m), 8.05 (2H, d).

The following compounds were synthesised according to Preparation 37 from potassium phthalimide and the appropriate α-bromoketone.

| Preparation | R | NMR |
|---|---|---|
| 38 | (3,4-difluorophenyl) | $\delta_H$(d$_6$ DMSO): 5.25 (2H, d), 7.60–7.75 (1H, m), 7.85–8.06 (5H, m), 8.10–8.24 (1H, m) |
| 39 | (4-chlorophenyl) | $\delta_H$(g$_6$ DMSO): 5.24 (2H, s), 7.66 (2H, d), 7.83–8.02 (4H, m), 8.10 (2H, d) |
| 40 | (4-fluorophenyl) | $\delta_H$(d$_6$ DMSO): 5.24 (2H, s), 7.36–7.52 (2H, m), 7.84–8.02 (4H, m), 8.11–8.25 (2H, m) |

Preparation 41: 2-[2-(4-Methoxyphenyl)-[1,3]dioxolan-2-ylmethyl]isoindole-1,3-dione

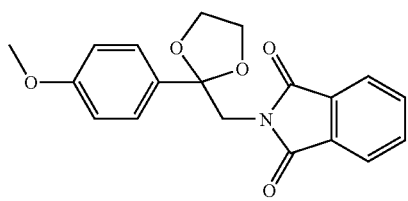

2-[2-(4-Methoxyphenyl)-2-oxoethyl]isoindole-1,3-dione (Preparation 37, 6.35 g, 21.5 mmol) was suspended in toluene (50 mL) and ethylene glycol (12 mL) added. p-Toluenesulfonic acid (300 mg, 1.58 mmol) was added and the resulting mixture heated under reflux for 40 h, removing water with a Dean-Stark trap. The reaction mixture was allowed to cool to rt then partitioned between ethyl acetate (200 mL) and saturated aqueous sodium bicarbonate solution (100 mL). The organic layer was washed with brine (50 mL), dried (MgSO$_4$), filtered and concentrated under reduced pressure, to give the title compound as an off-white solid. $\delta_H$ (d$_6$ DMSO): 3.66 (2H, t), 3.72 (3H, s), 3.87 (4H, m), 6.88 (2H, d), 7.32 (2H, d), 7.83 (4H, m).

The following compounds were synthesised according to Preparation 41 from ethylene glycol and the appropriate ketone.

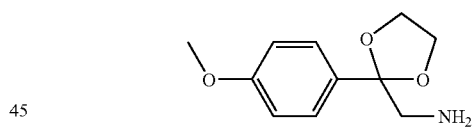

| Preparation | R | NMR |
|---|---|---|
| 42 | (3,4-difluorophenyl) | $\delta_H$(d$_6$ DMSO): 3.69–3.81 (2H, m), 3.85–4.04 (4H, m), 7.15–7.30 (1H, m), 7.32–7.49 (2H, m), 7.74–7.96 (4H, m) |
| 43 | (4-chlorophenyl) | $\delta_H$(d$_6$ DMSO): 3.62–3.78 (2H, m), 3.84–3.99 (4H, m), 7.32–7.49 (4H, m), 7.74–7.94 (4H, m) |
| 44 | (4-fluorophenyl) | $\delta_H$(d$_6$ DMSO): 3.64–3.80 (2H, m), 3.85–4.03 (4H, m), 7.08–7.24 (2H, m), 7.35–7.52 (2H, m), 7.75–7.93 (4H, m) |

Preparation 45: [2-(4-Methoxyphenyl)-[1,3]dioxolan-2-yl]methylamine

2-[2-(4-Methoxyphenyl)-[1,3]dioxolan-2-ylmethyl]isoindole-1,3-dione (Preparation 41, 2.0 g, 5.90 mmol) and hydrazine hydrate (5 mL) were combined. The stirred reaction mixture was heated under reflux for 48 h then allowed to cool to rt. Aqueous sodium hydroxide (2M, 10–15 mL) and water (20 mL) were added and the mixture stirred until a solution was formed. Diethyl ether (20 mL) was added and the biphasic mixture stirred vigorously for 16 h. The layers were separated and the aqueous layer was extracted with diethyl ether (3×20 mL), then the combined organic extracts were washed with brine (20 mL). The ethereal solution was passed through a filter paper then evaporated to dryness in vacuo to give the title compound as a yellow oil, which solidified on standing. $\delta_H$ (CDCl$_3$): 1.42 (2H, br s), 3.06 (2H, s), 3.97 (3H, s), 4.00 (2H, t), 4.21 (2H, t), 7.04 (2H, d), 7.53 (2H, d).

The following compounds were synthesised according to Preparation 45 from hydrazine hydrate and the corresponding phthalimide.

| Preparation | R | NMR |
|---|---|---|
| 46 | 3,4-difluorophenyl | δ$_H$(CDCl$_3$): 1.31 (2H, br s), 2.87 (2H, s), 3.79–3.87 (2H, m), 3.99–4.08 (2H, m), 7.00–7.20 (2H, m), 7.23–7.29 (1H, m) |
| 47 | 4-chlorophenyl | δ$_H$(CDCl$_3$): 1.23 (2H, br s), 2.89 (2H, s), 3.75–3.87 (2H, m), 3.99–4.10 (2H, m), 7.29–7.33 (2H, m), 7.36–7.40 (2H, m) |
| 48 | 4-fluorophenyl | δ$_H$(d$_6$ DMSO): 2.72 (2H, s), 3.25 (2H, br s), 3.67–3.78 (2H, m), 3.93–4.06 (2H, m), 7.11–7.18 (2H, m), 7.37–7.44 (2H, m) |

Preparation 49: 5-Chloro-1H-pyrrolo[2,3-c]pyridine-2-carboxylic acid [2-(4-methoxyphenyl)-[1,3]-dioxolan-2-ylmethyl]amide

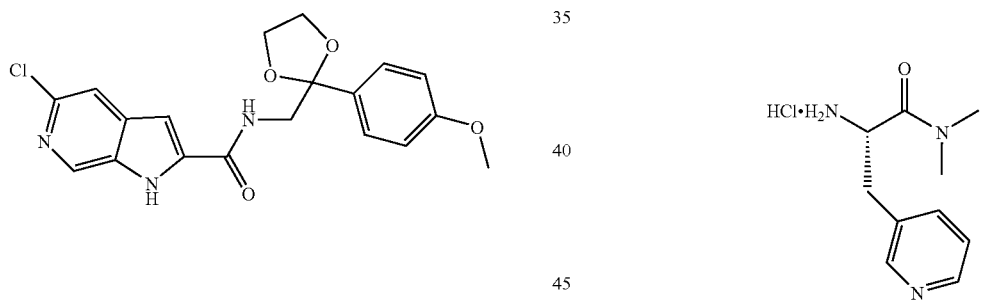

To a solution of [2-(4-methoxyphenyl)-[1,3]-dioxolan-2-yl]methylamine (Preparation 45, 0.117 g, 0.56 mmol) in dichloromethane (5 mL) was added DIPEA (213 μL, 1.22 mmol), 5-chloro-1H-pyrrolo[2,3-c]pyridine-2-carboxylic acid (Preparation 18, 0.100 g, 0.51 mmol) and HOBT (0.076 g, 0.56 mmol). The resulting solution was stirred for 2 min then EDCI (0.117 g, 0.61 mmol) was added and stirring was continued for 18 h at rt. The reaction mixture was partitioned between dichloromethane (30 mL) and water (20 mL) and the layers separated. The aqueous phase was extracted with dichloromethane (3×20 mL) then the combined organics were washed with brine (20 mL), dried (MgSO$_4$), filtered and concentrated in vacuo. Recrystallisation from methanol/dichloromethane gave the title compound as an orange solid. δ$_H$ (CDCl$_3$): 3.81 (3H, s), 3.84-3.91 (4H, m), 4.05 (2H, m), 6.56 (1H, t), 6.76 (1H,s), 6.89 (2H, d), 7.44 (2H, d), 7.57 (1H, s), 8.68 (1H, s), 9.94 (1H, br s).

The following compounds were synthesised according to Preparation 49 from 5-chloro-1H-pyrrolo[2,3-c]pyridine-2-carboxylic acid (Preparation 18) and the appropriate amine.

| Preparation | R | m/z |
|---|---|---|
| 50 | 3,4-difluorophenyl | m/z (ES$^+$) = 394 [M + H]$^+$; RT = 3.49 min |
| 51 | 4-chlorophenyl | m/z (ES$^+$) = 392 [M + H]$^+$; RT = 1.48 min |
| 52 | 4-fluorophenyl | m/z (ES$^+$) = 376 [M + H]$^+$; RT = 3.26 min |

Preparation 53: (S)-2-Amino-N,N-dimethyl-3-pyridin-3-yl-propionamide hydrochloride To a solution of (S)-2-tert-butoxycarbonylamino-3-pyridin-3-ylpropionic acid (500 mg, 1.88 mmol) in DMF (10 mL) was added dimethylamine hydrochloride (153 mg, 1.88 mmol), DIPEA (1.2 mL, 6.57 mmol) and TBTU (602 mg, 1.88 mol). The reaction mixture was stirred at rt for 16 h. The solvent was removed in vacuo and the residue dissolved in methanol (20 mL). To this was added 4M hydrochloric acid in dioxane (20 mL) and the reaction was stirred for 16 h at rt. The solvent was removed in vacuo and the residue was partitioned between water (100 mL) and ethyl acetate (2×100 mL). The aqueous layer was evaporated to dryness and the residue recrystallised from ethanol/ethoxyethanol (9:1), to give the title compound as a white solid. δ$_H$ (CD$_3$OD): 2.99 (3H, s), 3.06 (3H, s), 3.35–3.42 (1H, m), 3.45–3.53 (1H, m), 4.87–4.94 (1H, m), 8.04–8.10 (1H, m), 8.48–8.53 (1H, m), 8.84–8.90 (2H, m).

Preparation 54: (S)-2-Amino-3-pyridin-3-yl-1-pyrrolidin-1-ylpropan-1-one hydrochloride

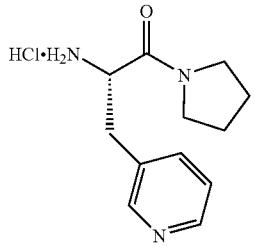

To a solution of pyrrolidine (157 µL, 1.88 mmol) in DMF (10 mL) was added DIPEA (817 µL, 4.69 mmol), (S)-2-tert-butoxycarbonylamino-3-pyridin-3-ylpropionic acid (500 mg, 1.88 mmol) and TBTU (663 mg, 2.06 mmol). The reaction was stirred at rt for 72 h. The solvent was removed in vacuo and the residue was dissolved in methanol (15 mL). To this was added 4M hydrochloric acid in dioxane (20 mL) and the reaction was stirred at rt for 16 h. The solvent was removed in vacuo and the residue was partitioned between water (100 mL) and ethyl acetate (2×100 mL). The aqueous layer was evaporated to dryness, to give the title compound as a green oil. $\delta_H$ (CD$_3$OD): 1.86–2.05 (4H, m), 3.20–3.28 (2H, m), 3.39–3.58 (2H, m), 3.68–3.78 (2H, m), 4.63–4.71 (1H, m), 8.11–8.17 (1H, m), 8.56–8.64 (1H, m), 8.85–8.93 (2H, m).

Preparation 55: (S)-2-Amino-N,N-dimethylamino-3-pyridin-2-ylpropionamide hydrochloride

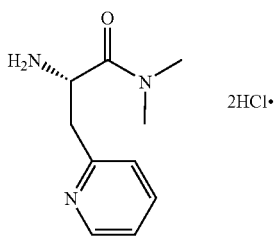

To a stirred solution of dimethylamine hydrochloride (153 g, 187 mmol) in DMF (8 mL) was added DIPEA (2 mL, 6.55 mmol), (S)-2-tert-butoxycarbonylamino-3-pyridin-2-ylpropionic acid (0.50 g, 1.87 mmol, Acros) and TBTU (0.60 g, 1.87 mmol). The reaction mixture was stirred at rt for 16 h. The solvent was removed in vacuo and the residue was dissolved in methanol (15 mL). To this was added 4M hydrochloric acid in dioxane (20 mL) and the reaction stiffed at rt for 16 h. The solvent was removed in vacuo and the residue partitioned between water (100 mL) and ethyl acetate (2×100 mL). The aqueous layer was evaporated to dryness to give a solid, which was recrystallised from ethanol to give the title compound as a pale brown solid. mr/z (ES$^+$)=194.

Preparation 56: 5-Chloro-3-iodopyridin-2-ylamine

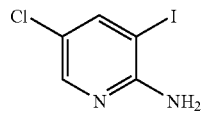

Silver sulfate (3.40 g, 10.9 mmol) and 2-amino-5-chloropyridine (1 g, 7.8 mmol) was added to a solution of iodine (2.76 g, 10.9 mmol) in ethanol (50 ml) and the reaction mixture stiffed at rt for 72 h. The mixture was filtered, washed with methanol and the filtrate concentrated in vacuo. The residue was partitioned between saturated Na$_2$S$_2$O$_3$ solution (50 ml) and DCM (2×50 ml). The combined organics were dried (MgSO$_4$), concentrated in vacuo and purified by chromatography on silica gel eluting with DCM to give the title compound as a beige solid. $\delta_H$ (CDCl$_3$): 4.95 (2H, br s), 7.84 (1H, d), 7.98 (1H, d).

Preparation 57: 5-Chloro-1H-pyrrolo[2,3-b]pyridine-2-carboxylic acid

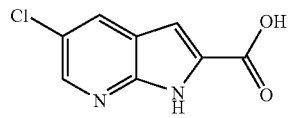

Pyruvic acid (0.43 ml, 6.24 mmol) was added to a solution of 5-chloro-3-iodopyridin-2-ylamine (Preparation 56, 500 mg, 2.08 mmol), palladium acetate (23 mg, 0.10 mmol) and DABCO (700 mg, 6.24 mmol) in anhydrous DMF (20 ml). The reaction mixture was degassed with argon for 20 min, then heated to 110° C. for 16 h. The solvent was removed in vacuo and the residue suspended in water (10 ml) and acetic acid (5 ml) and then filtered. The solid was dissolved in EtOAc (50 ml), extracted into 2N NaOH solution (50 ml) and the organic layer discarded. The aqueous solution was acidified with concentrated HCl and extracted into EtOAc (2×40 ml). The combined organics were dried (MgSO$_4$) and concentrated in vacuo to give the title compound as a beige solid. $\delta_H$ (CD$_3$OD): 7.14 (1H, s), 8.14 (1H, d), 8.35 (1H, d).

Preparation 58: 5-Trimethylsilylacetylene-1H-pyrrolo[2,3-c]pyridine-2-carboxylic acid ethyl ester

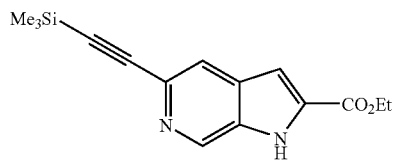

PdCl$_2$(PPh$_3$)$_2$ (0.026 g, 0.037 mmol) and Cu(I)I (0.007 g, 0.037 mmol) were added sequentially to 5-bromo-1H-pyrrolo[2,3-c]pyridine-2-carboxylic acid ethyl ester (Preparation 26, 0.100 g, 0.370 mmol) under an argon atmosphere.

1,4-Dioxane (7 mL, anhydrous) followed by diisopropylamine (0.063 mL, 0.45 mmol) were added and the stirred mixture was purged with argon for 5 min. Trimethylsilylacetylene (0.064 mL, 0.45 mmol) was added dropwise and the resulting mixture stirred at rt for 24 h. The reaction mixture was partitioned between water (50 mL) and ethyl acetate (100 mL) and the layers separated. The aqueous phase was extracted with ethyl acetate (3×30 mL). The combined organics were washed with brine (50 mL), dried (MgSO$_4$), filtered and concentrated in vacuo. The residue was dissolved in the minimum amount of dichloromethane and loaded onto a silica column. Purification via flash column chromatography (SiO$_2$, dichloromethane then 25% ethyl acetate/isohexane) gave a pale yellow solid. $\delta_H$ (CDCl$_3$): 0.28 (9H, s), 1.43 (3H, t), 4.45 (2H, q), 7.18 (1H, s), 7.83 (1H, s), 8.86 (1H, s), 9.21 (1H, br s).

Preparation 59:
5-Ethynyl-1H-pyrrolo[2,3-c]pyridine-2-carboxylic acid ethyl ester

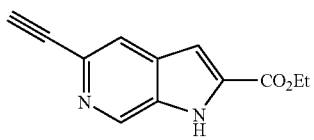

To a stirred solution of the ester (Preparation 58, 0.123 g) was added tetra-n-butylammonium fluoride (1.0M in THF, 5% wt H$_2$O, 0.47 mL, 0.47 mmol) and the solution immediately turned dark pink in colour. After 5 min the reaction was partitioned between ethyl acetate (60 mL) and water (40 mL). The layers were separated and the aqueous layer extracted with ethyl acetate (2×20 mL). Glacial acetic acid was added to the combined organics until the colour changed from pink to yellow. The solution was washed with water (20 mL), brine (20 mL) then dried (MgSO$_4$), filtered and concentrated in vacuo. The residue was dissolved in methanol and adsorbed onto silica gel. Purification via flash column chromatography (SiO$_2$, ethyl acetate:isohexane, 1:1, v/v) gave the title compound as a pale yellow powder. $\delta_H$ (CDCl$_3$): 1.44 (3H, t), 3.08 (1H, s), 4.46 (2H, q), 7.20 (1H, s), 7.85 (1H, s), 8.89 (1H, s), 9.33 (1H, s).

Preparation 60:
5-Ethynyl-1H-pyrrolo[2,3-c]pyridine-2-carboxylic acid

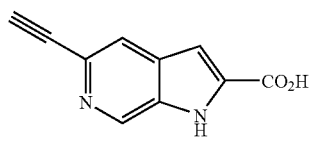

To a suspension of ester (Preparation 59, 0.065 g, 0.30 mmol) in ethanol (6 mL) was added sodium hydroxide (2M aqueous, 1.5 mL, 3.0 mmol) and the reaction mixture stirred at 50° C. for 3 h. The mixture was allowed to cool to rt and glacial acetic acid added, causing precipitation of a white solid. This was collected by filtration, washed with water (20 mL) and then diethyl ether (20 mL). The solid was air dried to give the title compound as a white powder. m/z (ES$^+$)=187 [M+H]$^+$; RT=1.85 min.

Preparation 61:
5-Cyano-1H-pyrrolo[2,3-c]pyridine-2-carboxylic acid ethyl ester

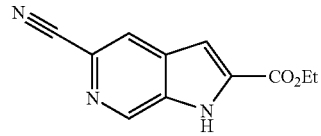

To a solution of 5-bromo-1H-pyrrolo[2,3-c]pyridine-2-carboxylic acid ethyl ester (Preparation 26, 0.160 g, 0.590 mmol) in DMF (anhydrous, 5 mL) was added zinc (II) cyanide (0.041 g, 0.35 mmol) then tetrakis-triphenylphosphine palladium (0). The reaction mixture was degassed by bubbling argon through it for 10 min. The reaction mixture was heated to reflux temperature for 4.5 h then allowed to cool to rt. Water (30 mL) was added and the mixture extracted with ethyl acetate (2×50 mL). The combined organics were washed with brine (30 mL), dried (MgSO$_4$), filtered and concentrated in vacuo. The residue was dissolved in ethyl acetate then adsorbed onto silica gel. Purification via flash column chromatography (SiO$_2$, ethyl acetate:isohexane, 1:3, v/v) gave the title compound as a white solid. $\delta_H$ (CDCl$_3$): 1.45 (3H, t), 4.49 (2H, quartet), 7.31 (1H, s), 8.09 (1H, s), 8.97 (1H, s), 9.60 (1H, br s); m/z (ES$^+$)=216 [M+H]$^+$; RT=3.03 min.

Preparation 62:
5-Cyano-1H-pyrrolo[2,3-c]pyridine-2-carboxylic acid

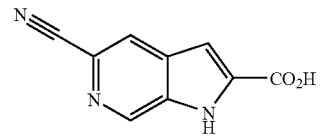

To a stirred suspension of ester (Preparation 61, 0.266 g, 1.24 mmol) in ethanol (6 mL) and water (0.6 mL) was added sodium hydroxide (0.108 g, 2.72 mmol). The reaction mixture was heated to 50° C. for 24 h then allowed to cool to rt. The reaction mixture was diluted with diethyl ether (30 mL), collected by filtration and washed with diethyl ether. The solid was washed with aqueous acetic acid (2×50 mL), then diethyl ether. The solid was air-dried to give the title compound as a white solid. $\delta_H$ (d$_6$ DMSO): 7.22 (1H, s), 8.37 (1H, s), 8.88 (1H, s), 12.88 (1H, s).

Preparation 63: 2,4-Dimethyl-5-nitropyridine

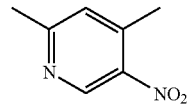

To a stirred suspension of 2-chloro-4-methyl-5-nitropyridine (9.419 g, 54.6 mmol) in dioxane (110 mL) was added tetrakis(triphenyl phosphine) palladium (6.330 g, 5.46 mmol)

and the mixture stirred for 15 min prior to the addition of trimethyl boroxine (7.68 mL, 54.6 mmol) and potassium carbonate (22.64 g, 164.0 mmol). The reaction mixture was heated under reflux for 6 h then allowed to cool to rt over 16 h. Ethyl acetate (200 mL) was added and the mixture stirred vigorously for 1 h. The mixture was filtered through celite, washing through with ethyl acetate/THF (1:1, v/v). Brine (100 mL) was added and attempted separation of layers resulted in a thick emulsion. After removal of all volatiles, ethyl acetate (300 mL) was added and the mixture filtered, giving rise to a biphasic mixture. The layers were separated and the aqueous phase was extracted with ethyl acetate (3×100 mL). The combined organics were washed with brine (100 mL), dried ($MgSO_4$), filtered and concentrated in vacuo. The resulting oil was dissolved in dichloromethane then purified via flash column chromatography ($SiO_2$, ethyl acetate/isohexane, 3:7, v/v) to give the title compound as an orange oil. $\delta_H$ ($CDCl_3$): 2.59 (3H, s), 2.60 (3H, s), 7.12 (1H, s), 9.07 (1H, s).

Preparation 64:
3-(2-Methyl-5-nitropyridin-4-yl)-2-oxopropionic acid ethyl ester

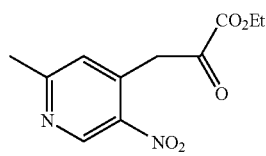

To a solution of potassium ethoxide (0.262 g, 2.96 mmol) in diethyl ether (10 mL) and ethanol (1 mL) was added diethyl oxalate (0.404 mL, 2.96 mmol) in one portion and the resulting solution stirred for 10 min at rt. 2,4-Dimethyl-5-nitropyridine (Preparation 63, 0.400 g, 2.63 mmol) was added as a suspension in diethyl ether (1 mL)/ethanol (1.5 mL) and stirring continued for 16 h at rt. The mixture was filtered, washing with cold diethyl ether. The collected precipitate was dissolved in water and the pH adjusted to 4 by the addition of glacial acetic acid. The resulting precipitate was collected by filtration and air dried. The solid was partitioned between ethyl acetate (150 mL) and water (50 mL) and the layers separated. The aqueous layer was extracted with ethyl acetate (3×20 mL) and the combined organics washed with brine (50 mL), dried ($MgSO_4$), filtered and concentrated under reduced pressure to give the title compound as a red solid which required no further purification. $\delta_H$ ($CDCl_3$): 1.40 (3H, t), 4.40 (2H, q), 4.52 (2H, s), 7.11 (1H, s), 9.25 (1H, s).

Preparation 65:
5-Methyl-1H-pyrrolo[2,3-c]pyridine-2-carboxylic acid ethyl ester

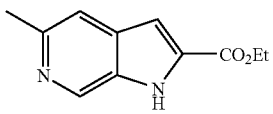

To a solution of the pyruvate (Preparation 64, 0.749 g, 2.97 mmol) in THF (30 mL) and ethanol (15 mL) was added saturated aqueous ammonium chloride solution (15 mL) and the suspension vigorously stirred at rt. Iron powder (1.38 g, 24.64 mmol) was added portionwise and the mixture heated under reflux for 2 h then allowed to cool prior to filtration through a celite plug, and washed through with warm methanol. The mixture was concentrated under reduced pressure, the residue partitioned between ethyl acetate (250 mL) and water (250 mL) and the layers separated. The aqueous phase was extracted with ethyl acetate (3×50 mL) then the combined organics were washed with brine (100 mL), dried ($MgSO_4$), filtered and concentrated in vacuo. The residue was adsorbed onto silica gel and purified via flash chromatography ($SiO_2$, ethyl acetate) to give the title compound as a pale orange solid. $\delta_H$ ($CDCl_3$): 1.42 (3H, t), 2.63 (3H, s), 4.43 (2H, q), 7.10 (1H, s), 7.40 (1H, s), 8.81 (1H, s), 9.08 (1H, br s).

Preparation 66:
5-Methyl-1H-pyrrolo[2,3-c]pyridine-2-carboxylic acid

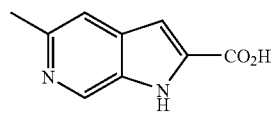

To a stirred solution of ester (Preparation 65, 117 mg, 0.574 mmol) in ethanol (10 mL) was added aqueous sodium hydroxide (2M, 0.43 mL, 0.861 mmol). The resulting solution heated to 55° C. for 4 h then allowed to cool to room temperature and stirred for 17 h. Excess glacial acetic acid was added then all volatiles were removed under reduced pressure. The residue was triturated with water and the resulting solid collected by filtration, washed with water then air dried. The title compound was isolated as a pale yellow solid. m/z ($ES^+$)=177 $[M+H]^+$; RT=1.60 min.

Preparation 67: 4-Methoxypiperidine-1-carboxylic acid tert-butyl ester

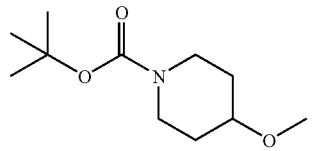

To a vigourosly stirred solution of 4-hydroxypiperidine-1-carboxylic acid tert-butyl ester (2.07 g, 10.3 mmol) in DMF (25 mL) was added a 60% sodium hydride dispersion in mineral oil (500 mg, 12.5 mmol). After stirring for 20 min, methyl iodide (0.9 mL, 14.5 mmol) was added and the resulting mixture stirred for 48 h before being added to a mixture of water and brine (250 mL, 1:1). Extraction with ethyl acetate (4×50 mL), washing of the combined extracts with brine (100 mL) and drying ($MgSO_4$) gave, after concentration, a residue which was purified via flash chromatography (silica gel, ethyl acetate/hexane, 1:1) to give the title compound as a colourless oil. $\delta_H$ ($CDCl_3$): 1.50 (9H, s), 1.52, 1.88 (4H, 2m) 3.12 (2H, ddd), 3.18 (1H, m), 3.19 (3H, s), 3.77 (2H, m); $R_f$ 0.33 (ethyl acetate/hexane: 1/1).

Preparation 68: 4-Methoxypiperidine hydrochloride

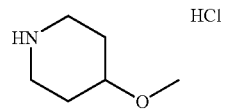

To a solution of 4-methoxypiperidine-1-carboxylic acid tert-butyl ester (Preparation 67, 1.58 g, 7.34 mmol) in methanol (20 mL) was added hydrochloric acid in 1,4-dioxane (4M, 10 mL) and the mixture stirred for 3 h at rt. Concentration in vacuo gave an oil which was redissolved in water (100 mL). The aqueous layer was washed with ethyl acetate (2×30 mL) and concentrated to give the title compound as colourless solid. $\delta_H$ (D$_2$O): 1.80, 2.14 (4H, 2m), 3.13 (2H, m), 3.38 (2H, m), 3.40 (3H, s), 3.68 (m, 1H).

Preparation 69: (R)-3-Methoxypyrrolidine-1-carboxylic acid tert-butyl ester

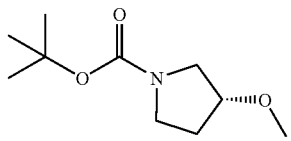

(R)-3-Hydroxypyrrolidine-1-carboxylic acid tert-butyl ester (Sigma-Aldrich) (1.04 g, 5.55 mmol) was methylated and purified in a similar way to Preparation 67 using 60% sodium hydride dispersion (267 mg, 6.68 mmol) and methyl iodide (0.5 mL, 8.06 mmol) in DMF (15 ml). $\delta_H$ (CDCl$_3$): 1.50 (9H, s),1.94–2.02 (2H, m), 3.37 (3H, s), 3.38–3.58 (4H, m), 3.95 (1H, m); R$_f$ 0.47 (ethyl acetate/hexane: 1/1).

Preparation 70: (R)-3-Methoxypyrrolidine hydrochloride

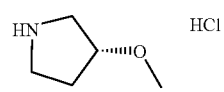

(R)-3-Methoxypyrrolidine-1-carboxylic acid tert-butyl ester (840 mg, 4.17 mmol) was deprotected and purified in a similar way to Preparation 68 using methanol (10 mL) and hydrochloric acid in 1,4-dioxane (4 M, 5.0 mL). $\delta_H$ (D$_2$O): 2.12 (2H, m), 3.10–3.56 (8H, m), 4.20 (1H, m).

Preparation 71: (S)-3-Methoxypyrrolidine-1-carboxylic acid tert-butyl ester

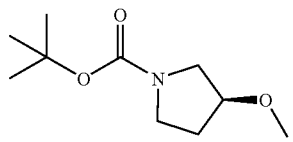

(S)-3-Hydroxypyrrolidine-1-carboxylic acid tert-butyl ester (Omega Chemical Company) (950 mg, 5.55 mmol) was methylated and purified in a similar way to Preparation 67 using 60% sodium hydride dispersion (260 mg, 6.50 mmol) and methyl iodide (0.5 mL, 8.06 mmol) in DMF (15 ml). $^1$H NMR and R$_f$ were identical to the (R)-enantiomer.

Preparation 72: (S)-3-Methoxypyrrolidine hydrochloride

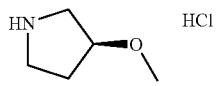

(S)-3-Methoxypyrrolidine-1-carboxylic acid tert-butyl ester (720 mg, 3.58 mmol) was deprotected and purified in a similar way to Preparation 68 using methanol (10 mL) and hydrochloric acid in 1,4-dioxane (4 M, 5.0 mL). $^1$-H NMR and R$_f$ were identical to (R)-enantiomer.

Preparation 73: 4-(2-Nitrobenzenesulfonylamino)piperidine-1-carboxylic acid tert-butyl ester

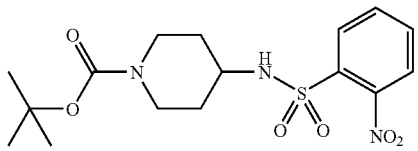

To a solution of 4-aminopiperidine-1-carboxylic acid tert-butyl ester (400 mg, 200 mmol) in anhydrous dichloromethane (14 mL) under argon was added triethylamine (340 µL, 2.4 mmol) and the solution cooled in an ice bath. 2-Nitrophenylsulfonyl chloride (443 mg, 2.0 mmol) was added and the reaction allowed to stir at rt for 16 h. The crude solution was washed with water (2×30 mL) before removing the solvent in vacuo. The crude material was purified by chromatography using ethyl acetate/petroleum ether (30–60%) as the eluent to give the title compound as an off-white powder. $\delta_H$ (d$_6$ DMSO): 8.43 (2H, m), 8.17 (1H, s), 8.09 (2H, m), 3.80–3.69 (2H, m), 3.31–3.23 (1H, m), 2.86–2.69 (2H, m), 1.63–1.51 (2H, m), 1.39 (9H, s), 1.29–1.17 (2H, m).

Preparation 74: 4-[Methyl-(2-nitrobenzenesulfonyl)amino]piperidine-1-carboxylic acid tert-butyl ester

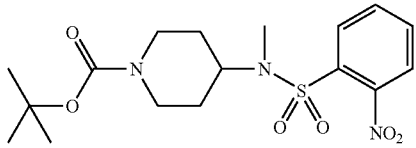

To a solution of 4-(2-nitrobenzenesulfonylamino)piperidine-1-carboxylic acid tert-butyl ester (Preparation 73) (400 mg, 1.04 mmol) in DMF (10 mL) was added caesium carbonate (507 mg, 1.56 mmol) and the mixture stirred at rt for 40 min. Iodomethane (323 μL, 5.19 mmol) was added and the mixture stirred for 16 h. Solvent was removed in vacuo and the crude residue partitioned between ethyl acetate (20 mL) and water (20 mL). The organic layer was separated and washed with 1M HCl (2×20 mL), water (20 mL), then brine (2×20 mL) before being dried (MgSO$_4$). The solvent was removed in vacuo to give the title compound as a yellow powder. $\delta_H$ (d$_6$ DMSO): 8.43 (2H, m), 8.01 (2H, m), 4.00–3.89 (3H, m), 2.83–2.67 (5H, m), 1.54–1.43 (2H, m), 1.39 (9H, s), 1.34–1.24 (2H, m).

Preparation 75: N-Methyl-2-nitro-N-piperidin-4-yl benzenesulfonamide

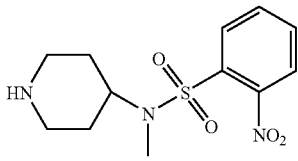

Prepared according to EXAMPLE 182 from 4-[methyl(2-nitrobenzenesulfonyl)amino]piperidine-1-carboxylic acid tert-butyl ester (Preparation 74). $\delta_H$ (d$_6$-DMSO): 8.44 (2H, m), 8.13 (2H, m), 4.20–7.07 (1H, m), 3.29–3.17 (2H, m), 3.03–2.90 (2H, m), 2.77 (3H, s), 2.00–1.84 (2H, m), 1.51–1.43 (2H, m).

Preparation 76: 5-Chloro-1H-pyrrolo[2,3-c]pyridine-2-carboxylic acid (1-(S)-(4-fluorobenzyl)-2-{4-[methyl(2-nitrobenzenesulfonyl)amino]piperidin-1-yl}-2-oxoethyl)amide

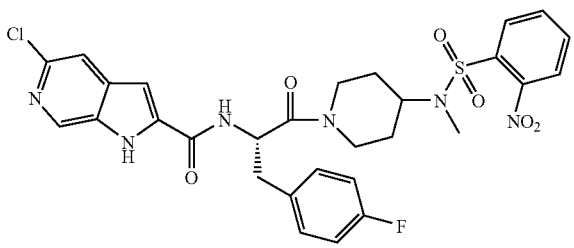

Prepared according to EXAMPLE 231 from 2-(S)-[(5-chloro-1H-pyrrolo[2,3-c]pyridine-2-carbonyl)amino]-3-(4-fluorophenyl)-propionic acid (EXAMPLE 230) and N-methyl-2-nitro-N-piperidin-4-yl-benzenesulfonamide hydrochloride (Preparation 75). m/z (ES$^+$)=643.36 [M+H]$^+$.

Preparation 77: Thiomorpholine 1,1-dioxide

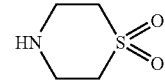

To a solution of thiomorpholine (1.0 g, 9.69 mmol) in acetic acid (11.5 mL) cooled to 0° C. (ice bath) was added aqueous hydrogen peroxide solution (30% w/v, 4 mL) and the reaction heated to 100° C. for 16 h. The mixture was cooled and solvent removed in vacuo before trituration of the residue with methanol gave a white precipitate. The solid was filtered and washed with methanol to give the title compound as an off-white powder. m/z (ES$^+$)=136.06 [M+H]$^+$.

Preparation 78: Piperidine-4-carboxylic acid methyl ester hydrochloride

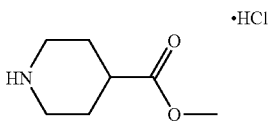

To a cooled solution of anhydrous methanol (100 mL) was added acetyl chloride (7.1 mL, 0.1 mol) and the solution stirred for 75 min. Piperidine-4-carboxylic acid (150 mg, 1.16 mmol) was dissolved in the prepared solution (10 mL) and the reaction stirred for 16 h. The solvent was removed in vacuo to give the title compound as its hydrochloride salt. m/z (ES$^+$)=144.12 [M+H]$^+$.

Preparation 79: 2-(S)-Carbamoyl-piperidine-1-carboxylic acid tert-butyl ester

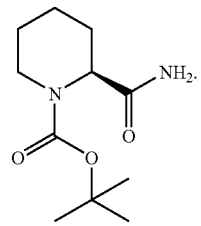

To a solution of N-Boc-L-pipecolinic acid (200 mg, 0.87 mmol) in DMF (3.5 mL) was added TBTU (336 mg, 1.05 mmol), ammonium chloride (93 mg, 1.74 mmol) then DIPEA (182 μL, 1.05 mmol) and the reaction stirred for 16 h. The mixture was partitioned between ethyl acetate (2×30 mL) and water (30 mL), and the organics combined before being washed with 1M sodium hydroxide (3×30 mL) and brine (3×30 mL). The organic solution was dried (MgSO$_4$) and solvent removed in vacuo to give the title compound as a white solid. $\delta_H$ (d$_6$ DMSO): 7.23 (1H, s), 6.97 (1H, s), 4.56–4.39 (1H, br m), 3.43–3.74 (1H, d), 3.14–2.90 (1H, br m), 2.09–2.00 (1H, d), 1.63–1.47 (3H, m), 1.30–1.17 (2H, m).

Preparation 80: (S)-Piperidine-2-carboxylic acid amide hydrochloride

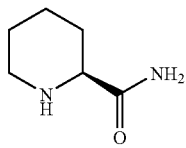

Piperidine-2-carboxylic acid amide was prepared according to the method of Johnson et.al., (*J. Med. Chem.*, 1986, 29, 2100–2104) to give the title compound as an off-white solid. $\delta_H$ (CD$_3$OD): 3.87–3.75 (1H, m), 3.43–3.34 (1H, m), 3.09–2.96 (1H, br m), 2.31–2.16 (1H, m), 1.97–1.81 (2H, br m), 1.77–1.57 (3H, br m).

Preparation 81: 4-(2-Methoxyethoxy)piperidine-1-carboxylic acid tert-butyl ester

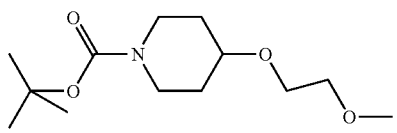

To a solution of tert-butyl-4-hydroxy-1-piperidine carboxylate (300 mg, 1.49 mmol) in DMF (2 mL) was added 1-bromo-2-methoxyethane (168 μL, 1.79 mmol) followed by potassium iodide (25 mg, 0.15 mmol) and sodium hydride (83.5 mg, 2.09 mmol) and the reaction stirred at rt for 16 h. Solvent was removed in vacuo and crude residue was partitioned between ethyl acetate (10 mL) and water (10 mL). The organic layer was washed with 1M HCl (10 mL), 1M NaOH (10 mL) then brine (2×10 mL) before being dried (MgSO$_4$) and removing the solvent in vacuo. Purification by chromatography using dichloromethane/methanol (97:3) as the eluent gave the title compound as a yellow oil. $\delta_H$ (CDCl$_3$): 3.89–3.77 (2H, m), 3.66 (2H, m), 2.57 (2H, m), 3.54–3.46 (1H, m), 3.43 (3H, s), 3.11–3.03 (2H, m), 1.93–1.83 (2H, m), 1.60–1.46 (11H, m).

Preparation 82: 4-(2-Methoxyethoxy)piperidine hydrochloride

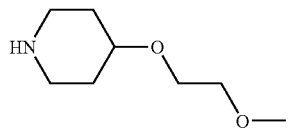

To a solution of 4-(2-methoxyethoxy)-piperidine-1-carboxylic acid tert-butyl ester (Preparation 81, 114 mg, 0.44 mmol) in methanol (3 mL) was added 4M HCl in dioxane (550 μL, 2.20 mmol) and the reaction stirred at rt for 16 h. Solvent was removed in vacuo and the crude residue dissolved in water (10 mL). The aqueous solution was extracted with ethyl acetate (2×10 mL) then concentrated in vacuo. Purification by trituration in ethyl acetate gave the title compound as the hydrochloride salt. $\delta_H$(CD$_3$OD): 3.74–3.67 (1H, m), 3.64 (2H, m), 3.56 (2H, m), 3.40–2.39 (7H, m), 2.11–1.96 (2H, m), 1.93–1.83 (2H, m).

Preparation 83: [1-(R)-(4-Fluorobenzyl)-2-(4-hydroxypiperidin-1-yl)-2-oxoethyl] carbamic acid tert-butyl ester

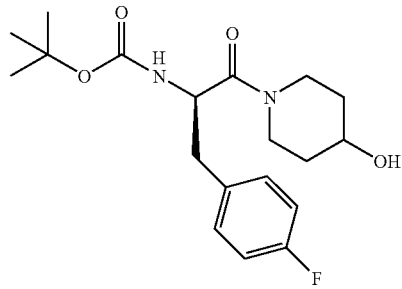

The title compound was prepared according to EXAMPLE 231 but using Boc-3-(4-fluorophenyl)-(R)-alanine and 4-hydroxypiperidine. m/z (ES$^+$)=367.34 [M+H]$^+$.

Preparation 84: 2-(R)-Amino-3-(4-fluorophenyl)-1-(4-hydroxypiperidin-1-yl)propan-1-one hydrochloride

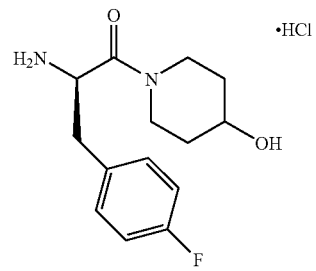

The title compound was prepared according to Preparation 20 from [1-(R)-(4-fluorobenzyl)-2-(4-hydroxypiperidin-1-yl)-2-oxoethyl] carbamic acid tert-butyl ester (Preparation 83). m/z (ES$^+$)=267.20 [M+H]$^+$.

Preparation 85: 4-(N-Benzyl-N-methylamino)piperidine-1-carboxylic acid tert-butyl ester

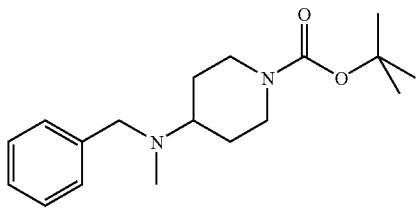

To a solution of N-benzylmethylamine (648 μL, 5.02 mmol) and 1-tert-butoxycarbonyl-4-piperidone (500 mg, 2.51 mmol) in THF (8 mL) was added sodium triacetoxyborohydride (798 mg, 3.76 mmol) followed by acetic acid (144 µL, 2.51 mmol) and the reaction stirred at rt for 40 h. Solvent was removed in vacuo and the residue partitioned between ethyl acetate (15 mL) and water (15 mL). The organic layer was washed with sodium bicarbonate solution (2×15 mL) then brine (2×20 mL), dried (MgSO$_4$) and the solvent removed in vacuo. The crude material was purified by chromatography using ethyl acetate/petroleum ether (2:1) as the eluent to give the title compound as yellow oil. m/z (ES$^+$) =305.32 [M+H]$^+$.

Preparation 86:
4-Methylaminopiperidine-1-carboxylic acid tert-butyl ester

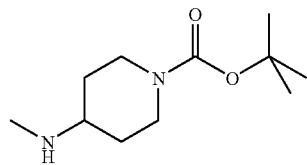

The title compound was prepared according to Preparation 23 from 4-(benzylmethylamino)piperidine-1-carboxylic acid tert-butyl ester (Preparation 85). δ$_H$ (CD$_3$OD): 4.13–4.03 (2H, m), 2.90–2.76 (2H, br m), 2.63–2.53 (1H, m), 2.40 (3H, s), 2.97–1.87 (2H, m), 1.49 (9H, s), 1.27–1.16 (2H, m).

Preparation 87:
Benzylmethyl(tetrahydropyran-4-yl)amine

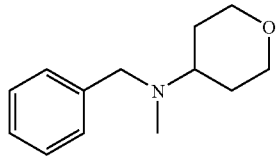

The title compound was prepared according to Preparation 85 from N-benzylmethylamine and tetrahydro-4H-pyran-4-one. Purification of the crude material by chromatography using dichloromethane/methanol (98:2) as the eluent gave the title compound as a yellow oil. δ$_H$ (CD$_3$OD): 7.50–7.40 (5H, m), 4.08 (2H, m), 4.06-(2H, s), 3.49–3.40 (2H, ddd), 3.23–3.14 (1H, m), 2.51 (3H, s), 2.03–1.97 (2H, m), 1.89–1.76 (2H, m).

Preparation 88: Methyl(tetrahydropyran-4-yl)amine hydrochloride

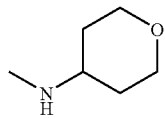

The title compound was prepared according to Preparation 23 from benzylmethyl(tetrahydropyran-4-yl)amine (Preparation 87). Crude material was dissolved in methanol and a solution of 1M HCl in ether was added dropwise to form a precipitate. The product was filtered and washed with ether to give the title compound as the hydrochloride salt as a white crystalline solid. δ$_H$ (CD$_3$OD): 4.11–4.00 (2H, m), 3.53–3.43 (2H, m), 3.37–3.27 (11H, m), 2.74 (3H, s), 2.11–2.03 (2H, m), 1.74–1.60 (2H, m).

Preparation 89:
1-Benzylpiperidin-4-yl-dimethylamine

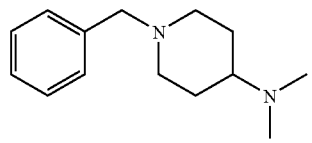

To a solution of 4-amino-1-benzylpiperidine (536 µL, 2.63 mmol) in formic acid (8.5 mL) at 0° C. was added formaldehyde solution (37%, 5.5 mL) and the mixture heated to reflux for 6 h. Solvent was removed in vacuo and the crude residue partitioned between ethyl acetate (20 mL) and water (20 mL). The aqueous layer was separated and taken to pH12 with 2M NaOH solution before being extracted with ethyl acetate (2×20 mL). The organic portion was washed with brine (30 mL) and dried (MgSO$_4$) before removing the solvent in vacuo to give the title compound as a yellow oil. m/z (ES$^+$)=219.25 [M+H]$^+$.

Preparation 90: Dimethylpiperidin4-yl amine

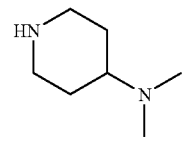

The title compound was prepared according to Preparation 23 from 1-benzylpiperidin-4-yl-dimethylamine (Preparation 89). δ$_H$ (CD$_3$OD): 3.17–3.09 (2H, m), 2.66–2.54 (2H, m), 2.30 (6H, s), 2.26 (1H, m), 1.94–1.86 (2H, m), 1.49–1.29 (2H, m).

Preparation 91:
4-Methanesulfonylamino-piperidine-1-carboxylic acid tert-butyl ester

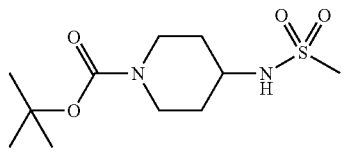

To a solution of 4-amino-1-Boc-piperidine (300 mg, 1.50 mmol) in dichloromethane (2.0 mL) was added a solution of methanesulfonyl chloride (348 µL, 4.49 mmol) in dichloromethane (1 mL) followed by a solution of pyridine (485 µL, 5.99 mmol) in dichloromethane (1 mL), and the reaction stirred at rt for 16 h. Water (10 mL) was added, the mixture separated and the organic layer washed with 1M HCl (10 mL), sodium bicarbonate solution (10 mL) then brine (2×10 mL). The solution was dried (MgSO₄) and solvent removed in vacuo. The crude material was purified by chromatography using dichloromethane/methanol (95:5) as the eluent to give the title compound as an off-white powder. $\delta_H$ (CD₃OD): 4.46–4.40 (1H, m), 4.09–3.97 (2H, m), 3.53–3.40 (1H, m), 3.0 (3H, s), 2.93–2.81 (2H, m), 2.01–1.93 (2H, m), 1.50–1.37 (2H, m).

Preparation 92: N-Piperidin-4-yl methanesulfonamide

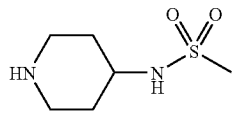

The title compound was prepared from 4-methanesulfonylaminopiperidine-1-carboxylic acid tert-butyl ester (Preparation 91) according to Preparation 82 as an off-white powder. $\delta_H$ (CD₃OD): 3.67–3.57 (1H, m), 3.47–3.40 (2H, m), 3.19–3.10 (2H, m), 3.03 (3H, s), 2.26–2.17 (2H, m), 1.87–1.76 (2H, m).

Preparation 93: 2-(S)-Amino-3-pyridin-4-yl propionic acid methyl ester hydrochloride

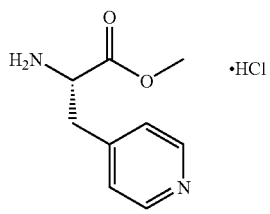

The title compound was prepared according to Preparation 78, using Boc-3-(4-pyridyl)-L-alanine as the starting acid. $\delta_H$ (CD₃OD): 8.90 (2H, br s), 8.16 (2H, br s), 4.73–4.60 (1H, m), 3.84 (3H, s), 3.73–3.50 (2H, m).

Preparation 94: 1,4-Dioxa-7-aza-spiro [4.5] decane

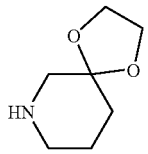

To a solution of 1-Boc-3-piperidone (700 mg, 3.51 mmol) in toluene (20 mL) was added ethylene glycol (588 µL, 10.54 mmol) followed by p-toluene sulfonic acid hydrate (1.0 g, 5.27 mmol) and the reaction heated to reflux using Dean-Stark apparatus for 7 h. To the mixture was added NaHCO₃ solution, and the organic layer was removed. The aqueous phase was evaporated to dryness and the resulting residue dissolved in THF. Filtration through celite and removal of the solvent in vacuo gave the desired product as light brown oil. $\delta_H$ (CD₃OD): 3.99 (2H, s), 3.73–3.57 (2H, m), 3.63 (4H, m), 2.77 (1H, m), 2.73 (1H, m), 1.76 (2H, m).

Preparation 95: 2-Phenyl-1-(S)-(2-phenyl-[1,3]dioxolan-2-yl)ethylamine

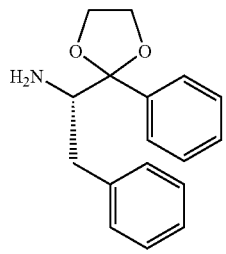

To a solution of commercially available 2-(S)-(N-tert-butyloxycarbonyl)-amino-1,3-diphenyl-1-propanone (250 mg, 0.768 mmol) in toluene (100 mL) was added ethylene glycol (1.0 mL, 17.9 mmol) and p-toluenesulfonic acid monohydrate (262 mg, 1.38 mmol). The resulting mixture was heated under reflux for 48 h, removing water with a Dean-Stark trap. After cooling to ambient temperature the mixture was diluted with ethyl acetate (200 mL) and successively washed with diluted sodium hydroxide solution (1M, 2×50 mL) and brine (50 mL). The solution was dried (MgSO₄) and concentrated to an oil that was purified by flash chromatography on silica gel (eluent:ethyl acetate) to give the title compound as colourless oil. $\delta_H$ (CDCl₃): 2.07 (2H, br s), 2.37 (1H, dd), 2.92 (1H, dd), 3.36 (1H, m), 3.85–4.35 (4H, 3m), 7.14–7.59 (10H, m); m/z (ES⁺)=270.20 [M+H]⁺; RT=2.63 min.

Preparation 96: 5-Chloro-1H-pyrrolo[2,3-c]pyridine-2-carboxylic acid [2-phenyl-1-(S)-(2-phenyl-[1,3]dioxolan-2-yl)ethyl]amide

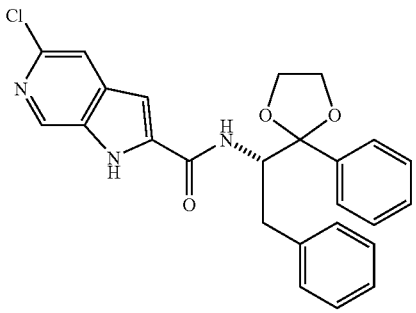

To a solution of 5-chloro-1H-pyrrolo[2,3-c]pyridine-2-carboxylic acid (Preparation 18, 88 mg, 0.403 mmol) and 2-phenyl-1-(S)-(2-phenyl-[ 1,3]dioxolan-2-yl)ethylamine (Preparation 95, 104 mg, 0.386 mmol) in DMF (5 mL) was added HOBt (65 mg, 0.424 mmol), DIPEA (0.155 mL, 0.890 mmol) and EDCI (90 mg, 0.469 mmol). After stirring at rt for 12 h the mixture was added to diluted brine (100 mL, water/brine:1/1). Extraction with ethyl acetate (4×25 mL), washing of the combined extracts with diluted hydrochloric acid (1M, 30 mL), diluted aqueous sodium hydroxide solution (1M, 30 ml) and brine (5 mL) followed by drying (MgSO₄) gave after concentration a residue which was purified by flash chromatography on silica gel (eluent:hexane/ethyl acetate: 50/50). The title compound was obtained as a colourless oil. $\delta_H$ (CDCl₃): 2.73 (1H, dd), 3.10 (1H, dd), 3.84–4.22 (4H, 4m), 5.01 (1H, ddd), 6.37 (1H, d), 6.72 (1H, s), 7.05–7.62 (1.1H, 3m), 8.64 (1H, s), 10.48 (1H, s); m/z (ES$^+$)=448.24 [M+H]$^+$; RT=3.64 min.

Preparation 97: 2-(2-Oxo-2-pyridin-3-yl-ethyl)isoindole-1,3-dione

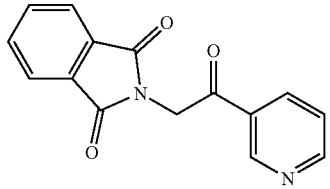

A solution of bromomethylpyridin-3-yl ketone (4.55 g, 16.2 mmol) and potassium phthalimide (6.0 g, 32.4 mmol) in DMF (50 mL) was stirred for 3 days at rt before the added to diluted brine (500 ml, 1:1). The solution was made acidic (pH 2) with diluted hydrochloric acid (1M) before washed with ethyl acetate (2×100 ml). The aqueous layer was then made alkaline (pH 12) again with sodium hydroxide solution (2 M) and extracted with DCM (4×200 ml). The extracts were combined and dried (MgSO$_4$) before concentrated in vacuo. Recrystallisation from methanol (2×) allows to remove crystalline phthalimide and to enrich the title compound in the mother liquer. The crude product was used in Preparation 98 without further purification. $\delta_H$(d$_6$ DMSO): 5.33 (2H, s), 7.64 (1H, dd), 7.92, 7.97 (4H, 2m), 8.43 (1H, m), 8.88 (1H, m), 9.28 (1H, s); m/z (ES$^+$)=308.13 [M+MeCN +H]$^+$; RT=2.39 min.

Preparation 98: 2-Amino-1-pyridin-3-ylethanol

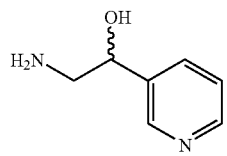

To a solution of crude 2-(2-oxo-2-pyridin-3-ylethyl)isoindole-1,3-dione (Preparation 97, 5.0 g, ~19.0 mmol) in aqueous isopropanol (210 ml, water/IPA:1/6) was added sodium borohydride (10.2 g, 270 mmol) in 2 portions. The mixture was stirred at rt for 12 h before being carefully acidified (pH 2) with dilute hydrochloric acid (1M). After removal of the solvent the residue was taken up in destillated water (100 mL) and passed down a column filled with ion-exchange resin (Amberlite IR 120, H$^+$-form, 300 g, eluent: 500 mL water then 1L of 2 M aqueous ammonia solution). Concentration of the alkaline fractions gave the title compound as a yellow oil. $\delta_H$(d$_6$ DMSO): 2.74, 2.85 (2H, 2m), 4.66 (11H, m), 5.15 (3H, br s), 7.36 (1H, dd), 7.75 (1H, m), 8.46 (1H, m), 8.56 (1H, m); m/z (ES$^+$)=139.11 [M+H]$^+$; RT=0.21 min.

Preparation 99: 2-(S)-Amino-3-(tert-butyldimethylsilanyloxy)-1-(S)-phenylpropan-1-ol

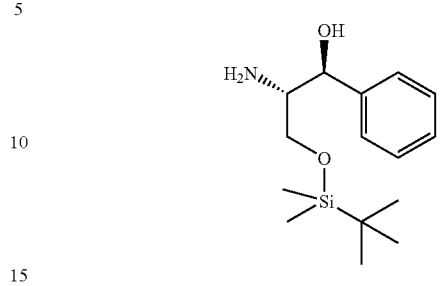

To a solution of (1S,2S)-2-amino-1-phenyl-1,3-propanediol (2.07 g, 12.4 mmol) in DMF (10 mL) was added imidazole (1.0 g, 14.7 mmol) and tert-butyldimethylsilyl chloride (2.30 g, 15.3 mmol). After stirring at rt for 12 h the mixture was added to diluted brine (150 mL, water/brine:1/1). Extraction with ethyl acetate (4×30 mL), washing of the combined extracts with brine (30 mL) and drying (MgSO$_4$) gave after concentration a residue which was purified by flash chromatography on silica gel (eluent: ethyl acetate). The title compound was obtained as colourless oil. $\delta_H$ (CDCl$_3$): 0.24, 0.26 (6H, 2s), 1.12 (9H, s), 2.50–2.78 (3H, br s), 3.16 (1H, ddd), 3.78 (1H, dd), 3.85 (1H, dd), 4.84 (1H, d), 7.49–7.55 (5H, m); m/z (ES$^+$)=282.32 [M+H]$^+$; RT=2.87 min.

Preparation 100: 5-Chloro-1H-pyrrolo[2,3-c]pyridine-2-carboxylic acid [1-(S)-(tert-butyldimethylsilanyloxymethyl)-2-(S)-hydroxy-2-phenylethyl]amide

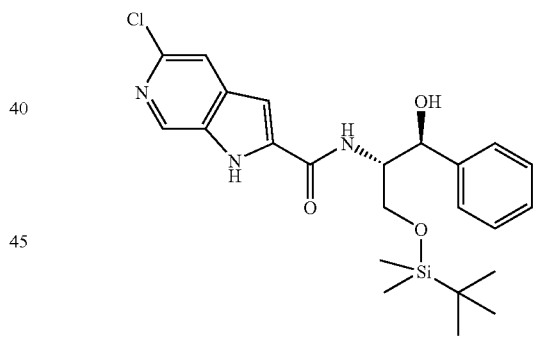

To a solution of 5-chloro-1H-pyrrolo[2,3-c]pyridine-2-carboxylic acid (Preparation 18, 520 mg, 2.65 mmol) and 2-amino-3-(tert-butyldimethylsilanyloxy)-1-phenylpropan-1-ol (Preparation 99, 780 mg, 2.77 mmol) in DMF (15 mL) was added HOBt (411 mg, 2.68 mmol), DIPEA (0.96 mL, 5.51 mmol) and EDCI (589 mg, 3.07 mmol). After stirring at rt for 12 h the mixture was added to diluted brine (150 mL, water/brine:1/1). Extraction with ethyl acetate (4×50 mL), washing of the combined extracts with diluted hydrochloric acid (1M, 50 ml), diluted aqueous sodium hydroxide solution (1M, 50 ml) and brine (50 mL) followed by drying (MgSO$_4$) gave after concentration a residue which was purified by flash chromatography on silica gel (eluent:hexane/ethyl acetate: 50/50). The title compound was obtained as colourless oil. $\delta_H$ (CD$_3$OD): 0.00, 0.01 (6H, 2s), 0.84 (9H, s), 3.60 (1H, dd), 3.84 (1H, dd), 4.33 (1H, ddd), 4.98 (1H, d), 7.05 (1H, s), 7.12–7.37 (5H, 3m), 7.60 (1H, s), 8.49 (11H, s); m/z (ES$^+$)= 460.36 [M+H]$^+$; RT=4.16 min.

Preparation 101: 5-Chloro-1H-pyrrolo[2,3-c]pyridine-2-carboxylic acid [1-(S)-(tert-butyldimethylsilanyloxymethyl)-2-oxo-2-phenylethyl]amide

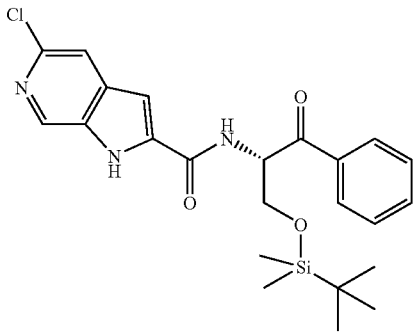

To a solution of 5-chloro-1H-pyrrolo[2,3-c]pyridine-2-carboxylic acid [1-(S)-(tert-butyldimethylsilanyloxymethyl)-2-(S)-hydroxy-2-phenylethyl]amide (Preparation 100, 304 mg, 0.661 mmol) in dry DCM (10 mL) was added Dess-Martin periodinane (342 mg, 0.806 mmol). After stirring for 3 h at room temperature alkaline sodium thiosulfate solution was added (5.4 g $Na_2SO_3$ dissolved in 20 mL saturated $NaHCO_3$ solution) and the emulsion vigorously stirred for an additional 30 min. Ethyl acetate (150 ml) was added and the aqueous layer removed. The organic layer was washed with brine (50 ml), dried ($MgSO_4$) and concentrated to a residue which was purified by flash chromatography on silica gel (eluent: hexane/ethyl acetate:50/50) to give the title compound as colourless solid. m/z ($ES^+$)=458.34 $[M+H]^+$; RT=4.32 min.

Preparation 102: [1-(S)-(4-Fluorobenzyl)-2-(3-(S)-hydroxypyrrolidin-1-yl)-2-oxoethyl]carbamic acid tert-butyl ester

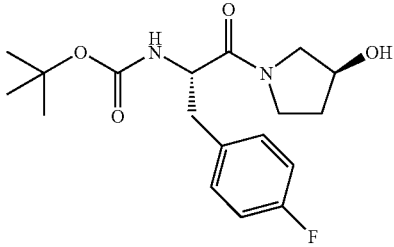

To a stirred solution of (S)-N-Boc-4-fluorophenylalanine (5.08 g, 17.9 mmol) and (S)-3-hydroxypyrrolidine (1.05 mL, 19.7 mmol) in anhydrous DMF (200 mL), was added DIPEA (6.87 mL, 39.5 mmol) and $HOBt.H_2O$ (3.02 g, 19.7 mmol). The reaction mixture was stirred for 10 min at room temperature then EDCI (4.13 g, 21.5 mmol) was added and the resulting mixture stirred for 20 h at rt. The volatiles were removed in vacuo then the residue partitioned between water (200 mL) and ethyl acetate (200 mL). The layers were separated and the aqueous layer extracted with ethyl acetate (3×50 mL). The combined organics were washed with aqueous sodium hydroxide solution (2M, 3×50 mL), brine (100 mL), dried ($MgSO_4$), filtered and concentrated in vacuo. The oily residue was purified via flash chromatography ($SiO_2$, methanol/dichloromethane, 1:19, v/v) to give the title compound as a colourless oil which became a white solid on standing. m/z ($ES^+$)=353 $[M+H]^+$; RT=3.17 min.

Preparation 103: 2-(S)-Amino-3-(4-fluorophenyl)-1-(3-(S)-hydroxypyrrolidin-1-yl)propan-1-one hydrochloride

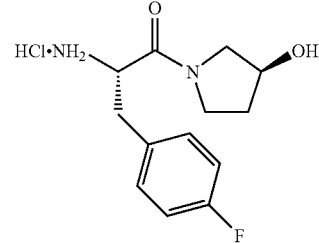

To a solution of ester (Preparation 102, 5.25 g, 14.9 mmol) in methanol (anhydrous, 30 mL) was added 4M HCl in dioxane (7.64 mL, 30.6 mmol) and the resulting solution stirred for 18 h at rt then the solvents removed in vacuo. The residue was partitioned between ethyl acetate (150 mL) and water (100 mL). The layers were separated and the organic layer extracted with water (2×50 mL). The combined aqueous extracts were washed once with ethyl acetate (30 mL), then the combined organic extracts were evaporated to dryness under reduced pressure to give the title compound as a white foam. $\delta_H$ ($CD_3OD$): 1.47–1.62 (0.5H, m), 1.67–1.80 (1H, m), 1.83–1.96 (0.5H, m), 2.72–2.87 (1H, m), 2.96–3.12 (2H, m), 3.19–3.29 (1H, m), 3.30–3.62 (2H, m), 4.14–4.39 (2H, m), 6.91–7.08 (2H, m), 7.22 (2H, dd).

Preparation 104: (6-Chloropyridin-3-yl)carbamic acid tert-butyl ester

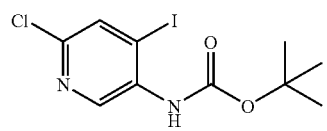

The title compound was prepared according to the method described by Dinnell et al (US 2002/0022624 A1). $\delta_H$ ($CDCl_3$): 1.52(9H, s), 6.52(1H, s), 7.26 (1H, d), 7.97 (1H, d), 8.23 (1H, d).

Preparation 105: (6-Chloro-4-iodopyridin-3-yl)carbamic acid tert-butyl ester

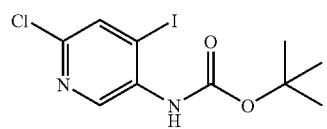

The title compound was prepared according to the method described by Dinnell et al (US 2002/0022624 A1) from the compound of Preparation 104. $\delta_H$ ($CDCl_3$): 1.54 (9H, s), 6.62 (1H, s), 7.72 (1H, s), 8.93 (1H, s).

Preparation 106: 6-Chloro4-iodopyridin-3-ylamine

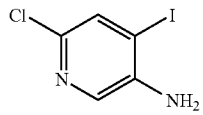

The title compound was prepared according to the method described by Dinnell et al (US 2002/0022624 A1) from the compound of Preparation 105. $\delta_H$ (CDCl$_3$): 4.12 (2H, br s), 7.60 (1H, s), 7.79 (1H, s).

Preparation 107: N-(6-Chloropyridin-2-yl)-2,2-dimethyl propionamide

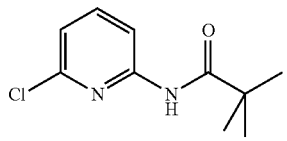

To a solution of 2-amino-6-chloropyridine (3.0 g, 23.3 mmol) in dichloromethane (45 mL) under argon was added triethylamine (4.10 mL, 29.2 mmol) and the reaction cooled to 0° C. (ice bath). A solution of trimethylacetyl chloride (3.16 mL, 25.7 mmol) in dichloromethane (10 mL) was added dropwise over 20 min before stirring for 30 min at 0° C. The reaction was brought up to rt and stirred for a further 5 h, then water (30 mL) was added. The organics were separated and washed with Na$_2$CO$_3$ solution (2×50 mL), dried,(MgSO$_4$) and solvent removed in vacuo. Purification by column chromatography (SiO$_2$, CH$_2$Cl$_2$) gave the title compound. m/z (ES$^+$)=213.04 [M+H]$^+$.

Preparation 108: N-(6-Chloro-3-iodopyridin-2-yl)-2,2-dimethyl propionamide

To a dry solution of N-(6-chloropyridin-2-yl)-2,2-dimethyl propionamide (Preparation 107, 8.0 g, 37.6 mmol) in THF (120 mL), cooled to −78° C., was added dropwise, a solution of tert-butyllithium in pentane (1.7M, 48.7 mL, 82.8 mmol) over 40 min. The reaction was stirred at −78° C. for 3 h before adding a solution of iodine (11.46 g, 45.1 mmol) in THF (40 mL) dropwise. The mixture was brought up to rt and stirred for 16 h. 2M HCl (3 mL) was added to the reaction, and after 20 min the solvent was removed in vacuo. Crude material was partitioned between ethyl acetate (200 mL) and water (150 mL). Organics were separated and washed with 10% sodium thiosulfate solution (4×100 mL) then NaHCO$_3$ solution (2×100 mL), dried (MgSO$_4$) and the solvent removed in vacuo. The residue was purified by column chromatography (SiO$_2$, CH$_2$Cl$_2$) to give the title compound. m/z (ES$^+$)=338.93 [M+H]$^+$.

Preparation 109: 6-Chloro-3-iodopyridin-2-ylamine

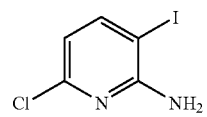

A suspension of N-(6-chloro-3-iodopyridin-2-yl)-2,2-dimethyl propionamide (Preparation 108, 5.0 g, 14.8 mmol) in 1M HCl was heated to reflux for 4.5 h. The reaction was cooled to rt and then extracted with diethyl ether (2×50 mL). The organics were washed with Na$_2$CO$_3$ solution (2×50 mL) before being dried (MgSO$_4$) and the solvent removed in vacuo. Purification by column chromatography (SiO$_2$, CH$_2$Cl$_2$) afforded the title compound. $\delta_H$(CDCl$_3$): 7.76 (1H, d), 6.46 (1H, d), 5.43–5.20 (2H, br s).

Preparation 110: 6-Chloro-1H-pyrrolo[2,3b]pyridine-2-carboxylic acid

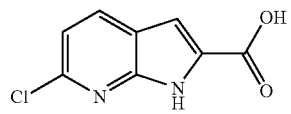

To a dry solution of 6-chloro-3-iodo-pyridin-2-ylamine (Preparation 109, 2.80 g, 11.0 mmol) in DMF (8 mL) under argon was added pyruvic acid (2.29 mL, 33.0 mmol), DABCO (3.70 g, 33.0 mmol) then palladium(II)acetate (124 mg, 0.55 mmol) and the mixture purged with argon for 20 min. The reaction was heated to 105° C. (bath temp.) for 3 h before being allowed to cool to rt. Solvent was removed in vacuo then crude material partitioned between ethyl acetate (100 mL) and water (75 mL). The organic layer was separated and washed with water (2×75 mL) before being extracted into 2M NaOH (2×75 mL). The aqueous layer was acidified to pH 3 with 2M HCl and extracted into ethyl acetate (2×100 mL). Organic layers were combined, dried (MgSO$_4$) and concentrated in vacuo. The residue was suspended in water and the filtrate removed to give the title compound. m/z (ES$^+$)= 196.91 [M+H]$^+$, RT=3.07 min.

Preparation 111: [1-(S)-(4-Fluorobenzyl)-2-oxo-2-(5-oxo-[1,4]diazepam-1-yl)ethyl]carbamic acid tert-butyl ester

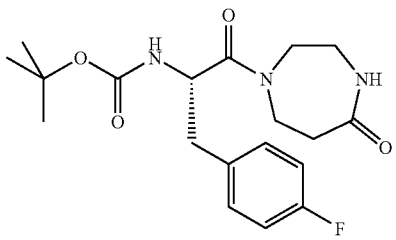

DIPEA (2.08 mL, 11.95 mmol), BOC-L-phenylalanine (1.128 g, 3.98 mmol) and HOBt (592 mg, 4.38 mmol) was added to a solution of [1,4]-diazepan-5-one (500 mg, 4.38 mmol) in DMF (10 mL) and the mixture stirred for 5 min. EDCI (992 mg, 5.18 mmol) was added and the reaction stirred for 16 h before removing the solvent in vacuo. Purification by column chromatography (SiO$_2$, 9:1 CH$_2$Cl$_2$/MeOH) gave the title compound. m/z (ES$^+$)=380.00 [M+H]$^+$.

Preparation 112: 1-(S)-[2-Amino-3-(4-fluorophenyl)propionyl][1,4]diazepan-5-one

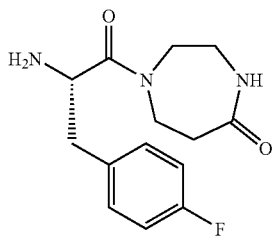

To a solution of [1-(S)-(4-fluorobenzyl)-2-oxo-2-(5-oxo-[1,4]diazepam-1-yl)ethyl]carbamic acid tert-butyl ester (Preparation 111, 1.23 g, 3.24 mmol) in methanol (15 mL) was added a solution of 4M HCl in dioxane (6.48 mL, 25.9 mmol) and the reaction stirred for 3.5 h. Solvent was removed in vacuo then crude material taken into water (20 mL). The aqueous layer was extracted with ethyl acetate (15 mL) then water removed in vacuo to afford the title compound as its hydrochloride salt. m/z (ES$^+$)=279.95 [M+H]$^+$.

Preparation 113: 2-(S)-tert-Butoxycarbonylamino-3-(4-fluorophenyl)propionic acid tert-butyl ester

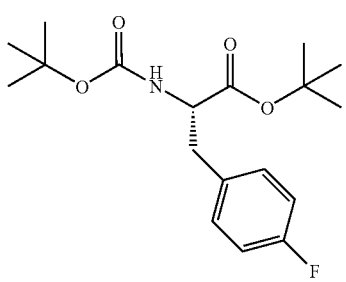

To a stirred solution of (S)-N-Boc-4-fluorophenylalanine (2.83 g, 10.0 mmol), DMAP (0.12 g, 1.0 mmol) in DCM (20 mL) and 2-methyl-2-propanol (1.05 mL, 11.0 mmol), was added DCC (2.27 g, 11.0 mmol). The reaction mixture was stirred at rt for 16 h. The reaction mixture was filtered and washed several times with DCM. The filtrate was concentrated in vacuo and chromatographed on silica gel eluting with ethyl acetate:isohexane (1:4) to give the title compound. δ$_H$ (CDCl$_3$): 1.39 (9H, s), 1.41 (9H, s), 3.01 (2H, m), 4.41 (1H, m), 4.98 (1H, m), 6.95 (2H, m), 7.12 (2H, m).

Preparation 114: 2-(S)-Amino-3-(4-fluorophenyl)propionic acid tert-butyl ester hydrochloride

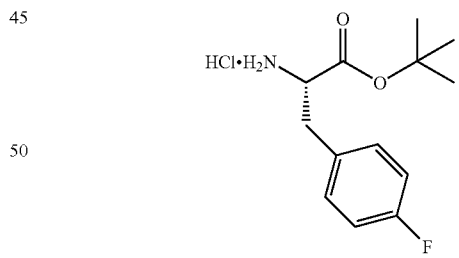

A stirred solution of ethyl acetate (10 mL) and methanol (0.60 mL, 14.7 mmol) was cooled to 0° C. under an argon atmosphere. Acetyl chloride (1.05 mL, 14.7 mmol) was added dropwise, and the solution warmed to rt and stirred for 30 min. 2-(S)-tert-butoxycarbonylamino-3-(4-fluorophenyl)propionic acid tert-butyl ester (Preparation 113, 1 g, 2.95 mmol) was added, and the reaction mixture stirred at rt for 4 h. The reaction mixture was filtered, washed several times with diethyl ether and dried under vacuum to give the title compound. δ$_H$ (DMSO): 1.30 (9H, s), 3.01 (1H, dd), 3.20 (1H, dd), 4.08 (1H, m), 7.15 (2H, m), 7.32 (2H, m), 8.64 (3H, br s).

Preparation 115: 2-Chloro-5-iodopyridin-4-ylamine

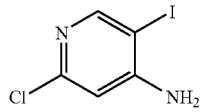

Silver sulfate (7.1 g, 22.8 mmol) and 4-amino-2-chloropyridine (4.06 g, 31.6 mmol) were added to a solution of iodine (5.65 g, 22.3 mmol) in ethanol (100 mL) and the reaction mixture stirred at rt for 72 h. The bright yellow suspension was filtered, washed with methanol and the filtrate concentrated in vacuo. The residue was partitioned between saturated $Na_2CO_3$ solution (200 mL) and ethyl acetate (200 ml). After separation the organic layer was washed with $Na_2S_2O_3$ solution (50 mL, 25%) and brine (50 mL), dried ($MgSO_4$), concentrated in vacuo and purified by chromatography on silica gel eluting with iso-hexane/ethyl acetate (3:1 to 2.5:1) to give the title compound. $\delta_H$ ($CDCl_3$): 4.81 (2H, br s), 6.63 (1H, s), 8.38 (1H, s); m/z ($ES^+$)=254.86 $[M+H]^+$; RT=2.51 min.

Preparation 116: 6-Chloro-1H-pyrrolo[3,2-c]pyridine-2-carboxylic acid

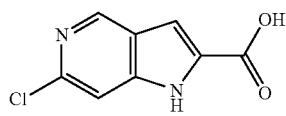

Pyruvic acid (0.86 mL, 12.4 mmol) was added to a solution of 2-chloro-5-iodo-pyridin-4-ylamine (Preparation 115, 1.05 mg, 4.13 mmol), palladium acetate (56 mg, 0.25 mmol) and DABCO (1.39 g, 12.4 mmol) in anhydrous DMF (30 ml). The reaction mixture was degassed with argon for 20 min, then heated to 145° C. for 2 h. The solvent was removed in vacuo and the residue taken up in water (200 mL). The suspension was made alkaline (pH 9–10) with dilute NaOH solution (1M) and filtered through Celite. After washing of the filtrate with ethyl acetate (50 mL) and ether (50 mL) the pH was adjusted to 3 with dilute HCl solution (1M). Extraction with ethyl acetate (5×50 mL), drying of the combined extracts ($MgSO_4$) and concentration gave the title compound. $\delta_H$ ($d_6$ DMSO): 7.24 (1H, s), 7.42 (1H, s), 8.80 (1H, s); m/z ($ES^-$)= 195.02 $[M-H]^-$; RT=2.36 min.

Preparation 117: 4(S)-(4-Fluorobenzyl)oxazolidine-2,5-dione

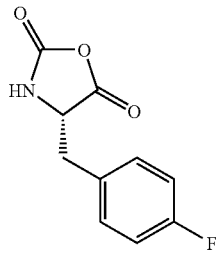

To a solution of 2(S)-tert-butoxycarbonylamino-3-(4-fluorophenyl)propionic acid (1.5 g, 5.29 mmol) in ethyl acetate (100 mL) under an argon atmosphere was added triphosgene (628 mg, 2.12 mmol). To the solution was added triethylamine (0.8 mL 5.76 mmol,) over 1 min, and the reaction stirred for 72 h at rt. The reaction mixture was filtered, and the filtrate concentrated in vacuo to yield an oily residue. The crude material was crystallised from cold dichloromethane and petroleum ether to give the title compound. $\delta_H$ ($CD_3OD$): 7.20 (2H, m), 7.10 (2H, m), 5.86 (1H, s, (NH)), 4.58 (1H, s), 3.33–3.23 (2H, m), 3.11–3.00 (1H, m).

EXAMPLE 1

5-Chloro-1H-pyrrolo[3,2-b]pyridine-2-carboxylic acid (1-dimethylcarbamoyl-2-(S)-phenylethyl)amide

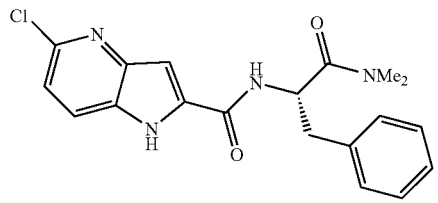

To a solution of 5-chloro-1H-pyrrolo[3,2-b]pyridine-2-carboxylic acid (Preparation 6, 36 mg, 0.18 mmol) in DMF (4 mL, anhydrous), was added 2-(S)-amino-N,N-dimethyl-3-phenylpropionamide hydrochloride (Preparation 8, 46 mg, 0.20 mmol), DIPEA (105 μL, 6.05 mmol) and HOBt (25 mg, 0.18 mmol) sequentially. The solution was stirred for 5 min prior to the addition of EDCI (42 mg, 0.22 mmol) in one portion. The resulting solution was stirred for 16 h at rt. The reaction mixture was partitioned between ethyl acetate (50 mL) and brine (20 mL). The layers were separated and the aqueous phase extracted with ethyl acetate (3×20 mL), then the combined organics were washed with water (3×10 mL) and brine (10 mL). The organic phase was dried ($MgSO_4$), filtered and concentrated in vacuo. Purification via flash column chromatography eluting with methanol/dichloromethane (1:19) gave an orange oil which was triturated with diethyl ether/hexane to give the title compound as an orange solid. δ$_H$ (CDCl$_3$): 2.71 (3H, s), 2.93 (3H, s), 3.05–3.21 (2H, m), 5.28–5.39 (1H, m), 7.00 (1H, s), 7.17–7.36 (6H, m), 7.69 (1H, d, 9.23 Hz), 9.27 (1H, s); m/z (ES$^+$)=371.15 [M+H]$^+$; RT=3.28 min.

EXAMPLE 2

1H-pyrrolo [3,2-c]pyridine-2-carboxylic acid (1-dimethylcarbamoyl-2(S)-phenylethyl)amide

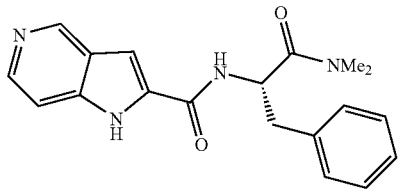

To a solution of 1H-pyrrolo[3,2-c]pyridine-2-carboxylic acid (Preparation 12, 100 mg, 0.62 mmol) in DMF (15 mL) was added 2-(S)-amino-N,N-dimethyl-3-phenylpropionamide hydrochloride (Preparation 8, 141 mg, 0.62 mmol), HOBt (83 mg, 0.62 mmol) and DIPEA (0.21 mL, 1.23 mmol). After 30 min, EDCI (154 mg, 0.80 mmol) was added and the mixture was stirred at rt for 72 h. The solvent was removed in vacuo and the solid partitioned between water (50 mL) and ethyl acetate (3×50 mL). The combined organic layer was dried (MgSO$_4$), concentrated in vacuo and purified by chromatography on silica gel using methanol/dichloromethane (6:94) as eluant to give the title compound as a beige solid. δ$_H$ (CD$_3$OD): 3.06–3.19 (2H, m), 4.83 (6H, s), 5.27 (1H, t), 7.20–7.32 (5H, m), 7.34 (1H, s), 7.45 (1H, d), 8.20 (1H, d), 8.87 (1H, s); m/z (ES$^+$)=337 [M+H]$^+$.

EXAMPLE 3

1H-Pyrrolo[2,3-c]pyridine-2-carboxylic acid (1-dimethylcarbamoyl-2(S)-phenylethyl)amide

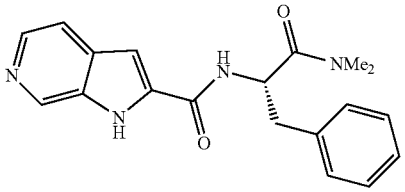

To a solution of 1H-pyrrolo[2,3-c]pyridine-2-carboxylic acid (Preparation 15, 100 mg, 0.62 mmol) in DMF (15 mL), was added 2-(S)-amino-N,N-dimethyl-3-phenylpropionamide hydrochloride (Preparation 8, 141 mg, 0.62 mmol), HOBt (83 mg, 0.62 mmol) and DIPEA (0.21 mL, 1.23 mmol). The reaction was stirred at rt for 0.5 h, followed by addition of EDCI (154 mg, 0.80 mmol). The mixture was stirred at rt for 72 h then partitioned between water (50 mL) and ethyl acetate (3×50 mL). The combined organic fractions were dried (MgSO$_4$), concentrated in vacuo and chromatographed on silica gel eluting with methanol/dichloromethane (1:19) to give the title compound as a yellow solid. δ$_H$ (CD$_3$OD): 2.88 (6H, s), 3.07–3.20 (2H, m), 5.28 (1H, t), 7.20 (1H, s), 7.22–7.31 (5H, m), 7.65 (1H, d), 8.10 (1H, d), 8.76 (1H, s); m/z (ES$^+$)=337 [M+H]$^+$.

EXAMPLE 4

5-Chloro-1H-pyrrolo[2,3-c]pydridine-2-carboxylic acid (1-dimethylcarbamoyl-2(S)-phenylethyl)amide

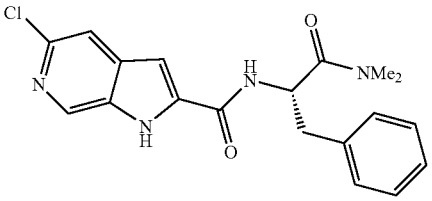

To a solution of 5-chloro-1H-pyrrolo[2,3-c]pyridine-2-carboxylic acid (Preparation 18, 100 mg, 0.51 mmol) in DMF (15 mL) was added 2-(S)-amino-N,N-dimethyl-3-phenylpropionamide hydrochloride (Preparation 8, 116 mg, 0.51 mmol), HOBt (69 mg, 0.51 mmol) and DIPEA (0.18 mL, 1.02 mmol). After 15 min, EDCI (127 mg, 0.66 mmol) was added and the mixture stirred at rt for 15 h. The solvent was removed in vacuo and the solid partitioned between water (50 mL) and ethyl acetate (3×50 mL). The combined organic phases were dried (MgSO$_4$), concentrated in vacuo and purified by chromatography on silica gel eluting with methanol/dichloromethane (1:19) to give the title compound as a beige solid. δ$_H$ (CD$_3$OD): 2.89 (6H, s), 3.05–3.19 (2H, m), 5.27 (1H, t), 7.16 (1H, s), 7.20–7.32 (5H, m), 7.67 (1H, s), 8.56 (1H, s); m/z (ES$^+$)=371 [M+H]$^+$.

EXAMPLE 5

5-Chloro-1H-pyrrolo[2,3-c]pyridine-2-carboxylic acid [1-(S)-(4-fluorobenzyl)-2-(4-hydroxypiperidin-1-yl)-2-oxoethyl]amide

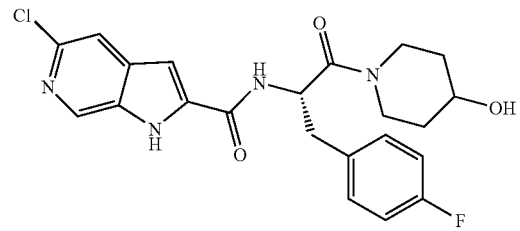

Route A: To a solution of 2-(S)-[(5-chloro-1H-pyrrolo[2,3-c]pyridine-2-carbonyl)amino]-3-(4-fluorophenyl)propionic acid (EXAMPLE 228, 1.4 g, 3.87 mmol) in DMF (35 mL) was added HATU (1.77 g, 4.64 mmol) and the reaction stirred for 10 min. 4-Hydroxypiperidine (0.43 g, 4.26 mmol) was added, followed by DIPEA (0.8 mL, 4.64 mmol,) and the reaction stirred at rt for 16 h. Solvent was removed in vacuo and the crude material partitioned between ethyl acetate (50 mL) and water (50 mL). The organics were washed with sodium bicarbonate (2×30 mL) and brine (2×30 mL), dried (MgSO$_4$) and the solvent removed in vacuo. Purification by column chromatography (SiO$_2$, 96:4 dichloromethane/methanol) gave the title compound. m/z (ES$^+$)=445.15 [M+H]$^+$; RT=3.24 min.

Route B: The title compound was prepared as outlined in EXAMPLE 1 from 5-chloro-1H-pyrrolo[2,3-c]pyridine-2-carboxylic acid (Preparation 18) and 2-(S)-amino-3-(4-fluorophenyl)-1-(4-hydroxypiperidin-1-yl)propan-1-one hydrochloride (Preparation 20). The product was purified by chromatography on silica gel eluting with methanol/dichloromethane (1:19) to give the title compound as a pale yellow solid. $\delta_H$ (CD$_3$OD): 1.08–1.19 (0.5H, m), 1.29–1.51 (1.5H, m), 1.54–1.62 (0.5H, m), 1.73–1.84 (1.5H, m), 3.06–3.36 (4H, m), 3.67–3.95 (2.5H, m), 4.03–4.10 (0.5H, m), 5.32 (1H, t), 6.97–7.04 (2H, m), 7.14 (1H, s), 7.26–7.33 (2H, m), 7.66 (1H, s), 8.55 (1H, s); m/z (ES$^+$)=445 [M+H]$^+$; RT=3.27 min.

EXAMPLE 6

5-Chloro-1H-pyrrolo[2,3-c]pyridine-2-carboxylic acid [1-(S)-benzyl-3-(cis-3,4-dihydroxypyrrolidin-1-yl)-2(R)-hydroxy-3-oxopropyl]amide

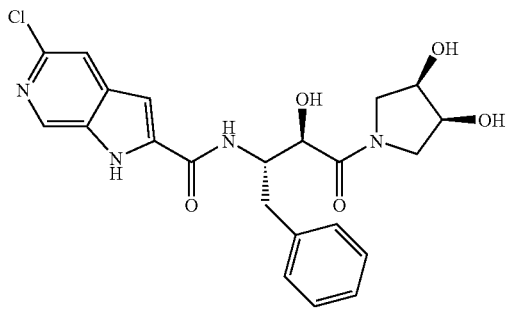

To a solution of (S)-3-[(5-chloro-1H-pyrrolo[2,3-c]pyridine-2-carbonyl)amino]-2-(R)-hydroxy-4-phenylbutyric acid (EXAMPLE 44, 50 mg, 0.13 mmol), cis-3,4-dihydroxypyrrolidine (Preparation 23, 15 mg, 0.15 mmol) and HOBt (27 mg, 0.20 mmol) in DMF (5 mL), was added DIPEA (47 µL, 0.27 mmol). After stirring for 5 min, EDCI (28 mg, 0.15 mmol) was added and the reaction stirred at rt for 72 h. The solvent was removed in vacuo and the residue partitioned between water (30 mL) and ethyl acetate (3×30 mL). The combined organic fractions were dried (MgSO$_4$), concentrated in vacuo and the residue purified by chromatography on silica gel eluting with methanol/dichloromethane (1:9) to give the title compound as a white solid. m/z (ES$^+$)=459 [M+H]$^+$. RT=3.07 min.

EXAMPLE 7

5-Bromo-1H-pyarrolo[2,3-c]pyridine-2-carboxylic acid (1-dimethylcarbamoyl-2-(S)-phenylethyl)amide

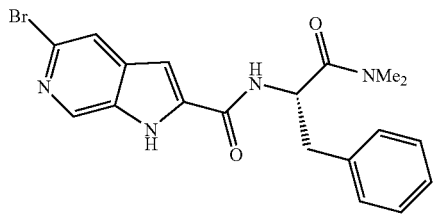

To a solution of 5-bromo-1H-pyrrolo[2,3-c]pyridine-2-carboxylic acid (Preparation 27, 50 mg, 0.21 mmol) in DMF (5 mL), was added 2-(S)-amino-N,N-dimethyl-3-phenylpropionamide hydrochloride (Preparation 8, 52 mg, 0.23 mmol), HOBt (31 mg, 0.23 mmol) and DIPEA (72 µL, 0.41 mmol). After 5 min, EDCI (44 mg, 0.23 mmol) was added and the reaction was stirred at rt for 16 h. The solvent was removed in vacuo and the residue partitioned between water (30 mL) and ethyl acetate (3×30 mL). The combined organic fractions were dried (MgSO$_4$), concentrated in vacuo and the residue purified by chromatography on silica gel eluting with methanol/dichloromethane (3:97) to give the title compound as an off-white solid. $\delta_H$ (CD$_3$OD): 2.88 (6H, s), 3.06–3.18 (2H, m), 5.27 (1H, t), 7.13 (1H, s), 7.19–7.29 (5H, m), 7.80 (1H, s), 8.53 (1H, s); m/z (ES$^+$)=415 [M+H]$^+$.

EXAMPLE 8

1H-Pyrrolo[2,3-b]pyridine-2-carboxylic acid (1-dimethylcarbamoyl-2-(S)-phenylethyl)amide

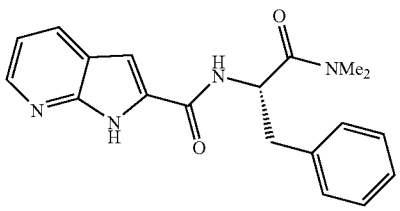

Triethylamine (82 µL, 0.59 mmol) was added to 2-(S)-amino-N,N-dimethyl-3-phenylpropionamide hydrochloride (Preparation 8, 117 mg, 0.51 mmol) in DCM (5 mL) at rt under nitrogen. The mixture was cooled to 0° C. and 1H-pyrrolo[2,3-b]pyridine-2-carboxylic acid (Preparation 28, 75 mg, 0.51 mmol) was added followed by HOBt (102 mg, 0.765 mmol) and then EDCI (98 mg, 0.51 mmol). The reaction mixture was then left to warm to rt, stirred for 4 days and then diluted with ethyl acetate (25 mL), washed with aqueous sodium hydroxide solution (2M, 2×25 mL), aqueous hydrochloric acid (2N, 2×25 mL) and dried (MgSO$_4$). The organic solution was concentrated in vacuo to give a beige foam which was purified by column chromatography eluting with methanol/dichloromethane (2:98) to give the title compound as a white solid. $\delta_H$ (CDCl$_3$): 2.74 (3H, s), 2.95 (3H, s), 3.17 (2H, m), 5.41 (1H, dd), 6.90 (1H, s), 7.08–7.48 (7H, m), 7.98 (1H, d), 8.55 (1H, d); m/z (ES$^+$)=337.2 [M+H]+, RT=1.38 min.

EXAMPLE 9

5-Chloro-1H-pyrrolo[2,3-c]pyridine-2-carboxylic acid (2-phenoxyethyl)amide

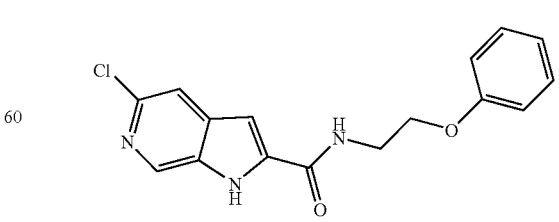

The title compound was prepared as outlined in EXAMPLE 1 from 5-chloro-1H-pyrrolo[2,3-c]pyridine-2- carboxylic acid (Preparation 18) and 2-phenoxyethylamine. The product was purified by chromatography on silica gel eluting with methanol/dichloromethane (1:19) to give the title compound as a yellow solid. $\delta_H$ (CD$_3$OD): 3.79 (2H, t), 4.17 (2H, t), 6.88–6.97 (3H, m), 7.08 (1H, s), 7.16 (2H, t), 7.67 (1H, s), 8.58 (1H, s); m/z (ES$^+$)=316 [M+H]$^+$.

EXAMPLE 10

5-Chloro-1H-pyrrolo[2,3-c]pyridine-2-carboxylic acid (2-morpholin4-ylethyl)amide

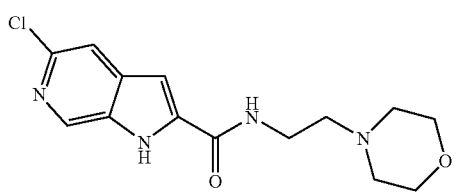

The title compound was prepared as outlined in EXAMPLE 1 from 5-chloro-1H-pyrrolo[2,3-c]pyridine-2-carboxylic acid (Preparation 18) and 2-morpholin-4-ylethylamine. The product was purified by chromatography on silica gel eluting with methanol/dichloromethane (1:19) to give the title compound as a yellow solid.

$\delta_H$(CD$_3$OD): 2.54–2.60 (4H, m), 2.64 (2H, t), 3.58 (2H, t), 3.69–3.73 (4H, m), 7.05 (1H, s), 7.66 (1H, s), 8.58 (1H, s); m/z (ES$^+$)=309 [M+H]$^+$.

EXAMPLE 11

5-Chloro-1H-pyrrolo[2,3-c]pyridine-2-carboxylic acid [2-(4-methoxyphenoxy)ethyl]amide

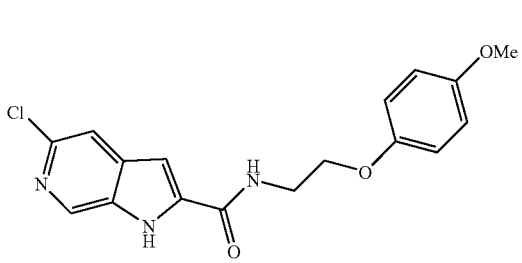

The title compound was prepared as outlined in EXAMPLE 1 from 5-chloro-1H-pyrrolo[2,3-c]pyridine-2-carboxylic acid (Preparation 18) and 2-(4-methoxyphenoxy) ethylamine. The product was purified by chromatography on silica gel eluting with methanol/dichloromethane (3:97) to give the title compound as a yellow solid. $\delta_H$ (CD$_3$OD): 3.71 (3H, s), 3.77 (2H, t), 4.12 (2H, t), 6.81–6.91 (4H, m), 7.09 (1H, s), 7.67 (1H, s), 8.58 (1H, s); m/z (ES$^+$)=346 [M+H]$^+$.

EXAMPLE 12

5-Chloro-1H-pyrrolo[2,3-c]pyridine-2-carboxylic acid (2-thiophen-2-ylethyl)amide

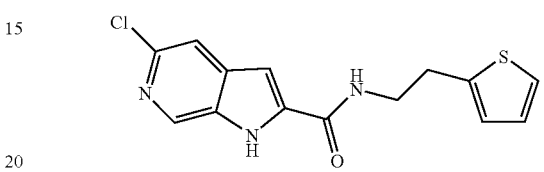

The title compound was prepared as outlined in EXAMPLE 1 from 5-chloro-1H-pyrrolo[2,3-c]pyridine-2-carboxylic acid (Preparation 18) and 2-thiophen-2-ylethylamine. The product was purified by chromatography on silica gel eluting with methanol/dichloromethane (3:97) to give the title compound as a yellow solid. $\delta_H$ (CD$_3$OD): 3.16 (2H, t), 3.65 (2H, t), 6.89–6.94 (2H, m), 7.03 (1H, s), 7.20 (1H, d), 7.66 (1H, s), 8.57 (1H, s); m/z (ES$^+$)=306 [M+H]$^+$.

EXAMPLE 13

5-Chloro-1H-pyrrolo[2,3-c]pyridine-2-carboxylic acid [2-(2-methoxyphenyl)ethyl]amide

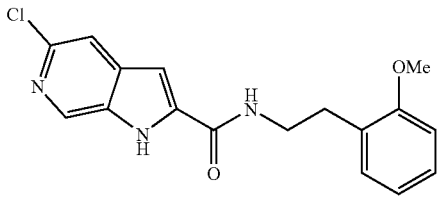

The title compound was prepared as outlined in EXAMPLE 1 from 5-chloro-1H-pyrrolo[2,3-c]pyridine-2-carboxylic acid (Preparation 18) and 2-(2-methoxyphenyl) ethylamine. The product was purified by chromatography on silica gel eluting with methanol/dichloromethane (3:97) to give the title compound as a yellow solid. $\delta_H$ (CD$_3$OD): 2.94 (2H, t), 3.59 (2H, t), 3.78 (3H, s), 6.84 (1H, t), 6.89 (1H, d), 6.97 (1H, s), 7.12–7.18 (2H, m), 7.60 (1H, s), 8.55 (1H, s); m/z (ES$^+$)=330 [M+H]$^+$.

EXAMPLE 14

5-Chloro-1H-pyrrolo[2,3-c]pyridine-2-carboxylic acid (2-oxo-2-phenylethyl)amide

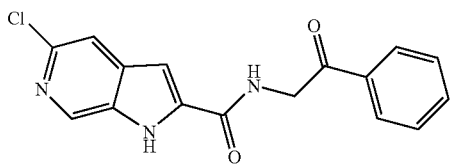

The title compound was prepared as outlined in EXAMPLE 1 from 5-chloro-1H-pyrrolo[2,3-c]pyridine-2-carboxylic acid (Preparation 18) and 2-oxo-2-phenylethylamine. The product was purified by mass directed purification to give the title compound as an orange solid. m/z (ES$^+$)= 314 [M+H]$^+$; RT=3.30 min.

EXAMPLE 15

5-Chloro-1H-pyrrolo[2,3-c]pyridine-2-carboxylic acid (1H-benzoimidazol-2-ylmethyl)amide

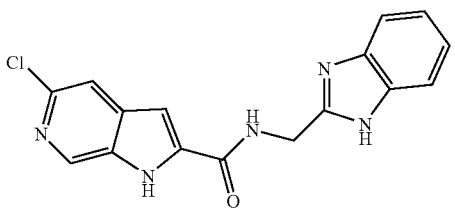

The title compound was prepared as outlined in EXAMPLE 1 from 5-chloro-1H-pyrrolo[2,3-c]pyridine-2-carboxylic acid (Preparation 18) and 2-oxo-2-phenylethylamine. The product was purified by mass directed purification to give the title compound as a yellow solid. m/z (ES$^+$)= 326 [M+H]$^+$; RT=2.66 min.

EXAMPLE 16

5-Chloro-1H-pyrrolo[2,3-c]pyridine-2-carboxylic acid phenethylamide

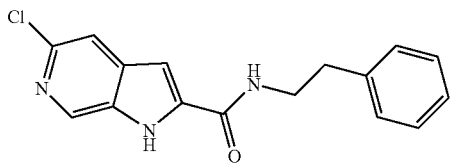

The title compound was prepared as outlined in EXAMPLE 1 from 5-chloro-1H-pyrrolo[2,3-c]pyridine-2-carboxylic acid (Preparation 18) and phenethylamine. The product was purified by mass directed purification to give the title compound as an orange solid. $\delta_H$ (CD$_3$OD): 2.94 (2H, t), 3.63 (2H, t), 7.00 (1H, s), 7.15–7.30 (5H, m), 7.64 (1H, s), 8.57 (1H, s); m/z (ES$^+$)=300 [M+H]$^+$.

EXAMPLE 17

5-Chloro-1H-pyrrolo[2,3-c]pyridine-2-carboxylic acid [2-(4-fluorophenyl)ethyl]amide

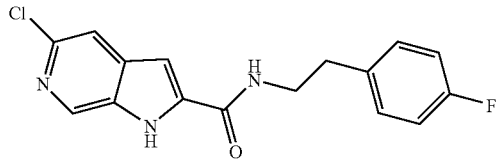

The title compound was prepared as outlined in EXAMPLE 1 from 5-chloro-1H-pyrrolo[2,3-c]pyridine-2-carboxylic acid (Preparation 18) and 4-fluorophenethylamine. The product was purified by mass directed purification to give the title compound as an orange solid. $\delta_H$ (CD$_3$OD): 2.93 (2H, t), 3.60 (2H, t), 6.97–7.04 (3H, m), 7.24–7.30 (2H, m), 7.65 (1H, s), 8.56 (1H, s); m/z (ES$^+$)=318 [M+H]$^+$.

EXAMPLE 18

5-Chloro-1H-pyrrolo[2,3-c]pyridine-2-carboxylic acid [2-(2-chloro-6-fluorobenzalsulfanyl)ethyl]amide

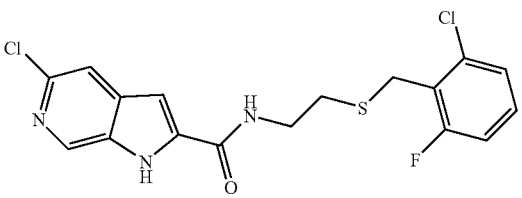

The title compound was prepared as outlined in EXAMPLE 1 from 5-chloro-1H-pyrrolo[2,3-c]pyridine-2-carboxylic acid (Preparation 18) and 2-(2-chloro-6-fluorobenzylsulfanyl)ethylamine. The product was purified by mass directed purification to give the title compound as a yellow solid. $\delta_H$ (CD$_3$OD): 2.82 (2H, t), 3.64 (2H, t), 3.95 (2H, s), 7.04–7.09 (2H, m), 7.20–7.25 (2H, m), 7.67 (1H, s), 8.58 (1H, s); m/z (ES$^+$)=398 [M+H]$^+$.

EXAMPLE 19

5-Chloro-1H-pyrrolo[2,3-c]pyridine-2-carboxylic acid (2,3-dihydrobenzo[1,4]dioxin-2-ylmethyl)amide

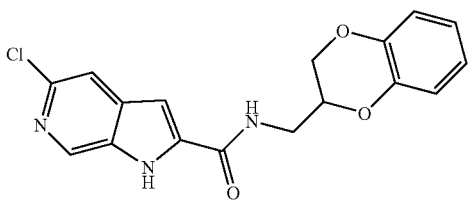

The title compound was prepared as outlined in EXAMPLE 1 from 5-chloro-1H-pyrrolo[2,3-c]pyridine-2-carboxylic acid (Preparation 18) and 2,3-dihydrobenzo[1,4]

dioxin-2-ylmethylamine. The product was purified by mass directed purification to give the title compound as a yellow solid. $\delta_H$ (CD$_3$OD): 3.69–3.73 (2H, m), 3.97–4.03 (1H, m), 4.32–4.42 (2H, m), 6.77–6.88 (4H, m), 7.10 (1H, s), 7.67 (1H, s), 8.58 (1H, s); m/z (ES$^+$)=344 [M+H]$^+$.

EXAMPLE 20

5-Chloro-1H-pyrrolo[2,3-c]pyridine-2-carboxylic acid [2-(naphthalen-1-ylamino)ethyl]amide

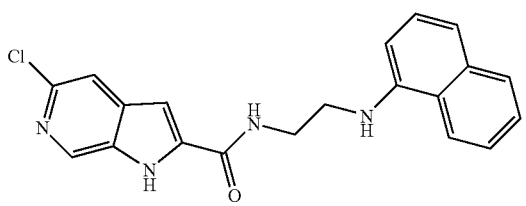

The title compound was prepared as outlined in EXAMPLE 1 from 5-chloro-1H-pyrrolo[2,3-c]pyridine-2-carboxylic acid (Preparation 18) and 2-(naphthalen-1-ylamino)ethylamine. The product was purified by mass directed purification to give the title compound as a brown solid. $\delta_H$ (CD$_3$OD): 3.55 (2H, t), 3.80 (2H, t), 6.68 (1H, d), 7.04 (1H, s), 7.14 (1H, d), 7.28 (1H, t), 7.36–7.42 (2H, m), 7.65 (1H, s), 7.70–7.74 (1H, m), 7.98–8.02 (1H, m), 8.58 (1H, s); m/z (ES$^+$)=365 [M+H]$^+$.

EXAMPLE 21

1H-Pyrrolo[2,3-c]pyridine-2-carboxylic acid (2-phenylaminoethyl)amide

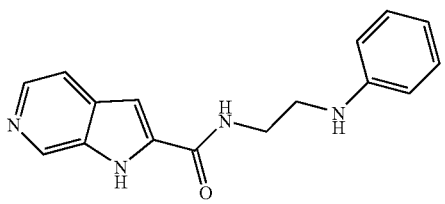

The title compound was prepared as outlined in EXAMPLE 1 from 1H-pyrrolo[2,3-c]pyridine-2-carboxylic acid (Preparation 15) and 2-phenylaminoethylamine to give the title compound as a pale yellow solid.

$\delta_H$ (CD$_3$OD): 3.37 (2H, t), 3.63 (2H, t), 6.61 (1H, t), 6.69 (2H, d), 7.08–7.13 (2H, m), 7.64 (1H, d), 8.10 (1H, d), 8.78 (1H, s); m/z (ES$^+$)=281 [M+H]$^+$.

EXAMPLE 22

1H-Pyrrolo[2,3-c]pyridine-2-carboxylic acid (2-phenoxyethyl)amide

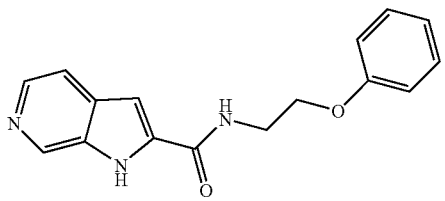

The title compound was prepared as outlined in EXAMPLE 1 from 1H-pyrrolo[2,3-c]pyridine-2-carboxylic acid (Preparation 15) and 2-phenoxyethylamine to give the title compound as a pale yellow solid. $\delta_H$ (CD$_3$OD): 3.81 (2H, t), 4.18 (2H, t), 6.89–6.97 (3H, m), 7.14 (1H, s), 7.26 (2H, t), 7.65 (1H, d), 8.10 (1H, d), 8.78 (1H, s); m/z (ES$^+$)=282 [M+H]$^+$.

EXAMPLE 23

5-Methoxy-1H-pyrrolo[3,2-b]pyridine-2-carboxylic acid (1-dimethylcarbamoyl-2-(S)-phenylethyl)amide

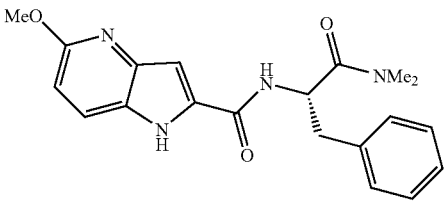

To a solution of 5-methoxy-1H-pyrrolo[3,2-b]pyridine-2-carboxylic acid (Preparation 36, 50 mg, 0.26 mmol) in DMF (3 mL), was added DIPEA (100 µL, 0.57 mmol), HOBt (35 mg, 0.26 mmol) and EDCI (60 mg, 0.31 mmol) sequentially. The reaction mixture was stirred for 5 min prior to the addition of 2-(S)-amino-N,N-dimethyl-3-phenylpropionamide hydrochloride (Preparation 8, 65 mg, 0.29 mmol) in one portion. The reaction mixture was stirred for 21 h at rt then water (15 mL) and dichloromethane (30 mL) were added. The mixture was stirred vigorously for 10 min and the layers separated. The aqueous phase was extracted with dichloromethane (3×15 mL) and the combined organics washed with brine (30 mL), dried (MgSO$_4$), filtered and concentrated in vacuo. Purification via flash column chromatography (SiO$_2$, ethyl acetate/isohexane, 1:1) gave a yellow oil. Trituration with water followed by filtration and drying gave the title compound as a white solid. $\delta_H$ (CD$_3$OD): 2.88 (6H, 2×s), 3.12 (2H, m), 3.94 (3H, s), 5.26 (1H, dd), 6.71 (1H, d), 7.13 (1H, s), 7.25 (5H, m), 7.74 (1H, d); m/z (ES$^+$)=367 [M+H]$^+$; RT=3.20 min.

EXAMPLE 24

1H-Pyrrolo[3,2-b]pyridine-2-carboxylic acid (1-dimethylcarbamoyl-2-(S)-phenylethyl)amide

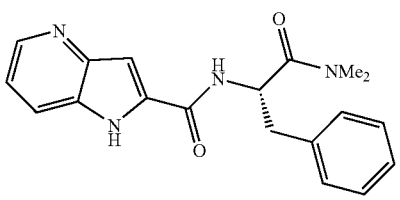

Prepared as outlined in EXAMPLE 1 from 1H-pyrrolo[3,2-b]pyridine-2-carboxylic acid (Preparation 32) and 2-(S)-amino-N,N-dimethyl-3-phenyl-propionamide hydrochloride (Preparation 8, 78 mg, 0.34 mmol). The title compound was isolated as a white solid. $\delta_H$ (d$_6$ DMSO): 2.82 (3H, s), 2.98 (3H, s), 3.03 (2H, m), 5.12 (1H, m), 7.16 (2H, m), 7.24 (2H, m), 7.32 (2H, m), 7.40 (1H, d), 7.74 (1H, d), 8.37 (1H, dd), 8.93 (1H, d); m/z (ES$^+$)=337 [M+H]$^+$; RT=3.10 min.

EXAMPLE 25

1H-Pyrrolo[3,2-b]pyridine-2-carboxylic acid (2-phenoxyethyl)amide

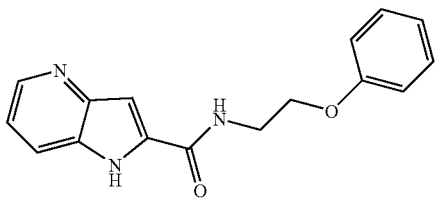

To a solution of 1H-pyrrolo[3,2-b]pyridine-2-carboxylic acid (Preparation 32, 50 mg, 0.31 mmol) in DMF (5 mL), was added 2-phenoxyethylamine (44 μL, 0.34 mmol), DIPEA (118 μL, 0.68 mmol) and HOBt (42 mg, 0.31 mmol) sequentially. The reaction mixture was stirred for 5 min prior to the addition of EDCI (42 mg, 0.22 mmol) in one portion. The resulting mixture was stirred for 20 h at rt and partitioned between ethyl acetate (50 mL) and water (20 mL). The layers were separated and the aqueous phase extracted with ethyl acetate (2×30 mL). The combined organic fractions were washed with brine (20 mL), dried (MgSO$_4$), filtered and concentrated in vacuo to give an oil. Trituration with diethyl ether/isohexane and collection by filtration gave, after air-drying, the title compound as a cream coloured solid. $\delta_H$ (d$_6$ DMSO): 3.48 (2H, m), 4.14 (2H, t), 6.94 (3H, m), 7.17 (1H, dd), 7.28 (3H, m), 7.77 (1H, d), 8.37 (1H, dd), 8.86 (1H, t); m/z (ES$^+$)=282 [M+H]$^+$; RT=2.60 min.

EXAMPLE 26

1H-Pyrrolo[3,2-b]pyridine-2-carboxylic acid (2-phenylaminoethyl)amide

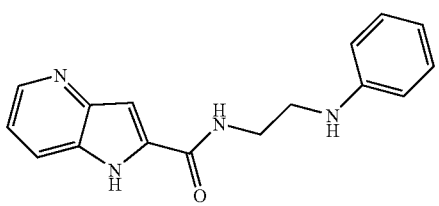

The title compound was prepared as outlined in EXAMPLE 25 except N-phenylethylenediamine (44 μL, 0.34 mmol) was used in place of 2-phenoxyethylamine. The title compound was isolated as a cream solid. $\delta_H$ (d$_6$ DMSO): 3.23 (2H, m), 3.37 (2H, m), 5.70 (1H, t), 6.52 (1H, t), 6.63 (2H, dd), 7.07 (2H, dd), 7.17 (1H, dd), 7.22 (1H, s), 7.77 (1H, d), 8.37 (1H, dd), 8.73 (1H, t); m/z (ES$^+$)=281 [M+H]$^+$; RT=2.36 min.

EXAMPLE 27

5-Chloro-1H-pyrrolo[3,2-b]pyridine-2-carboxylic acid (2-phenoxyethyl)amide

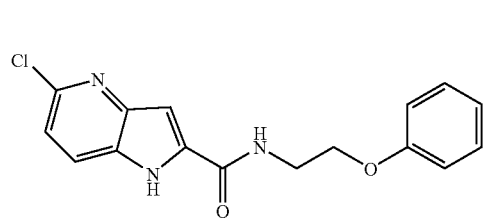

The title compound was prepared as outlined in EXAMPLE 1 from 5-chloro-1H-pyrrolo[3,2-b]pyridine-2-carboxylic acid (Preparation 6) and 2-phenoxyethylamine. On completion of the reaction, the mixture was partitioned between water and dichloromethane on a hydrophobic frit, washing with dichloromethane. The organic filtrate was concentrated in vacuo then triturated with dichloromethane/methanol/ethyl acetate to give the title compound as a white solid.

$\delta_H$ (d$_6$ DMSO): 3.68 (2H, m), 4.13 (2H, m), 6.94 (3H, m), 7.25 (4H, m), 7.83 (1H, d), 8.95 (1H, t), 12.09 (1H, s). m/z (ES$^+$)=316 [M+H]$^+$; RT=3.45 min.

EXAMPLE 28

5-Chloro-1H-pyrrolo[2,3-c]pyridine-2-carboxylic acid [2-(4-benzylpiperazin-1-yl)ethyl]amide

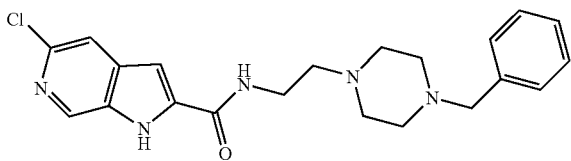

The title compound was prepared as outlined in EXAMPLE 1 from 5-chloro-1H-pyrrolo[2,3-c]pyridine-2-carboxylic acid (Preparation 18) and 4-benzylpiperazin-lyl-ethylamine. The product was purified by mass directed purification to give the title compound as an orange solid. m/z (ES$^+$)=398 [M+H]$^+$; RT=2.75 min.

EXAMPLE 29

5-Chloro-1H-pyrrolo [2,3-c]pyridine-2-carboxylic acid (2-benzylaminoethyl)amide

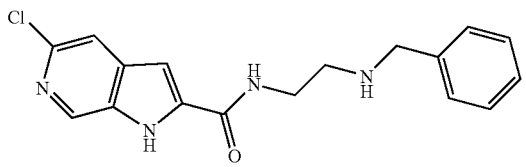

The title compound was prepared as outlined in EXAMPLE 1 from 5-chloro-1H-pyrrolo[2,3-c]pyridine-2-carboxylic acid (Preparation 18) and 2-benzylaminoethylamine. The product was purified by mass directed purification to give the title compound as an off-white solid. m/z (ES$^+$)=329 [M+H]$^+$; RT=2.75 min.

EXAMPLE 30

5-Chloro-1H-pyrrolo[2,3-c]pyridine-2-carboxylic acid phenylcarbamoylmethylamide

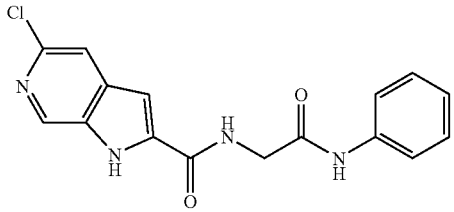

To a solution of [(5-chloro-1H-pyrrolo[2,3-c]pyridine-2-carbonyl)amino] acetic acid (EXAMPLE 40, 30 mg, 0.12 mmol) in DMF (2 mL) was added aniline (12 µL, 0.13 mmol), HOBt (16 mg, 0.12 mmol) and DIPEA (41 µL, 0.24 mmol). After 5 min, EDCI (29 mg, 0.15 mmol) was added, and the reaction stirred at rt for 16 h. The solvent was removed in vacuo and the solid partitioned between water (20 mL) and ethyl acetate (3×20 mL). The combined organic fractions were dried (MgSO$_4$), concentrated in vacuo and the residue purified by chromatography on silica gel eluting with methanol/dichloromethane (1:19) to give the title compound as a yellow solid. m/z (ES$^+$)=329 [M+H]$^+$; RT=3.17 min.

EXAMPLE 31

5-Chloro-1H-pyrrolo[2,3-c]pyridine-2-carboxylic acid [(tetrahydropyran-4-ylcarbomoyl)methyl]amide

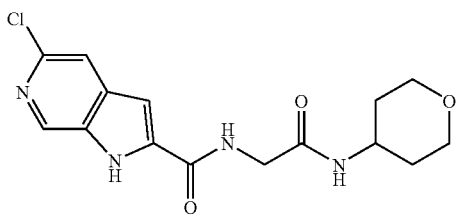

The title compound was prepared according to the procedure of EXAMPLE 30 except 4-aminotetrahydropyran was used in place of aniline. After 16 h the reaction mixture was poured into water and left for a further 16 h. The solid was filtered and dried to give the title compound as a white crystalline solid. m/z (ES$^+$)=337 [M+H]$^+$; RT=2.72 min.

EXAMPLE 32

5-Chloro-1H-pyrrolo[2,3-c]pyridine-2-carboxylic acid {[(thiophen-2-ylmethyl)carbamoyl]methyl}amide

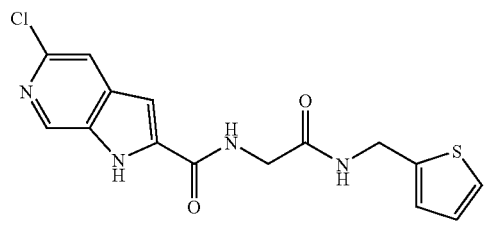

The title compound was prepared according to EXAMPLE 30 except 2-aminomethylthiophene was used in place of aniline. After stirring for 16 h the reaction mixture was poured into water and the precipitate was filtered and dried to give the title compound as a white solid. m/z (ES$^+$)=349 [M+H]$^+$; RT=3.07 min.

EXAMPLE 33

5-Chloro-1H-pyrrolo[2,3-c]pyridine-2-carboxylic acid [(4-methoxyphenylcarbamoyl)methyl]amide

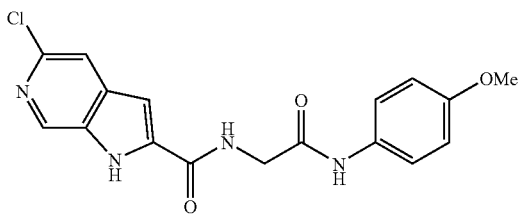

The title compound was prepared according to EXAMPLE 30 except p-anisidine was used in place of aniline. After stirring for 16 h, the reaction mixture was poured into water and the precipitate was filtered and dried to give the title compound as a beige solid. m/z (ES$^+$)=359 [M+H]$^+$; RT=3.22 min.

EXAMPLE 34

5-Chloro-1H-pyrrolo[2,3-c]pyridine-2-carboxylic acid (1-(S)-benzyl-2-oxo-2-pyrrolidin-1-ylethyl)amide

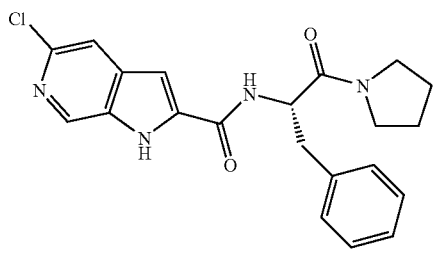

To a solution of 2-(S)-[(5-chloro-1H-pyrrolo[2,3-c]pyridine-2-carbonyl)amino]-3-phenylpropionic acid (EXAMPLE 42, 50 mg, 0.15 mmol) in DMF (3 mL) was added pyrrolidine (13 μL, 0.16 mmol), HOBt (20 mg, 0.15 mmol) and DIPEA (51 μL, 0.29 mmol). After 5 min, EDCI (36 mg, 0.19 mmol) was added and the reaction was stirred at rt for 16 h. The solvent was removed in vacuo and the solid was triturated with water, filtered and dried to give the title compound as a beige solid. m/z (ES$^+$)=397 [M+H]$^+$; RT=3.38 min.

EXAMPLE 35

5-Chloro-1H-pyrrolo[2,3-c]pyridine-2-carboxylic acid [1-(S)-benzal-2-(3-(S)-hydroxypyrrolidin-1-yl-2-oxoethyl]amide

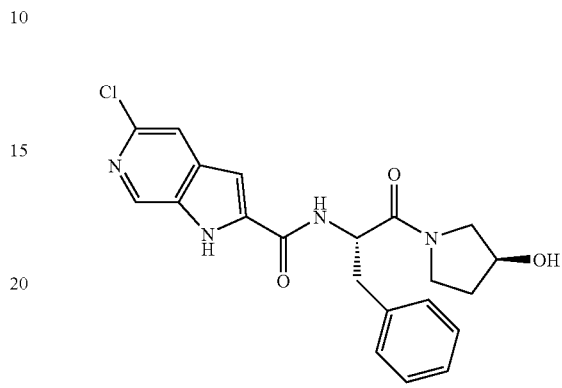

To a solution of 2-(S)-[(5-chloro-1H-pyrrolo[2,3-c]pyridine-2-carbonyl)amino]-3-phenylpropionic acid (EXAMPLE 42, 50 mg, 0.15 mmol) in DMF (3 mL) was added 3-(S)-hydroxypyrrolidine (13.9 mg, 0.16 mmol), HOBt (20 mg, 0.15 mmol) and DIPEA (51 μL, 0.29 mmol). After 5 min, EDCI (36 mg, 0.19 mmol) was added and the reaction stirred at rt for 16 h. The solvent was removed in vacuo and the residue partitioned between water (20 mL) and ethyl acetate (3×20 mL), dried (MgSO$_4$) and concentrated in vacuo. Purification via chromatography on silica gel eluting with methanol/dichloromethane (4:96) gave the title compound as a white solid. m/z (ES$^+$)=413 [M+H]$^+$; RT=3.20 min.

EXAMPLE 36

5-Chloro-1H-pyrrolo[2,3-c]pyridine-2-carboxylic acid [1-(S)-benzyl-2-(3,4-dihydroxypyrrolidin-1-yl)-2-oxo-ethyl]amide

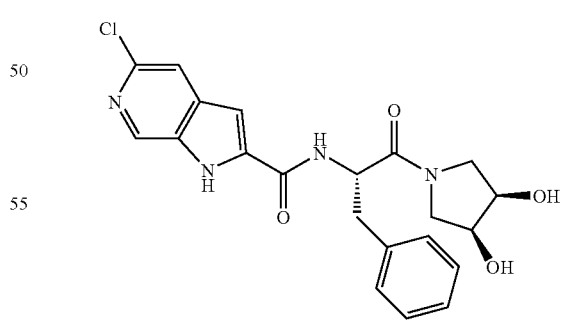

The title compound was prepared according to EXAMPLE 35 except cis-3,4-dihydroxypyrrolidine was used in place of 3-(S)-hydroxypyrrolidine. Purification via chromatography on silica gel eluting with a gradient of methanol/dichloromethane (4:96 to 1:9) gave the title compound as a white solid. m/z (ES$^+$)=429 [M+H]$^+$; RT=3.12 min.

EXAMPLE 37

5-Chloro-1H-pyrrolo[2,3-c]pyridine-2-carboxylic acid (1-(S)-benzal-2-oxo-2-thiomorpholin-4-ylethyl)amide

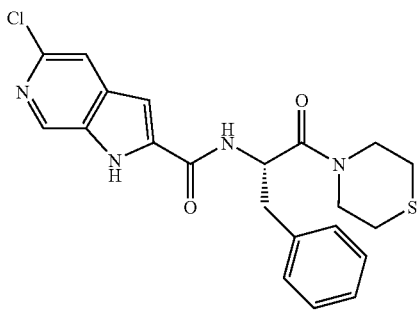

The title compound was prepared according to the procedure used for EXAMPLE 35 except thiomorpholine was used in place of 3-(S)-hydroxypyrrolidine. Purification via chromatography on silica gel eluting with methanol/dichloromethane (3:97) gave the title compound as a white solid. m/z (ES$^+$)=429 [M+H]$^+$; RT=3.54 min.

EXAMPLE 38

5-Chloro-1H-pyrrolo[2,3-c]pyridine-2-carboxylic acid [2-phenyl-1-(S)-(tetrahydropyran-4-ylcarbamoyl)ethyl]amide

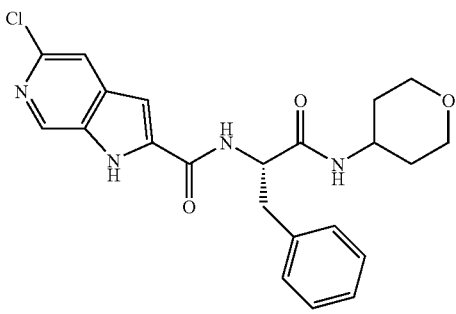

The title compound was prepared according to EXAMPLE 35 except 4-aminotetrahydropyran was used in place of 3-(S)-hydroxypyrrolidine. The product was recrystallised from methanol/dichloromethane (3:97) to give the title compound as a white solid. m/z (ES$^+$)=427 [M+H]$^+$; RT=3.23 min.

EXAMPLE 39

[(5-Chloro-1H-pyrrolo[2,3-c]pyridine-2-carbonyl amino]acetic acid ethyl ester

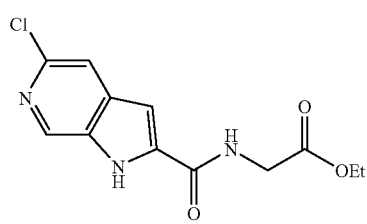

To a solution of 5-chloro-1H-pyrrolo[2,3-c]pyridine-2-carboxylic acid (Preparation 18, 800 mg, 4.1 mmol) in DMF (40 mL) was added glycine ethyl ester hydrochloride (625 mg, 4.5 mmol), HOBt (0.55 g, 4.1 mmol) and DIPEA (2.13 mL, 12.2 mmol). After 5 min, EDCI (1.01 g, 5.3 mmol) was added and the reaction stirred at rt for 16 h. The solvent was removed in vacuo and the solid partitioned between water (100 mL) and ethyl acetate (3×80 mL). The combined organic fractions were dried (MgSO$_4$), concentrated in vacuo and purified by chromatography on silica gel eluting with methanol/dichloromethane (4:96) to give the title compound as a yellow solid. $\delta_H$ (CD$_3$OD): 1.28 (3H, t), 4.14 (2H, s), 4.23 (2H, q), 7.10 (1H, s), 7.68 (1H, s), 8.59 (1H, s); m/z (ES$^+$)=282 [M+H]$^+$.

EXAMPLE 40

[(5-Chloro-1H-pyrrolo[2,3-c]pyridine-2-carbonyl)amino]acetic acid

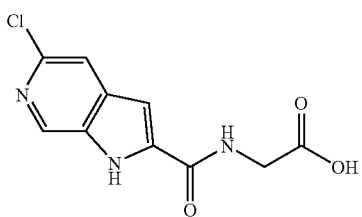

To a solution of [(5-chloro-1H-pyrrolo[2,3-c]pyridine-2-carbonyl)amino] acetic acid ethyl ester (EXAMPLE 39, 500 mg, 1.8 mmol) in THF (30 mL) was added sodium hydroxide solution (1.8 mL, 2M, 3.6 mmol) and the reaction stirred at rt for 4 h. The solvent was removed in vacuo and the solid partitioned between hydrochloric acid (1M, 100 mL) and ethyl acetate (2×100 mL). The aqueous layer was concentrated in vacuo and the solid residue suspended in water (10 mL), filtered and dried to give the title compound as an off-white solid. $\delta_H$ (d$_6$ DMSO): 3.97 (2H, d), 7.18 (1H, s), 7.76 (1H, s), 8.57 (1H, s), 9.17 (1H, t), 12.32 (1H, s); m/z (ES$^+$)=254 [M+H]$^+$.

EXAMPLE 41

2-(S)-[(5-Chloro-1H-pyrrolo[2,3-c]pyridine-2-carbonyl)amino]-3-phenylpropionic acid ethyl ester

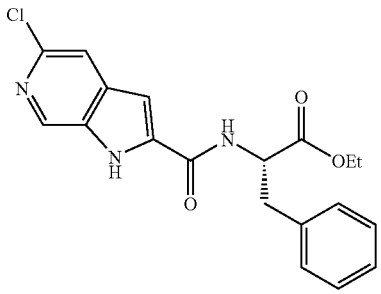

To a solution of 5-chloro-1H-pyrrolo[2,3-c]pyridine-2-carboxylic acid (Preparation 18, 2.00 g, 10.2 mmol) in DMF (50 mL) was added L-phenylalanine ethyl ester hydrochloride (2.45 g, 10.7 mmol), HOBt (1.37 g, 10.2 mmol) and DIPEA (5.3 mL, 30.5 mmol). After 5 min, EDCI (2.54 g, 13.2 mmol) was added and the reaction mixture stirred at rt for 16 h. The solvent was removed in vacuo and the solid dissolved in ethyl acetate (150 mL) and washed with water (200 mL). The organic phase was dried (MgSO$_4$), concentrated in vacuo and purified by chromatography on silica gel eluting with methanol/dichloromethane (3:97) to give the title compound as a pale yellow solid. $\delta_H$ (CD$_3$OD): 1.21 (3H, t), 3.13 (1H, dd), 3.28 (1H, dd), 4.17 (2H, q), 4.86 (1H, m), 7.09 (1H, s), 7.16–7.26 (5H, m), 7.65 (1H, s), 8.55 (1H, s); m/z (ES$^+$)=372 [M+H]$^+$.

EXAMPLE 42

2-(S)-[(5-Chloro-1H-pyrrolo[2,3-c]pyridine-2-carbonyl)amino]-3-phenylpropionic acid

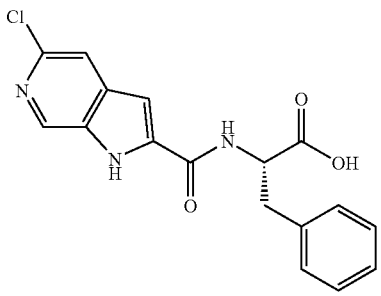

Sodium hydroxide solution (2.5 mL, 2M, 5.1 mmol) was added to a solution of 2-(S)-[(5-chloro-1H-pyrrolo[2,3-c]pyridine-2-carbonyl)amino]-3-phenylpropionic acid ethyl ester (EXAMPLE 41, 940 mg, 2.5 mmol) in THF (30 mL) and the reaction mixture was stirred at rt for 16 h. The solvent was removed in vacuo and the solid partitioned between hydrochloric acid (2M, 40 mL) and ethyl acetate (3×40 mL). The combined organic fractions were dried (MgSO$_4$) and concentrated in vacuo to give the title compound as a yellow solid. m/z (ES$^+$)=344 [M+H]$^+$; RT=3.29 min.

EXAMPLE 43

(S)-3-[(5-Chloro-1H-pyrrolo[2,3-c]pyridine-2-carbonyl)amino]-(R)-2-hydroxy-4-phenylbutyric acid methyl ester

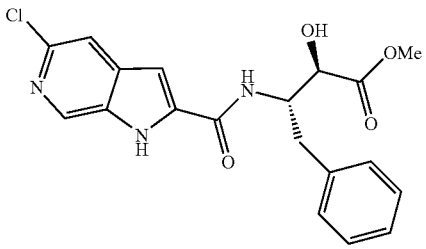

To a solution of 5-chloro-1H-pyrrolo[2,3-c]pyridine-2-carboxylic acid (Preparation 18, 165 mg, 0.84 mmol) and (3S,2R)-3-amino-2-hydroxy-4-phenylbutyric acid methyl ester (Preparation 21, 175 mg, 0.84 mmol) in DMF (10 mL) was added HOBt (125 mg, 0.92 mmol), DIPEA (0.29 mL, 1.68 mmol) and EDCI (177 mg, 0.92 mmol) and the reaction stirred at rt for 72 h. The reaction solvent was removed in vacuo, and the residue partitioned between water (40 mL) and ethyl acetate (3×40 mL). The combined organic fractions were dried (MgSO$_4$), concentrated in vacuo and the residue purified by chromatography on silica gel eluting with methanol/dichloromethane (3:97) to give the title compound as a yellow solid. $\delta_H$ (CD$_3$OD): 2.97–3.12 (2H, m), 3.67 (1H, s), 4.25 (1H, d), 4.70–4.75 (1H, m), 7.08 (1H, s), 7.15–7.21 (1H, m), 7.25–7.34 (4H, m), 7.65 (1H, s), 8.55 (1H, s); m/z (ES$^+$)=388 [M+H]$^+$.

EXAMPLE 44

(S)-3-[(5-Chloro-1H-pyrrolo[2,3-c]pyridine-2-carbonyl)amino]-(R)-2-hydroxy-4-phenylbutyric acid

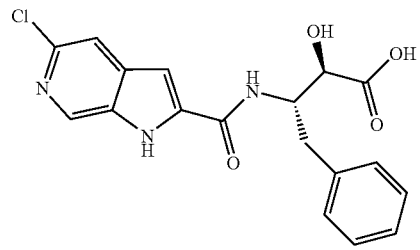

Sodium hydroxide solution (0.24 mL, 2M, 0.48 mmol) was added to a solution of (S)-3-[(5-chloro-1H-pyrrolo[2,3-c]pyridine-2-carbonyl)amino]-(R)-2-hydroxy-4-phenylbutyric acid methyl ester (EXAMPLE 43, 170 mg, 0.44 mmol) in methanol (5 mL) and the reaction stirred at rt for 24 h. The solvent was removed in vacuo and the residue partitioned between hydrochloric acid (1N, 30 mL) and ethyl acetate (3×3 mL). The combined organic fractions were dried (MgSO$_4$) and concentrated in vacuo to give the title compound as a yellow solid. $\delta_H$ (DMSO): 2.71 (1H, dd), 2.91 (1H, dd), 3.56 (1H, d), 4.38–4.46 (1H, m), 4.77 (1H, s), 6.76 (1H, s), 7.11–7.16 (1H, m), 7.19–7.27 (4H, m), 7.45 (1H, s), 8.44–8.52 (2H, m); m/z (ES$^+$)=374 [M+H]$^+$.

EXAMPLE 45

5-Chloro-1H-pyrrolo[2,3-c]pyridine-2-carboxylic acid [2-(4-methoxyphenyl)-2-oxoethyl]amide

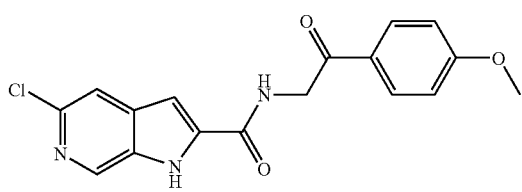

Aqueous hydrochloric acid (2.1 mL, 2M) was added to a solution of 5-chloro-1H-pyrrolo[2,3-c]pyridine-2-carboxylic acid [2-(4-methoxyphenyl)[1,3]dioxolan-2-ylmethyl]amide (Preparation 49, 160 mg, 0.41 mmol) in acetone (20 mL). The mixture was heated under reflux for 90 min then allowed to cool to rt. The suspension was filtered then washed with acetone and air dried, to give the title compound as a pale yellow solid. $\delta_H$ (d$_6$ DMSO): 3.86 (3H, s), 4.79 (2H, d), 7.08 (2H, d), 7.23 (1H, s), 7.77 (1H, s), 8.03 (2H, d), 8.58 (1H, s), 9.14 (1H, t), 12.31 (1H, br s). m/z (ES$^+$)=344 [M+H]$^+$; RT=3.34 min.

The following compounds were synthesised according to the method of EXAMPLE 45 using the appropriate ketal and aqueous hydrochloric acid.

| Example | R | m/z |
|---|---|---|
| 46 | 3,4-difluorophenyl | m/z (ES$^+$) = 350 [M + H]$^+$; RT = 3.20 min |
| 47 | 4-chlorophenyl | m/z (ES$^+$) = 348 [M + H]$^+$; RT = 3.32 min |
| 48 | 4-fluorophenyl | m/z (ES$^+$) = 332 [M + H]$^+$; RT = 3.25 min |

EXAMPLE 49

5-Chloro-1H-pyrrolo[2,3-c]pyridine-2-carboxylic acid [2-(4-fluorophenyl)-2-hydroxyethyl]amide

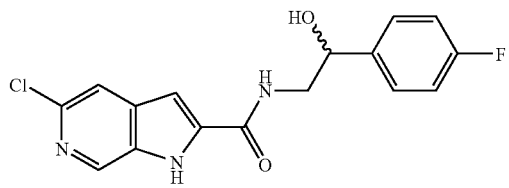

To a stirred suspension of 5-chloro-1H-pyrrolo[2,3-c]pyridine-2-carboxylic acid [2-(4-fluorophenyl)-2-oxoethyl]amide EXAMPLE 48 (0.05 g, 151 mmol) in ethanol (5 mL, absolute) was added polymer-supported borohydride (2.5 mmol/g, 0.09 g, 226 mmol) and the mixture sonicated with gentle warming until the ketone had dissolved. The reaction mixture was stirred for 2 days at rt then filtered, washing with methanol. The filtrate was evaporated to dryness in vacuo to give a colourless oil. Purification via flash column chromatography (SiO$_2$, ethyl acetate:isohexane, 1:1, v/v) gave the title compound as a white solid. m/z (ES$^+$)=334 [M+H]$^+$; RT=2.93 min.

EXAMPLE 50

5-Chloro-1H-pyrrolo[2,3-c]pyridine-2-carboxylic acid (1-dimethylcarbamoyl-2-(S)-pyridin-3-yl-ethyl)amide

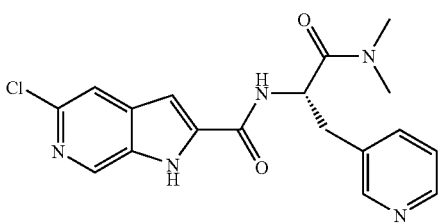

To a solution of (S)-2-amino-N,N-dimethyl-3-pyridin-3-ylpropionamide hydrochloride (Preparation 53, 170 mg, 0.74 mmol) in DMF (5 mL) was added DIPEA (0.45 mL, 2.58 mmol), 5-chloro-1H-pyrrolo[2,3-c]pyridine-2-carboxylic acid (Preparation 18, 145 mg, 0.74 mmol) and TBTU (262 mg, 0.82 mmol). The reaction mixture was stirred at rt for 16 h. The solvent was removed in vacuo and the remainder was purified by preparative HPLC, to give the title compound as an off-white solid. $\delta_H$ (CD$_3$OD): 2.95 (3H, s), 3.08 (3H, s), 3.11–3.18 (1H, m), 3.22–3.28 (1H, m), 5.31–5.37 (1H, m), 7.12 (1H, s), 7.34–7.38 (1H, m), 7.65 (1H, s), 7.79–7.84 (1H, m), 8.37–8.41 (1H, m), 8.45–8.51 (1H, m), 8.54 (1H, s); m/z (ES$^+$)=372 [M+H]$^+$.

EXAMPLE 51

5-Chloro-1H-pyrrolo[2,3-c]pyridine-2-carboxylic acid (2-oxo-1-(S)-pyridin-3-ylmethyl-2-pyrrolidin-1-yl-ethyl)amide

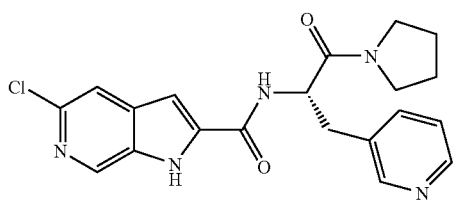

To a solution of (S)-2-amino-3-pyridin-3-yl-1-pyrrolidin-1-ylpropan-1-one hydrochloride (Preparation 54, 239 mg, 0.94 mmol) in DMF (5 mL) was added DIPEA (0.60 mL, 3.28 mmol), 5-chloro-1H-pyrrolo[2,3-c]pyridine-2-carboxylic acid (Preparation 18, 184 mg, 0.94 mmol) and TBTU (330 mg, 1.03 mmol). The reaction mixture was stirred at rt for 16 h. The solvent was removed in vacuo and the residue partitioned between ethyl acetate (100 mL) and sodium hydroxide solution (2×100 mL, 1N). The organic phase was dried (MgSO$_4$) and evaporated to dryness give the title compound as a brown solid. $\delta_H$ (CD$_3$OD): 1.74–1.94 (4H, m), 3.12–3.39 (4H, m), 3.41–3.48 (1H, m), 3.69–3.75 (1H, m), 5.07–5.12 (1H, m), 7.16 (1H, s), 7.34–7.39 (1H, m), 7.67 (1H, s), 7.79–7.83 (1H, m), 8.37–8.42 (1H, m), 8.45–8.51 (1H, m), 8.56 (1H, s); m/z (ES$^+$)=398 [M+H]$^+$.

EXAMPLE 52

5-Chloro-1H-pyrrolo[2,3-c]pyridine-2-carboxylic acid (1-dimethylcarbamoyl-2-(S)-pyridin-2-yl-ethyl)amide

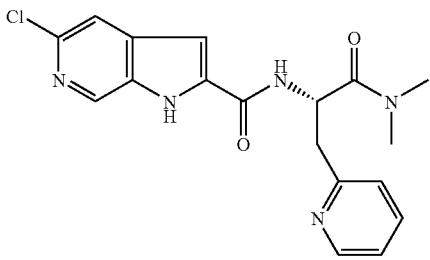

To a solution of 2-(S)-amino-N,N-dimethylamino-3-pyridin-2-yl-propionamide hydrochloride (Preparation 53, 0.15 g, 0.66 mmol) in DMF (5 mL) was added DIPEA (0.4 mL, 2.31 mmol), TBTU (0.212 g, 0.66 mmol) and 5-chloro-1H-indole-2-carboxylic acid (Preparation 18, 0.130 g, 0.66 mmol). The reaction mixture was stirred at rt for 16 h then concentrated under reduced pressure. The residue was dissolved in ethyl acetate (200 mL) and washed with sodium hydroxide solution (100 mL, 1N). The organic extract was dried and concentrated in vacuo. Purification by preparative hplc gave the title compound as a white solid. m/z (ES$^+$)=372 [M+H]$^+$; RT=2.47 min.

EXAMPLE 53

5-Chloro-1H-pyrrolo[2,3-c]pyridine-2-carboxylic acid [1-(S)-(4-fluorobenzyl)-2-(3-(S)-hydroxypyrrolidin-1-yl)-2-oxoethyl]amide

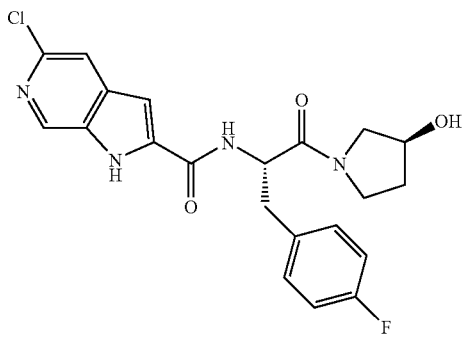

To a solution of carboxylic acid (Preparation 18, 2.66 g, 13.6 mmol) in DMF (anhydrous, 120 mL) was added amine-.HCl (Preparation 103, 4.30 g, 14.9 mmol), DIPEA (7.79 mL, 44.7 mmol) and HOBt.H$_2$O (2.280 g, 14.9 mmol). The resulting solution was stirred at rt for 10 min prior to the addition of EDCI (3.12 g, 16.3 mmol) and the reaction mixture stirred for 17 h at rt. The volatiles were removed in vacuo then the residue was partitioned between ethyl acetate (200 mL) and water (200 mL). The aqueous phase was extracted with ethyl acetate (3×50 mL) then the combined organics washed with sodium hydroxide solution (2M, 3×50 mL), hydrochloric acid (2M, 2×50 mL), brine (100 mL), dried (MgSO$_4$), filtered and concentrated in vacuo. The isolated solid was dissolved in methanol/dichloromethane (15:185, v/v) then purified via flash chromatography (SiO$_2$, dissolved in methanol/dichloromethane, 15:185, v/v) to give the title compound as a pale yellow powder. $\delta_H$ (CD$_3$OD): 1.72–2.02 (2H, m), 3.01–3.13 (1H, m), 3.13–3.26 (2H, m), 3.35–3.52 (1.5H, m), 3.55–3.65 (0.5H, m), 3.71–3.81 (0.5H, m), 3.84 (0.5H, dd), 4.23–4.33 (0.5H, m), 4.37–4.45 (0.5H, m), 4.99 (0.5H, t), 5.07 (0.5H, t), 6.90–7.07 (2H, m), 7.13 (1H, d), 7.31 (2H, dd), 7.66 (1H, s), 8.54 (1H, d); m/z (ES$^+$)=431 [M+H]$^+$; RT=3.17 min.

EXAMPLE 54

5-Chloro-1H-pyrrolo[2,3-c]pyridine-2-carboxylic acid [2-(S)-(4-fluorophenyl)-1-isopropylcarbamoyl-ethyl]amide

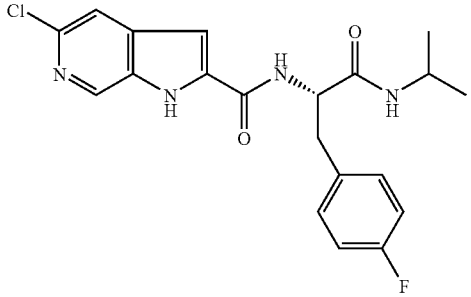

To a solution of 2-(S)-[(5-chloro-1H-pyrrolo[2,3-c]pyridine-2-carbonyl)-amino]-3-(4-fluorophenyl)propionic acid (30 mg, 0.08 mmol) in DMF (3 mL) was added DIPEA (17.3 µL, 0.10 mmol) and HATU (37.8 mg, 0.10 mmol). After 15 min, isopropylamine (7.1 µL, 0.08 mmol) was added. The reaction mixture was stirred at rt for 24 h then concentrated under reduced pressure (genevac). Purification by mass directed purification gave the title compound as a yellow solid. m/z (ES+)=403 [M+H]+; RT=3.39 min.

EXAMPLES 55–98

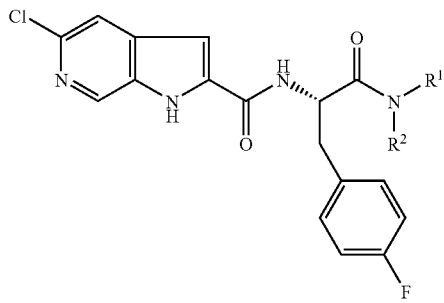

The following compounds were prepared according to the method of EXAMPLE 54 from 2-(S)-[(5-chloro-1H-pyrrolo[2,3-c]pyridine-2-carbonyl)amino]-3-(4-fluorophenyl)propionic acid and the appropriate amine.

| Example | NR¹R² | m/z | RT (min) |
|---|---|---|---|
| 55 | HN–(Me) | 375 | 3.11 |
| 56 | HN–Et | 389 | 3.24 |
| 57 | HN-cyclobutyl | 415 | 3.36 |
| 58 | HN-cyclopentyl | 429 | 3.51 |
| 59 | trans-2-hydroxycyclopentylamino | 443/445 | 3.11 |
| 60 | trans-2-hydroxycyclohexylamino | 457/459 | 3.22 |
| 61 | 2-(hydroxymethyl)cyclohexylamino | 471/473 | 3.29 |
| 62 | (tetrahydrofuran-2-ylmethyl)amino | 445 | 3.20 |
| 63 | (furan-2-ylmethyl)amino | 441 | 3.44 |
| 64 | azetidin-1-yl | 401 | 3.19 |
| 65 | pyrrolidin-1-yl | 415 | 3.31 |
| 66 | piperidin-1-yl | 429 | 3.51 |
| 67 | 2-(hydroxymethyl)pyrrolidin-1-yl | 445 | 3.24 |
| 68 | 2-(hydroxymethyl)pyrrolidin-1-yl | 445 | 3.14 |
| 69 | 2-(methoxymethyl)pyrrolidin-1-yl | 459 | 3.39 |
| 70 | 3-hydroxypyrrolidin-1-yl | 431 | 3.07 |
| 71 | 3-acetamidopyrrolidin-1-yl | 472 | 3.04 |
| 72 | morpholin-4-yl | 431 | 3.17 |
| 73 | 4-methylpiperazin-1-yl | 444 | 2.69 |
| 74 | HN–CH₂CH₂OH | 405 | 3.06 |
| 75 | HN–CH₂CH₂OMe | 419 | 3.19 |
| 76 | HN–CH₂CH₂SMe | 435 | 3.36 |
| 77 | HN–CH₂CH₂NMe₂ | 432 | 2.77 |

-continued

| Example | NR¹R² | m/z | RT (min) |
|---|---|---|---|
| 78 | HO-CH2CH2-N-CH2CH2-OH | 449 | 2.99 |
| 79 | N(CH3)2 | 389 | 3.24 |
| 80 | N(Et)2 | 417 | 3.37 |
| 81 | morpholinoethylamine | 474 | 2.67 |
| 82 | piperazinone | 444 | 3.04 |
| 83 | 3-pyridylmethylamine | 452 | 2.65 |
| 84 | aniline | 437 | 357 |
| 85 | 2,5-dimethylpyrrolidine | 443 | 3.52 |
| 86 | bis(2-methoxyethyl)amine | 477 | 3.31 |
| 87 | 3,4-dimethoxypyrrolidine | 475 | 3.11 |
| 88 | 3,4-dihydroxypyrrolidine | 447 | 2.99 |
| 89 | cyclohexylamine | 443 | 3.51 |
| 90 | thiazolidine | 433 | 3.32 |

-continued

| Example | NR¹R² | m/z | RT (min) |
|---|---|---|---|
| 91 | 4-aminotetrahydropyran | 445 | 3.19 |
| 92 | thiomorpholine | 447 | 3.37 |
| 93 | N,N-dimethylaminopropylamine | 446 | 2.64 |
| 94 | 3-aminopropanol | 419 | 3.04 |
| 95 | 1-(2-hydroxyethyl)piperazine | 474 | 2.64 |
| 96 | 4-(1-pyrrolidinyl)piperidine | 498 | 2.70 |
| 97 | 3-hydroxypiperidine | 445 | 3.14 |
| 98 | 4-piperidone | 443 | 3.20 |

EXAMPLE 99

5-Chloro-1H-pyrrolo[2,3-c]pyridine-2-carboxylic acid [1-cyclopropylcarbamoyl-2-(S)-(4-fluorophenyl)ethyl]amide

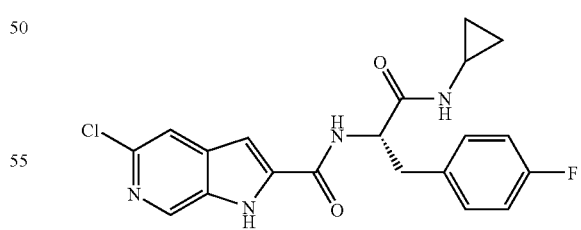

To a solution of 2-(S)-[(5-chloro-1H-pyrrolo[2,3-c]pyridine-2-carbonyl)-amino]-3-(4-fluorophenyl)propionic acid (100 mg, 0.28 mmol) in DMF (5 ml) was added cyclopropylamine (19.2 µl, 0.28 mmol), HOBt (37 mg, 0.28 mmol) and DIPEA (96 µl, 0.55 mmol). After 5 min, EDCI (69 mg, 0.36 mmol) was added and the reaction mixture stirred at rt for 16 h. The solvent was removed in vacuo and the residue triturated with water and chromatographed on silica gel eluting with methanol:dichloromethane (1:24) to give the title compound as an off-white solid. m/z (ES$^+$)=401 [M+H]$^+$; RT=3.22 min.

EXAMPLES 100–106

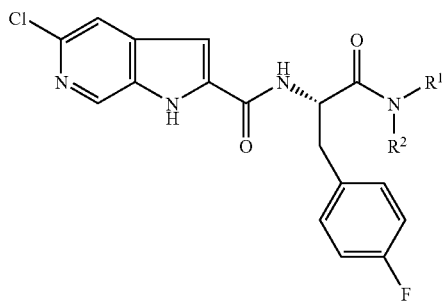

The following compounds were prepared according to the method of EXAMPLE 99 from 2-(S)-[(5-chloro-1H-pyrrolo[2,3-c]pyridine-2-carbonyl)amino]3-(4-fluorophenyl)propionic acid and the appropriate amine. All compounds were purified by chromatography on silica gel eluting with the described solvent system.

EXAMPLE 107

5-Chloro-1H-pyrrolo[2,3-c]pyridine-2-carboxylic acid [1-(S)-(4-fluorobenzyl)-2-(3-hydroxyazetidin-1-yl)-2-oxoethyl]amide

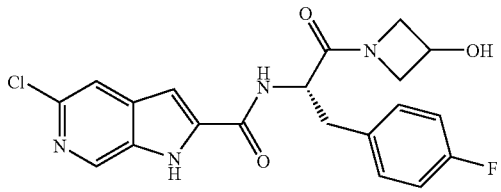

2-(S)-[(5-Chloro-1H-pyrrolo[2,3-c]pyridine-2-carbonyl)amino]-3-(4-fluorophenyl)propionic acid (100 mg, 0.28 mmol), 3-hydroxyazetidine hydrochloride (Heterocycles, 2002, 56(1–2), 433–442; 30 mg, 0.28 mmol) and HOBt (37 mg, 0.28 mmol) were dissolved in DMF (5 ml) and DIPEA (0.14 ml, 0.83 mmol). After 5 min, EDCI (69 mg, 0.36 mmol) was added and the reaction mixture stirred at rt for 16 h. The solvent was removed in vacuo and the residue triturated with water. Purification by chromatography on silica gel eluting

| Example | NR$^1$R$^2$ | Eluent | m/z | RT (min) |
|---|---|---|---|---|
| 100 | HN~~~OH | MeOH:DCM 1:19 | 433 | 3.06 |
| 101 | HN~~O~ | MeOH:DCM 3:97 | 433 | 3.20 |
| 102 | HN~(OH)~OH | MeOH:DCM 6:94 | 435 | 2.95 |
| 103 | HN~~~N(pyrrolidinone) | MeOH:DCM 3:97 | 486 | 3.15 |
| 104 | HN~~~NH-cyclohexyl | NH$_4$OH:MeOH:DCM 1:9:90 | 500 | 2.82 |
| 105 | azetidine-SO$_2$-morpholine | MeOH:DCM 1:19 | 550 | 3.24 |
| 106 | azetidine-SO$_2$-azetidine | MeOH:DCM 1:19 | 520 | 3.36 |

EXAMPLE 108

5-Chloro-1H-pyrrolo[2,3-c]pyridine-2-carboxylic acid [1-(S)-benzyl-2-(3-hydroxazetidin-1-yl)-2-oxo-ethyl]amide with methanol:dichloromethane (1:49 to 3:97) gave the title compound as a yellow solid. $\delta_H$ (CD$_3$OD): 3.08–3.21 (2H, m), 3.58–3.63 (0.5H, m), 3.84–3.91 (0.5H, m), 4.03–4.09 (0.5H, m), 4.25–4.32 (0.5H, m), 4.38–4.94 (4H, m), 7.03–7.12 (2H, m), 7.15–7.19 (1H, m), 7.30–7.38 (2H, m), 7.68 (1H, s), 8.59 (1H, s); RT=3.32 min.

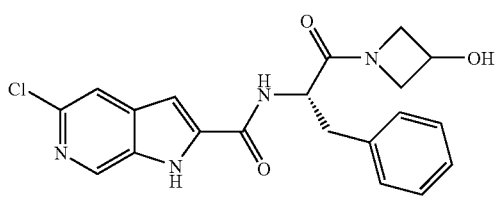

2-(S)-[(5-Chloro-1H-pyrrolo[2,3-c]pyridine-2-carbonyl)amino]-3-phenylpropionic acid (100 mg, 0.29 mmol), 3-hydroxyazetidine hydrochloride (32 mg, 0.29 mmol) and HOBt (39 mg, 0.29 mmol) were dissolved in DMF (5 ml) and DIPEA (0.15 ml, 0.87 mmol). After 5 min, EDCI (72 mg, 0.38 mmol) was added and the reaction mixture stirred at rt for 16 h. The solvent was removed in vacuo and the residue triturated with water. Purification by chromatography on silica gel eluting with methanol:dichloromethane (1:49 to 3:97) gave the title compound as an off-white solid. $\delta_H$ (CD$_3$OD): 3.12–3.20 (2H, m), 3.45–3.51 (0.5H, m), 3.83–3.90 (0.5H, m), 4.00–4.13 (1H, m), 4.35–4.52 (2H, m), 4.57–4.94 (2H, m), 7.18–7.22 (1H, m), 7.27–7.40 (5H, m), 7.68 (1H, s), 8.59 (1H, s); RT=3.27 min.

EXAMPLE 109

5-Chloro-1H-pyrrolo[2,3-c]pyridine-2-carboxylic acid [2-(3-hydroxyazetidin-1-yl)-2-oxoethyl]amide

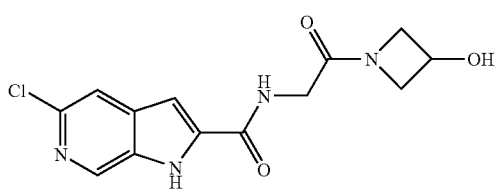

[(5-Chloro-1H-pyrrolo[2,3-c]pyridine-2-carbonyl)amino]acetic acid (30 mg, 0.12 mmol), 3-hydroxyazetidine hydrochloride (13 mg, 0.12 mmol) and HOBt (16 mg, 0.12 mmol) were dissolved in DMF (3 ml) and DIPEA (43 μl, 0.25 mmol). After 5 min, EDCI (30 mg, 0.15 mmol) was added and the reaction mixture stirred at rt for 16 h. The solvent was removed in vacuo and the residue partitioned between water (20 ml) and DCM (3×20 ml). The combined organics were dried (MgSO$_4$), concentrated in vacuo and the residue purified by chromatography on silica gel eluting with methanol:dichloromethane (1:24) to give the title compound as a white solid. $\delta_H$ (CD$_3$OD): 4.06–4.15 (3H, m), 4.40–4.46 (1H, m), 4.55–4.63 (1H, m), 4.77–4.94 (2H, m), 7.14 (1H, s), 7.71 (1H, s), 8.62 (1H, s); RT=2.82 min.

EXAMPLES 110–111

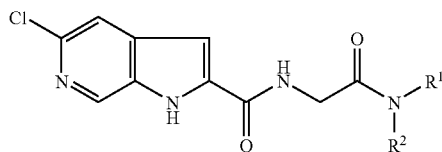

The following compounds were prepared according to the method of EXAMPLE 109 from [(5-chloro-1H-pyrrolo[2,3-c]pyridine-2-carbonyl)amino]acetic acid and the appropriate amine. All compounds were purified by chromatography on silica gel eluting with the described solvent system.

| Example | NR$^1$R$^2$ | Eluent | m/z | RT (min) |
|---|---|---|---|---|
| 110 | | MeOH:DCM 6:94 to 8:92 | 337 | 2.61 |
| 111 | | MeOH:DCM 1:24 | 323 | 2.65 |

EXAMPLE 112

2-[(5-Chloro-1H-pyrrolo[2,3-c]pyridine-2-carbonyl)amino]-3-oxo-3-phenylpropionic acid ethyl ester

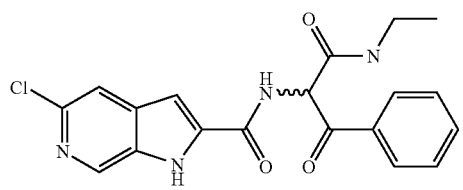

5-Chloro-1H-pyrrolo[2,3-c]pyridine-2-carboxylic acid (100 mg, 0.51 mmol) and 4-(4,6-dimethoxy[1.3.5]triazin-2-yl)-4-methylmorpholinium chloride (DMTMM) (183 mg, 0.66 mmol) were dissolved in THF (20 ml). After 5 min, 2-amino-3-oxo-3-phenylpropionic acid ethyl ester hydrochloride (Tetrahedron Lett., 1993, 34(2), 211–214; 124 mg, 0.51 mmol) and 4-methylmorpholine (56 μl, 0.51 mmol) were added and the reaction mixture stirred at rt for 72 h. The solvent was removed in vacuo and the residue partitioned between water (40 ml) and EtOAc (3×30 ml). The combined organics were dried (MgSO$_4$), concentrated in vacuo and purified by chromatography on silica gel eluting with methanol:dichloromethane (1:19). This material was further triturated with methanol:diethyl ether (1:19) to give the title compound as a pale yellow solid. m/z (ES$^+$)=386 [M+H]$^+$; RT=3.56 min.

EXAMPLE 113

5-Chloro-1H-pyrrolo[2,3-c]pyridine-2-carboxylic acid [2-(S)-(4-fluorophenyl)-1-(methylethylcarbamoyl)ethyl]amide

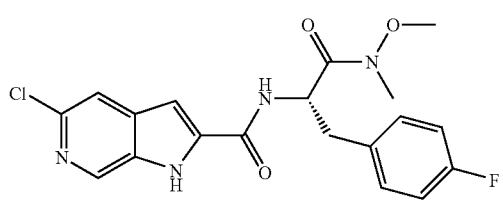

2-(S)-[(5-Chloro-1H-pyrrolo[2,3-c]pyridine-2-carbonyl)amino]-3-(4-fluorophenyl)propionic acid (80 mg, 0.22 mmol) and N,O-dimethylhydroxylamine hydrochloride (24 mg, 0.24 mmol) were dissolved in ethanol (10 ml) and 4-methylmorpholine (27 µl, 0.24 mmol). To this was added DMTMM (67 mg, 0.24 mmol) and the reaction mixture was stirred at rt for 16 h. Further N,O-dimethylhydroxylamine hydrochloride (12 mg, 0.12 mmol), 4-methylmorpholine (14 µl, 0.12 mmol) and DMTMM (34 mg, 0.12 mmol) were added and the reaction mixture was stirred at rt for 96 h. The solvent was removed in vacuo and the residue partitioned between water (40 ml) and EtOAc (2×40 ml). The combined organics were dried (MgSO$_4$), concentrated in vacuo and purified by chromatography on silica gel eluting with methanol:dichloromethane (1:19) to give the title compound as a white solid. m/z (ES$^+$)=405 [M+H]$^+$; RT=3.36 min.

EXAMPLE 114

5-Chloro-1H-pyrrolo[2,3-b]pyridine-2-carboxylic acid [1-(S)-(4-fluorobenzyl)-2-(4-hydroxypiperidin-1-yl)-2-oxoethyl]amide

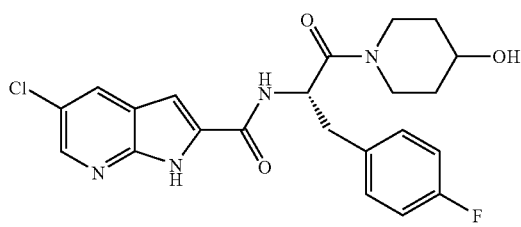

5-Chloro-1H-pyrrolo[2,3-b]pyridine-2-carboxylic acid (Preparation 57, 50 mg, 0.25 mmol), 2-(S)-amino-3-(4-fluorophenyl)-1-(4-hydroxypiperidin-1-yl)propan-1-one hydrochloride (85 mg, 0.25 mmol) and DMTMM (85 mg, 0.31 mmol) were dissolved in ethanol (5 ml) and 4-methylmorpholine (31 µl, 0.28 mmol). The reaction mixture was stirred at rt for 16 h. The solvent was removed in vacuo and the residue partitioned between water (30 ml) and EtOAc (3×25 ml). The combined organics were dried (MgSO$_4$), concentrated in vacuo and purified by chromatography on silica gel eluting with methanol:dichloromethane (1:19) to give the title compound as a beige solid. m/z (ES$^+$)=445 [M+H]$^+$; RT=3.31 min.

EXAMPLE 115

5-Chloro-1H-pyrrolo[2,3-b]pyridine-2-carboxylic acid (1-dimethylcarbamoyl-2-(S)-phenylethyl)amide

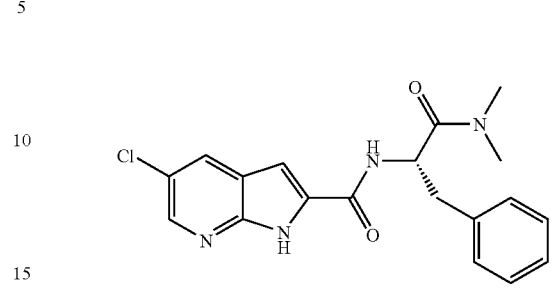

5-Chloro-1H-pyrrolo[2,3-b]pyridine-2-carboxylic acid (Preparation 57, 55 mg, 0.28 mmol), 2-(S)-amino-N,N-dimethyl-3-phenylpropionamide hydrochloride (70 mg, 0.31 mmol) and DMTMM (93 mg, 0.34 mmol) were dissolved in ethanol (5 ml) and 4-methylmorpholine (34 µl, 0.31 mmol). The reaction mixture was stirred at rt for 24 h. The solvent was removed in vacuo and the residue partitioned between water (40 ml) and EtOAc (2×40 ml). The combined organics were washed with 2N NaOH solution (40 ml), brine (40 ml), dried (MgSO$_4$), concentrated in vacuo and purified by chromatography on silica gel eluting with methanol:dichloromethane (3:97) to give the title compound as a yellow solid. m/z (ES$^+$)=371 [M+H]$^+$; RT=3.49 min.

EXAMPLE 116

5-Ethynyl-1H-pyrrolo[2,3-c]pyridine-2-carboxylic acid (1-(S)-dimethylcarbamoyl-2-phenylethyl)amide

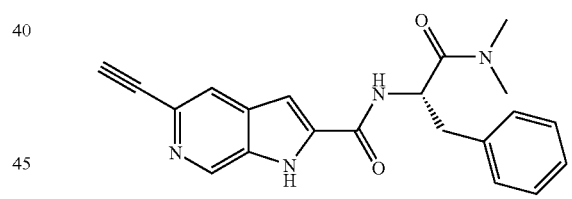

To a solution of 2-(S)-amino-N,N-dimethyl-3-phenylpropionamide hydrochloride (Preparation 8, 0.0135 g, 0.059 mmol) in DMF (anhydrous, 3 mL) was added DIPEA (0.031 mL, 0.177 mmol) then carboxylic acid (Preparation 60, 0.010 g, 0.054 mmol). To the stirred solution was added HOBt.H$_2$O (0.008 g, 0.059 mmol) then, after 10 min, EDCI (0.012 g, 0.065 mmol). The reaction mixture was stirred for 18 h then all volatiles were removed in vacuo. The residue was partitioned between ethyl acetate (30 mL) and water (20 mL). The layers were separated and the aqueous layer extracted with ethyl acetate (3×20 mL). The combined organics were washed with brine (30 mL), dried (MgSO$_4$), filtered and concentrated in vacuo. The residue was dissolved in methanol then adsorbed onto silica gel. Purification via flash column chromatography (SiO$_2$, CH$_2$Cl$_2$:MeOH, 19:1, v/v) gave the title compound as an off-white solid. $\delta_H$ (CD$_3$OD): 2.88 (3H, s), 2.89 (3H, s), 3.00–3.23 (2H, m), 3.50 (1H, s), 5.27 (1H, t), 7.10–7.37 (6H, m), 7.86 (1H, s), 8.70 (1H, s). m/z (ES$^+$)=361 [M+H]$^+$; RT=2.65 min.

EXAMPLE 117

5-Cyano-1H-pyrrolo[2,3-c]pyridine-2-carboxylic acid (1-(S)-dimethylcarbamoyl-2-phenylethyl)amide

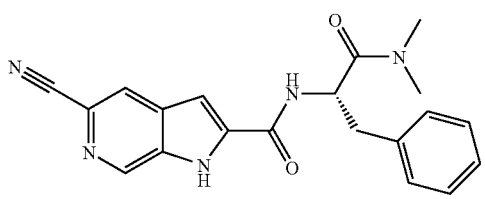

To a solution of 2-(S)-amino-N,N-dimethyl-3-phenylpropionamide hydrochloride (Preparation 8, 0.023 g, 0.100 mmol) in DMF (anhydrous, 4 mL) was added DIPEA (0.052 mL, 0.300 mmol) then carboxylic acid (Preparation 62, 0.017 g, 0.091 mmol). To the stirred solution was added HOBt.H$_2$O (0.0135 g, 0.100 mmol) then, after 10 min, EDCI (0.021 g, 0.109 mmol). The reaction mixture was stirred for 18 h then all volatiles were removed in vacuo. The residue was partitioned between ethyl acetate (30 mL) and water (20 mL). The layers were separated and the aqueous layer extracted with ethyl acetate (3×20 mL). The combined organics were washed with brine (30 mL), dried (MgSO$_4$), filtered and concentrated in vacuo. The residue was dissolved in ethyl acetate then adsorbed onto silica gel. Purification via flash column chromatography (SiO$_2$, ethyl acetate:isohexane, 1:1, v/v) gave the title compound as a pale brown solid. $\delta_H$ (CDCl$_3$): 2.77 (3H, s), 2.96 (3H, s), 3.08–8.20 (2H, m), 5.23–5.41 (1H, m), 6.99 (1H, s), 7.14–7.36 (5H, m), 7.65 (1H, d), 8.01 (1H, s), 8.87 (1H, s), 10.01 (1H, s); m/z (ES$^+$)=362 [M+H]$^+$; RT=3.11 min.

EXAMPLE 118

5-Cyano-1H-pyrrolo[2,3-c]pyridine-2-carboxylic acid [1-(S)-(4-fluorobenzyl)-2-(4-hydroxypiperidin-1-yl)-2-oxoethyl]amide

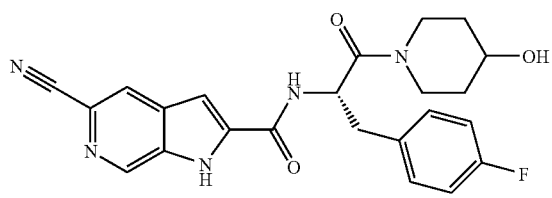

To a solution of 2-(S)-amino-3-(4-fluorophenyl)-1-(4-hydroxypiperidin-1-yl)propan-1-one hydrochloride (Preparation 20, 0.036 g, 0.118 mmol) in DMF (anhydrous, 5 mL) was added DIPEA (0.061 mL, 0.353 mmol) then carboxylic acid (Preparation 62, 0.020 g, 0.107 mmol). To the stirred solution was added HOBt.H$_2$O (0.016 g, 0.107 mmol) then, after 10 min, EDCI (0.025 g, 0.128 mmol). The reaction mixture was stirred for 18 h then all volatiles were removed in vacuo. The residue was partitioned between CH$_2$Cl$_2$ (30 mL) and water (20 mL). The layers were separated then the aqueous was extracted with CH$_2$Cl$_2$ (2×30 mL). The combined organics were washed with brine (50 mL), dried (MgSO$_4$), filtered and concentrated in vacuo. The residue was dissolved in methanol then adsorbed onto silica gel. Purification via flash column chromatography (SiO$_2$, methanol:dichloromethane, 7:93, v/v) gave the title compound as a white solid. $\delta_H$ (d$_6$ DMSO): 1.05–1.32 (2H, m), 1.49–1.72 (2H, m), 2.86–3.42 (4H, m), 3.53–3.87 (2.5H, m), 3.93–4.05 (0.5H, m), 4.69 (1H, d), 5.07–5.21 (1H, m), 6.97–7.12 (2H, m), 7.26–7.39 (2H, m), 7.47 (1H, s), 8.41 (1H, s), 8.81 (1H, s), 9.01–9.41 (1H, m), 12.64 (1H, s); m/z (ES$^+$)=436 [M+H]$^+$; RT=1.51 min.

EXAMPLE 119

5-Methyl-1H-pyrrolo[2,3-c]pyridine-2-carboxylic acid (1-dimethylcarbamoyl-2-(S)-phenylethyl)amide

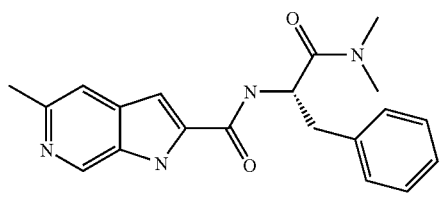

To a solution of 2-(S)-amino-N,N-dimethyl-3-phenylpropionamide hydrochloride (Preparation 8, 0.0286 g, 0.125 mmol) in DMF (anhydrous, 5 mL) was added DIPEA (0.071 mL, 0.409 mmol) then carboxylic acid (Preparation 66, 0.020 g, 0.114 mmol). To the stirred solution was added HOBt.H$_2$O (0.017 g, 0.125 mmol) then, after 10 min, EDCI (0.026 g, 0.136 mmol). The reaction mixture was stirred for 16 h at room temperature then all volatiles were removed in vacuo. The residue was partitioned between CH$_2$Cl$_2$ (50 mL) and water (50 mL). The layers were separated then the aqueous layer extracted with CH$_2$Cl$_2$ (3×20 mL). The combined organics were washed with brine (30 mL), dried (MgSO$_4$), filtered and concentrated in vacuo. The residue was dissolved in CH$_2$Cl$_2$ then purified via flash column chromatography (SiO$_2$, CH$_2$Cl$_2$ then methanol:CH$_2$Cl$_2$, 1:19, v/v) to give the title compound as a pale yellow solid. $\delta_H$ (CDCl$_3$): 2.63 (3H, s), 2.77 (3H, s), 2.97 (3H, s), 3.11–3.25 (2H, m), 5.34–5.44 (1H, m), 6.85 (1H, s), 7.20–7.33 (6H, m), 7.34 (1H, s), 7.83 (1H, d), 8.78 (1H, s); m/z (ES$^+$)=351 [M+H]$^+$; RT=2.36 min.

EXAMPLE 120

5-Chloro-1H-pyrrolo[2,3-c]pyridine-2-carboxylic acid [1-(S)-(4-fluorobenzyl)-2-(4-methoxypiperidin-1-yl)-2-oxoethyl]amide

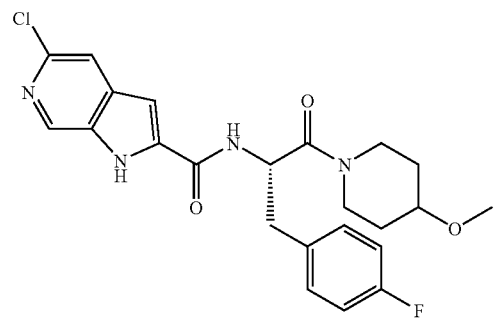

To a solution of 2-(S)-[(5-chloro-1H-pyrrolo[2,3-c]pyridine-2-carbonyl)amino]-3-phenylpropionic acid (EX- AMPLE 42, 150 mg, 0.42 mmol) and 4-methoxypiperidine hydrochloride (Preparation 68, 86 mg, 0.57 mmol) in DMF (5 mL) was added HOBt (66 mg, 0.43 mmol), DIPEA (0.23 mL, 1.34 mmol) and EDCI (102 mg, 0.53 mmol). After stirring at rt for 12 h the mixture was added to diluted brine (100 mL, water/brine: 1/1). Extraction with ethyl acetate (4×25 mL), washing of the combined extracts with brine (50 mL) and drying (MgSO$_4$) gave, after concentration, a residue which was purified by recrystallisation from methanol to give the title compound as a colourless solid. m/z (ES$^+$)=459.38 [M+H]$^+$; RT=3.40 min.

EXAMPLE 121

5-Chloro-1H-pyrrolo[2,3-c]pyridine-2-carboxylic acid [1-(S)-(4-fluorobenzyl)-2-(3-(R)-methoxypyrrolidin-1-yl)-2-oxoethyl]amide

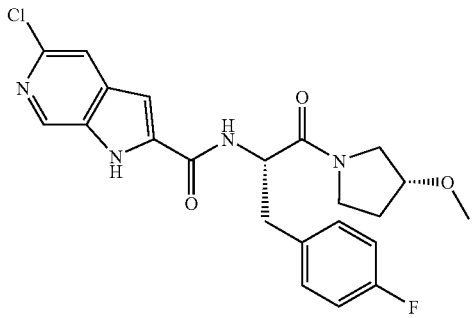

To a solution of 2-(S)-[(5-chloro-1H-pyrrolo[2,3-c]pyridine-2-carbonyl)amino]-3-phenylpropionic acid (EXAMPLE 42, 104 mg, 0.29 mmol) and (R)-3-methoxypyrrolidine hydrochloride (Preparation 70, 40 mg, 0.29 mmol) in DMF (5 mL) was added HOBt (44 mg, 0.29 mmol), DIPEA (0.15 mL, 0.88 mmol) and EDCI (66 mg, 0.344 mmol). After stirring at rt for 12 h the mixture was added to diluted brine (100 mL, water/brine: 1/1). Extraction with ethyl acetate (4×25 mL), washing of the combined extracts with brine (50 mL) and drying (MgSO$_4$) gave, after concentration, a residue which was recrystallised from acetonitrile to give the title compound as a colourless solid. m/z (ES$^+$)=445.31 [M+H]$^+$; RT=3.36 min.

EXAMPLE 122

5-Chloro-1H-pyrrolo[2,3-c]pyridine-2-carboxylic acid [(1-(S)-(4-fluorobenzyl)-2-(3-(S)-methoxypyrrolidin-1-yl)-2-oxoethyl]amide

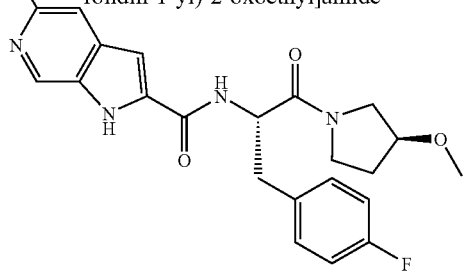

To a solution of 2-(S)-[(5-chloro-1H-pyrrolo[2,3-c]pyridine-2-carbonyl)amino]-3-phenylpropionic acid (EXAMPLE 42, 53 mg, 0.15 mmol) and (S)-3-methoxypyrrolidine hydrochloride (Preparation 72, 20 mg, 0.15 mmol) in DMF (5 mL) was added HOBt (25 mg, 0.16 mmol), DIPEA (76 μL, 0.44 mmol) and EDCI (34 mg, 0.18 mmol). After stirring at rt for 12 h the mixture was added to diluted brine (100 mL, water/brine: 1/1). Extraction with ethyl acetate (4×25 mL), washing of the combined extracts with brine (50 mL) and drying (MgSO$_4$) gave, after concentration, a residue which was purified via flash chromatography (silica gel, dichloromethane/methanol, 95:5) to give the title compound as a colourless solid. m/z (ES$^+$)=445.34 [M+H]$^+$; RT=3.34 min.

EXAMPLE 123

3-(S)-[(5-Chloro-1H-pyrrolo[2,3-c]pyridine-2-carbonyl)amino]-2-(S)-hydroxy-4-phenylbutyric acid methyl ester

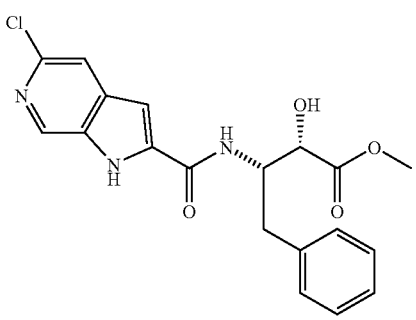

5-Chloro-1H-pyrrolo[2,3-c]pyridine-2-carboxylic acid (Preparation 18, 170 mg, 0.86 mmol) and (3S,2S)-3-amino-2-hydroxy-4-phenylbutyric acid methyl ester (Preparation 21A, 174 mg, 0.83 mmol) were coupled under similar conditions to EXAMPLE 43 using HOBt (142 mg, 0.93 mmol), EDCI (200 mg, 1.04 mmol), DIPEA (0.32 ml, 1.87 mmol) in DMF (10 ml). The crude product was purified by chromatography on silica gel eluting with hexane/ethyl acetate (25:75) to give the title compound as a colourless oil. δ$_H$ (CDCl$_3$): 3.04 (4H, 2dd), 3.74 (3H, s), 4.36 (1H, br s), 4.63 (1H, m), 4.98 (1H, ddd), 6.66 (1H, s), 6.96 (1H, d), 7.18–7.35 (5H, m), 7.48 (1H, s), 8.63 (1H, s).

EXAMPLE 124

3-(S)-[(5-Chloro-1H-pyrrolo[2,3-c]pyridine-2-carbonyl)amino]-2-(S)-hydroxy-4-phenylbutyric acid

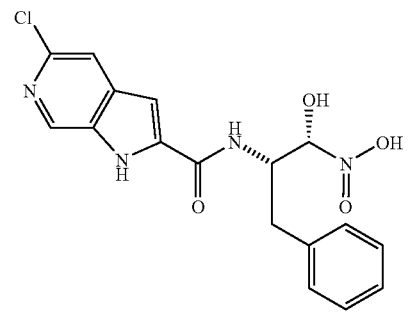

3-(S)-[(5-Chloro-1H-pyrrolo[2,3-c]pyridine-2-carbonyl)amino]-2-(S)-hydroxy-4-phenylbutyric acid methyl ester (152 mg, 0.39 mmol) was hydrolysed in a similar way to EXAMPLE 44 using sodium hydroxide solution (0.44 ml, 1N, 0.44 mmol) in methanol (10 mL). δ$_H$ (d$_6$ DMSO): 2.83, 2.95 (2H, 2dd), 4.19 (1H, d), 4.52 (1H, m), 5.75 (1H, br s), 7.10-7.33 (6H, 2m), 7.68 (1H, s), 8.54 (1H, s), 8.72 (1H, d).

EXAMPLE 125

5-Chloro-1H-pyrrolo[2,3-c]pyridine-2-carboxylic acid (1-(S)-benzyl-2-dimethylcarbamoyl-2-(S)-hydroxyethyl)amide

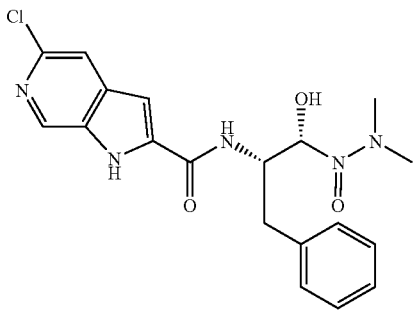

Dimethylamine hydrochloride (7 mg, 0.085 mmol) was added to a solution of 3-(S)-[(5-chloro-1H-pyrrolo[2,3-c]pyridine-2-carbonyl)amino]-2-(S)-hydroxy-4-phenylbutyric acid (EXAMPLE 124, 30 mg, 0.080 mmol), HOBt (14 mg, 0.091 mmol), DIPEA (31 µL, 0.18 mmol) and EDCI (18 mg, 0.094 mmol) in DMF (3 mL). After the addition of DIPEA (14 ml, 0.080 mmol) the mixture was stirred for 12 h before adding to diluted brine (100 mL, water/brine: 1/1). Extraction with ethyl acetate (4×25 mL), washing of the combined extracts with brine (50 mL) and drying (MgSO$_4$) gave, after concentration, a residue which was purified by preparative LCMS to give the title compound as a colourless solid. m/z (ES$^+$)=401.28 [M+H]$^+$; RT=3.06 min.

EXAMPLE 126

5-Chloro-1H-pyrrolo[2,3-c]pyridine-2-carboxylic acid (1-(S)-benzyl-2-(S)-hydroxy-3-oxo-3-pyrrolidin-1-ylpropyl)amide

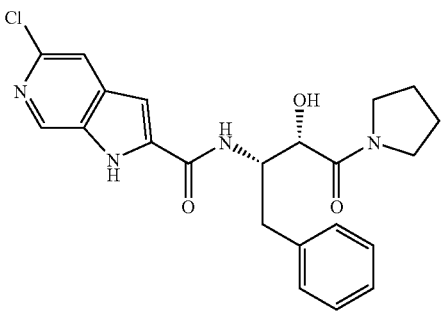

Pyrrolidine (7 µg, 0.084 mmol) was added to a solution of 3-(S)-[(5-chloro-1H-pyrrolo[2,3-c]pyridine-2-carbonyl)amino]-2-(S)-hydroxy-4-phenylbutyric acid (EXAMPLE 124, 30 mg, 0.080 mmol), HOBt (14 mg, 0.091 mmol), DIPEA (31 µL, 0.18 mmol) and EDCI (18 mg, 0.094 mmol) in DMF (3 mL). After stirring for 12 h the mixture was added to diluted brine (100 mL, water/brine: 1/1). Extraction with ethyl acetate (4×25 mL), washing of the combined extracts with brine (50 mL) and drying (MgSO$_4$), gave, after concentration, a residue which was purified by preparative LCMS to give the title compound as a colourless solid. m/z (ES$^+$)= 427.31 [M+H]$^+$; RT=3.27 min.

EXAMPLE 127

5-Chloro-1H-pyrrolo[2,3-c]pyridine-2-carboxylic acid [1-(S)-benzyl-3-(3,4-dihydroxypyrrolidin-1-yl)-2-(S)-hydroxy-3-oxopropyl]amide

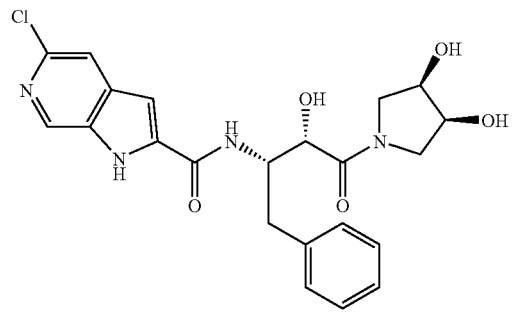

cis-3,4-Dihydroxypyrrolidine (Preparation 23, 9 mg, 0.087 mmol) was added to a solution of 3-(S)-[(5-chloro-1H-pyrrolo[2,3-c]pyridine-2-carbonyl)amino]-2-(S)-hydroxy-4-phenylbutyric acid (EXAMPLE 124, 30 mg, 0.080 mmol), HOBt (14 mg, 0.091 mmol), DIPEA (31 µL, 0.18 mmol) and EDCI (18 mg, 0.094 mmol) in DMF (3 mL). After stirring for 12 h the mixture was added to diluted brine (100 mL, water/brine: 1/1). Extraction with ethyl acetate (4×25 mL), washing of the combined extracts with brine (50 mL) and drying (MgSO$_4$) gave, after concentration, a residue which was purified by preparative LCMS to give the title compound as a colourless solid. m/z (ES$^+$)=459.29 [M+H]$^+$; RT=2.87 min.

EXAMPLE 128

5-Chloro-1H-pyrrolo[2,3-c]pyridine-2-carboxylic acid (1-(S)-benzyl-2-(R)-hydroxy-2-propylcarbamoylethyl)amide

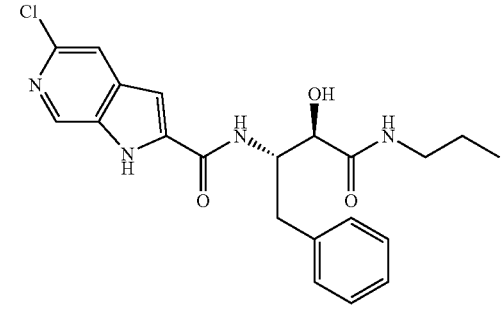

n-Propylamine (16 µL, 0.19 mmol) was added to a solution of 3-(S)-[(5-chloro-1H-pyrrolo[2,3-c]pyridine-2-carbonyl)amino]-2-(R)-hydroxy-4-phenylbutyric acid (EXAMPLE 44, 40 mg, 0.11 mmol), HOBt (16.4 mg, 0.11 mmol), DIPEA (41 µL, 0.24 mmol) and EDCI (25 mg, 0.13 mmol) in DMF (3 mL). After stirring for 72 h at room temperature the solvent was removed in vacuo and the remaining residue was purified by preparative LCMS to give the title compound as colourless solid. m/z (ES⁺)=415.34 [M+H]⁺; RT=3.10 min.

EXAMPLES 129–147

The following compounds were prepared according to the method of EXAMPLE 128 from 3-(S)-[(5-chloro-1H-pyrrolo[2,3-c]pyridine-2-carbonyl)-amino]-2-(R)-hydroxy-4-phenylbutyric acid and the appropriate amine.

| Example | Structure | RT (min) | m/z |
|---|---|---|---|
| 129 | 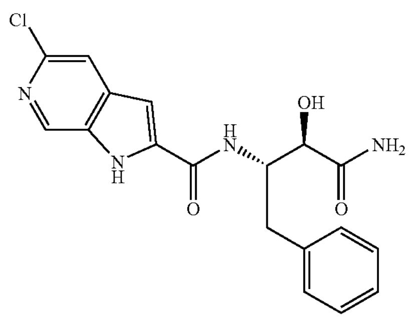 | 2.87 | 373.26 |
| 130 | 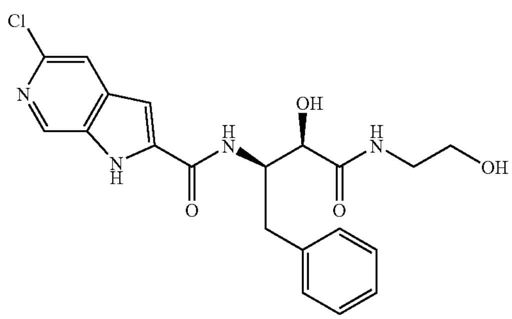 | 2.89 | 417.31 |
| 131 | 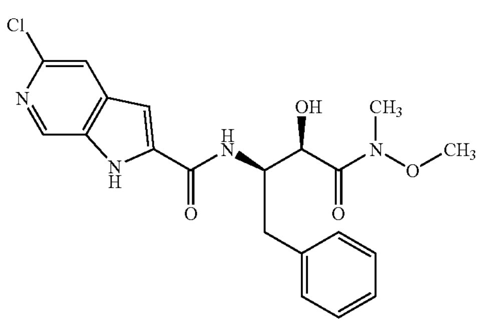 | 3.09 | 417.32 |
| 132 | 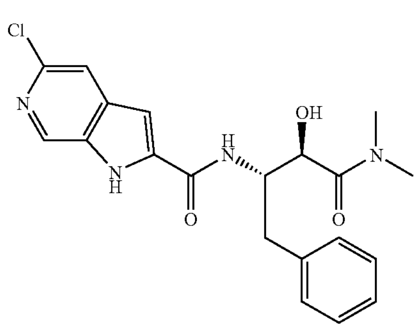 | 3.23 | 401.29 |

-continued

| Example | Structure | RT (min) | m/z |
|---|---|---|---|
| 133 | 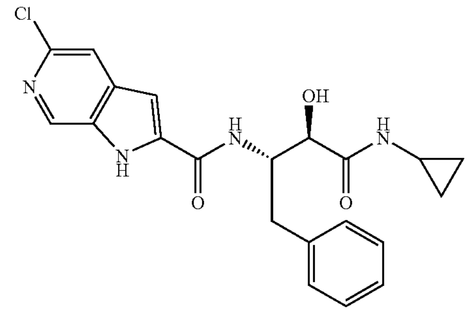 | 3.03 | 413.33 |
| 134 | 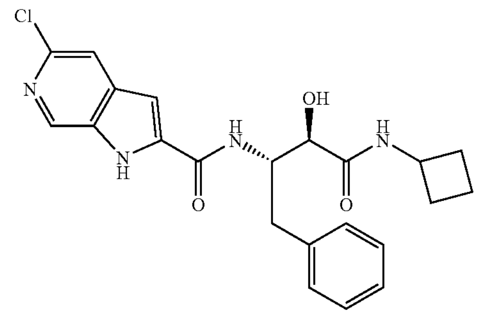 | 3.20 | 427.34 |
| 135 | 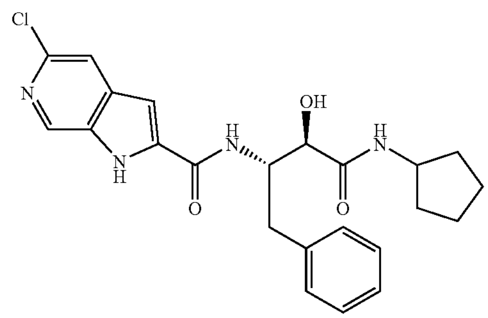 | 3.22 | 441.37 |
| 136 | 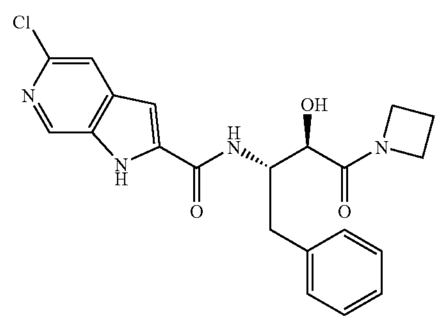 | 3.19 | 413.32 |
| 137 | 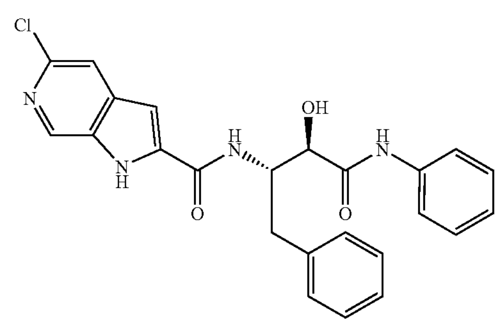 | 3.65 | 449.34 |

-continued

| Example | Structure | RT (min) | m/z |
|---|---|---|---|
| 138 | 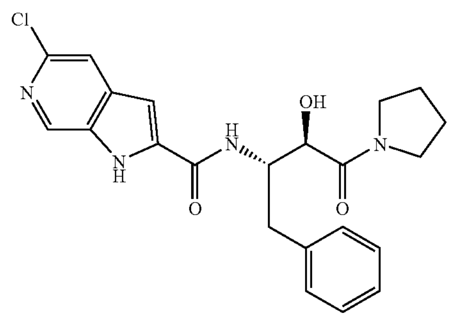 | 3.09 | 427.30 |
| 139 | 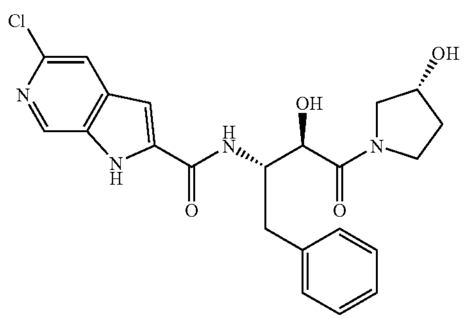 | 3.12 | 443.33 |
| 140 | 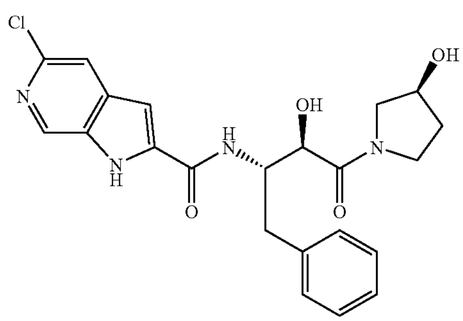 | 2.87 | 443.33 |
| 141 | 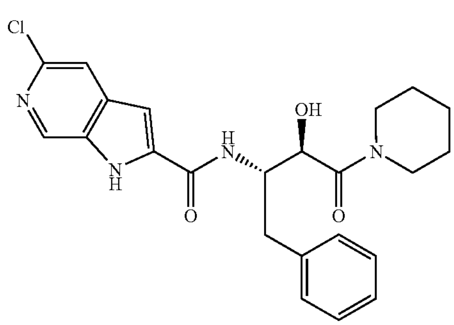 | 3.41 | 441.32 |

-continued

| Example | Structure | RT (min) | m/z |
|---|---|---|---|
| 142 | 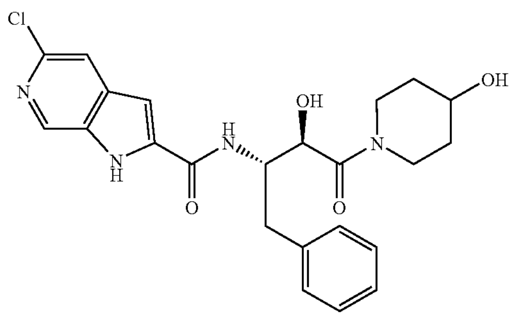 | 2.91 | 457.30 |
| 143 | 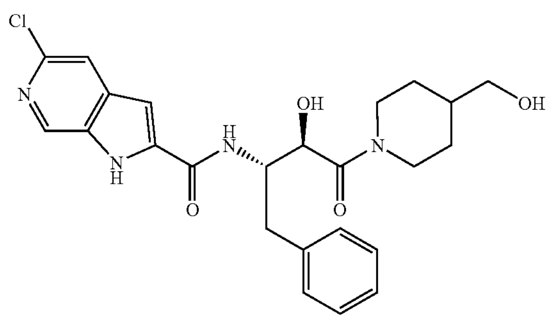 | 3.21 | 471.40 |
| 144 | 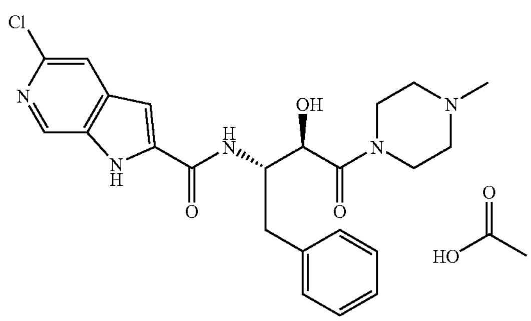 | 2.63 | 456.39 |
| 145 | 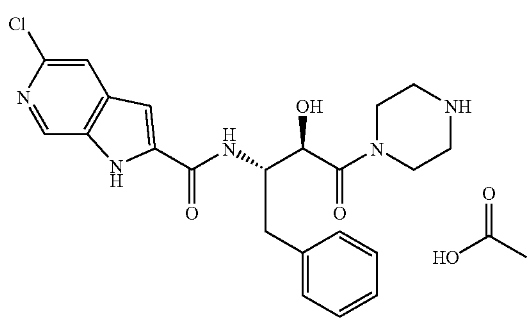 | 2.57 | 442.37 |
| 146 | 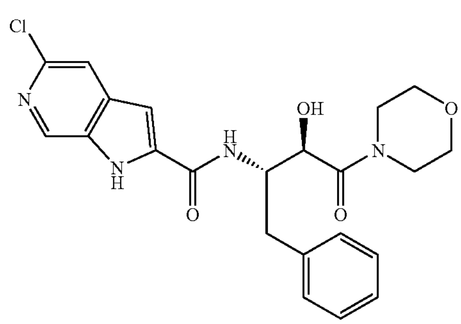 | 3.06 | 443.35 |

-continued

| Example | Structure | RT (min) | m/z |
|---|---|---|---|
| 147 | 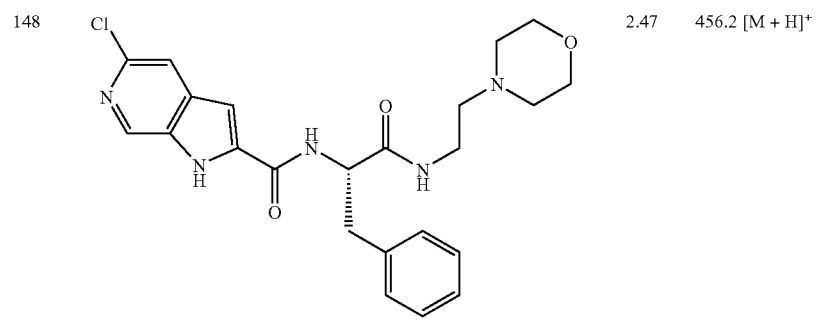 | 3.16 | 484.37 |

EXAMPLES 148–174

The following compounds were prepared according to the procedure outlined below from 5-chloro-1H-pyrrolo[2,3-c]pyridine-2-carboxylic acid (Preparation 18) and the appropriate amine.

To a solution of 5-chloro-1H-pyrrolo[2,3-c]pyridine-2-carboxylic acid (0.12 mmol, 1.5 eq) in 1:1.2 DMF/DCM (2 ml), HOBT (0.16 mmol, 2 eq) was added, followed by PS-carbodiimide (0.16 mmol, 2 eq). The reaction mixture was shaken for 15 min and a solution of amine (0.08 mmol, 1 eq) in DCM (0.5 ml) was added. The reaction mixture was shaken overnight. HOBT and unreacted starting material acid were scavenged with MP-Trisamine (0.36 mmol, 4.5 eq). MP-Trisamine was added to the reaction mixture and the mixture shaken for 5 h. The resin was filtered and washed with a solution of 1:1 DMF/DCM (2×4 ml). The filtrate was concentrated to give the product amide.

| Example | Structure | RT (min) | m/z (ES⁺) |
|---|---|---|---|
| 148 | 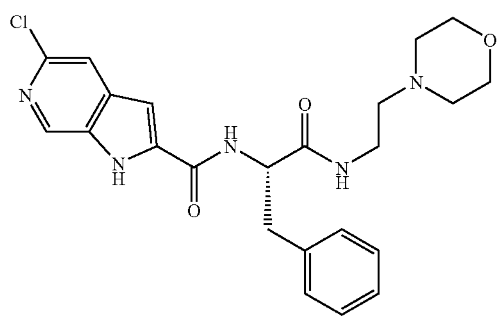 | 2.47 | 456.2 [M + H]⁺ |
| 149 | 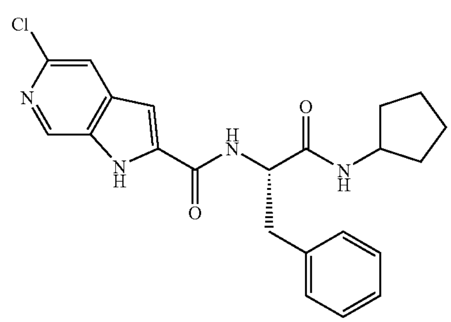 | 3.51 | 411.3 [M + H]⁺ |

| Example | Structure | RT (min) | m/z (ES⁺) |
|---|---|---|---|
| 150 | 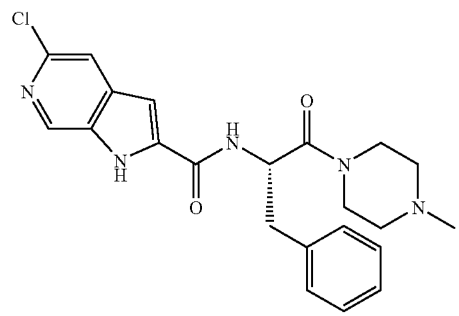 | 2.57 | 426.3 [M + H]⁺ |
| 151 | 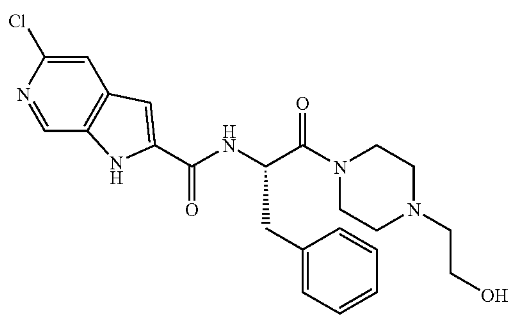 | 2.53 | 456.3 [M + H]⁺ |
| 152 | 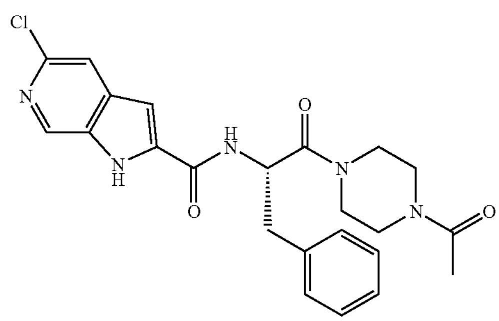 | 3.26 | 454.4 [M + H]⁺ |
| 153 | 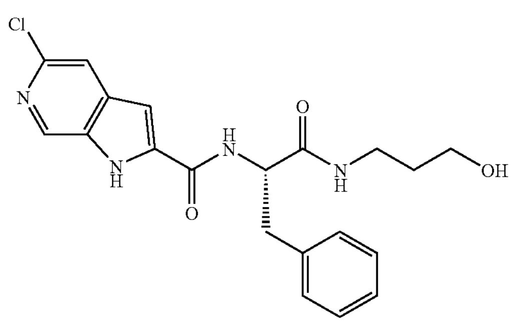 | 2.94 | 401.3 [M + H]⁺ |
| 154 | 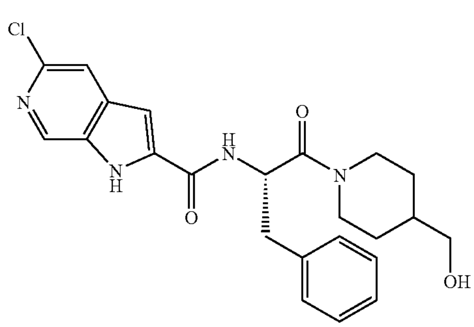 | 3.11 | 441.2 [M + H]⁺ |

-continued

| Example | Structure | RT (min) | m/z (ES+) |
|---|---|---|---|
| 155 | 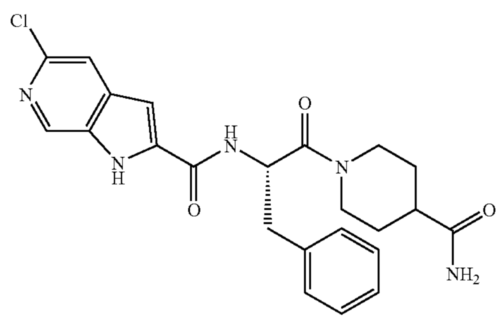 | 2.97 | 454.4 [M + H]+ |
| 156 | 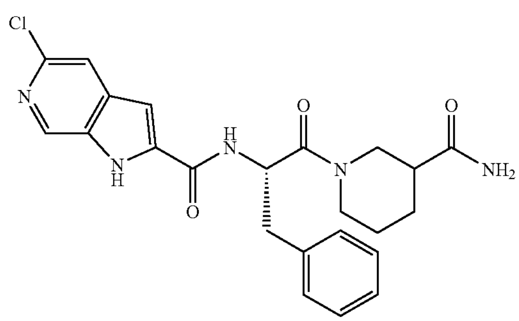 | 2.9 | 454.4 [M + H]+ |
| 157 | 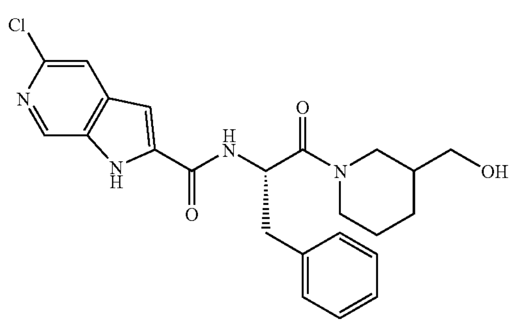 | 3.04 | 441.4 [M + H]+ |
| 158 | 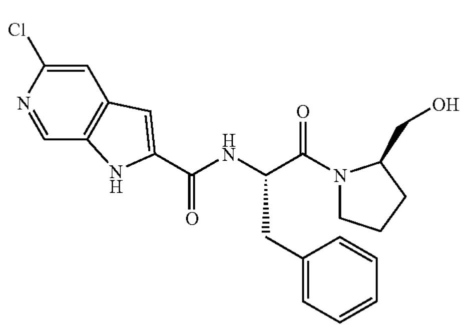 | 2.99 | 427.3 [M + H]+ |

-continued

| Example | Structure | RT (min) | m/z (ES⁺) |
|---------|-----------|----------|-----------|
| 159 | 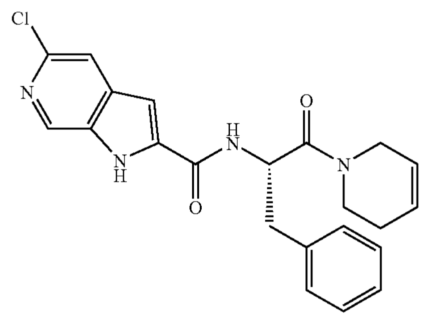 | 3.42 | 409.3 [M + H]⁺ |
| 160 | 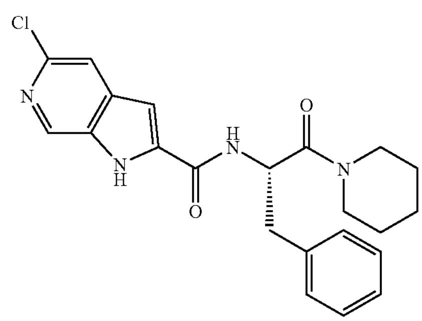 | 3.7 | 411.3 [M + H]⁺ |
| 161 | 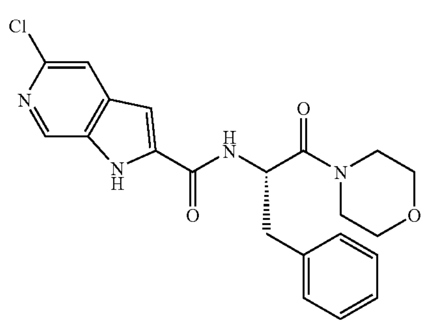 | 3.17 | 413.3 [M + H]⁺ |
| 162 | 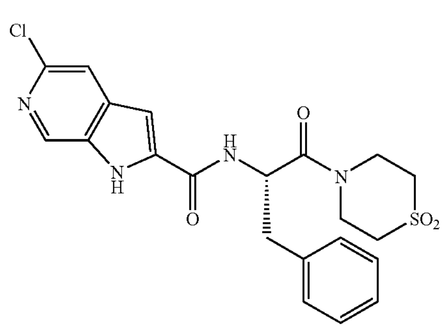 | 3.15 | 461.3 [M + H]⁺ |

-continued

| Example | Structure | RT (min) | m/z (ES+) |
|---|---|---|---|
| 163 | 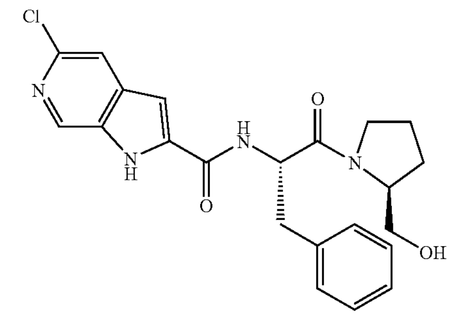 | 3.12 | 427.3 [M + H]+ |
| 164 | 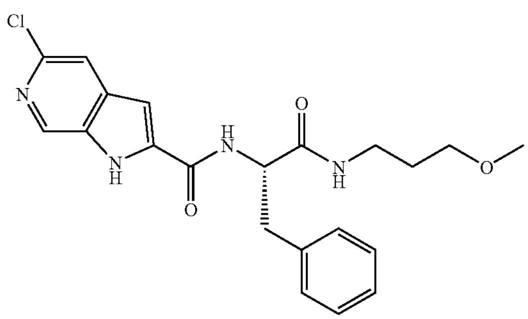 | 3.34 | 415.3 [M + H]+ |
| 165 | 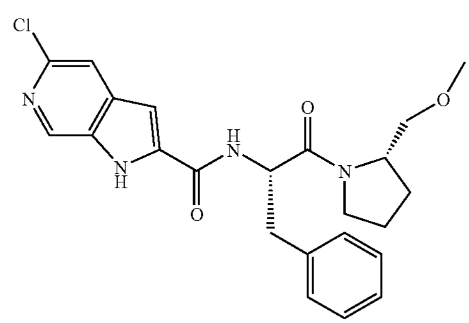 | 3.45 | 441.3 [M + H]+ |
| 166 | 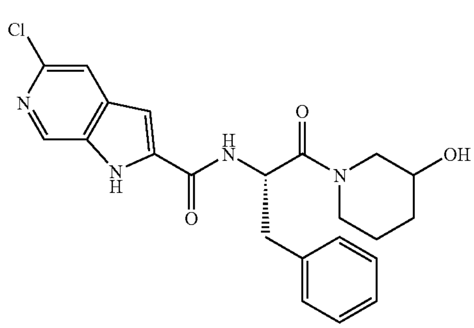 | 3.06 | 427.4 [M + H]+ |

-continued
| Example | Structure | RT (min) | m/z (ES+) |
|---|---|---|---|
| 167 | 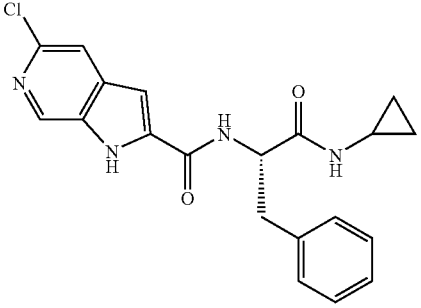 | 3.14 | 383.3 [M + H]+ |
| 168 | 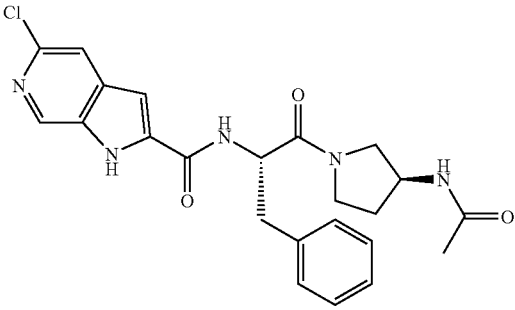 | 3.17 | 454.3 [M + H]+ |
| 169 | 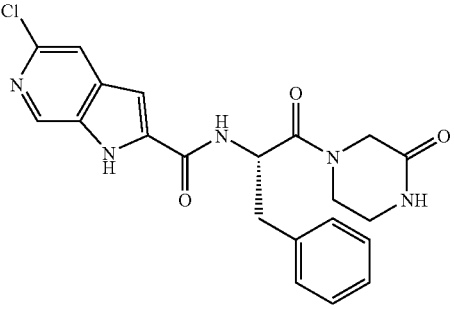 | 2.94 | 426.3 [M + H]+ |
| 170 | 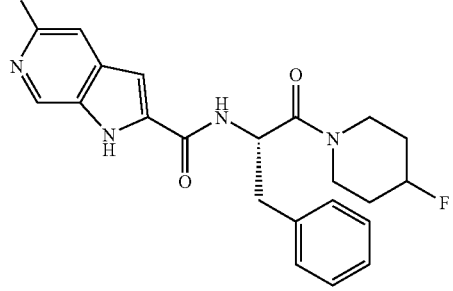 | 3.37 | 429.4 [M + H]+ |

-continued

| Example | Structure | RT (min) | m/z (ES+) |
|---|---|---|---|
| 171 | 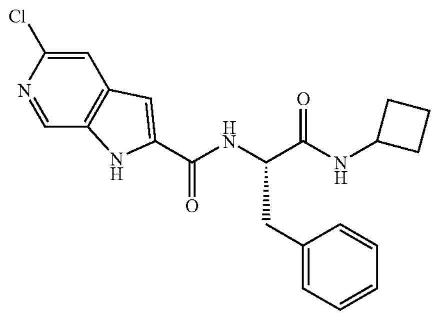 | 3.57 | 397.3 [M + H]+ |
| 172 | 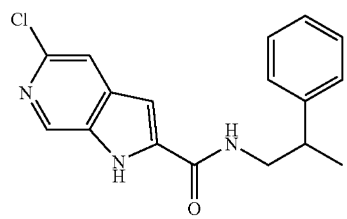 | 3.39 | 314.2 [M + H]+ |
| 173 | 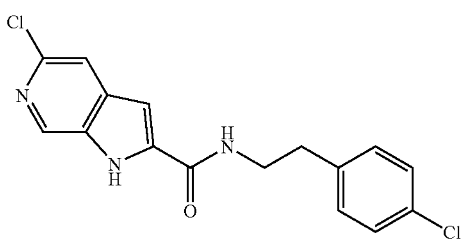 | 3.7 | 334.2 [M + H]+ |
| 174 | 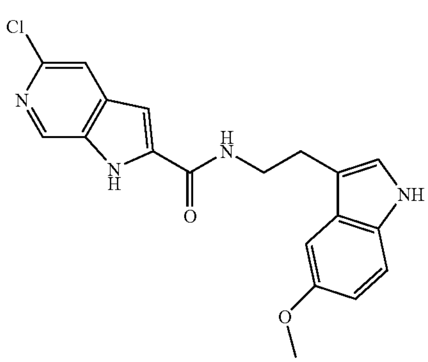 | 3.24 | 369.3 [M + H]+ |

EXAMPLE 175

5-Chloro-1H-pyrrolo[2,3-c]pyridine-2-carboxylic acid [2-(4-benzyloxypiperidin-1-yl)-1-(S)-(4-fluorobenzyl)-2-oxoethyl]amide

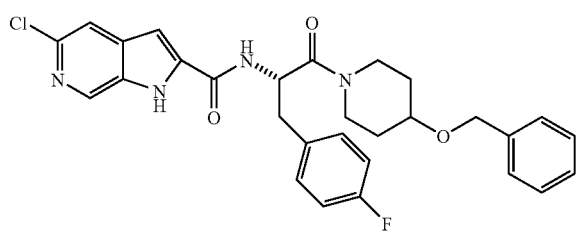

To 5-chloro-1H-pyrrolo[2,3-c]pyridine-2-carboxylic acid [1-(S)-(4-fluorobenzyl)-2-(4-hydroxypiperidin-1-yl)-2-oxoethyl]amide (EXAMPLE 5, 50 mg, 0.11 mmol) in anhydrous DMF (3 mL) under argon was added benzylbromide (16 µl, 0.13 mmol) followed by sodium hydride (6.3 mg, 0.16 mmol) and the reaction stirred for 16 h. Solvent was removed in vacuo and the residue partitioned between ethyl acetate (2×20 mL) and water (20 mL). The organic fractions were washed with 1M HCl (20 mL), NaHCO₃ (2×20 mL) then brine (2×20 mL), dried (MgSO₄) and the solvent removed in vacuo. Crude material was purified by chromatography on silica gel with dichloromethane/methanol (9:1) as the eluent to give the title compound as an off-white powder. m/z (ES⁺)=535.33 [M+H]⁺; RT=3.44 min.

EXAMPLE 176

1-[2-(S)-[5-Chloro-1H-pyrrolo[2,3-c]pyridine-2-carbonyl)amino]-3-(4-fluorophenyl)propionyl]piperidine-4-carboxylic acid

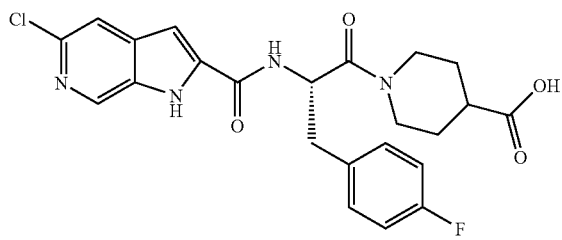

To a solution of 1-[2-(S)-[5-chloro-1H-pyrrolo[2,3-c]pyridine-2-carbonyl)amino]-3-(4-fluorophenyl)propionyl]piperidine-4-carboxylic acid methyl ester (EXAMPLE 239, 48 mg, 0.1 mmol) in THF (2.0 mL) was added 1M sodium hydroxide solution (0.11 mL, 0.11 mmol) and the reaction stirred at rt for 3 h. Solvent was removed in vacuo and the crude material partitioned between diethyl ether (20 mL) and water (2×20 mL). The aqueous layers were combined and acidified to pH2 with 2M HCl, and organics were extracted into ethyl acetate (2×20 mL). Organic layers were combined and washed with brine (2×15 mL), dried (MgSO₄) and solvent removed in vacuo. The crude material was crystallised from ethyl acetate/petroleum ether to give the title compound as a white powder. m/z (ES⁺)=473.30 [M+H]⁺; RT=3.20 min.

EXAMPLES 177 AND 178 WERE PREPARED IN A SIMILAR WAY TO EXAMPLE 176

| EXAMPLE | Amine | m/z | RT (min) |
|---|---|---|---|
| 177 | ![structure] | 473.29 | 3.26 |
| 178 | ![structure] | 473.3 | 3.33 |

EXAMPLE 179

Acetic acid 1-[2-(S)-[5-chloro-1H-pyrrolo[2,3-c]pyridine-2-carbonyl)amino]-3-(4-fluorophenyl)propionyl]piperidin4-yl ester

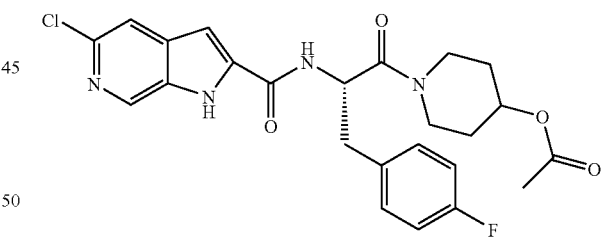

The title compound was prepared from 5-chloro-1H-pyrrolo[2,3-c]pyridine-2-carboxylic acid [1-(S)-(4-fluorobenzyl)-2-(4-hydroxypiperidin 1-yl)-2-oxoethyl] amide (EXAMPLE 5). To a solution of the starting amide (50 mg, 0.14 mmol) in anhydrous pyridine (2 mL) under argon was added acetic anhydride (1 mL) and the reaction stirred at rt over 4 h. Solvent was removed in vacuo and the crude material dissolved in ethyl acetate (30 mL). Organics were washed with 1M HCl (2×15 mL), water (15 mL) then brine (2×15 mL), dried (MgSO₄) and solvent removed in vacuo. The residue was purified by chromatography with dichloromethane/methanol (99:1) as the eluent to give the title compound as a white powder. m/z (ES⁺)=487.26 [M+H]⁺; RT=3.38 min.

EXAMPLE 180

5-Chloro-1H-pyrrolo[2,3-c]pydridine-2-carboxylic acid [2-(4-aminopiperidin-1-yl-1-(S)-(4-fluorobenzl)-2-oxoethyl]amide

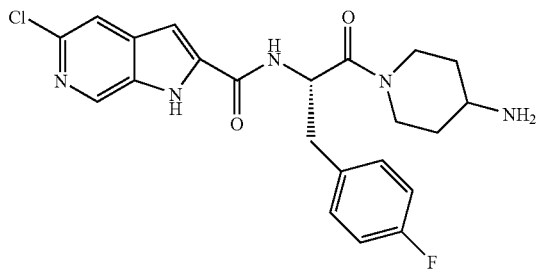

To a suspension of {1-[2-(S)-[(5-chloro-1H-pyrrolo[2,3-c]pyridine-2-carbonyl)amino]-3-(4-fluorophenyl)propionyl]piperidin-4-yl}carbamic acid tert-butyl ester (EXAMPLE 230, 500 mg, 0.92 mmol) in methanol (12 mL) was added a solution of 4M HCl in dioxane (0.69 mL, 2.76 mmol) and the reaction stirred for 48 h. The resulting precipitate was filtered and washed with ethyl acetate to give the title compound as the hydrochloride salt as a pale yellow powder. m/z (ES$^+$)= 444.16 [M+H]$^+$; RT=2.65 min. The product was dissolved in saturated sodium bicarbonate solution. Solvent was removed in vacuo and the crude material dissolved in THF (30 mL). The solution was filtered through celite and solvent removed in vacuo to give the title compound as a yellow powder. m/z (ES$^+$)=444.32 [M+H]$^+$; RT=2.59 min.

EXAMPLES 181–189 where prepared according to EXAMPLE 180 from the appropriate Boc-protected amine:

| EXAMPLE | Structure | m/z | RT (min) |
|---|---|---|---|
| 181 | 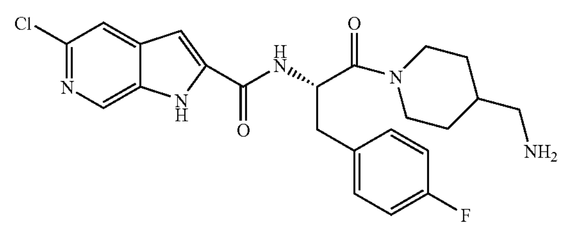 | 458.3 | 2.66 |
| 182 | 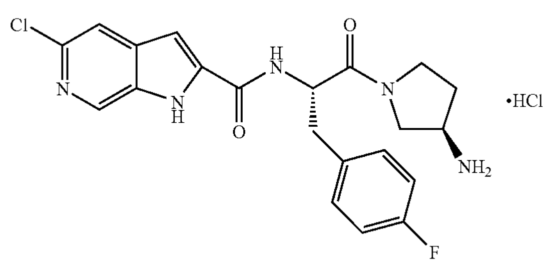 | 430.35 | 2.66 |
| 183 | 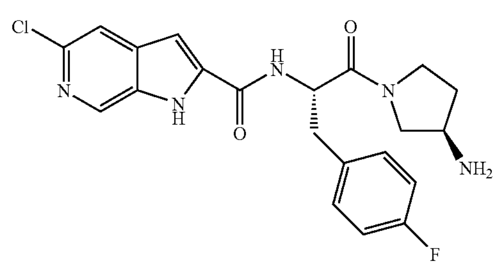 | 430.39 | 2.62 |
| 184 | 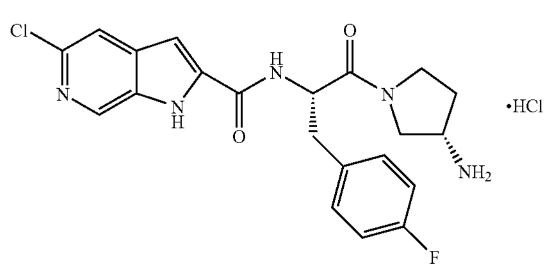 | 430.34 | 2.73 |

-continued

| EXAMPLE | Structure | m/z | RT (min) |
|---|---|---|---|
| 185 | 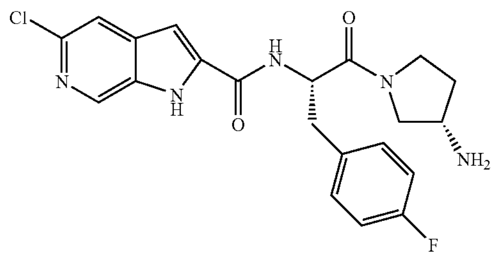 | 430.38 | 2.69 |
| 186 | ·HCl | 444.37 | 2.65 |
| 187 | 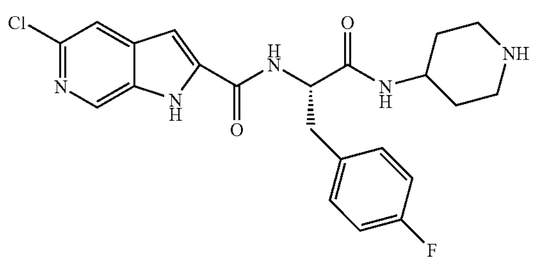 | 444.41 | 2.59 |
| 188 | ·HCl | 444.37 | 2.84 |
| 189 | 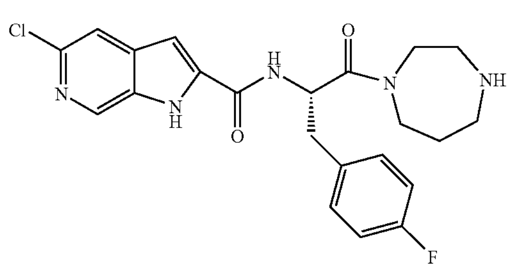 | 444.4 | 2.78 |

EXAMPLE 190

5-Chloro-1H-pyrrolo[2,3-c]pyridine-2-carboxylic acid [2-(4-diacetylaminopiperidin-1-yl)-1-(S)-(4-fluorobenzyl)-2-oxoethyl]amide

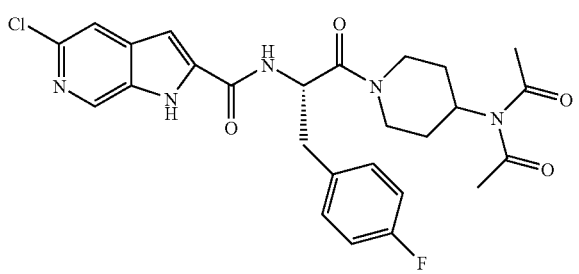

Prepared from 5-chloro-1H-pyrrolo[2,3-c]pyridine-2-carboxylic acid [2-(4-aminopiperidin-1-yl)-1-(S)-(4-fluorobenzyl)-2-oxoethyl]amide (EXAMPLE 180). The compound was synthesised according to EXAMPLE 179 and purified by preparative HPLC to give the title compound as a white powder. m/z (ES$^+$)=486.28 [M–CH$_3$CO$_2$H+NH$_4$]$^+$; RT=3.18 min.

EXAMPLE 191

5-Chloro-1H-pyrrolo[2,3-c]pyridine-2-carboxylic acid [1-(S)-(4-fluorobenzyl)-2-(4-methylaminopiperidin-1-yl)-2-oxoethyl]amide

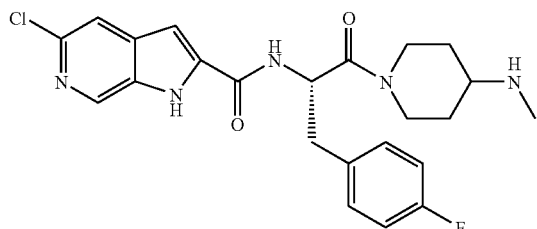

To a solution of 5-chloro-1H-pyrrolo[2,3-c]pyridine-2-carboxylic acid (1-(S)-(4-fluorobenzyl)-2-{4-[methyl-(2-nitrobenzenesulfonyl)amino]piperidin-1-yl}-2-oxoethyl)amide (Preparation 76, 82 mg, 0.13 mmol) in acetonitrile (6 mL) was added phenylthiol (145 µL, 1.4 mmol) followed by potassium carbonate (230 mg, 1.66 mmol) and the reaction heated to 50° C. for 24 h. To the mixture was added diethyl ether (10 mL) and 1M HCl (15 mL) and stirred for 5 min. The organic layer was separated and washed with 1M HCl (15 mL) before combining the aqueous layers. The solution was basified to pH9 with solid potassium carbonate and extracted with ethyl acetate (2×20 mL). Organic layers were combined, washed with brine (2×20 mL) and dried (MgSO$_4$). Removal of the solvent in vacuo provided the desired product as an off-white powder. m/z (ES$^+$)=458.40 [M+H]$^+$; RT=2.67 min. A small portion of the product (10 mg) was dissolved in methanol (2 mL) and 1M HCl added to bring the solution to pH 1–2. After stirring for 20 min the solvent was removed in vacuo to give the title compound as the hydrochloride salt as a yellow powder. m/z (ES$^+$)=458.38 [M+H]$^+$; RT=2.64 min.

EXAMPLE 192

5-Chloro-1H-pyrrolo[2,3-c]pyridine-2-carboxylic acid [1-(S)-(4-fluorobenzyl)-2-(4-methylaminomethylpiperidin-1-yl)-2-oxoethyl]amide

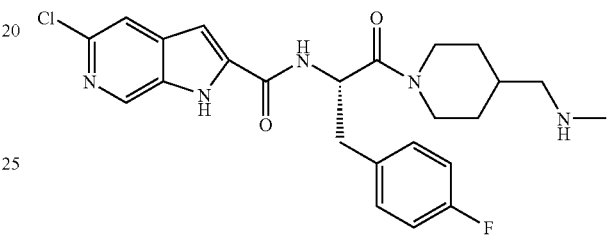

Prepared according to EXAMPLE 191 from 5-chloro-1H-pyrrolo[2,3-c]pyridine-2-carboxylic acid [1-(S)-(4-fluorobenzyl)-2-(4-{[methyl-(2-nitrobenzenesulfonyl)amino]methyl}piperidin-1-yl)-2-oxoethyl]amide (synthesised according to Preparations 73-76 from the 4-aminomethylpiperidine-1-carboxylic acid tert-butyl ester starting material). m/z (ES$^+$) free base=472.33 [M+H]$^+$; RT=2.80 min. m/z (ES$^+$) HCl salt=430.43 [M+H]$^+$; RT=2.72 min.

EXAMPLE 193

5-Chloro-1H-pyrrolo[2,3-c]pyridine-2-carboxylic acid [1-(S)-benzyl-2-(3-(R)-hydroxypyrrolidin-1-yl)-2-oxoethyl]amide

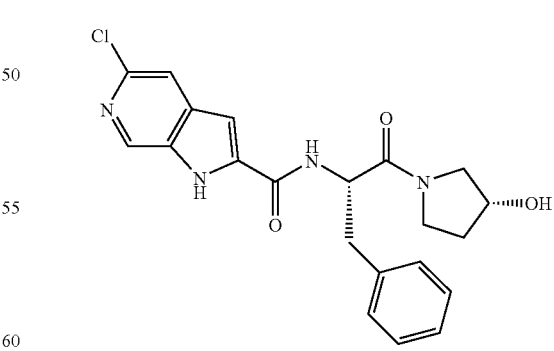

Prepared according to EXAMPLE 35, using 3-(R)-hydroxypyrrolidine in place of 3-(S)-hydroxypyrrolidine. Purification via chromatography using dichloromethane/methanol (95:5) as the eluent gave the title compound as an off-white powder. m/z (ES$^+$)=413.22 [M+H]$^+$; RT=3.13 min.

EXAMPLE 194

5Chloro-1H-pyrrolo[2,3-c]pyridine-2-carboxylic acid [1-(S)-(4-fluorobenzyl)-2-oxo-2-(4-trifluoromethylpiperidin-1-yl)ethyl]amide

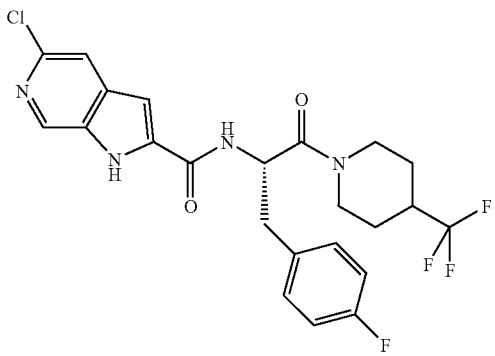

To 4-trifluoromethyl piperidine (17 mg, 0.11 mmol) was added a solution of 2-(S)-[(5-chloro-1H-pyrrolo[2,3-c]pyridine-2-carbonyl)amino]-3-(4-fluorophenyl)propionic acid (EXAMPLE 228, 40 mg, 0.11 mmol) in DMF (400 μL) followed by a solution of HATU (50 mg, 0.13 mmol) in DMF (400 μL) and finally a solution of DIPEA (23 μL, 0.13 mmol) in DMF (200 μL). The resulting mixture was stirred at rt for 96 h then solvent was removed in vacuo. The crude material was purified by crystallisation from THF/petroleum ether to give the title compound as a yellow powder. (ES$^+$)=497.23 [M+H]$^+$; RT=3.50 min.

EXAMPLES 195–225 were prepared the same way as EXAMPLE 194:

| EXAMPLE | Amine | Purification | m/z | RT (min) |
|---|---|---|---|---|
| 195 | piperidine-4-carboxylic acid ethyl ester | Crystallisation (THF/PE) | 501.26 | 3.43 |
| 196 | 3-(hydroxymethyl)piperidine | MDP | 459.3 | 3.13 |
| 197 | 4-(piperidin-1-yl)piperidine | MDP | 512.37 | 2.77 |
| 198 | 1-(piperidin-4-yl)ethanone | MDP | 471.3 | 3.24 |
| 199 | 4-fluoropiperidine | MDP | 447.27 | 3.37 |
| 200 | piperidine-4-carboxamide | MDP | 472.3 | 3.03 |
| 201 | 2-(piperidin-4-yl)ethanol | MDP | 473.32 | 3.09 |

-continued
| EXAMPLE | Amine | Purification | m/z | RT (min) |
|---|---|---|---|---|
| 202 | 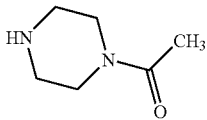 | MDP | 472.29 | 3.08 |
| 203 | 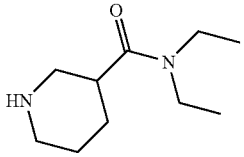 | MDP | 528.38 | 3.3 |
| 204 | 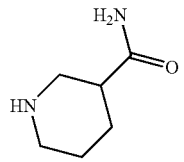 | MDP | 472.3 | 3.09 |
| 205 | 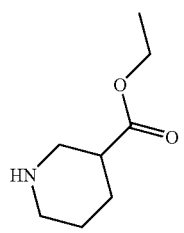 | MDP | 501.32 | 3.55 |
| 206 | 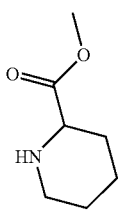 | MDP | 487.3 | 3.57 |
| 207 | 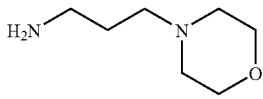 | MDP | 488.34 | 2.75 |
| 208 | 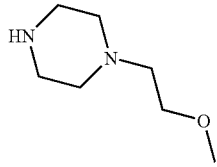 | MDP | 488.4 | 2.59 |
| 209 | 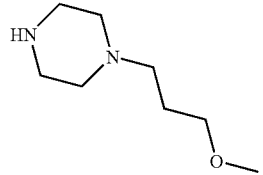 | MDP | 502.38 | 2.77 |
| 210 | 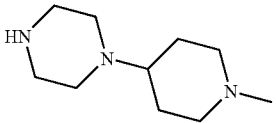 | MDP | 527.37 | 2.47 |

-continued
| EXAMPLE | Amine | Purification | m/z | RT (min) |
|---|---|---|---|---|
| 211 | 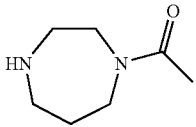 | MDP | 486.29 | 3.09 |
| 212 | 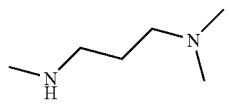 | MDP | 460.4 | 2.65 |
| 213 | 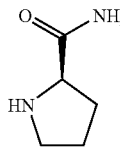 | MDP | 458.36 | 3.18 |
| 214 | 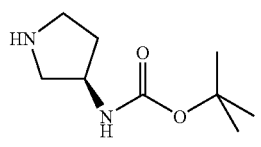 | MDP | 530.45 | 3.52 |
| 215 | 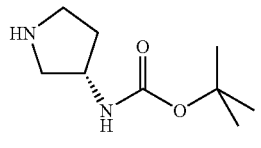 | MDP | 530.45 | 3.46 |
| 216 | 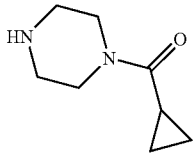 | MDP | 498.4 | 3.23 |
| 217 | 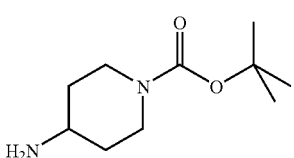 | MDP | 544.48 | 3.61 |
| 218 | 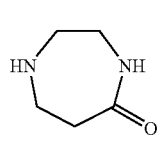 | MDP | 458.35 | 3 |
| 219 | 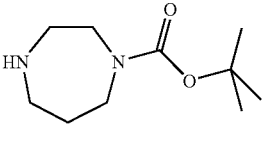 | MDP | 544.46 | 3.61 |
| 220 | 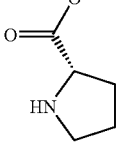 | Chromatography (DCM/MeoH 98:2) | 473.33 | 3.48 |

-continued

| EXAMPLE | Amine | Purification | m/z | RT (min) |
|---|---|---|---|---|
| 221 | ![piperazine ethyl carbamate] | Chromatography (DCM/MeoH 98:2) | 502.38 | 3.43 |
| 222 | ![piperazine Boc] | Trituration (EtOAc) | 530.39 | 3.65 |
| 223 | ![N-methyl homopiperazine] | Trituration (EtOAc) | 458.32 | 2.8 |
| 224 | ![piperazine propanol] | Prep HPLC | 488.35 | 2.63 |
| 225 | ![piperazine dimethylaminoethyl] | Crystallisation (MeOH) | 501.4 | 2.62 |

EXAMPLE 226

5Chloro-1H-pyrrolo[2,3-c]pyridine-2-carboxylic acid [1-(S)-(4-fluorobenzyl)-2-oxo-2-piperazin-1-ylethyl]amide

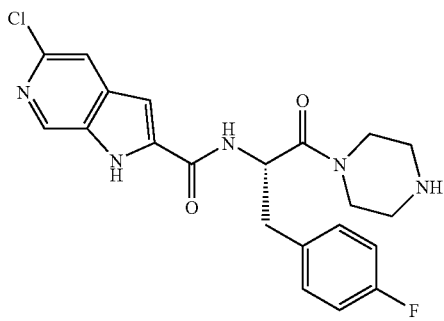

Prepared according to EXAMPLE 180 from 4-[2-(S)-[5-chloro-1H-pyrrolo[2,3-c]pyridine-2-carbonyl)amino]-3-(4-fluorophenyl)propionyl]piperazine-1-carboxylic acid tert-butyl ester (prepared according to EXAMPLE 222). Purification gave the title compound as a yellow powder. m/z (ES$^+$)=430.34 [M+H]$^+$; RT=2.56 min.

EXAMPLE 227

2-(S)-[(5-Chloro-1H-pyrrolo[2,3-c]pyridine-2-carbonyl)amino]-3-(4-fluorophenyl)propionic acid ethyl ester

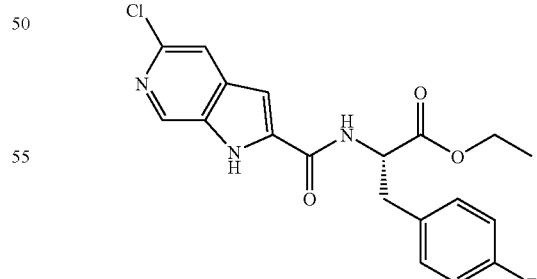

Prepared according to EXAMPLE 41 using p-fluoro-L-phenylalanine ethyl ester hydrochloride instead of L-phenylalanine ethyl ester hydrochloride. Chromatography gave the title compound as a yellow powder. m/z (ES$^+$)=390.27 [M+H]$^+$; RT=3.71 min.

EXAMPLE 228

2-(S)-[(5-Chloro-1H-pyrrolo[2,3-c]pyridine-2-carbonyl)amino]-3-(4-fluorophenyl)propionic acid

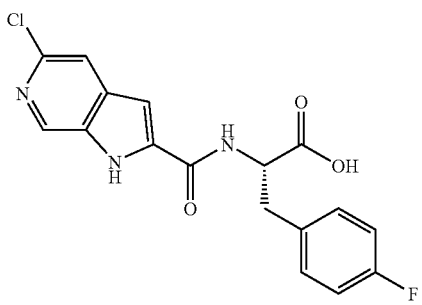

The title compound was prepared according to EXAMPLE 42 using 2-(S)-[(5-chloro-1H-pyrrolo[2,3-c]pyridine-2-carbonyl)amino]-3-(4-fluorophenyl)propionic acid ethyl ester (EXAMPLE 227). Solvent was removed in vacuo and the residue taken into water. The aqueous layer was extracted with ethyl acetate (3x) then acidified with 2M HCl solution to pH 2. The precipitate was filtered and washed thoroughly with water to give the title compound as a cream-coloured powder. (ES$^+$)=362.24 [M+H]$^+$; RT=3.21 min.

EXAMPLE 229

5-Chloro-1H-pyrrolo[2,3-c]pyridine-2-carboxylic acid [2-(1,4-dioxa-8-azaspiro[4.5]dec-8-yl)-1-(S)-(4-fluorobenzyl)-2-oxoethyl]amide

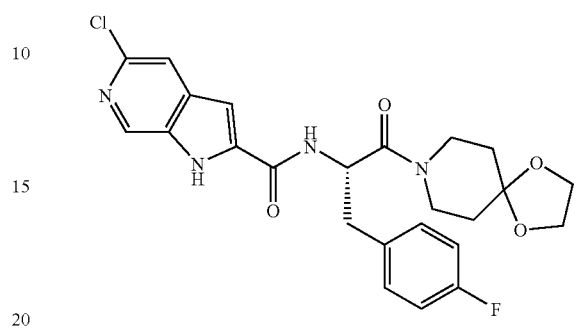

To a solution of 2-(S)-[(5-chloro-1H-pyrrolo[2,3-c]pyridine-2-carbonyl)amino]-3-(4-fluorophenyl)propionic acid (EXAMPLE 228, 40 mg, 0.11 mmol) in DMF (4 mL) was added HATU (50 mg, 0.13 mmol) and the reaction stirred for 10 min. 4-Piperidone ethylene ketal (19 mg, 0.13 mmol) was added, followed by DIPEA (23 µL, 0.13 mmol) and the reaction stirred at rt for 16 h. Solvent was removed in vacuo and the crude material partitioned between ethyl acetate (15 mL) and water (15 mL). The organic layer was washed with 1M HCl solution (15 mL), sodium bicarbonate solution (2x20 mL) then brine (2x20 mL), dried (MgSO$_4$) and the solvent removed in vacuo. Purification by chromatography using dichloromethane/methanol (9:1) as the eluent gave the title compound as a pale yellow powder. (ES$^+$)=487.30 [M+H]$^+$; RT=3.28 min.

EXAMPLES 230–237 were prepared in a similar way to EXAMPLE 229:

| EXAMPLE | Amine | Purification | m/z | RT (min) |
|---|---|---|---|---|
| 230 | ![piperidine-NH-Boc carbamate] | Chromatography (DCM/MeOH 9:1) | 544.45 | 5.39 |
| 231 | ![piperidine-CH2-NH-Boc carbamate] | Chromatography (DCM/MeOH 9:1) | 558.22 | 3.67 |
| 232 | ![piperidine-morpholine] | Chromatography (DCM/MeOH 9:1) | 514.28 | 2.67 |

-continued

| EXAMPLE | Amine | Purification | m/z | RT (min) |
|---|---|---|---|---|
| 233 | 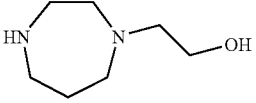 | Chromatography (DCM/MeOH 9:1) | 488.38 | 2.69 |
| 234 | 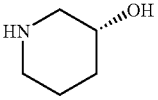 | Chromatography (DCM/MeOH 9:1) | 445.28 | 3.17 |
| 235 | 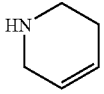 | Chromatography (EtOAc/PE 3:1) | 427.35 | 3.5 |
| 236 | 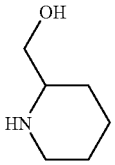 | prep. HPLC | 459.4 | 3.2 |
| 237 |  | Chromatography (EtOAc) | 413.2 | 3.31 |

EXAMPLE 238

5-Chloro-1H-pyrrolo[2,3-c]pyridine-2-carboxylic acid [2-(1,1-dioxo-1,6-thiomorpholin-4-yl)-1-(S)-(4-fluorobenzyl)-2-oxoethyl]amide

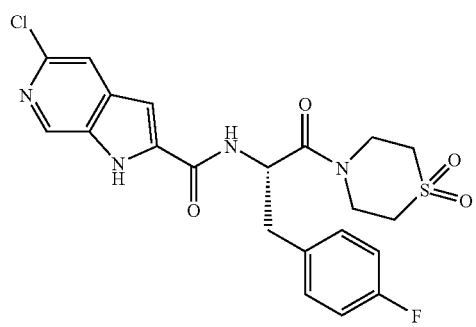

Prepared according to EXAMPLE 229 from 2-(S)-[(5-chloro-1H-pyrrolo[2,3-c]pyridine-2-carbonyl)amino]-3-(4-fluorophenyl)propionic acid (EXAMPLE 228) and thiomorpholine-1,1-dioxide (Preparation 77). Purification by trituration with methanol gave the title compound as a pale yellow powder. (ES$^+$)=479.24 [M+H]$^+$; RT=3.17 min.

EXAMPLE 239

1-[2-(S)-[(5-Chloro-1H-pyrrolo[2,3-c]pyridine-2-carbonyl)amino]-3-(4-fluorophenyl)propionly]piperidine-4-carboxylic acid methyl ester

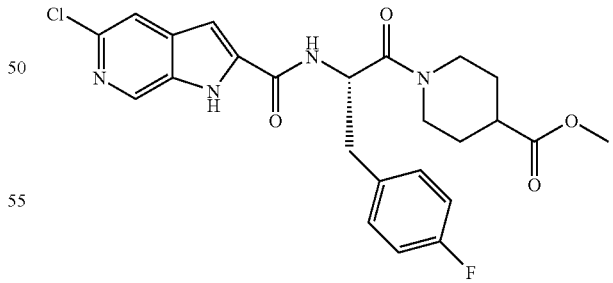

Prepared according to EXAMPLE 229 from 2-(S)-[(5-chloro-1H-pyrrolo[2,3-c]pyridine-2-carbonyl)amino]-3-(4-fluorophenyl)propionic acid (EXAMPLE 228) and piperidine-4-carboxylic acid methyl ester hydrochloride (Preparation 78). Purification by chromatography using ethyl acetate/petroleum ether (70:30) as the eluent gave the title compound as a pale yellow powder. m/z (ES$^+$)=487.32 [M+H]$^+$; RT=3.44 min.

EXAMPLE 240 WAS PREPARED IN A SIMILAR WAY TO EXAMPLE 239:

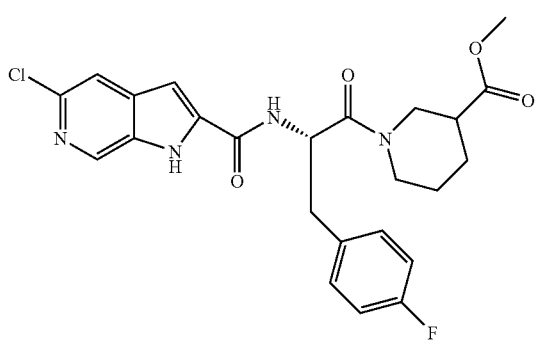

m/z (ES$^+$)=487.35 [M+H]$^+$; RT=3.88 min.

EXAMPLE 241

5-Chloro-1H-pyrrolo[2,3-c]pyridine-2-carboxylic acid [1-(S)-benzyl-2-(4-hydroxypiperidin-1-yl)-2-oxoethyl]amide

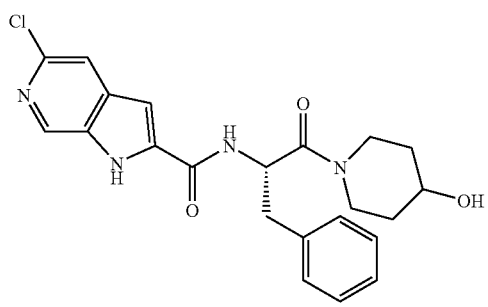

The title compound was prepared according to EXAMPLE 229 using 2-(S)-[(5-chloro-1H-pyrrolo[2,3-c]pyridine-2-carbonyl)amino]-3-phenylpropionic acid (EXAMPLE 42) and 4-hydroxypiperidine. Purification by chromatography using dichloromethane/methanol (9:1) as the eluent gave the title compound as an orange powder. m/z (ES$^+$)=427.35 [M+H]$^+$; RT=2.99 min.

EXAMPLE 242

5-Chloro-1H-pyrrolo[2,3-c]pyridine-2-carboxylic acid [2-(2-carbamoylpiperidin-1-yl)-1-(S)-(4-fluorobenzyl)-2-oxoethyl]amide

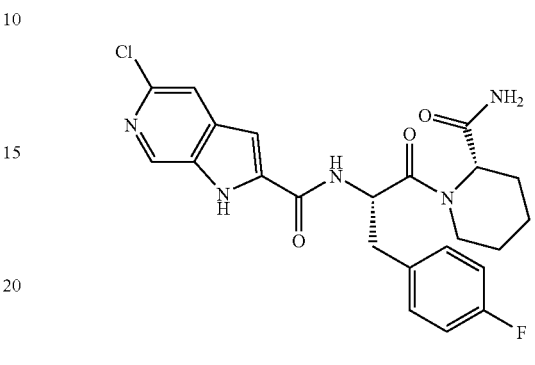

To a solution of piperidine-2-carboxylic acid amide hydrochloride (Preparation 80, 24 mg, 0.17 mmol) in DMF (3 mL) was added 2-(S)-[(5-chloro-1H-pyrrolo[2,3-c]pyridine-2-carbonyl)amino]-3-(4-fluorophenyl)propionic acid (EXAMPLE 230, 52 mg, 0.14 mmol), followed by HATU (65.6 mg, 0.17 mmol) and DIPEA (63 µL, 0.36 mmol), and the reaction stirred at rt for 16 h. Solvent was removed in vacuo, purification via preparative HPLC gave the title compound as an off-white powder. m/z (ES$^+$)=472.31 [M+H]$^+$; RT=3.19 min.

EXAMPLE 243

5-Chloro-1H-pyrrolo[2,3-c]pyridine-2-carboxylic acid {1-(S)-(4-fluorobenzl)-2-[4-(2-methoxyethoxy)piperidin-1-yl]-2-oxoethyl}amide

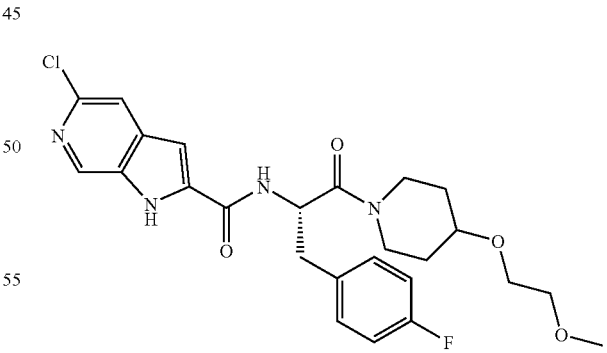

The title compound was prepared according to EXAMPLE 229 from 2-(S)-[(5-chloro-1H-pyrrolo[2,3-c]pyridine-2-carbonyl)amino]-3-(4-fluorophenyl)propionic acid (EXAMPLE 228) and 4-(2-methoxyethoxy)piperidine hydrochloride (Preparation 82). Purification by chromatography using dichloromethane/methanol (95:5) as the eluent gave the title compound as an off-white powder. m/z (ES$^+$)=503.26 [M+H]$^+$; RT=3.31 min.

EXAMPLE 244

5-Chloro-1H-pyrrolo[2,3-c]pyridine-2-carboxylic acid {1-(S)-(4-fluorobenzyl)-2-[4-(3-methoxypropoxy)piperidin-1-yl]-2-oxoethyl}amide

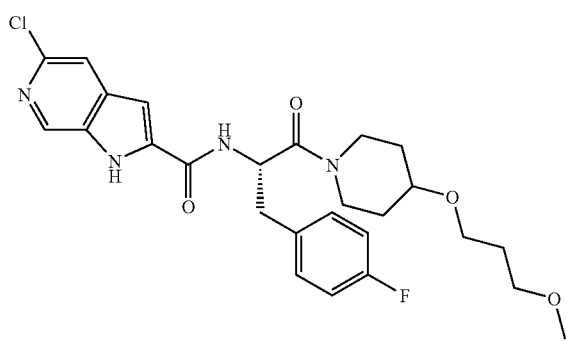

The title compound was prepared according to EXAMPLE 229 using 4-(3-methoxypropoxy)piperidine hydrochloride, synthesised from the appropriate starting materials (Preparations 81 and 82). Purification by chromatography using dichloromethane/methanol (9:1) as the eluent gave the title compound as an off-white powder. m/z (ES$^+$)=517.36 [M+H]$^+$; RT=3.41 min.

EXAMPLE 245

5-Chloro-1H-pyrrolo[2.3-c]pyridine-2-carboxylic acid [2-(4-acetylaminopiperidin-1-yl)-1-(S)-(4-fluorobenzyl)-2-oxoethyl]amide

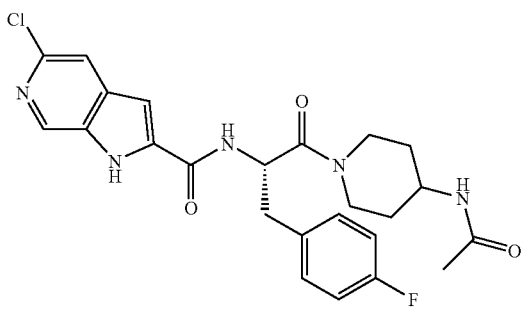

To a solution of acetic acid (7.5 µL, 0.13 mmol) in DMF (5 mL) was added EDCI (33 mg, 0.17 mmol), HOBt (19.5 mg, 0.14 mmol), 5-chloro-1H-pyrrolo[2,3-c]pyridine-2-carboxylic acid [2-(4-aminopiperidin-1-yl)-1-(S)-(4-fluorobenzyl)-2-oxoethyl]amide (EXAMPLE 180, 70 mg, 0.16 mmol) and DIPEA (57 µL, 0.33 mmol), and the reaction stirred at rt for 16 h. Solvent was removed in vacuo then crude material partitioned between ethyl acetate (15 mL) and water (15 mL). The organic layer was washed with NaHCO$_3$ (2×20 mL) and brine (2×30 mL), dried (MgSO$_4$) and the solvent removed in vacuo. Purification by chromatography using dichloromethane/methanol (95:5) as the eluent gave the title compound as an off-white powder. m/z (ES$^+$)=486.27 [M+H]$^+$; RT=3.16 min.

EXAMPLE 246

5-Chloro-1H-pyrrolo[2,3-c]pyridine-2-carboxylic acid [2-[4-(acetylaminomethyl)piperidin-1-yl]-1-(S)-(4-fluorobenzyl)-2-oxoethyl]amide

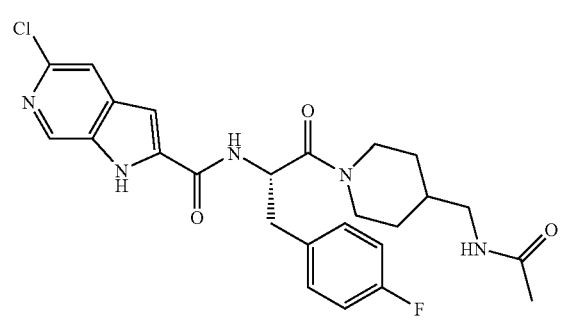

The title compound was prepared from 5-chloro-1H-pyrrolo[2,3-c]pyridine-2-carboxylic acid [2-(4-aminomethylpiperidin-1-yl)-1-(S)-(4-fluorobenzyl)-2-oxyethyl]amide (EXAMPLE 229 then 180 from the appropriate piperidin-4-ylmethylcarbamic acid tert-butyl ester). Purification by preparative HPLC gave the title compound as a white powder. m/z (ES$^+$)=500.38 [M+H]$^+$; RT=3.14 min.

EXAMPLE 247

5-Chloro-1H-pyrrolo[2,3-c]pyridine-2-carboxylic acid [1-(R)-(4-fluorobenzyl)-2-(4-hydroxypiperidin-1-yl)-2-oxoethyl]amide

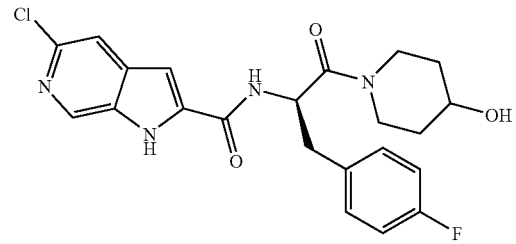

The title compound was prepared according to EXAMPLE 1 from 5-chloro-1H-pyrrolo[2,3-c]pyridine-2-carboxylic acid (Preparation 18) and 2-(R)-amino-3-(4-fluorophenyl)-1-(4-hydroxypiperidin-1-yl) propan-1-one hydrochloride (Preparation 84). Purification by chromatography using dichloromethane/methanol (92:8) as the eluent gave the title compound as a pale yellow powder. m/z (ES$^+$)=445.34 [M+H]$^+$; RT=3.10 min.

EXAMPLE 248

4-{[2-(S)-[(5-Chloro-1H-pyrrolo[2,3-c]pyridine-2-carbonyl)amino]-3-(4-fluorophenyl)propionyl]methylamino}piperidine-1-carboxylic acid tert-butyl ester

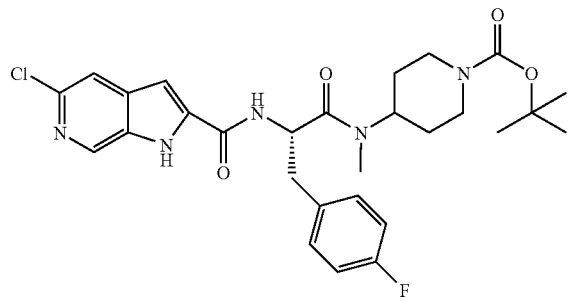

The title compound was prepared according to EXAMPLE 229 from 2-(S)-[(5-chloro-1H-pyrrolo[2,3-c]pyridine-2-carbonyl)amino]-3-(4-fluorophenyl)-propionic acid (EXAMPLE 228) and 4-methylaminopiperidine-1-carboxylic acid tert-butyl ester (Preparation 86). Purification by chromatography using dichloromethane/methanol (95:5) as the eluent gave the title compound as a pale yellow powder. m/z (ES$^+$)=558.48 [M+H]$^+$; RT=3.82 min.

EXAMPLE 249

5-Chloro-1H-pyrrolo[2,3-c]pyridine-2-carboxylic acid [2-(S)-(4-fluorophenyl)-1-(methylpiperidin-4-yl carbamoyl)ethyl]amide

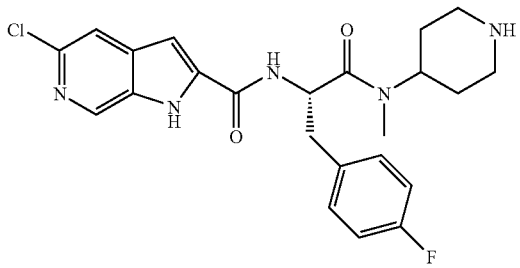

The title compound was prepared according to Preparation 82, from 4-{[2-(S)-[(5-chloro-1H-pyrrolo[2,3-c]pyridine-2-carbonyl)amino]-3-(4-fluorophenyl)propionyl]methylamino}piperidine-1-carboxylic acid tert-butyl ester (EXAMPLE 248), to give the title compound as the hydrochloride salt as a yellow crystalline solid. m/z (ES$^+$)=458.30 [M+H]$^+$; RT=2.86 min. The product was dissolved in saturated sodium bicarbonate solution and extracted into ethyl acetate. Organic solvent was removed in vacuo to give the title compound as the free base as a yellow powder. m/z (ES$^+$)= 458.33 [M+H]$^+$; RT=2.82 min.

EXAMPLE 250

5-Chloro-1H-pyrrolo2,3-c]pyridine-2-carboxylic acid {2-(S)-(4-fluorophenyl)-1-[methyl(tetrahydropyran-4-yl)carbamoyl]ethyl}amide

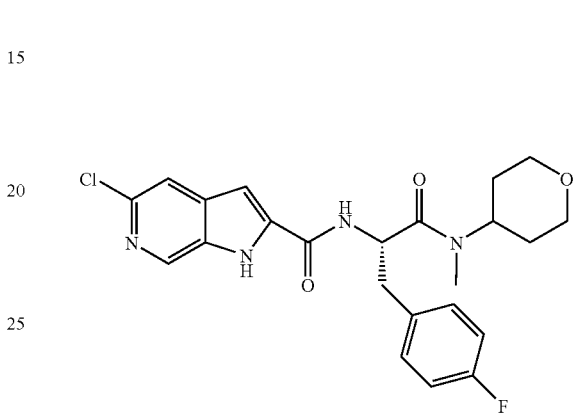

The title compound was prepared according to EXAMPLE 229 from 2-(S)-[(5-chloro-1H-pyrrolo[2,3-c]pyridine-2-carbonyl)amino]-3-(4-fluorophenyl)propionic acid (EXAMPLE 228) and methyl(tetrahydropyran-4-yl) amine hydrochloride (Preparation 88). m/z (ES$^+$)=459.27 [M+H]$^+$; RT=3.41 min.

EXAMPLE 251

5-Chloro-1H-pyrrolo2,3-c]pyridine-2-carboxylic acid [2-(4-dimethylaminopiperidin-1-yl)-1-(S)-(4-fluorobenzyl)-2-oxoethyl]amide

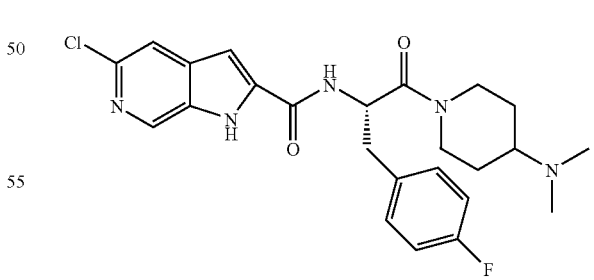

The title compound was prepared according to EXAMPLE 35 from 2-(S)-[(5-chloro-1H-pyrrolo[2,3-c]pyridine-2-carbonyl)amino]-3-(4-fluorophenyl)propionic acid (EXAMPLE 228) and dimethylpiperidin-4-yl amine (Preparation 90). Purification by preparative HPLC gave the title compound as a yellow crystalline solid. m/z (ES$^+$)=472.34 [M+H]$^+$; RT=2.64 min.

EXAMPLE 252

5-Chloro-1H-pyrrolo[2,3-c]pyridine-2-carboxylic acid [1-(S)-(4-fluorobenzyl)-2-(4-methanesulfonylaminopiperidin-1-yl)-2-oxoethyl]amide

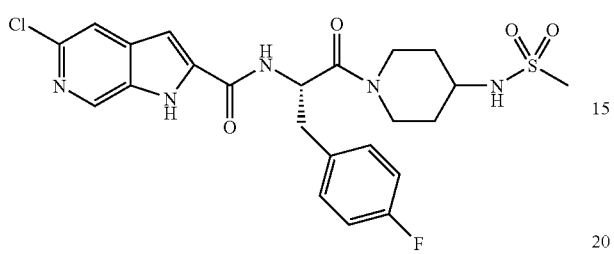

The title compound was prepared according to EXAMPLE 229 from 2-(S)-[(5-chloro-1H-pyrrolo[2,3-c]pyridine-2-carbonyl)amino]-3-(4-fluorophenyl)propionic acid (EXAMPLE 228) and N-piperidin-4-yl methanesulfonamide hydrochloride (Preparation 92). Purification gave the title compound as an off-white powder. m/z (ES$^+$)=522.30 [M+H]$^+$; RT=3.29 min.

EXAMPLE 253

2-(S)-[(5-Chloro-1H-pyrrolo[2,3-c]pyridine-2-carbonyl)-amino]-3-pyridin-4yl-propionic acid methyl ester

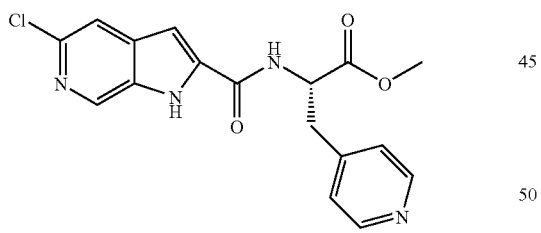

To a solution of 5-chloro-1H-pyrrolo[2,3-c]pyridine-2-carboxylic acid (Preparation 18, 185 mg, 0.94 mmol) in DMF (7 mL) was added 2-(S)-amino-3-pyridin-4-yl propionic acid methyl ester hydrochloride (Preparation 93, 204 mg, 0.94 mmol) followed by TBTU (333 mg, 1.04 mmol) and DIPEA (740 µL, 4.24 mmol), and the reaction stirred at rt for 16 h. Solvent was removed in vacuo and the residue partitioned between ethyl acetate (30 mL) and water (30 mL). The organic layer was washed with water (2×30 mL), NaHCO$_3$ solution (3×40 mL) then brine (3×50 mL), dried (MgSO$_4$) and the solvent removed in vacuo. Purification by chromatography (SiO$_2$, EtOAc) gave the title compound as a pink powder. m/z (ES$^+$)=359.11 [M+H]$^+$; RT=2.42 min.

EXAMPLE 254

5-Chloro-1H-pyrrolo2,3-c]pyridine-2-carboxylic acid (1-dimethylcarbamoyl-2-(S)-pyridin-4-yl-ethyl) amide

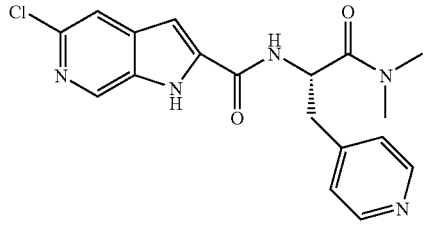

The title compound was prepared according to EXAMPLE 253 from 2-(S)-[(5-chloro-1H-pyrrolo[2,3-c]pyridine-2-carbonyl)amino]-3-pyridin-4-yl-propionic acid (EXAMPLE 259) and dimethylamine hydrochloride. Purification by preparative HPLC gave the title compound as an off-white powder. m/z (ES$^+$)=372.13 [M+H]$^+$; RT=2.31 min.

EXAMPLE 255 was prepared in a similar way to 254:

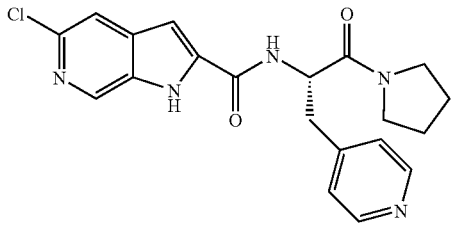

m/z (ES$^+$)=398.15 [M+H]$^+$; RT=2.53 min.

EXAMPLE 256

5-Chloro-1H-pyrrolo[2,3-c]pyridine-2-carboxylic acid [2-(1,4-dioxa-7-aza-spiro[4.5]dec-7-yl)-1-(S)-(4-fluorobenzyl)-2-oxoethyl]amide

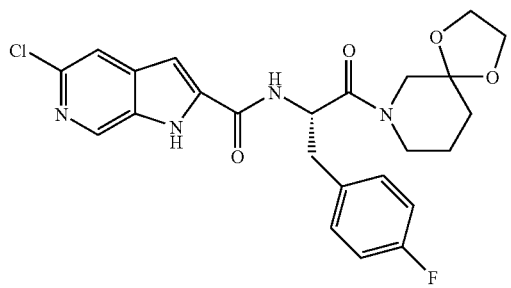

To a suspension of 2-(S)-[(5-chloro-1H-pyrrolo[2,3-c]pyridine-2-carbonyl)amino]-3-(4-fluorophenyl)propionic acid (EXAMPLE 228, 80 mg, 0.22 mmol) in ethanol (6 mL) was added DMTMM (78 mg, 0.27 mmol) and the reaction stirred for 5 min. To the mixture was added 1,4-dioxa-7-aza-spiro[4.5]decane (Preparation 94, 35 mg, 0.24 mmol) and stirring continued for 16 h. Solvent was removed in vacuo and the crude material partitioned between ethyl acetate and water. The organic layer was washed with NaHCO$_3$ solution (2×20 mL) then brine (2×20 mL), dried (MgSO$_4$) and the solvent removed in vacuo. Purification by chromatography using dichloromethane/methanol (95:5) as the eluent gave the title compound as a pale yellow powder. m/z (ES$^+$)=487.21 [M+H]$^+$; RT=3.50 min.

EXAMPLE 257

5-Chloro-1H-pyrrolo[2,3-c]pyridine-2-carboxylic acid [2-(3R,4R) dihydroxypyrrolidin-1-yl)-1-(S)-(4-fluorobenzyl)-2-oxoethyl]amide

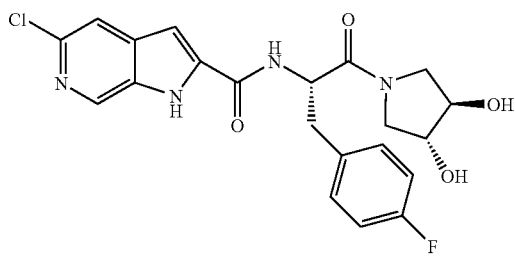

The title compound was prepared according to EXAMPLE 229 using (3R,4R)-dihydroxypyrrolidine (prepared according to Preparation 23 from the commercially available benzyl derivative). Additional crystallisation from methanol gave the title compound as colourless crystals. m/z (ES$^+$)=447.33 [M+H]$^+$; RT=2.99 min.

EXAMPLE 258

5-Chloro-1H-pyrrolo[2,3-c]pyridine-2-carboxylic acid [2-(3-(S)-4-(S) dihydroxypyrrolidin-1-yl)-1-(S)-(4-fluorobenzyl)-2-oxoethyl]amide

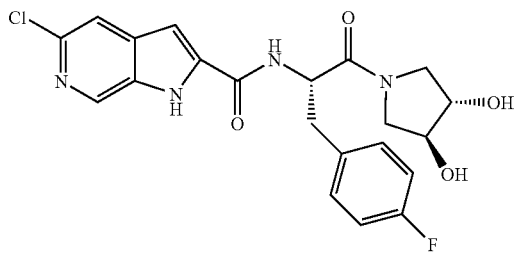

The title compound was prepared according to EXAMPLE 229 using 3-(S)-4-(S)-dihydroxypyrrolidine (prepared according to Preparation 23). Additional crystallisation from methanol gave the title compound as colourless crystals. m/z (ES$^+$)=447.33 [M+H]$^+$; RT=3.07 min.

EXAMPLE 259

2-(S)-[(5-Chloro-1H-pyrrolo[2,3-c]pyridine-2-carbonyl)amino]-3-pyridin-4-yl-propionic acid

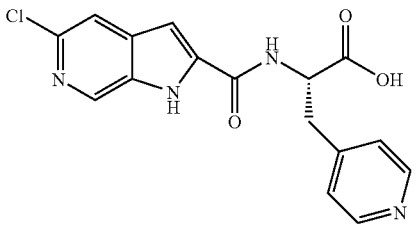

The title compound was prepared according to EXAMPLE 42 from 2-(S)-[(5-chloro-1H-pyrrolo[2,3-c]pyridine-2-carbonyl)amino]-3-pyridin-4-yl-propionic acid methyl ester (EXAMPLE 253). m/z (ES$^+$)=345.09 [M+H]$^+$.

EXAMPLE 260

5-Chloro-1H-pyrrolo[2,3-c]pyridine-2-carboxylic acid (1-(S)-benzyl-2-oxo-2-phenylethyl)amide

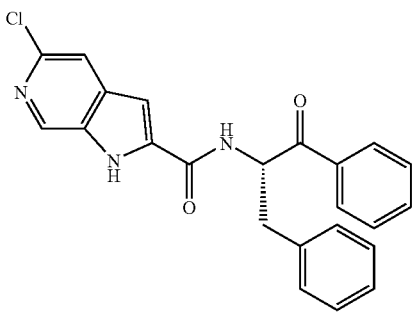

To a solution of 5-chloro-1H-pyrrolo[2,3-c]pyridine-2-carboxylic acid [2-phenyl-1-(S)-(2-phenyl-[1,3]dioxolan-2-yl)ethyl]amide (Preparation 96, 47 mg, 0.105 mmol) in acetone (20 mL) was added aqueous hydrochloric acid (1 mL, 1M). After stirring under reflux for 3 days the solvent was removed in vacuo. The residue was distributed between ethyl acetate (100 mL) and saturated sodium carbonate solution (50 mL). After separation the organic layer was washed with brine (50 ml), dried (MgSO$_4$) and concentrated to a residue which was purified by flash chromatography on silica gel (eluent: hexane/ethyl acetate: 50/50) to give the title compound as colourless solid. m/z (ES$^+$)=404.21 [M+H]$^+$; RT=3.58 min.

EXAMPLE 261

5-Chloro-1H-pyrrolo[2,3-c]pyridine-2-carboxylic acid (2-hydroxy-2-pyridin-3-yl-ethyl)amide

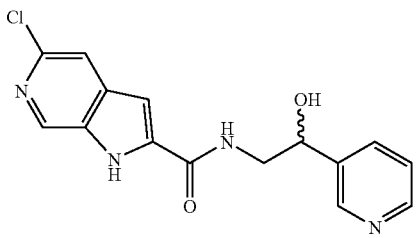

To a solution of 5-chloro-1H-pyrrolo[2,3-c]pyridine-2-carboxylic acid (Preparation 18, 296 mg, 1.51 mmol) and 2-amino-1-pyridin-3-ylethanol (Preparation 98, 214 mg, 1.55 mmol) in DMF (10 mL) was added HOBt (225 mg, 1.47 mmol), DIPEA (0.55 mL, 3.16 mmol) and EDCI (340 mg, 1.77 mmol). After stirring at rt for 12 h the solvent was removed in vacuo and the residue then taken up in THF (150 mL) and washed with diluted sodium hydroxide solution (1M, 50 mL) and brine (2×50 mL). The solution was dried (MgSO$_4$) and concentrated to an oil that was further purified by flash chromatography on silica gel (eluent: DCM/methanol: 90/10+0.5% triethylamine) to give the title compound as off-white solid. $\delta_H$ (d$_6$ DMSO): 3.53 (2H, m), 4.85 (1H, m), 5.75 (1H, d), 7.15 (1H, s), 7.37 (1H, dd), 7.75 (2H, m), 8.47 (1H, m), 8.57 (1H, s), 8.89 (1H, appt), 12.24 (1H, s); m/z (ES$^+$)=317.17 [M+H]$^+$; RT=2.71 min.

EXAMPLE 262

5-Chloro-1H-pyrrolo[2,3-c]pyridine-2-carboxylic acid (2-(S)-hydroxy-1-(S)-methoxymethyl-2-phenyl-ethyl)amide

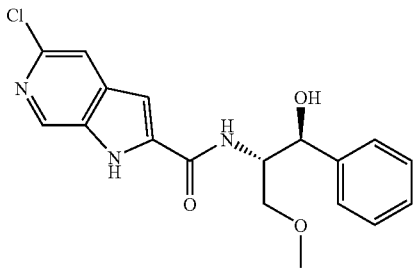

To a solution of 5-chloro-1H-pyrrolo[2,3-c]pyridine-2-carboxylic acid (Preparation 18, 223 mg, 1.13 mmol) and commercially available (1S,2S)-(+)-2-amino-3-methoxy-1-phenyl-1-propanol (200 mg, 1.10 mmol) in DMF (5 mL) was added HOBt (173 mg, 1.13 mmol), DIPEA (0.42 mL, 2.41 mmol) and EDCI (260 mg, 1.36 mmol). After stirring at rt for 12 h the mixture was added to diluted brine (100 mL, water/brine: 1/1). Extraction with ethyl acetate (4×25 mL), washing of the combined extracts with diluted hydrochloric acid (1M, 30 ml), diluted aqueous sodium hydroxide solution (1M, 30 ml) and brine (30 mL) followed by drying over magnesium sulphate gave after concentration a residue which was purified by flash chromatography on silica gel (eluent: ethyl acetate). The title compound was obtained as colourless solid. $\delta_H$ (CD$_3$OD): 3.37 (3H, s), 3.34 (1H, dd), 3.66 (1H, dd), 4.53 (1H, ddd), 5.03 (1H, d), 7.15 (1H, s), 7.25-7.45 (5H, 3m), 7.68 (1H, s), 8.58 (1H, s); m/z (ES$^+$)=360.22 [M+H]$^+$; RT=3.12 min.

EXAMPLE 263

5-Chloro-1H-pyrrolo[2,3-c]pyridine-2-carboxylic acid (1-(S)-hydroxymethyl-2-oxo-2-phenylethyl)amide

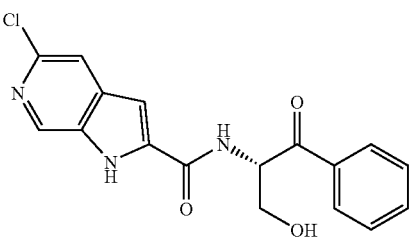

To a solution of 5-chloro-1H-pyrrolo[2,3-c]pyridine-2-carboxylic acid [1-(S) -(tert-butyldimethylsilanyloxymethyl)-2-oxo-2-phenylethyl]amide (Preparation 101, 220 mg, 0.48 mmol) in THF (10 mL) was added acetic acid (60 μL) and tetrabutylammonium fluoride solution (1 ml, 1M in THF) at rt. After stirring for 3 h the reaction mixture was distributed between ethyl acetate (100 mL) and water (30 mL). The organic layer was separated, then washed with brine (50 ml), dried (MgSO$_4$) and concentrated to a solid residue. Recrystallisation from THF gave the title compound.

m/z (ES$^+$)=344.21 [M+H]$^+$; RT=3.02 min.

EXAMPLE 264

5-Chloro-1H-pyrrolo[2,3-c]pyridine-2-carboxylic acid (1-(S)-methoxymethyl-2-oxo-2-phenylethyl)amide

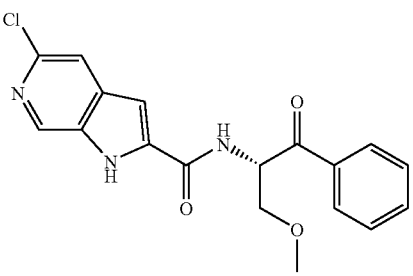

5-Chloro-1H-pyrrolo[2,3-c]pyridine-2-carboxylic acid (2-(S)-hydroxy-1-(S)-methoxymethyl-2-phenylethyl)amide (EXAMPLE 262, 101 mg, 0.281 mmol) was oxidised and isolated in a similar way to Preparation 101 using Dess-Martin periodinane (240 mg, 0.566 mmol) in DCM (10 mL). The title compound was obtained by recrystallisation of the crude product from methanol. m/z (ES$^+$)=358.24 [M+H]$^+$; RT=3.18 min.

EXAMPLE 265

5-Chloro-1H-pyrrolo[2,3-c]pyridine-2-carboxylic acid (2-oxo-2-pyridin-3-ylethyl)amide

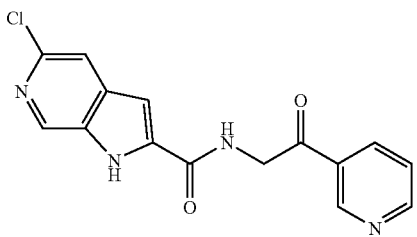

To a solution of racemic 5-chloro-1H-pyrrolo[2,3-c]pyridine-2-carboxylic acid (2-hydroxy-2-pyridin-3-ylethyl)amide (EXAMPLE 261, 80 mg, 0.253 mmol) in dry THF (20 mL) was added Dess-Martin periodinane (307 mg, 0.724 mmol). After stirring for 4 h at rt alkaline sodium thiosulfate solution was added (5.4 g $Na_2SO_3$ dissolved in 20 mL saturated $NaHCO_3$ solution) and the emulsion was vigorously stirred for additional 30 min before further diluted with water (~150 mL). Extraction with THF (4×50 mL), washing of the combined extracts with saturated sodium hydrogen carbonate (50 mL) and brine (50 mL) gave a solution which was concentrated after drying ($MgSO_4$). Purification of the residue by flash chromatography on silica gel (eluent: DCM/methanol: 90/10) gave the title compound as off-white solid. m/z ($ES^+$)=315.19 $[M+H]^+$; RT=2.65 min.

EXAMPLE 266

6-Chloro-1H-pyrrolo[2,3-b]pyridine-2-carboxylic acid (1-dimethylcarbamoyl-2-(S)-phenethyl)amide

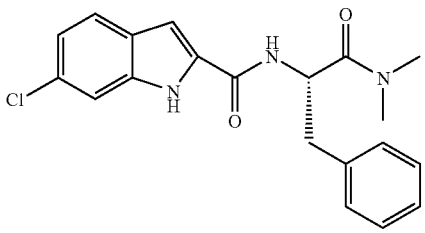

DIPEA (155 µL, 0.89 mmol), HOBt (43 mg, 0.28 mmol) and 6-chloro-1H-pyrrolo[2,3b]pyridine-2-carboxylic acid (Preparation 110, 50 mg, 0.25 mmol) was added to a stirred solution of 2-(S)-amino-N,N-dimethyl-3-phenyl propionamide hydrochloride (Preparation 8, 61 mg, 0.27 mmol) in DMF (4 mL). After 5 min EDCI (63 mg, 0.33 mmol) was added and the reaction stirred for 22 h. Purification by column chromatography ($SiO_2$, 95:5 $CH_2Cl_2$/MeOH) afforded the title compound. m/z ($ES^+$)=370.93 $[M+H]^+$; RT=3.62 min.

EXAMPLE 267

6-Chloro-1H-pyrrolo[2,3-b]pyridine-2-carboxylic acid [1-(S)-(4-fluorobenzyl)-2-(3-(S)-hydroxypyrrolidin-1-yl)-2-oxoethyl]amide

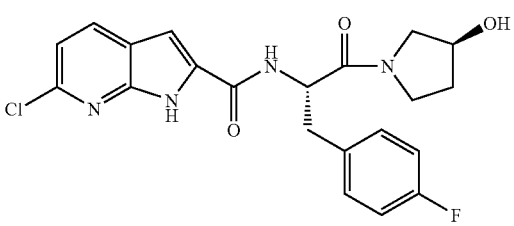

The title compound was prepared according to EXAMPLE 266 but using 2-(S)-amino-3-(4-fluorophenyl)-1-(3-(S)-hydroxypyrrolidin-1-yl)-propan-1-one hydrochloride (Preparation 103) instead of 2-(S)-amino-N,N-dimethyl-3-phenyl propionamide hydrochloride. m/z ($ES^+$)=430.94 $[M+H]^+$; RT=4.31 min.

EXAMPLE 268

6-Chloro-1H-pyrrolo[2,3-b]pyridine-2-carboxylic acid [1-(S)-(4-fluorobenzyl)-2-(4-hydroxypiperidin-1-yl)-2-oxoethyl]amide

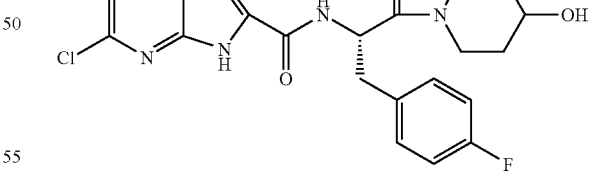

The title compound was prepared according to EXAMPLE 266 but using 2-(S)-amino-3-(4-fluorophenyl)-1-(4-hydroxypiperidin-1-yl)-propan-1-one hydrochloride (Preparation 20) instead of 2-(S)-amino-N,N-dimethyl-3-phenyl propionamide hydrochloride. Purification by column chromatography ($SiO_2$, 9:1 $CH_2Cl_2$/MeOH) gave the title compound. m/z ($ES^+$)=444.91 $[M+H]^+$; RT=3.55 min.

EXAMPLE 269

6-Chloro-1H-pyrrolo[2,3-b]pyridine-2-carboxylic acid [1-(S)-(4-fluorobenzyl)-2-oxo-2-(5-oxo-[1,4]diazepam-1-yl)ethyl]amide

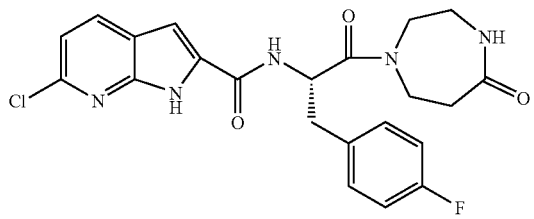

The title compound was prepared according to EXAMPLE 266 but using 1-[2-(S)-amino-3-(4-fluorophenyl)propionyl]-[1,4]diazepan-5-one hydrochloride (Preparation 112) instead of 2-(S)-amino-N,N-dimethyl-3-phenyl propionamide hydrochloride. Purification by column chromatography (SiO$_2$, 94:6 CH$_2$Cl$_2$/MeOH) gave the title compound. m/z (ES$^+$)=457.91 [M+H]$^+$; RT=3.74 min.

EXAMPLE 270

6-Chloro-1H-pyrrolo[2,3-b]pyridine-2-carboxylic acid (2-oxo-2 phenethyl)amide

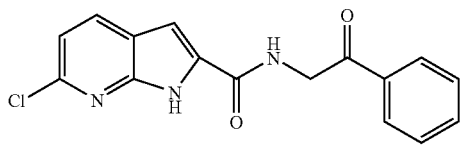

To a solution of 6-chloro-1H-pyrrolo[2,3b]pyridine-2-carboxylic acid (Preparation 110, 60 mg, 0.31 mmol) in ethanol (5 mL) was added 2-aminoacetophenone hydrochloride (58 mg, 0.34 mmol), N-methylmorpholine (74 µL, 0.67 mmol) and DMTMM (198 mg, 0.67 mmol) and the reaction stirred at rt for 16 h. Solvent was removed in vacuo and the resulting residue partitioned between ethyl acetate (20 mL) and water (20 mL). Organics were washed with 1M HCl (20 mL), water (20 mL), NaHCO$_3$ solution (2×20 mL) then brine (20 mL) before being dried (MgSO$_4$) and solvent concentrated in vacuo. Purification by column chromatography (SiO$_2$, 2:1 Pet. Ether/EtOAc then 97:3 CH$_2$Cl$_2$/MeOH) gave the title compound.

EXAMPLE 271

2-(S)-[(6-Chloro-1H-pyrrolo[2,3-b]pyridine-2-carbonyl)amino]-3-(4-fluorophenyl) propionic acid ethyl ester

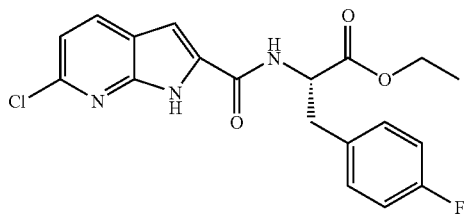

To a solution of 6-chloro-1H-pyrrolo[2,3b]pyridine-2-carboxylic acid (Preparation 110, 450 mg, 2.29 mmol) in DMF (20 mL) was added 4-fluoro phenylalanine ethyl ester hydrochloride (624 mg, 2.52 mmol), DIPEA (1.40 mL, 8.01 mmol) and HOBt. (386 mg, 2.52 mmol) and the reaction stirred. After 5 min EDCI (570 mg, 2.98 mmol) was added and stirring continued for 16 hr. Solvent was removed in vacuo then crude material partitioned between ethyl acetate (75 mL) and water (50 mL). Organics were washed with NaHCO$_3$ solution (3×50 mL) then brine (2×50 mL), dried (MgSO$_4$) and THE solvent removed in vacuo to give the title compound. m/z (ES$^+$)=389.90 [M+H]$^+$; RT=3.79 min.

EXAMPLE 272

2-(S)-[(6-Chloro-1H-pyrrolo[2,3-b]pyridine-2-carbonyl)amino]-3-(4-fluorophenyl)propionic acid

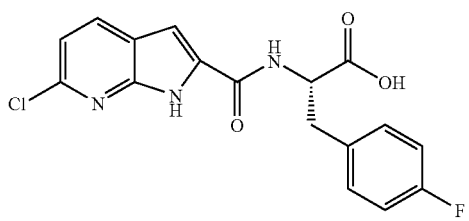

To a solution of 2-[(6-chloro-1H-pyrrolo[2,3-b]pyridine-2-carbonyl)amino]-3-(4-fluorophenyl)propionic acid ethyl ester (EXAMPLE 271, 780 mg, 2.0 mmol) in methanol (15 mL) was added 2M NaOH (2 mL, 4.0 mmol) and the reaction was stirred for 16 hr. Solvent was removed in vacuo and crude residue dissolved in water (20 mL). The aqueous phase was washed with ethyl acetate (2×20 mL), then acidified to Ph 3 with 2M HCl. The organics were extracted into ethyl acetate (2×30 mL), and then dried (MgSO$_4$) before concentrating the solvent in vacuo to provide the title compound. m/z (ES$^+$)= 361.88 [M+H]$^+$.

EXAMPLE 273

6-Chloro-1H-pyrrolo[2,3-b]pyridine-2-carboxylic acid [1-(S)-(4-fluorobenzyl)-2-oxo-2-pyrrolidin-1-yl-ethyl]amide

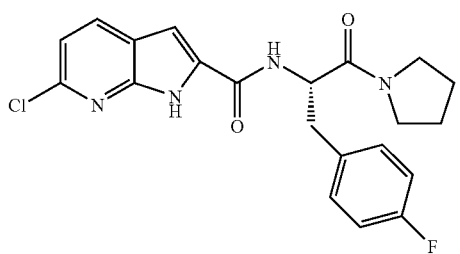

To pyrrolidine (11.5 mg, 0.14 mmol) was added a solution of DIPEA (60 µL, 0.35 mmol) in DMF (500 µL) followed by 2-(S)-[(6-chloro-1H-pyrrolo[2,3-b]pyridine-2-carbonyl) amino]-3-(4-fluorophenyl) propionic acid (EXAMPLE 272, 50 mg, 0.14 mmol) in DMF (500 µL) and HOBt (23 mg, 0.15 mmol) in DMF (500 µL) and the mixture stirred. After 5 min EDCI (34.5 mg, 0.18 mmol) in DMF (500 µL) was added and the reaction stirred for 16 hr. Solvent was removed in vacuo then crude material purified by mass-directed purification to give the title compound. m/z (ES$^+$)=414.93 [m+H]$^+$; RT=3.77 min.

EXAMPLES 274–276 were prepared in the same way:

| Example | Structure | m/z | RT (min) |
|---|---|---|---|
| 274 | 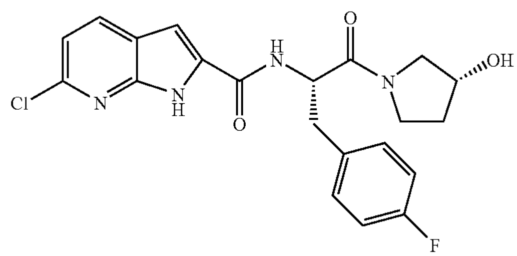 | 430.92 | 3.46 |
| 275 | 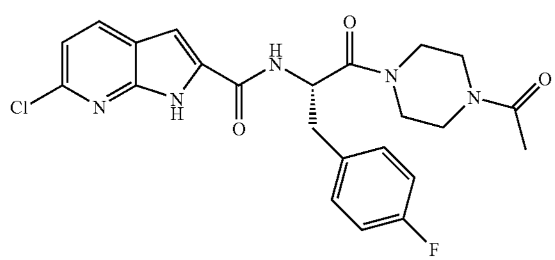 | 471.92 | 3.51 |
| 276 | 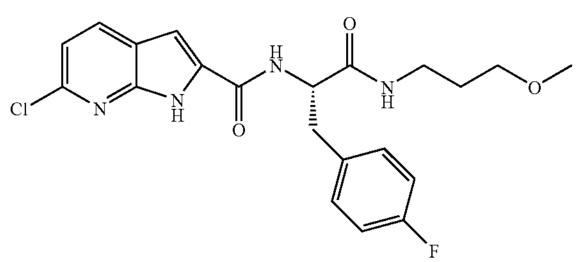 | 432.92 | 3.79 |

EXAMPLES 277–280 were prepared in the same way, but purification was by trituration from menthol:

| Example | Structure | m/z | RT (min) |
|---|---|---|---|
| 277 | 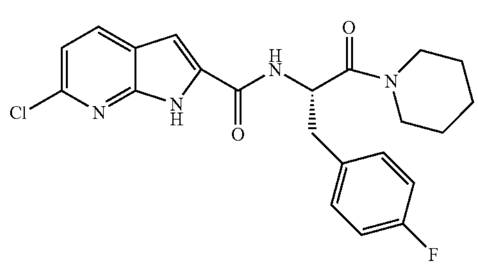 | 428.95 | 5.06 |

-continued

| Example | Structure | m/z | RT (min) |
|---|---|---|---|
| 278 | 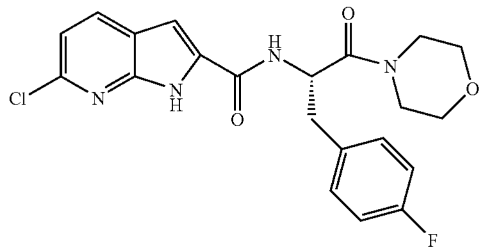 | 430.93 | 3.65 |
| 279 | 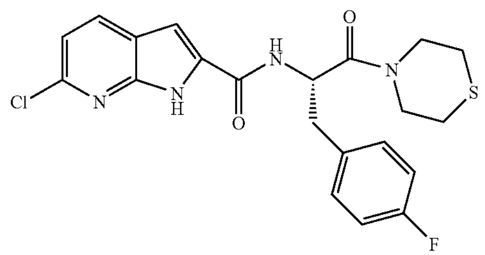 | 446.9 | 3.9 |
| 280 | 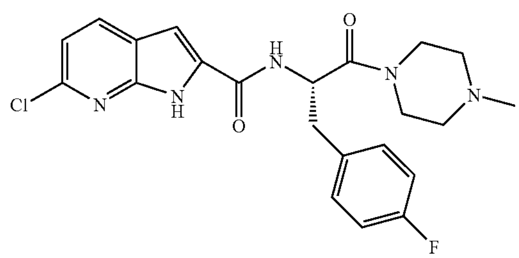 | 443.92 | 3.05 |

EXAMPLE 281

2-(S)-[(5-Chloro-1H-pyrrolo[2,3-b]pyridine-2-carbonyl)amino]-3-(4-fluorophenyl)-propionic acid tert-butyl ester

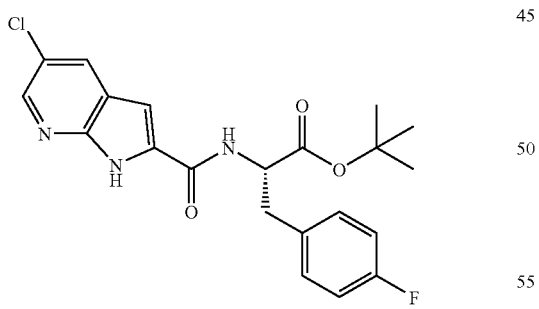

To a solution of 5-chloro-1H-pyrrolo[2,3-b]pyridine-2-carboxylic acid (Preparation 57, 500 mg, 2.54 mmol) in DMF (20 mL) was added 2-(S)-amino-3-(4-fluorophenyl)propionic acid tert-butyl ester hydrochloride (Preparation 114, 701 mg, 2.54 mmol), HOBt (344 mg, 2.54 mmol) and DIPEA (1.4 mL, 7.88 mmol). After 5 min, EDCI (634 mg, 3.31 mmol) was added and the reaction mixture stirred at rt for 72 h. The solvent was removed in vacuo and the solid partitioned between water (50 mL) and ethyl acetate (3×40 mL). The combined organic phase was washed with brine (20 mL), dried (MgSO$_4$), concentrated in vacuo and purified by chromatography on silica gel eluting with methanol:dichloromethane (1:99) to give the title compound. $\delta_H$ (CD$_3$OD): 1.42 (9H, s), 3.09 (1H, dd), 3.22 (1H, dd), 4.76 (1H, m), 6.98 (2H, m), 7.07 (1H, s), 7.27 (2H, m), 8.06 (1H, d), 8.28 (1H, d); m/z (ES$^+$)=418 [M+H]$^+$.

EXAMPLE 282

2-(S)-[(5-Chloro-1H-pyrrolo[2,3-b]pyridine-2-carbonyl)amino]-3-(4-fluorophenyl)-propionic acid

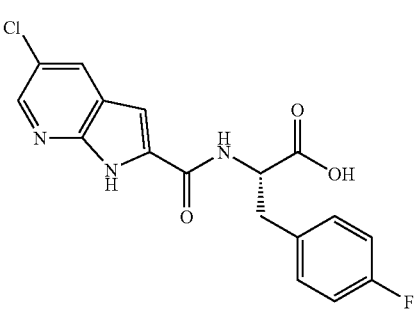

Trifluoroacetic acid (1.9 mL, 24.3 mmol) was added to a suspension of 2-(S)-[(5-chloro-1H-pyrrolo[2,3-b]pyridine-2-carbonyl)amino]-3-(4-fluorophenyl)-propionic acid tert-butyl ester (EXAMPLE 281, 507 mg, 1.21 mmol) in DCM (25 mL) and the reaction mixture was stirred at rt for 16 h. Further trifluoroacetic acid (2 mL) was added and the reaction was stirred at rt for 48 h. The solvent was removed in vacuo and the solid partitioned between 1N hydrochloric acid (50 mL) and ethyl acetate (3×30 mL). The combined organic fractions were washed with brine (20 mL), dried (MgSO$_4$) and concentrated in vacuo to give the title compound. $\delta_H$ (CD$_3$OD): 3.11 (1H, dd), 3.33 (1H, dd), 4.88 (1H, m), 6.97 (2H, m), 7.06 (1H, s), 7.28 (2H, m), 8.08 (1H, d), 8.29 (1H, d); m/z (ES$^+$)=362 [M+H]$^+$; $^{RT=}$3.67 min.

EXAMPLE 283

5-Chloro-1H-pyrrolo[2,3-b]pyridine-2-carboxylic acid [1-(S)-(4-fluoro-benzyl)-2-(3-hydroxy-pyrrolidin-1-yl)-2-oxo-ethyl]-amide

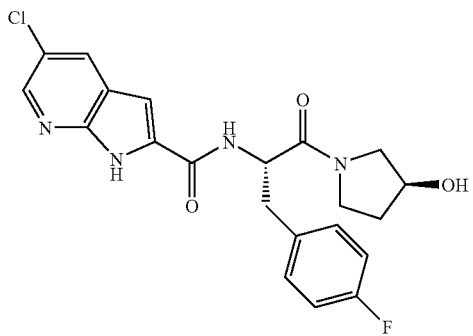

To a solution of 5-chloro-1H-pyrrolo[2,3-b]pyridine-2-carboxylic acid (Preparation 57, 34 mg, 0.17 mmol) in DMF (5 mL) was added 2-(S)-amino-3-(4-fluorophenyl)-1-(3-(S)-hydroxypyrrolidin-1-yl)propan-1-one hydrochloride (Preparation 103, 50 mg, 0.17 mmol), HOBt (23 mg, 0.17 mmol) and DIPEA (94 µL, 0.54 mmol). After 5 min, EDCI (43 mg, 0.23 mmol) was added and the reaction stirred at rt for 16 h. The solvent was removed in vacuo and the residue partitioned between water (25 mL) and ethyl acetate (3×20 mL). The combined organic layer was washed with 2N sodium hydroxide solution (2×10 mL), brine (10 mL), dried (MgSO$_4$) and concentrated in vacuo. Purification via chromatography on silica gel eluting with methanol:dichloromethane (7:93) gave the title compound. m/z (ES$^+$)=431 [M +H]$^+$; RT=3.49 min.

EXAMPLE 284

5-Chloro-1H-pyrrolo[2,3-b]pyridine-2-carboxylic acid (2-oxo-2-phenylethyl)amide

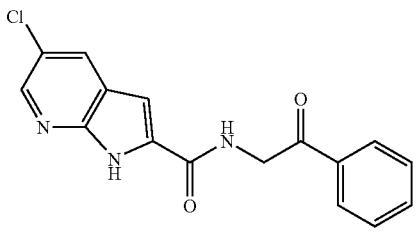

5-Chloro-1H-pyrrolo[2,3-b]pyridine-2-carboxylic acid (Preparation 57, 50 mg, 0.25 mmol), 2-aminoacetophenone hydrochloride (48 mg, 0.28 mmol) and DMTMM (85 mg, 0.31 mmol) were dissolved in THF (5 mL) and 4-methylmorpholine (31 µL, 0.28 mmol). The reaction mixture was stirred at rt for 16 h. The solvent was removed in vacuo and the residue partitioned between water (20 mL) and EtOAc (3×20 mL). The combined organics were dried (MgSO$_4$), concentrated in vacuo and purified by chromatography on silica gel eluting with methanol:dichloromethane (1:19) to give the title compound. m/z (ES$^+$)=314 [M+H]$^+$; RT=3.47 min.

EXAMPLE 285

5-Chloro-1H-pyrrolo[2,3-b]pyridine-2-carboxylic acid [2-(S)-(4-fluorophenyl)-1-(methoxymethylcarbamoyl)ethyl]amide

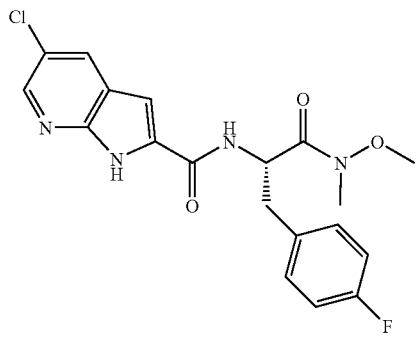

2-(S)-[(5-Chloro-1H-pyrrolo[2,3-b]pyridine-2-carbonyl)amino]-3-(4-fluorophenyl)propionic acid (EXAMPLE 282, 300 mg, 0.08 mmol) and N,O-dimethylhydroxylamine hydrochloride (8 mg, 0.08 mmol) were dissolved in THF (5 mL) and 4-methylmorpholine (9 µL, 0.08 mmol). To this was added DMTMM (28 mg, 0.10 mmol) and the reaction mixture was stirred at rt for 16 h. The solvent was removed in vacuo and the residue partitioned between water (30 mL) and EtOAc (3×30 mL). The combined organics were washed with 2N sodium hydroxide solution (2×20 ml), brine (20 ml), dried (MgSO$_4$) and concentrated in vacuo. The crude residue was purified by chromatography on silica gel eluting with methanol:dichloromethane (1:24) to give the title compound. m/z (ES$^+$)=405 [M+H]$^+$; RT=3.69 min.

EXAMPLE 286

5-Chloro-1H-pyrrolo[2,3-b]pyridine-2-carboxylic acid [1-(S)-(4-fluorobenzyl)-2-(3-hydroxy-pyrrolidin-1-yl-2-oxo-ethyl]-amide

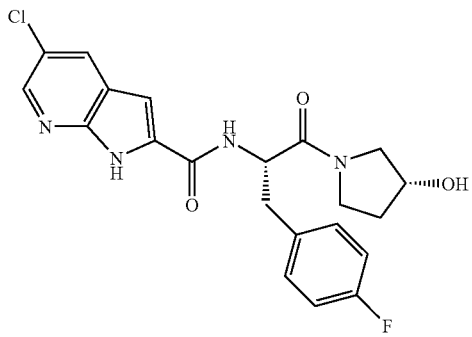

To a solution of 2-(S)-[(5-chloro-1H-pyrrolo[2,3-b]pyridine-2-carbonyl)amino]-3-(4-fluorophenyl)propionic acid (EXAMPLE 286, 30 mg, 0.08 mmol) in DMF (3 mL) was added (R)-(+)-3-hydroxypyrrolidine (7.2 mg, 0.08 mmol), HOBt (11.2 mg, 0.08 mmol) and DIPEA (30.3 µL, 0.17 mmol). After 5 min, EDCI (20.7 mg, 0.11 mmol) was added and the reaction was stirred at rt for 16 h. The solvent was removed in vacuo and the residue partitioned between water (20 mL) and ethyl acetate (3×20 mL). The combined organic fractions were washed with 2N sodium hydroxide solution (20 mL), brine (20 mL), dried (MgSO$_4$) and concentrated in vacuo. The crude product was triturated from methanol to give the title compound. m/z (ES$^+$)=431 [M+H]+; RT=3.44 min.

EXAMPLES 287–294

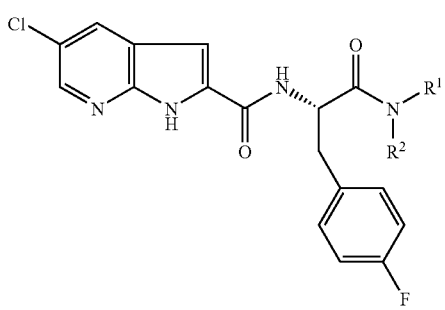

The following compounds were prepared according to the method of EXAMPLE 286 from 2-(S)-[(5-chloro-1H-pyrrolo[2,3-c]pyridine-2-carbonyl)amino]-3-(4-fluorophenyl) propionic acid (EXAMPLE 282) and the appropriate amine, with the exception that all compounds were purified by mass directed purification.

| Example | NR$^1$R$^2$ | m/z | RT (min) |
|---|---|---|---|
| 287 | morpholine | 431 | 3.47 |
| 288 | 4-methylpiperazine | 444 | 2.89 |
| 289 | HN-CH$_2$CH$_2$-OH | 405 | 3.20 |
| 290 | 4-(2-hydroxyethyl)piperazine | 474 | 2.92 |
| 291 | 4-acetylpiperazine | 472 | 3.37 |
| 292 | 3-hydroxypiperidine | 445 | 3.61 |
| 293 | HN-(CH$_2$)$_3$-OMe | 433 | 3.51 |
| 294 | HN-(CH$_2$)$_4$-OH | 433 | 3.34 |

EXAMPLE 295

6-Chloro-1H-pyrrolo[3,2-c]pyridine-2-carboxylic acid (1-dimethylcarbamoyl-2-(S)-phenylethyl)amide To a solution of 6-chloro-1H-pyrrolo[3,2-c]pyridine-2-carboxylic acid (Preparation 116, 47 mg, 0.24 mmol) in DMF (5 mL, anhydrous) was added 2-(S)-amino-N,N-dimethyl-3-phenylpropionamide hydrochloride (Preparation 8, 56 mg, 0.25 mmol), DIPEA (131 µL, 0.75 mmol) and HOBt (40 mg, 0.26 mmol) sequentially. The solution was stirred for 5 min prior to the addition of EDCI (55 mg, 0.29 mmol) in one portion. The resulting solution was stirred for 12 h at rt. The reaction mixture was partitioned between ethyl acetate (50 mL) and water/brine (150 mL, 1:1). The layers were separated and the aqueous phase extracted with ethyl acetate (3×50 mL), then the combined organics were washed with dilute HCl solution (1M, 50 mL), dilute NaOH solution (1M, 50 mL) and brine (50 mL). The organic phase was dried (MgSO$_4$), filtered and concentrated in vacuo. Purification via flash column chromatography eluting with toluene/acetone (3:1) gave the title compound. $\delta_H$ (CDCl$_3$): 2.88, 3.05 (6H, 2 s), 3.18, 3.28 (2H, 2 dd), 5.41 (2H, m), 7.02 (1H, s), 7.28–7.34 (6H, m), 8.17 (1H, d), 8.68 (1H, s), 10.58 (1H, br s); m/z (ES$^+$)=371.13 [M+H]$^+$; RT=3.28 min.

EXAMPLE 296

6-Chloro-1H-pyrrolo [3,2-c]pyridine-2-carboxylic acid [1-(S)-(4-fluorobenzyl)-2-(4-hydroxypiperidin-1-yl-2-oxoethyl]amide

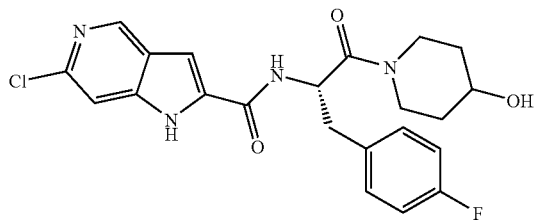

The title compound was prepared as outlined in EXAMPLE 295 from 6-chloro-1H-pyrrolo[3,2-c]pyridine-2-carboxylic acid (Preparation 116) and 2-(S)-amino-3-(4-fluorophenyl)-1-(4-hydroxypiperidin-1-yl)propan-1-one hydrochloride (Preparation 20). The product was purified by chromatography on silica gel eluting with methanol/dichloromethane (1:19) to give the title compound. $\delta_H$ (CD$_3$OD): 1.16–1.88 (4H, 3 m), 3.04–3.19 (4H, m), 3.69–4.16 (3H, 2m), 5.31 (1H, m), 7.00 (2H, m), 7.29 (3H, m), 7.42 (1H, s), 8.67 (11H, s); m/z (ES$^+$)=444.89 [M+H]$^+$; $^{RT=}$3.27 min.

EXAMPLE 297

6-Chloro-1H-pyrrolo [3.2-c]pyridine-2-carboxylic acid [1-(S)-(4-fluorobenzyl)-2-(3-(S)-hydroxypyrrolidin-1-yl)-2-oxoethyl]amide

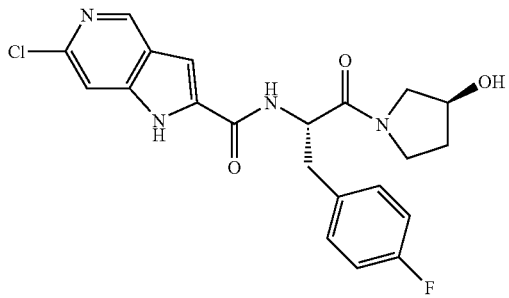

The title compound was prepared as outlined in EXAMPLE 295 from 6-chloro-1H-pyrrolo[3,2-c]pyridine-2-carboxylic acid (Preparation 116) and 2-(S)-amino-3-(4-fluorophenyl)-1-(3-(S)-hydroxypyrrolidin-1-yl)propan-1-one hydrochloride (Preparation 103). The crude product was recrystallised from ethyl acetate to give the title compound. $\delta_H$ (CD$_3$OD): 1.77–1.98 (2H, m), 3.08–3.88 (6H, 6 m), 4.30, 4.42 (1H, 2 m), 5.07, 5.09 (1H, 2m), 7.00 (2H, m), 7.30 (3H, m), 7.43 (1H, m), 8.67 (1H, s); m/z (ES$^+$)=430.90 [M+H]$^+$; RT=3.29 min.

EXAMPLE 298

5-Cyano-1H-pyrrolo[2,3-c]pyridine-2-carboxylic acid (2-oxo-2-phenylethyl)amide

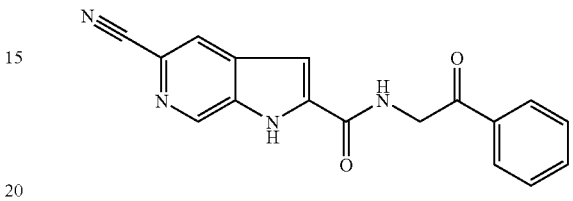

To a solution of 5-cyano-1H-pyrrolo[2,3-c]pyridine-2-carboxylic acid (Preparation 62, 0.035 g, 0.19 mmol) in THF (15 mL) under argon was added 2-aminoacetophenone hydrochloride (0.036 g, 0.21 mmol), N-methylmorpholine (25 μM, 0.23 mmol) and DMTMM (0.072 g, 0.27 mmol). The reaction mixture was stirred at rt for 16 h. The reaction mixture was concentrated to dryness in vacuo. The residue was partitioned between ethyl acetate (100 mL) and water (50 mL). The organic phase was separated and the aqueous phase was further extracted with ethyl acetate (100 mL). The combined organic extract was washed with 1N NaOH (40 mL), saturated sodium chloride (40 mL), dried (MgSO$_4$), filtered and concentrated in vacuo. Crude material was purified by chromatography in hexane/ethyl acetate (1:2) and recrystallised from methanol to give the title compound. m/z (ES$^+$)=304 [M+H]$^+$; RT=4.37.

EXAMPLE 299

2-[(5-Cyano-1H-pyrrolo[2,3-c]pyridine-2-carbonyl)amino]-3 (S)-(4-fluorophenyl)propionic acid ethyl ester

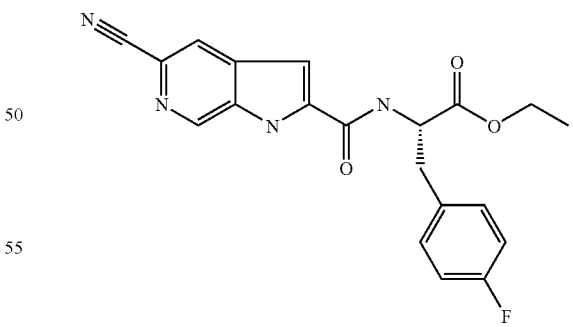

To a solution of 2-amino-3-(S)-(4-fluorophenyl)propionic acid ethyl ester hydrochloride (0.530 g, 2.14 mmol) in DMF (15 mL) was added DIPEA (1.3 mL, 7.49 mmol), HOBt (0.290 g, 2.14 mmol), 5-cyano-1H-pyrrolo[2,3-c]pyridine-2-carboxylic acid (Preparation 62, 0.400 g, 2.14 mmol) and EDCI (0.492 g, 2.57 mmol).

The reaction mixture was stirred at rt for 16 h. Reaction mixture was concentrated in vacuo and the residue was partitioned between water (150 mL) and ethyl acetate (200 mL). Organic phase was separated and the aqueous phase was further extracted with ethyl acetate (200 mL). The combined organic extracts were washed with saturated NaHCO$_3$ (75 mL), saturated sodium chloride (100 mL), dried (MgSO$_4$), filtered and concentrated in vacuo to give the title compound. m/z (ES$^+$)=381 [M+H]$^+$; RT=4.79 min.

EXAMPLE 300

2-[(5-Cyano-1H-pyrrolo[2,3-c]pyridine-2-carbonyl)aminol-3-(S)-(4-fluorophenyl)propionic acid

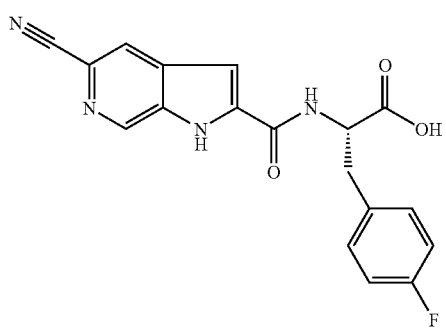

To a solution of 2-[(5-cyano-1H-pyrrolo[2,3-c]pyridine-2-carbonyl)amino]-3-(S)-(4-fluorophenyl)propionic acid ethyl ester (EXAMPLE 299, 0.800 g, 2.1 mmol) in methanol/water (2:1) was added 1N NaOH (4.2 mL, 4.2 mmol) and stirred at rt for 16 h. Reaction mixture was concentrated in vacuo to remove methanol. Water (150 mL) was added to the residue and washed with ethyl acetate (2×75 ml). The aqueous phase was cooled in an ice bath and acidified to pH 4 using 2N HCl. The precipitate formed was isolated and washed with water and ether to give the title compound. m/z (ES$^+$)=353 [M+H]$^+$; RT=3.27 min.

EXAMPLE 301

5-Cyano-1H-pyrrolo[2,3-c]pyridine-2-carboxylic acid [1-dimethylcarbamoyl-2-(S)-(4-fluorophenyl)ethyl]amide

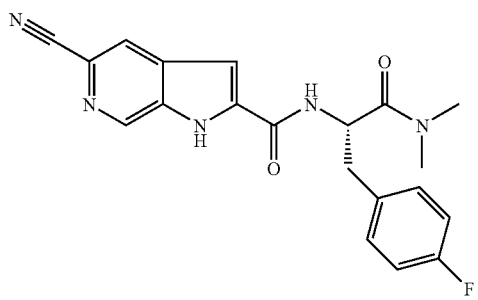

To a solution of N-dimethylamine hydrochloride (0.006 g, 0.07 mmol) in DMF (6 mL) was added DIPEA (37 μL, 0.21 mmol), HOBt (0.009 g, 0.07 mmol), 2-[(5-cyano-1H-pyrrolo[2,3-c]pyridine-2-carbonyl)amino]-3-(5)-(4-fluorophenyl)propionic acid (EXAMPLE 300, 0.025 g, 0.07 mmol) and EDCI (0.016 g, 0.084 mmol). The reaction mixture was stirred at rt for 16 h then concentrated in vacuo and the residue was partitioned between water (50 mL) and ethyl acetate (100 mL). The organic phase was separated and the aqueous phase was further extracted with ethyl acetate (100 mL). The combined organic extracts were washed with saturated NaHCO$_3$ (50 mL), saturated sodium chloride (75 mL), dried (MgSO$_4$), filtered and concentrated in vacuo to give the title compound. m/z (ES+)=380; RT=3.45.

EXAMPLES 302–307

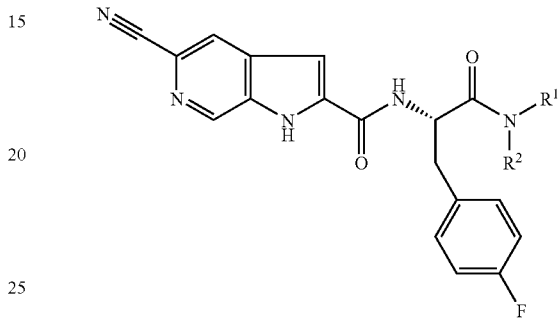

The following compounds were prepared according to the method of EXAMPLE 301 from 2-[(5-cyano-1H-pyrrolo[2,3-c]pyridine-2-carbonyl)amino]-3-(S)-(4-fluorophenyl)propionic acid (EXAMPLE 300) and the appropriate amine.

| Example | Amine | m/z | RT (min) |
|---|---|---|---|
| 302 | (3R)-hydroxypyrrolidine | 422 | 3.36 |
| 303 | (3S)-hydroxypyrrolidine | 422 | 3.32 |
| 304 | cyclopentylamine | 420 | 3.92 |
| 305 | morpholine | 422 | 3.44 |
| 306 | piperidine | 420 | 3.72 |
| 307 | homopiperazinone | 449 | 3.26 |

In vitro GP Activity

Materials

α-D-Glucose-1-phosphate (disodium salt), Glycogen, D-Glucose, Malachite Green Hydrochloride, Ammonium Molybdate tetrahydrate, BSA, HEPES and rabbit muscle phosphorylase a (P1261) were purchased from Sigma. All other reagents were analytical grade.

Method

Glycogen Phosphorylase Assay in vitro:

An assay for glycogen phosphorylase activity in the reverse direction was developed based on the method described by Engers et al., *Can. J. Biochem.*, 1970, 48, 746–754]. Rabbit muscle glycogen phosphorylase a (Sigma) was reconstituted at a stock concentration of 100 μg/mL in 25 mM Tris/HCl. The pH was measured in a 96-well plate in a final volume of 100 μL containing 50 mM Hepes pH 7.2, 7.5 mM glucose 0.5 mM glucose-1-phosphate and 1 mg/mL glycogen. After incubation at 3020 C. for 30 min, the inorganic phosphate released from glucose-1-phosphate was measured by the addition of 150 μL of malachite green/molybdate solution prepared as follows: 5 mL of 4.2% ammonium molybdate in 4N HCl, 15 mL of 0.045% malachite green, 50 μL of Tween 20. Following a 30 min incubation at rt, the absorbance was measured at 620 nm. For $IC_{50}$ determination, 10 μL of a serial dilution of compound (100 μM to 0.004 μM) in DMSO was added to each reaction in duplicate with the equivalent concentration of DMSO added to the control uninhibited reaction. Dose response curves were then obtained by plotting % inhibition versus $\log_{10}$ compound concentration. $IC_{50}$ is defined as the concentration of compound achieving 50% inhibition under the assay conditions described.

The EXAMPLES have an $IC_{50}$ of <1 mM. For example, EXAMPLES 1–20, 22, 27, and 30–48 demonstrated efficacy by measuring values of $IC_{50}$ in the range of 62.8–0.07 μM. Examples 21, 23–26, 28, and 29 yielded $IC_{50}$ 100 μM or higher. It is advantageous that the measured $IC_{50}$ be lower than 100 μM. It is still more advantageous for the $IC_{50}$ to be lower than 50 μM. It is even more advantageous for the $IC_{50}$ to be lower than 5 μM. It is yet more advantageous for the $IC_{50}$ to be lower than 0.5 μM.

What is claimed is:

1. A compound of Formula (I):

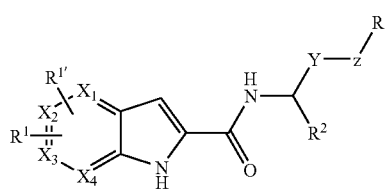

I or a stereoisomer, or a pharmaceutically acceptable salt thereof, wherein:

$X_3$ is N; and $X_1$, $X_2$, and $X_4$ are each C;

$R^1$ and $R^{1'}$ are each independently, halogen, hydroxy, cyano, $C_{0-4}$alkyl, $C_{1-4}$alkoxy, fluoromethyl, difluoromethyl, trifluoromethyl, ethenyl, or ethynyl;

$R^2$ is $C_{0-4}$alkyl, $COOR^6$, $COR^6$, $C_{1-4}$alkoxy$C_{1-4}$alkyl-, hydroxy$C_{1-4}$alkyl-, aryl$C_{0-4}$alkyl-, hetaryl$C_{0-4}$alkyl-, wherein any of the aryl or hetaryl rings are optionally substituted with 1–2 independent halogen, cyano, $C_{1-4}$alkyl, $C_{1-4}$alkoxy, —N($C_{0-4}$alkyl)($C_{0-4}$alkyl), —SO$_2$C$_{1-4}$alkyl, —SO$_2$N($C_{0-4}$alkyl)($C_{0-4}$alkyl), hydroxy, fluoromethyl, difluoromethyl, or trifluoromethyl substituents;

Y is $C_{0-2}$alkyl or —CH(OH)—;

Z is CH$_2$, —C(O)—, —O—, >N($C_{0-4}$alkyl), >N($C_{3-6}$cycloalkyl), or absent; but when Y is —CH(OH)—, Z or $R^3$ must be bonded to Y through a carbon-carbon bond;

$R^3$ is hydrogen, —COOC$_{0-4}$alkyl, $C_{1-4}$alkoxy, $C_{1-4}$alkyl, aryl$C_{1-4}$alkylthio-, —C$_{0-4}$alkylaryl, —C$_{0-4}$alkylhetaryl, —C$_{0-4}$alkylcycloalkyl or —C$_{0-4}$alkylheterocyclyl, wherein any of the rings is optionally substituted with 1–3 independent halogen, cyano, $C_{1-4}$alkyl, fluoromethyl, difluoromethyl, trifluoromethyl, —C$_{0-4}$alkylNHC(O)O($C_{1-4}$alkyl), —C$_{0-4}$alkylNR$^7$R$^8$, —C(O)R$^9$, $C_{1-4}$alkoxyC$_{0-4}$alkyl-, —COOC$_{0-4}$alkyl, —C$_{0-4}$alkylNHC(O)R$^9$, —C$_{0-4}$alkylC(O)N(R$^{10}$)$_2$, —C$_{1-4}$alkoxyC$_{1-4}$alkoxy, hydroxyC$_{0-4}$alkyl-, —NHSO$_2$R$^{10}$, —SO$_2$(C$_{1-4}$alkyl), —SO$_2$NR$^{11}$R$^{12}$, 5- to 6-membered heterocyclyl, phenylC$_{0-2}$alkoxy, or phenylC$_{0-2}$alkyl substituents, wherein phenyl is optionally substituted with 1–2 independent halogen, cyano, $C_{1-4}$alkyl, $C_{1-4}$alkoxy, —N($C_{0-4}$alkyl)($C_{0-4}$alkyl), —SO$_2$C$_{1-4}$alkyl, —SO$_2$N($C_{0-4}$alkyl)($C_{0-4}$alkyl), hydroxy, fluoromethyl, difluoromethyl or trifluoromethyl substituents, or two bonds on a ring carbon of the heterocyclyl group optionally can form an oxo (═O) substituent;

or $R^3$ is —NR$^4$(—C$_{0-4}$alkylR$^5$);

$R^4$ is $C_{0-3}$alkyl, —C$_{2-3}$alkyl-NR$^7$R$^8$, $C_{3-6}$cycloalkyl optionally substituted by hydroxyC$_{0-4}$alkyl- further optionally substituted by hydroxy, $C_{1-2}$alkoxyC$_{2-4}$alkyl-, or $C_{1-2}$alkyl-S(O)$_n$—C$_{2-3}$alkyl-;

n is 0, 1, or 2;

$R^5$ is hydrogen, hydroxyC$_{2-3}$alkyl-, $C_{1-2}$alkoxyC$_{0-4}$alkyl-, or aryl, hetaryl, or heterocyclyl;

wherein a heterocyclic nitrogen-containing $R^5$ ring optionally is mono-substituted on the ring nitrogen with $C_{1-4}$alkyl, benzyl, benzoyl, $C_{1-4}$alkyl-C(O)—, —SO$_2$C$_{1-4}$alkyl, —SO$_2$N($C_{0-4}$alkyl)($C_{0-4}$alkyl), $C_{1-4}$alkoxycarbonyl or aryl($C_{1-4}$alkoxy) carbonyl; and wherein the $R^5$ rings are optionally mono-substituted on a ring carbon with halogen, cyano, $C_{1-4}$alkyl-C(O)—, $C_{1-4}$alkyl-SO$_2$—, $C_{1-4}$alkyl, $C_{1-4}$alkoxy, hydroxy, —N($C_{0-4}$alkyl)($C_{0-4}$alkyl), hydroxyC$_{0-4}$alkyl-, or $C_{0-4}$alkylcarbamoyl-, provided that no quaternised nitrogen is included; or two bonds on a ring carbon of the heterocyclyl group optionally can form an oxo (═O) substituent;

$R^6$ is $C_{1-4}$alkyl, aryl, or hetaryl;

$R^7$ and $R^8$ are independently $C_{0-4}$alkyl, $C_{3-6}$cycloalkyl, or CO($C_{1-4}$alkyl);

$R^9$ is $C_{1-4}$alkyl, or $C_{3-6}$cycloalkyl;

$R^{10}$ is $C_{0-4}$alkyl, or $C_{3-6}$cycloalkyl;

$R^{11}$ and $R^{12}$ are independently $C_{0-4}$alkyl or together with the nitrogen to which they are attached may form a 4- to 6-membered heterocycle; and wherein there are no nitrogen-oxygen, nitrogen-nitrogen or nitrogen-halogen bonds in linking the three components —Y—Z—R$^3$ to each other.

2. A compound according to claim 1, or a stereoisomer, or a pharmaceutically acceptable salt thereof, wherein $R^1$ and $R^{1'}$ are each independently, halogen, cyano or hydrogen.

3. A compound according to claim 2, or a stereoisomer, or a pharmaceutically acceptable salt thereof, wherein one of $R^1$ and $R^{1'}$ is hydrogen and the other is a 5-halo or 5-cyano group.

4. A compound according to claim 1, or a stereoisomer, or a pharmaceutically acceptable salt thereof, wherein Y is $C_{0-2}$alkyl.

5. A compound according to claim 1, wherein Z is —C(O)—.

6. A compound according to claim 1, or a stereoisomer, or a pharmaceutically acceptable salt thereof, wherein $X_3$ is N;
Y is $C_{0-2}$alkyl; and
Z is —C(O)—.

7. A compound according to claim 4, or a stereoisomer, or a pharmaceutically acceptable salt thereof, wherein Y is a direct bond.

8. A compound according to claim 1, or a stereoisomer, or a pharmaceutically acceptable salt thereof, wherein $R^2$ is $C_{0-4}$alkyl or aryl$C_{0-4}$alkyl-, wherein the aryl ring is optionally substituted with 1–2 independent halogen, cyano, $C_{1-4}$alkyl, $C_{1-4}$alkoxy, —N($C_{0-4}$alkyl)($C_{0-4}$alkyl), —$SO_2C_{1-4}$alkyl, —$SO_2$N($C_{0-4}$alkyl)($C_{0-4}$alkyl), hydroxy, fluoromethyl, difluoromethyl, or trifluoromethyl substituents.

9. A compound according to claim 8, or a stereoisomer, or a pharmaceutically acceptable salt thereof, wherein $R^2$ is benzyl optionally substituted with 1–2 halogen substituents.

10. A compound according to claim 1, or a stereoisomer, or a pharmaceutically acceptable salt thereof, wherein $R^3$ is —$C_{0-4}$alkylheterocyclyl optionally substituted with 1–3 independent halogen, cyano, $C_{1-4}$alkyl, fluoromethyl, difluoromethyl, trifluoromethyl, —$C_{0-4}$alkylNHC(O)O($C_{1-4}$alkyl), —$C_{0-4}$alkylNR$^7$R$^8$, —C(O)R$^9$, $C_{1-4}$alkoxyC$_{0-4}$alkyl-, —COOC$_{0-4}$alkyl, —$C_{0-4}$alkylNHC(O)R$^9$, —$C_{0-4}$alkylC(O)N(R$^{10}$)$_2$, —$C_{1-4}$alkoxyC$_{1-4}$alkoxy, hydroxyC$_{0-4}$alkyl, —NHSO$_2$R$^{10}$, —SO$_2$(C$_{1-4}$alkyl), —SO$_2$NR$^{11}$R$^{12}$, 5- to 6-membered heterocyclyl, phenylC$_{0-2}$alkoxy or phenylC$_{0-2}$alkyl substituents, wherein phenyl is optionally substituted with 1–2 independent halogen, cyano, $C_{1-4}$alkyl, $C_{1-4}$alkoxy, —N($C_{0-4}$alkyl)($C_{0-4}$alkyl), —SO$_2$C$_{1-4}$alkyl, —SO$_2$N($C_{0-4}$alkyl)($C_{0-4}$alkyl), hydroxy, fluoromethyl, difluoromethyl, or trifluoromethyl substituents, or two bonds on a ring carbon of the heterocyclyl group optionally can form an oxo (=O) substituent; or $R^3$ is —NR$^4$(—C$_{0-4}$alkylR$^5$).

11. A compound according to claim 10, wherein $R^3$ is an optionally substituted nitrogen containing heterocyclyl group, linked to Z via a ring nitrogen atom; or $R^3$ is —NR$^4$(—C$_{0-4}$alkylR$^5$).

12. A compound according to claim 11, wherein $R^3$ is an optionally substituted 4–8-membered nitrogen containing heterocyclyl group.

13. A compound according to claim 12, or a stereoisomer, or a pharmaceutically acceptable salt thereof, wherein $R^3$ is pyrrolidin-1-yl or piperidin-1-yl optionally substituted with hydroxy.

14. A compound selected from the following:

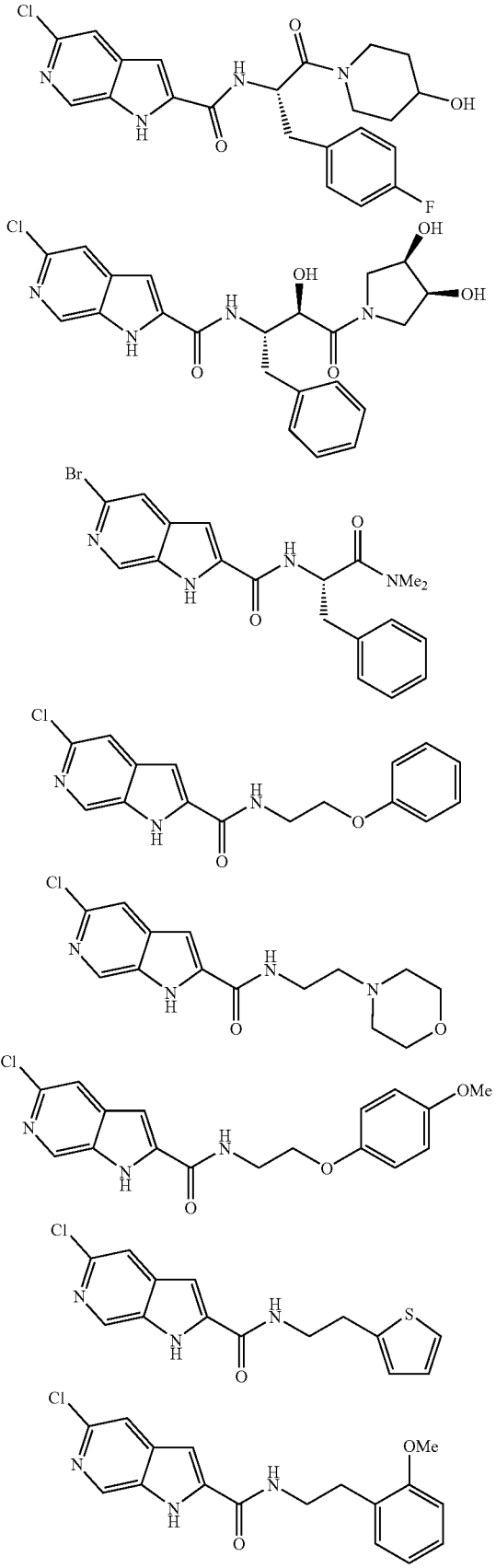

183
-continued
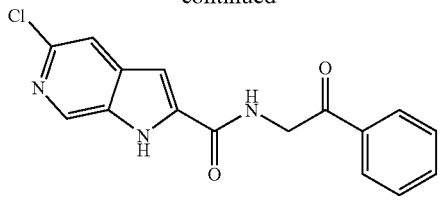
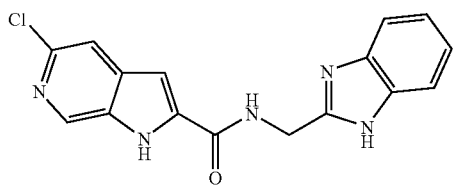
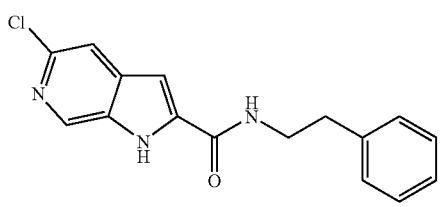
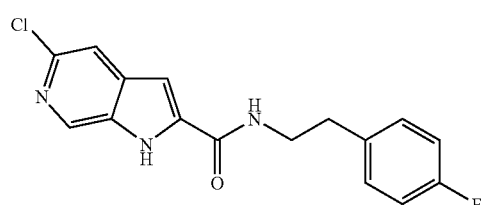
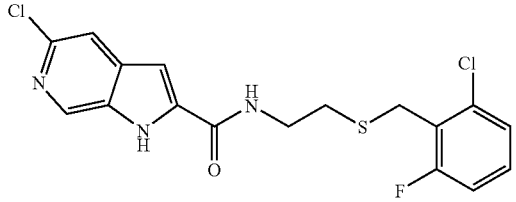
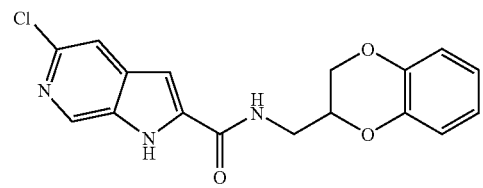
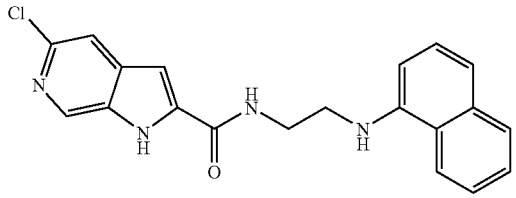
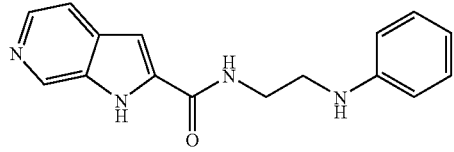
184
-continued
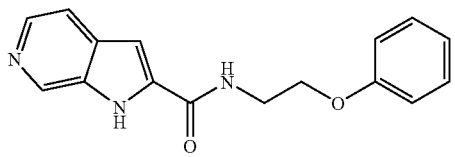
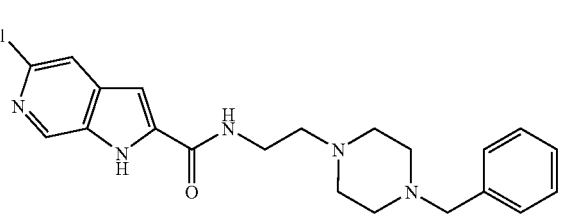
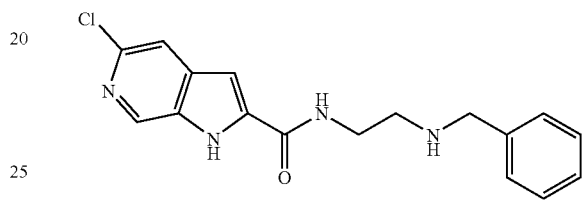
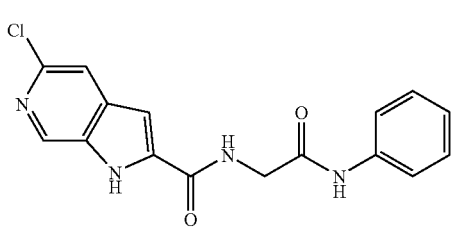
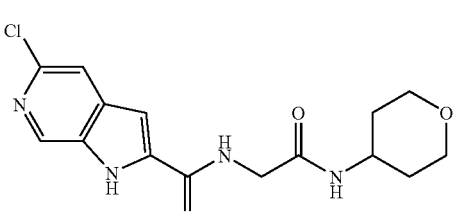
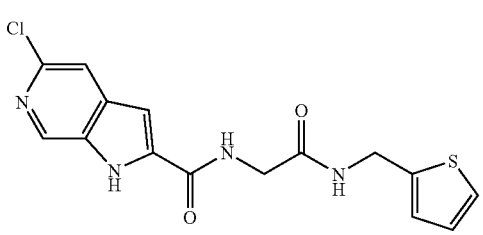
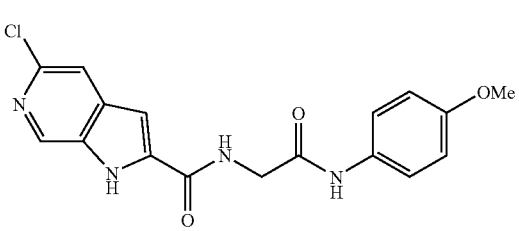

185
-continued
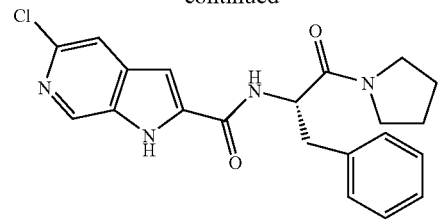
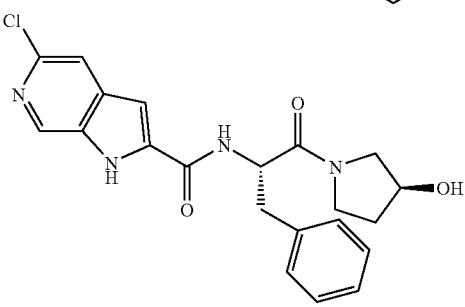
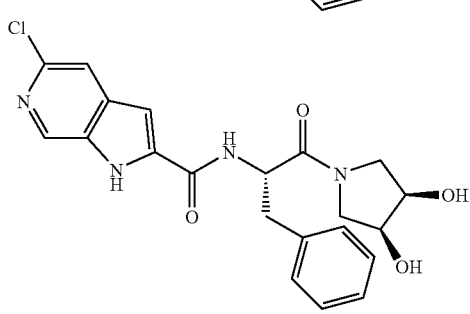
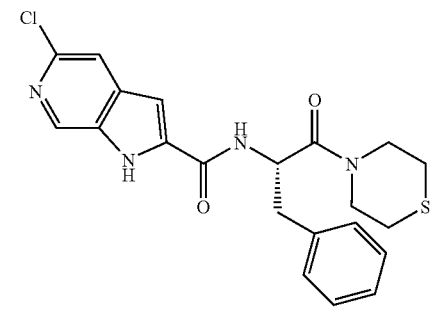
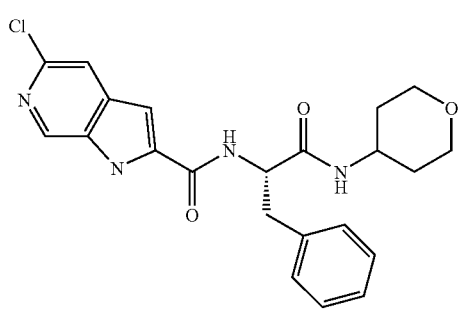
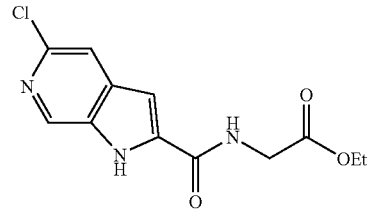
186
-continued
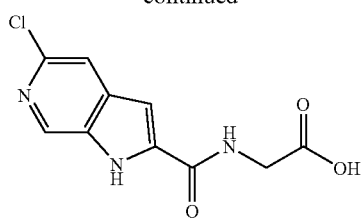
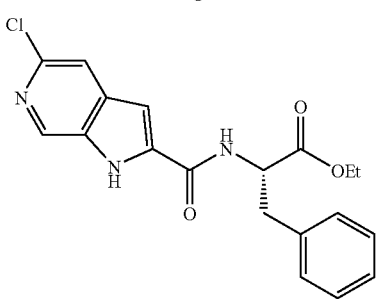
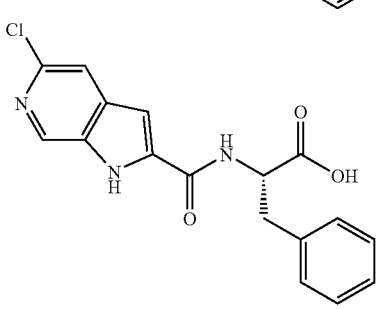
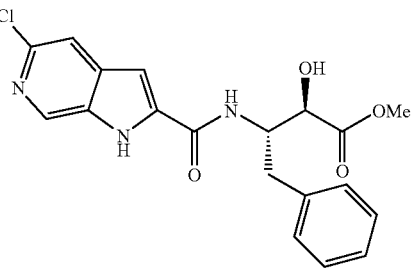
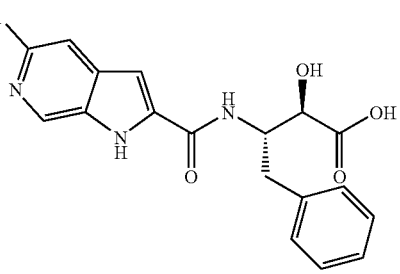
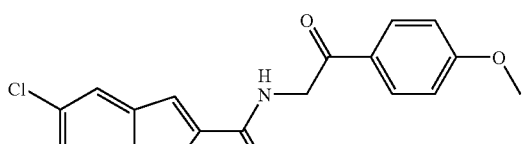

187
-continued
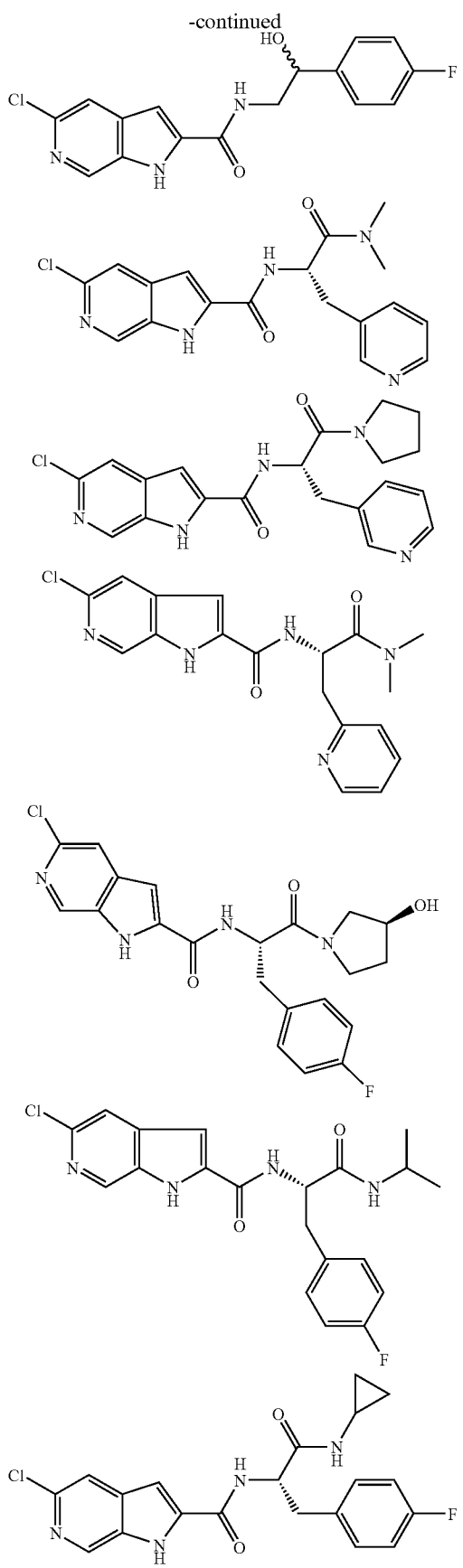
188
-continued
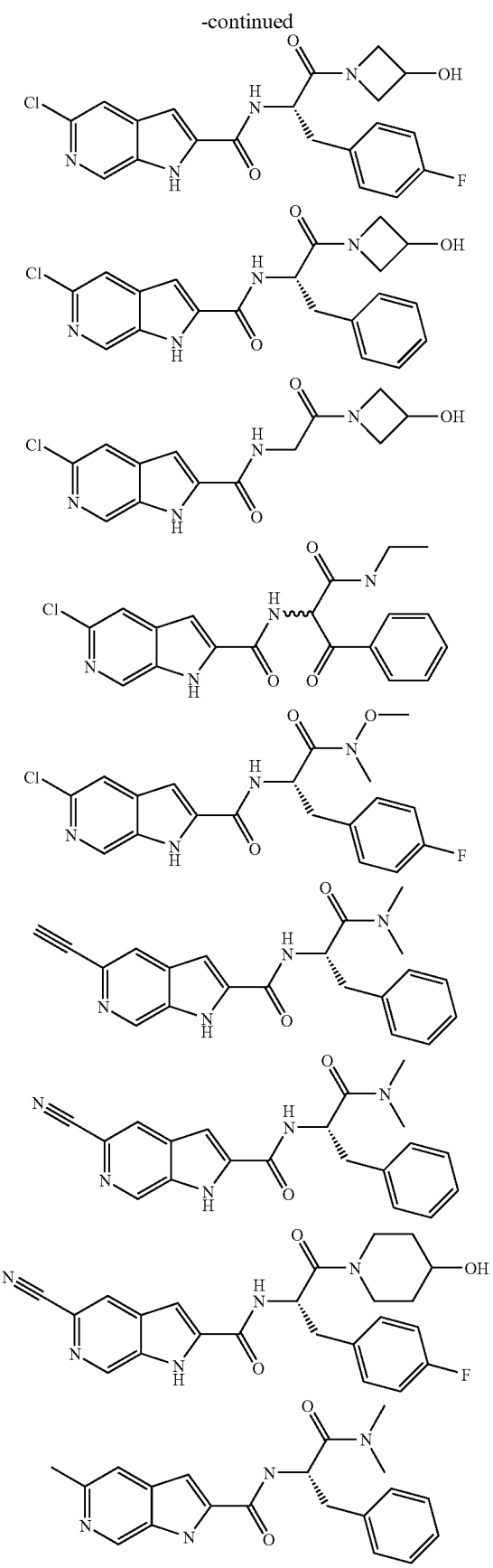

189
-continued
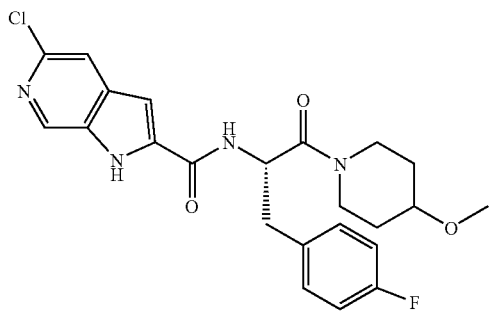
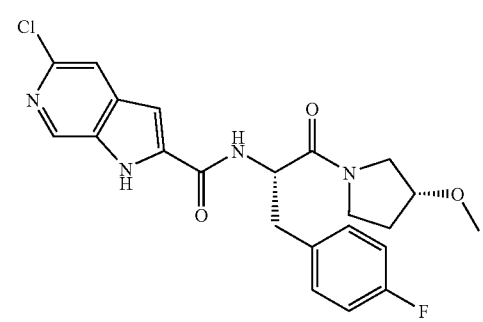
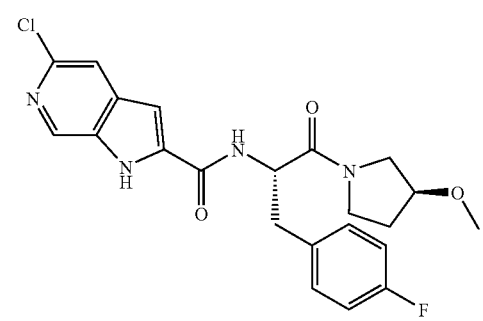
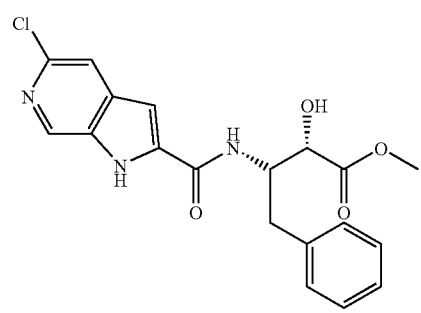
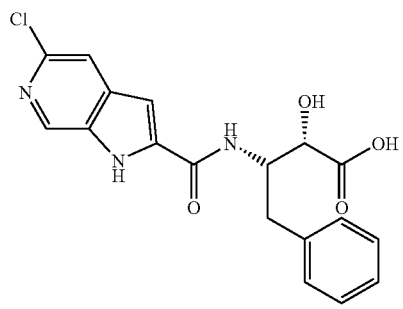
190
-continued
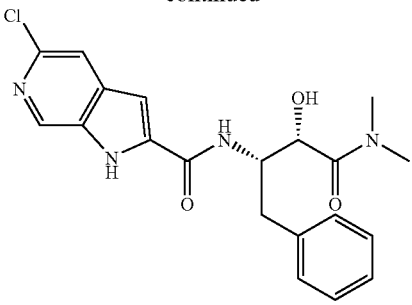
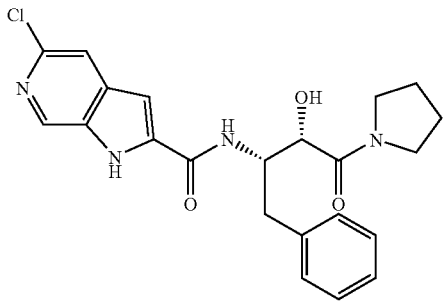
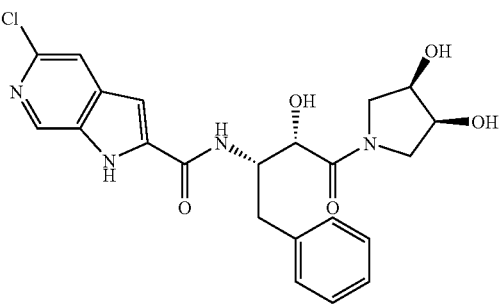
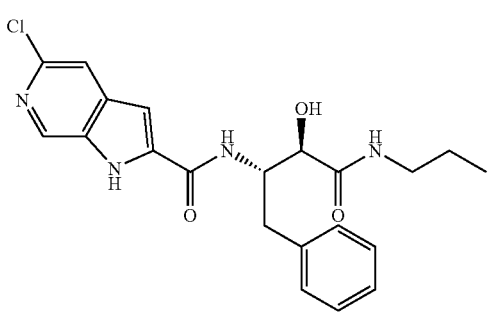
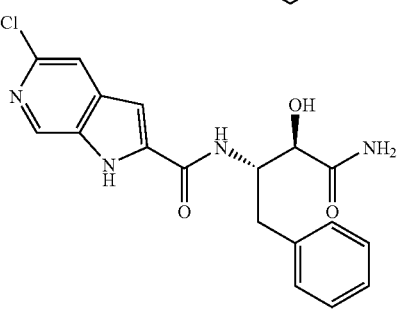

191
-continued
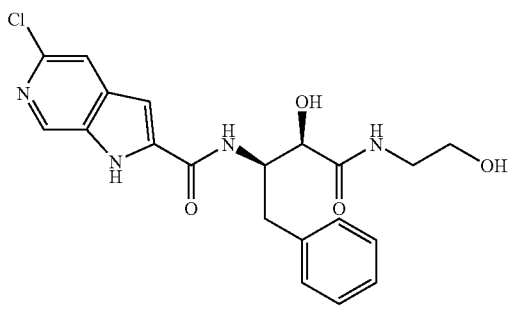
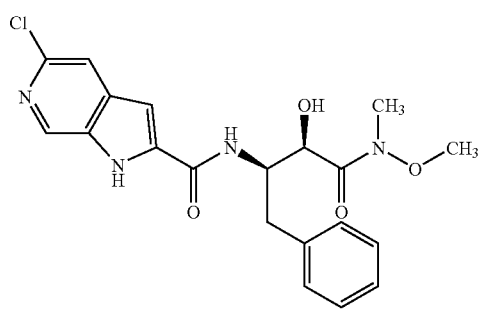
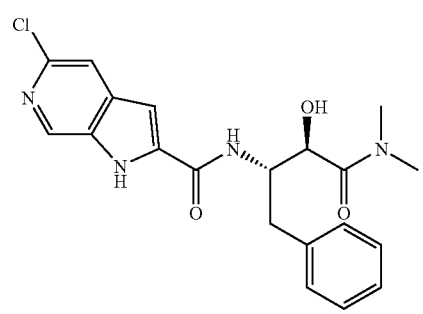
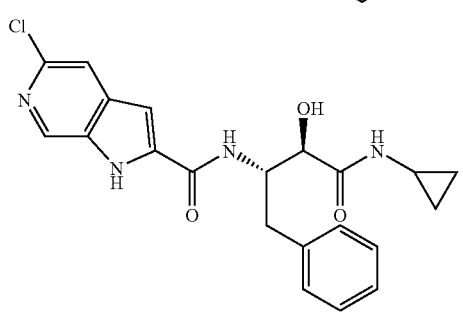
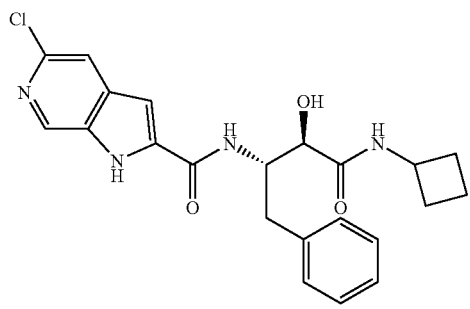
192
-continued
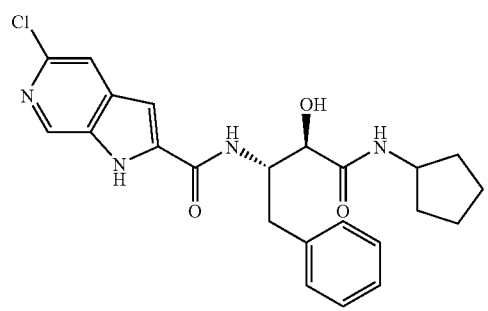
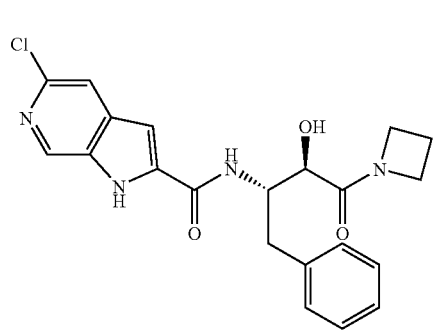
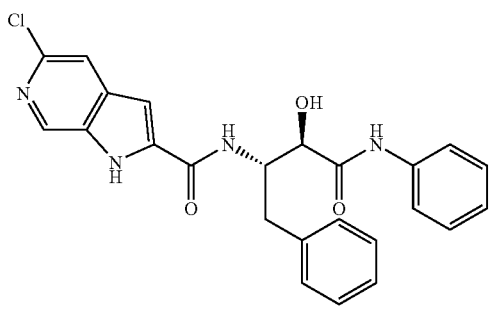
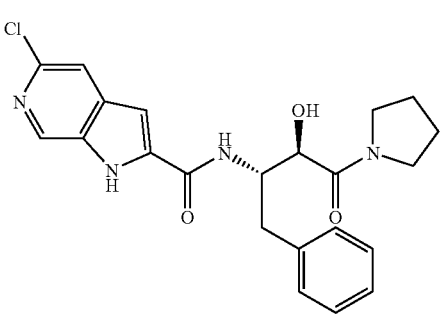

193
-continued
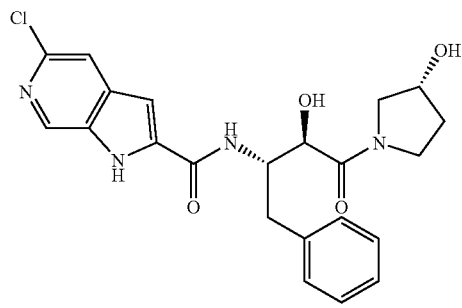
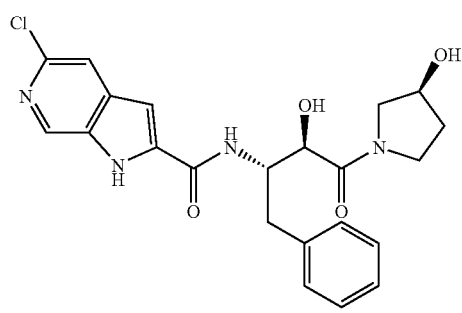
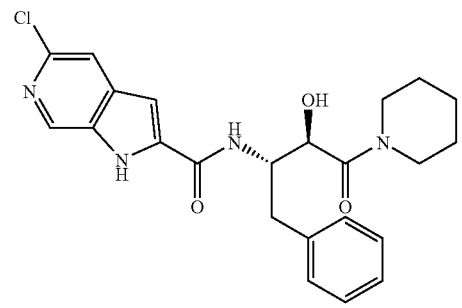
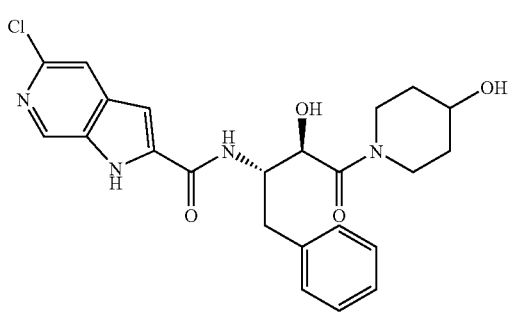
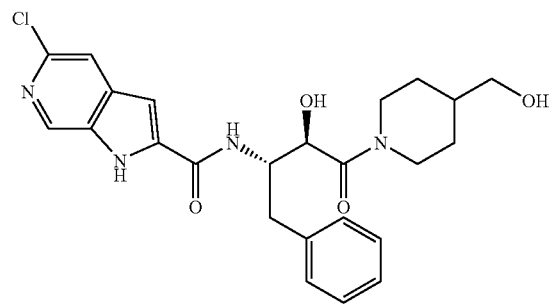
194
-continued
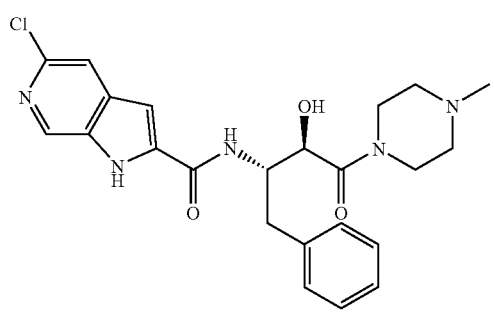
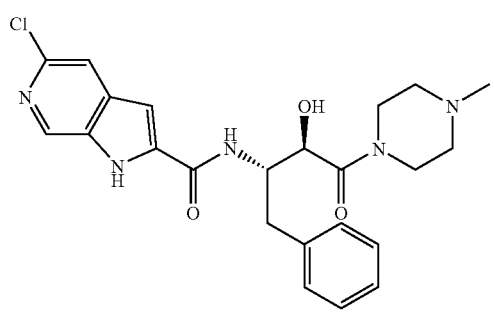
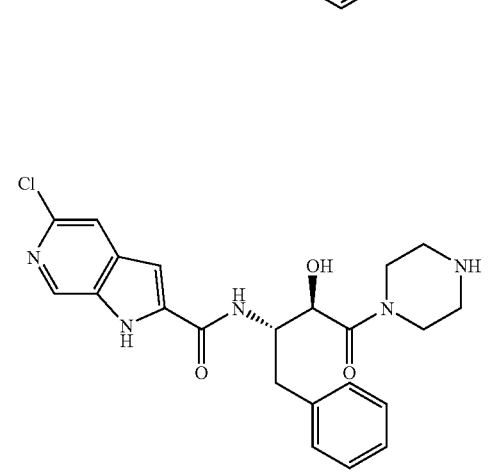

-continued
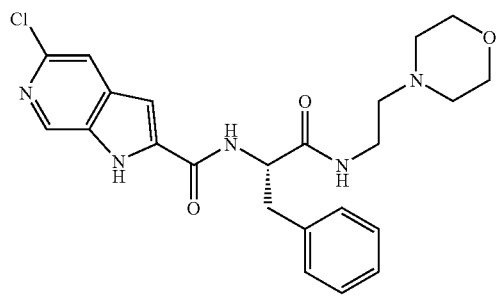
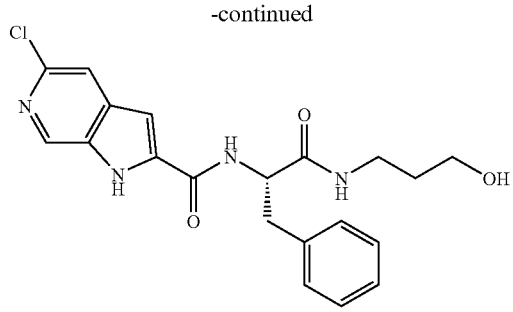
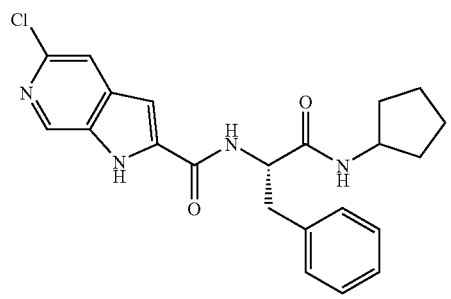
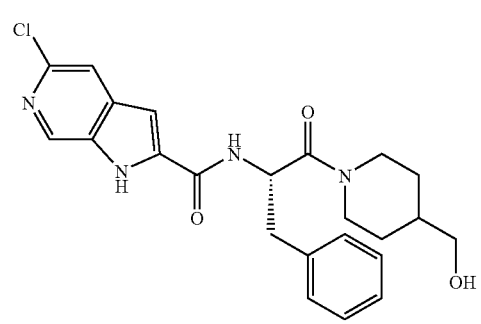
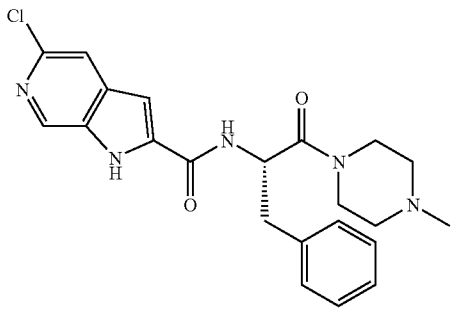
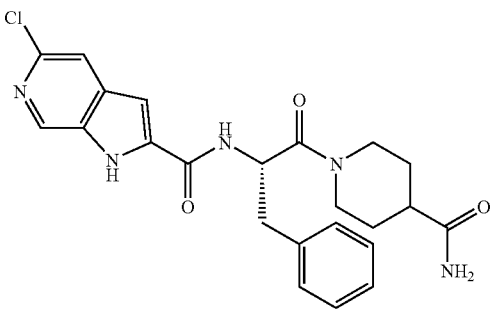
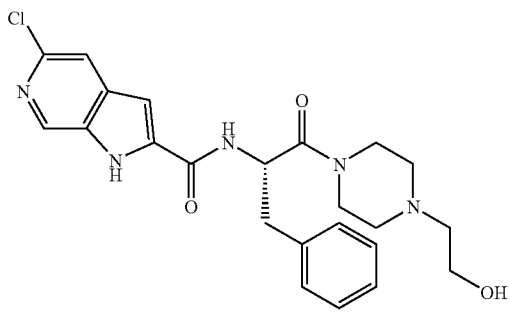
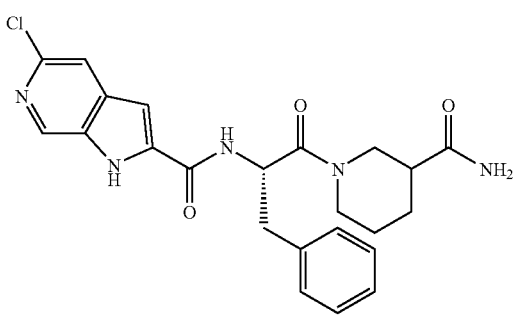
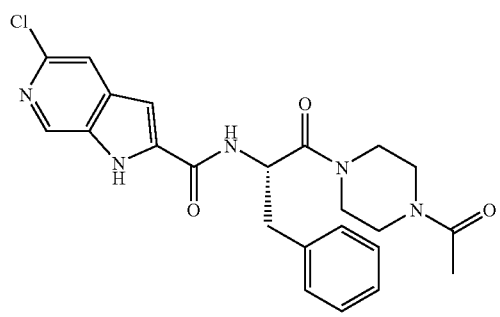
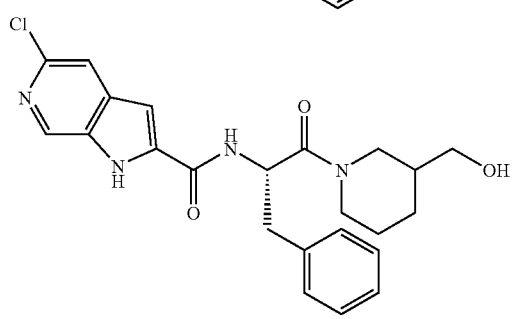

197
-continued
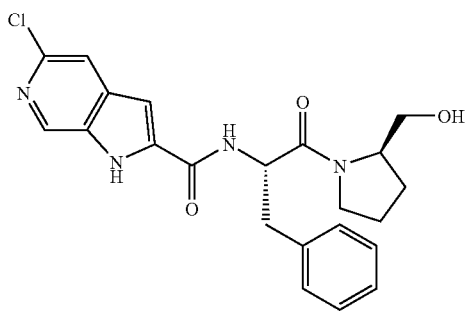
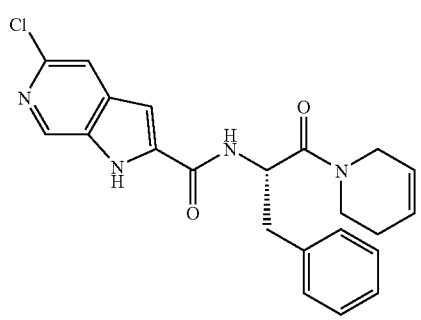
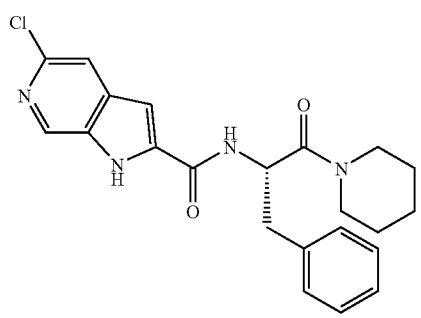
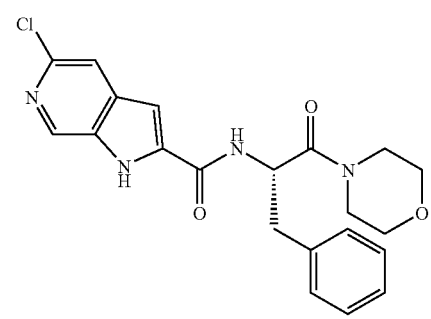
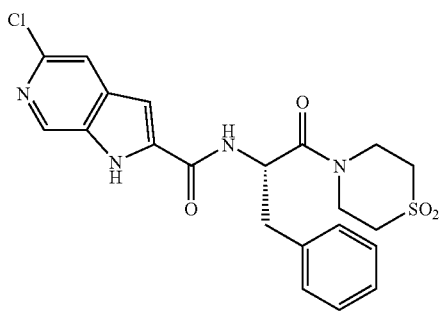
198
-continued
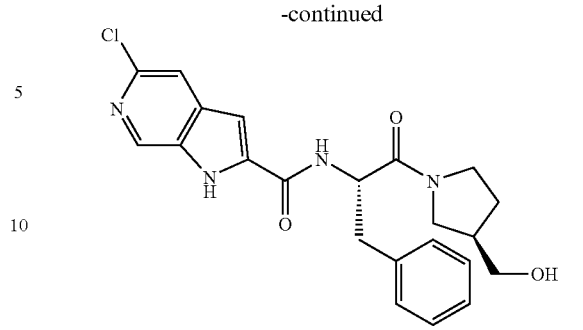
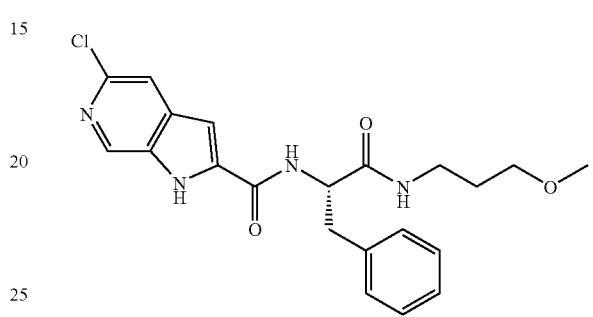
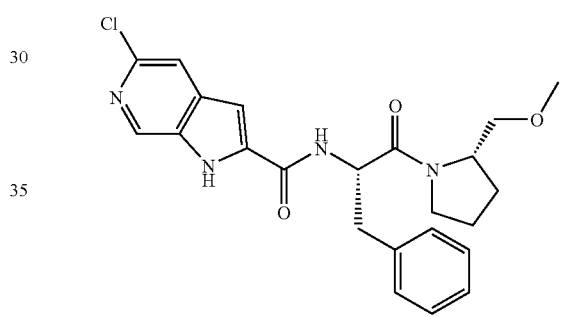
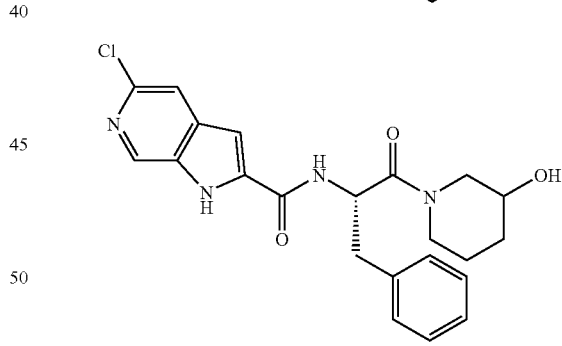
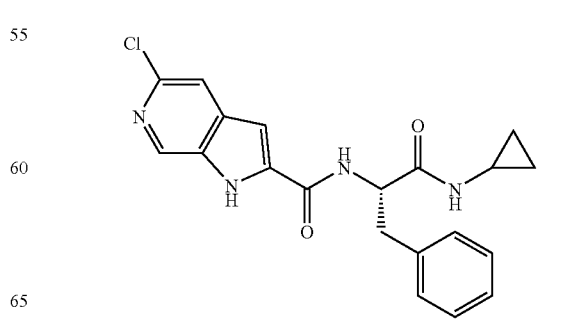

199
-continued
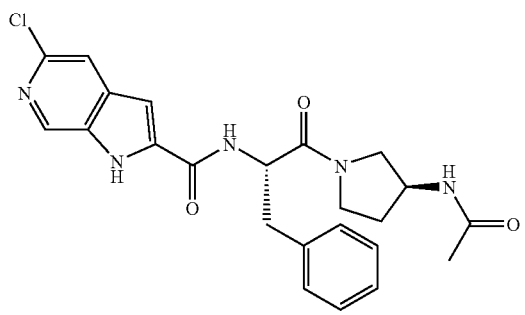
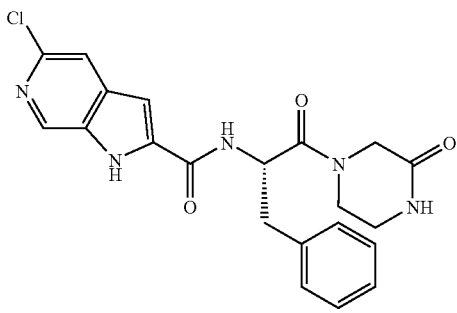
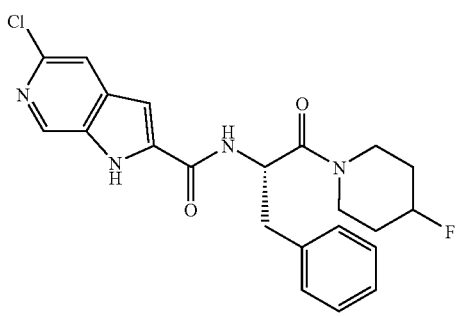
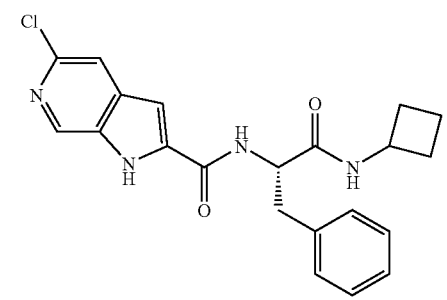
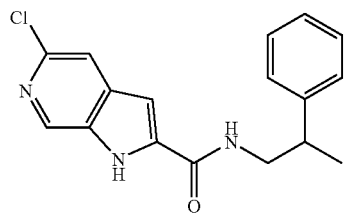
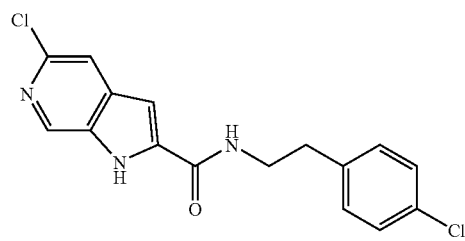
200
-continued
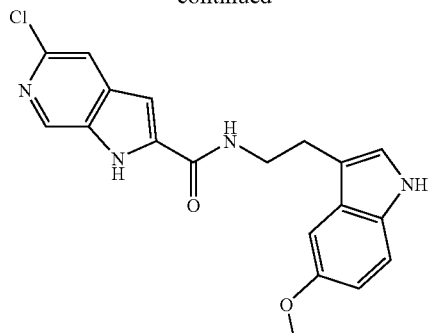
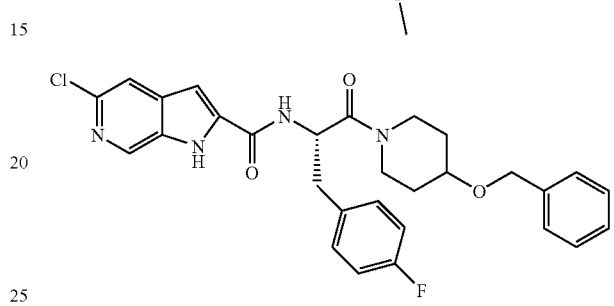
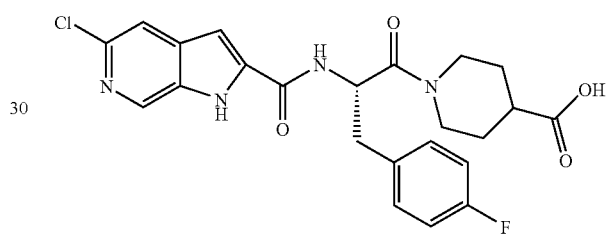
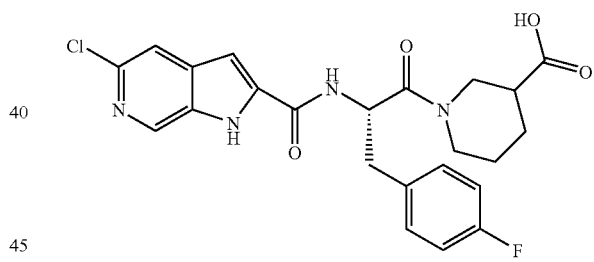
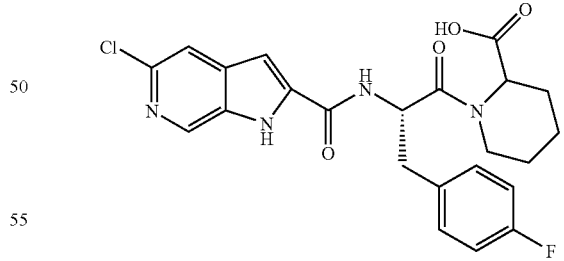
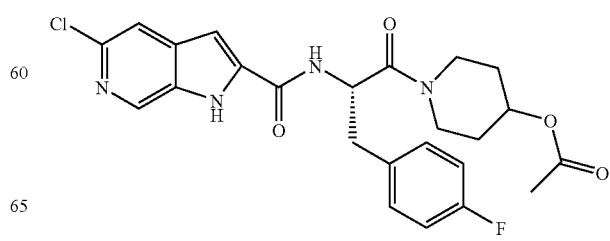

-continued
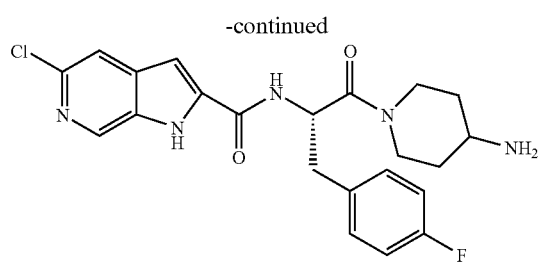
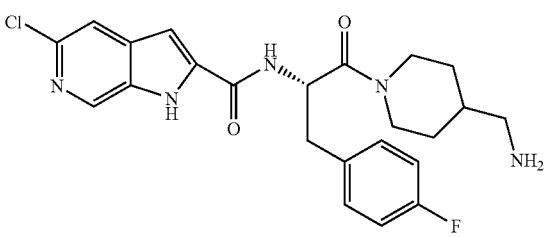
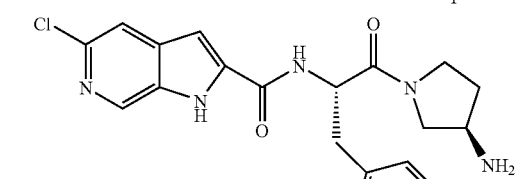
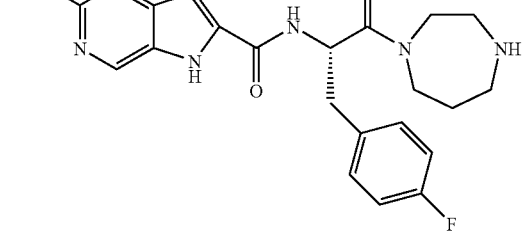
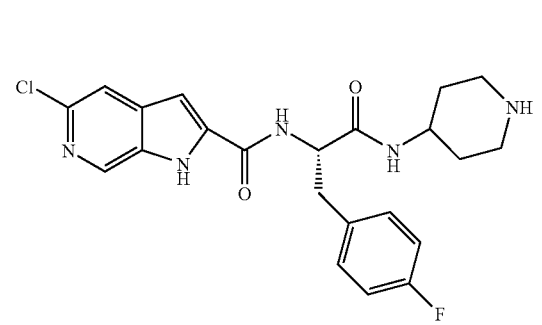
-continued
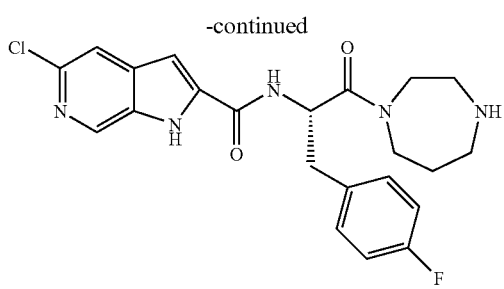
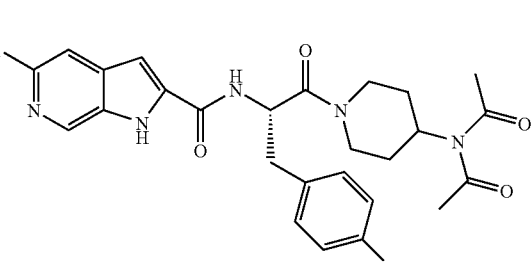
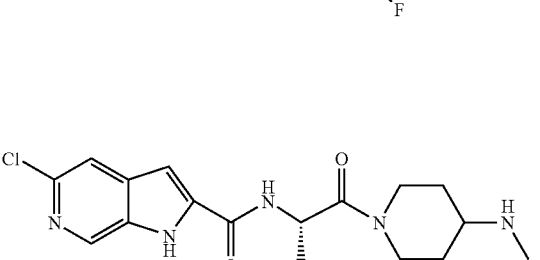
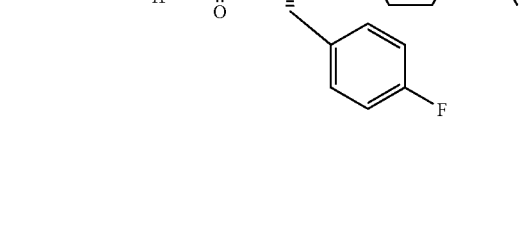
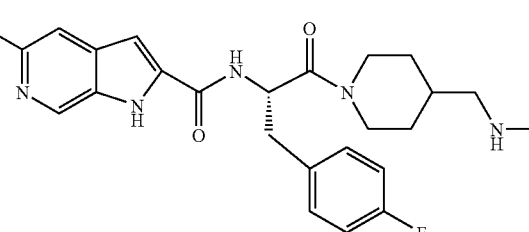
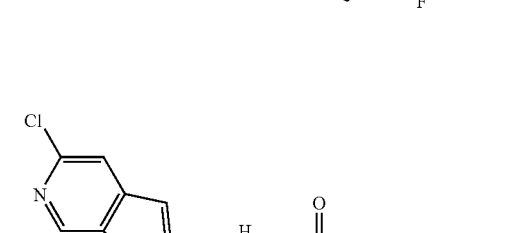

203
-continued
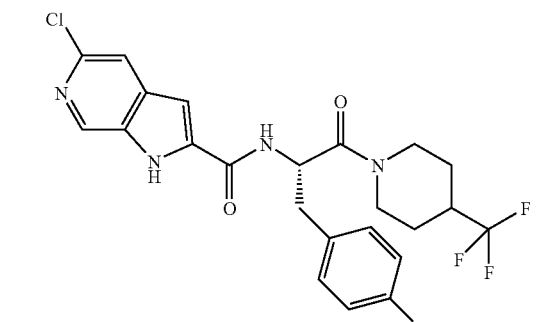
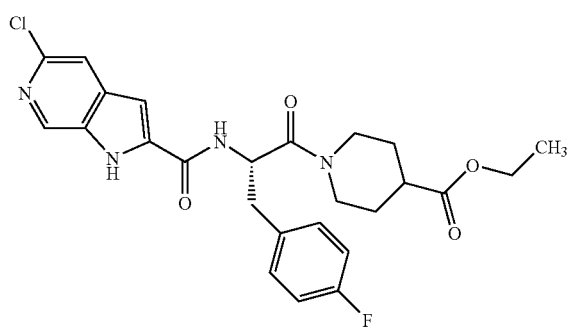
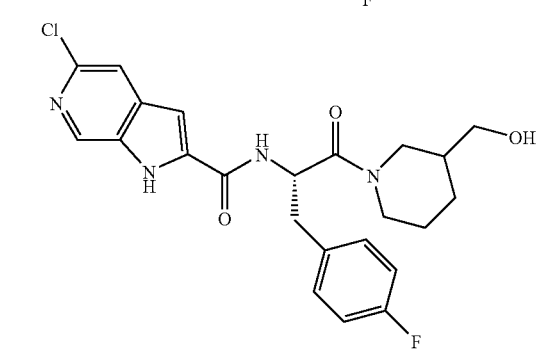
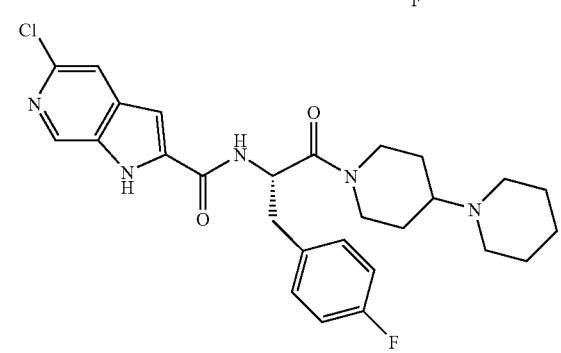
204
-continued

205
-continued
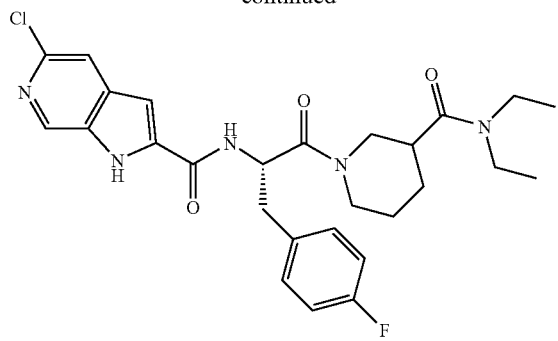
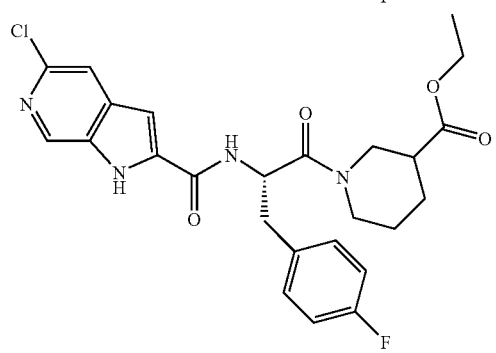
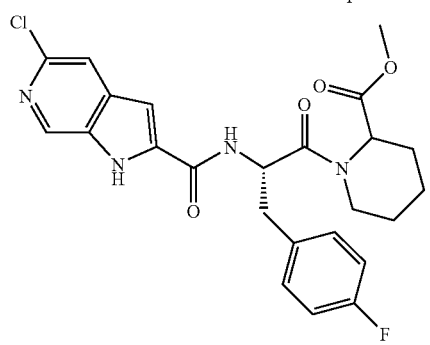
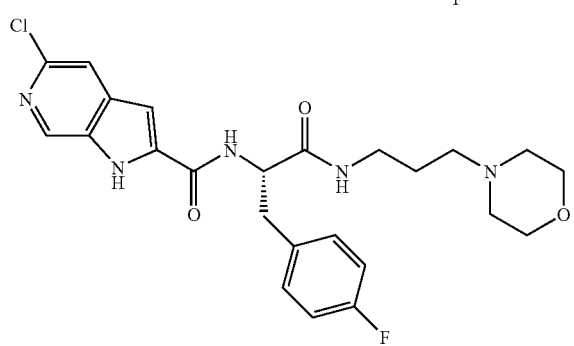
206
-continued
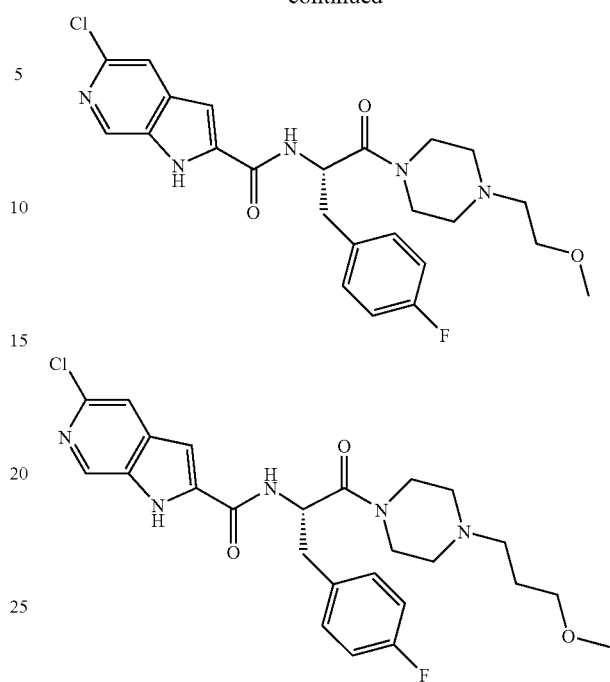
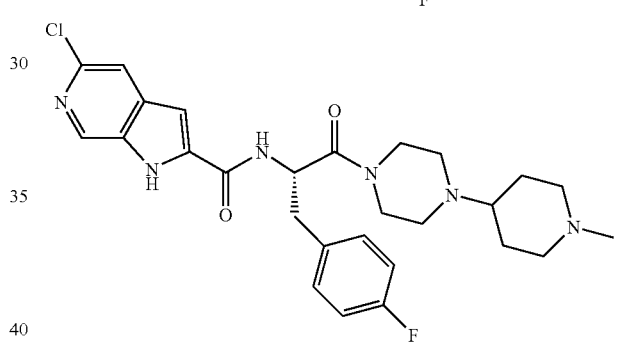
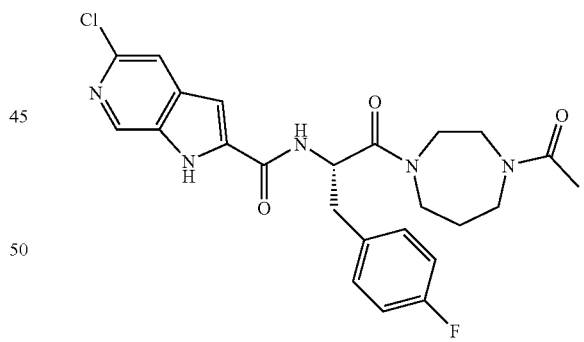
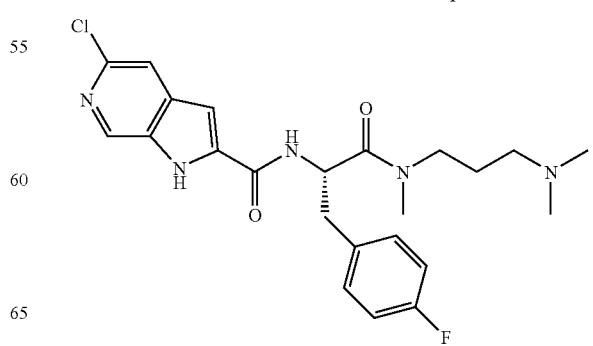

207
-continued
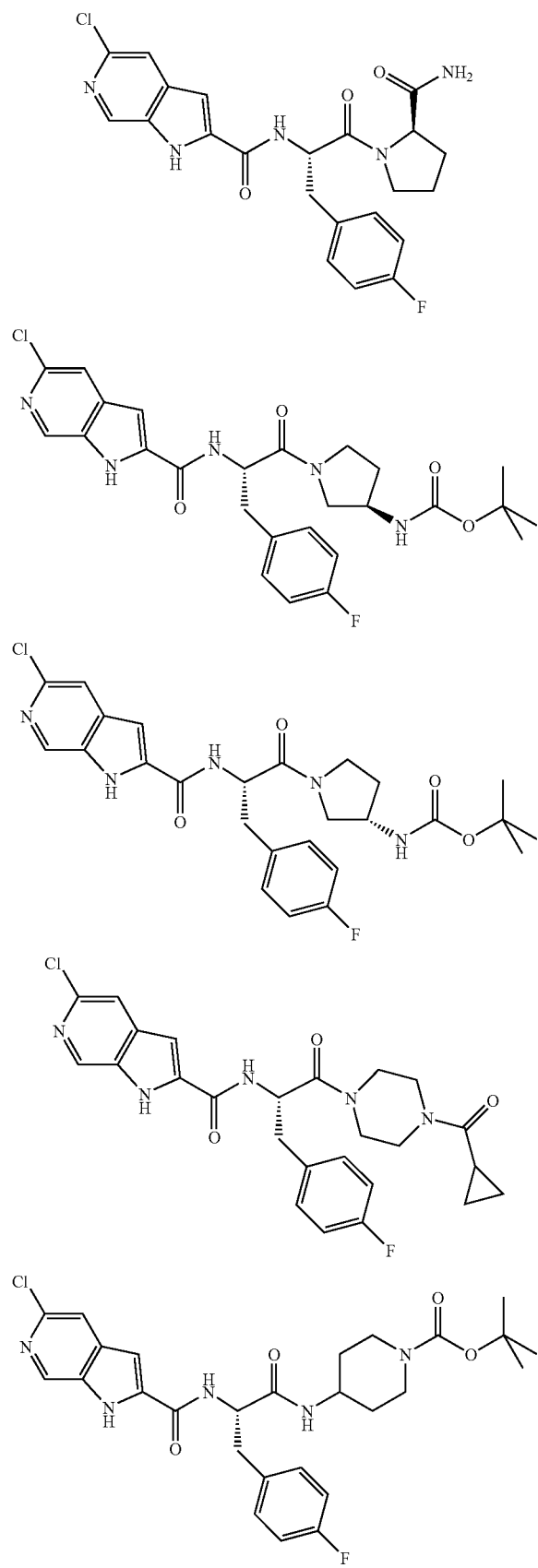
208
-continued
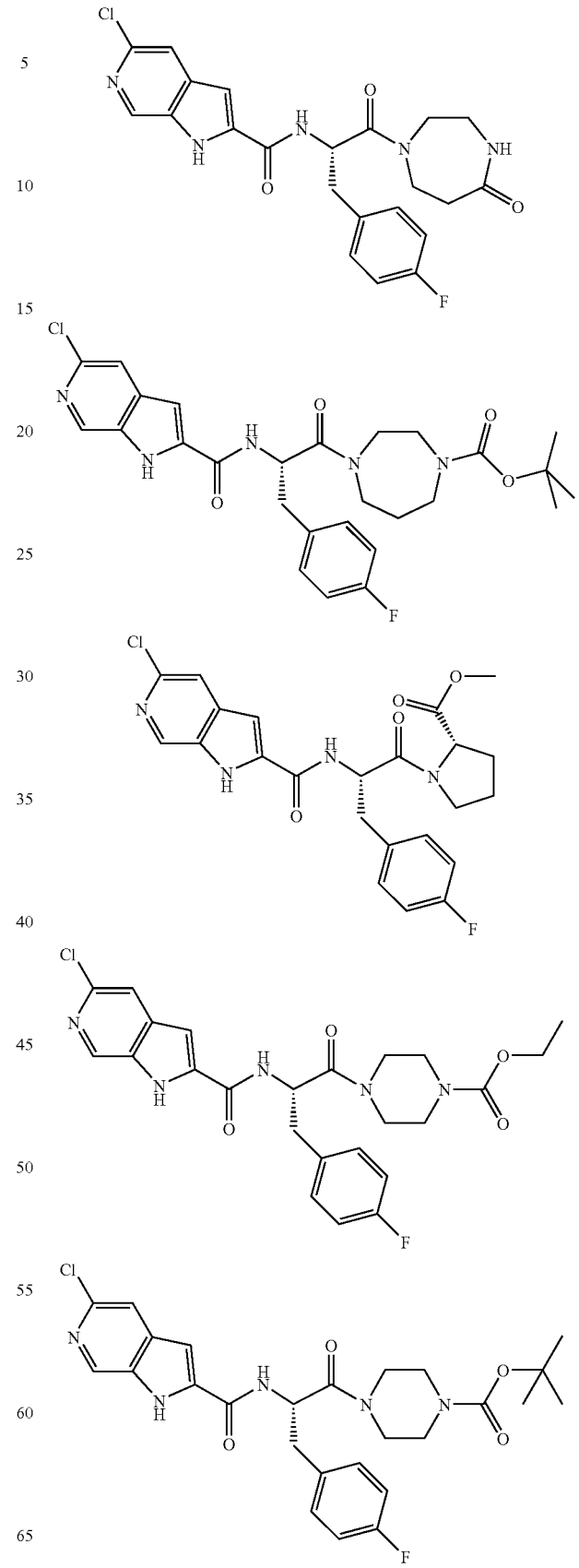

209 210
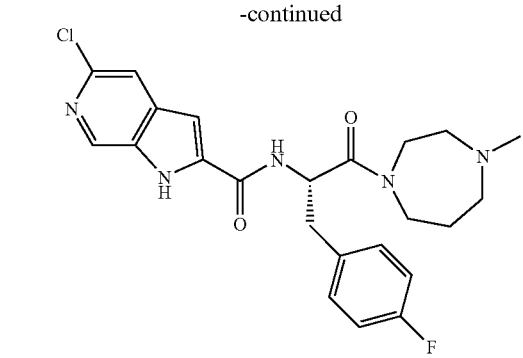
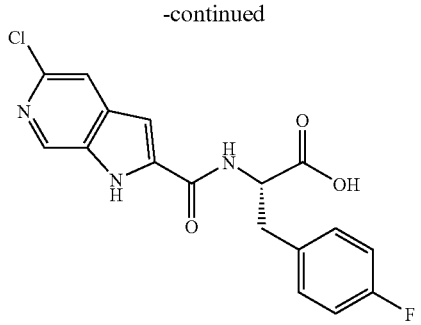
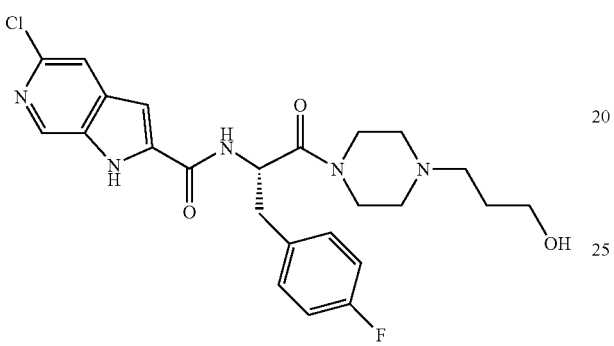
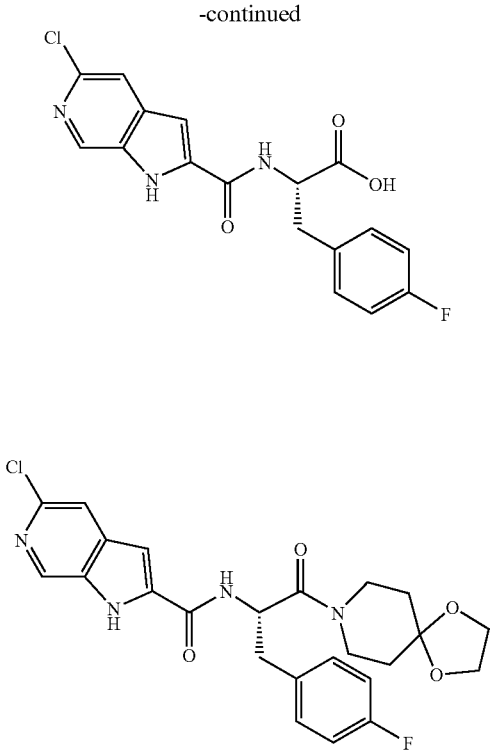
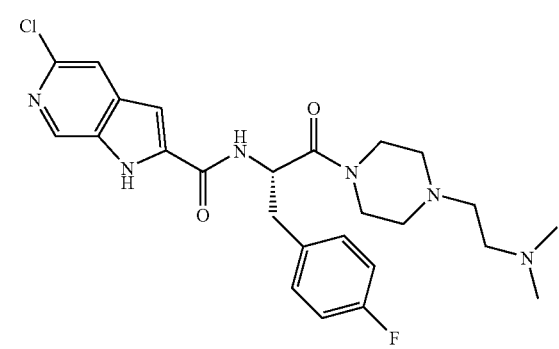
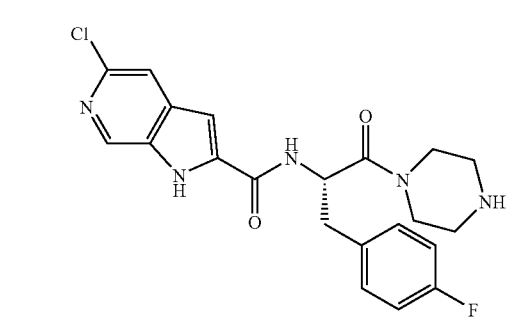
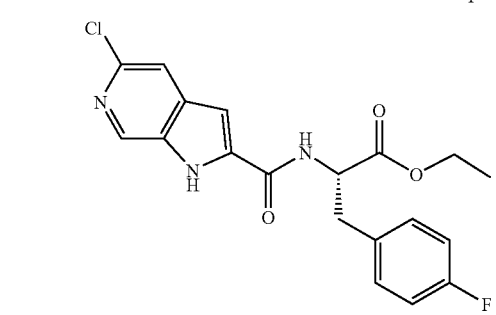
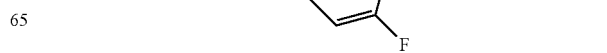

-continued
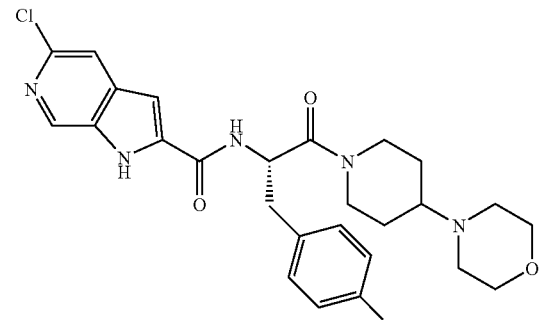
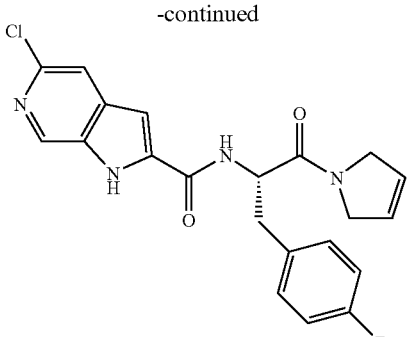
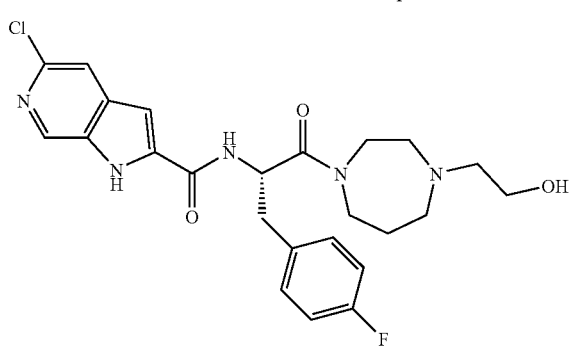
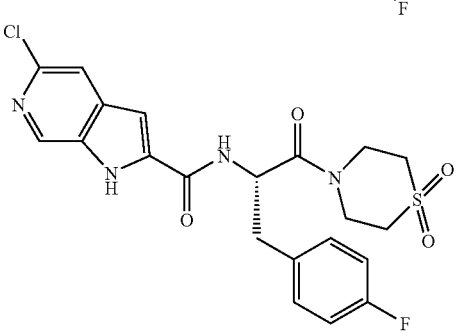
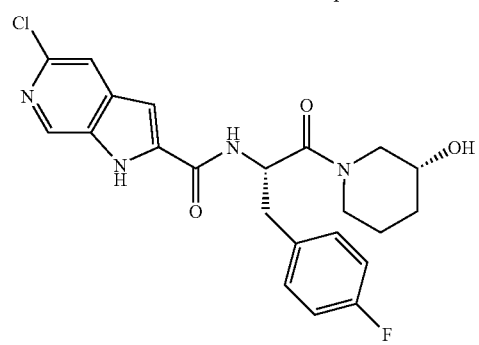
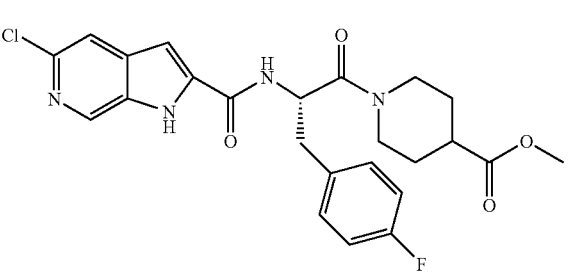
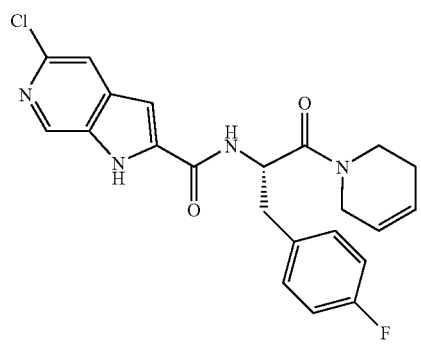
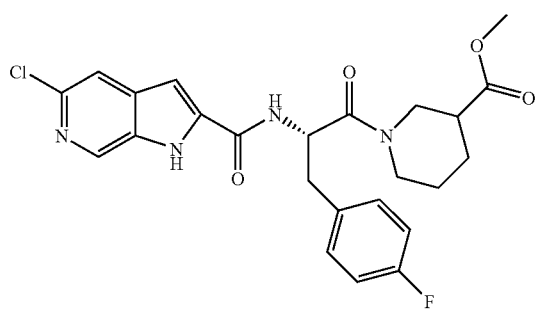
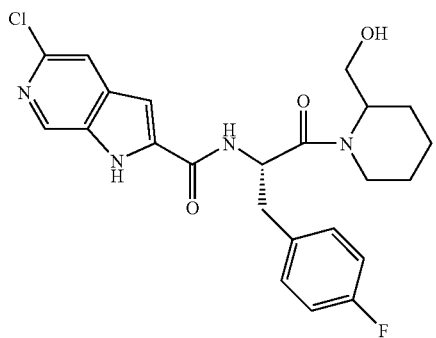
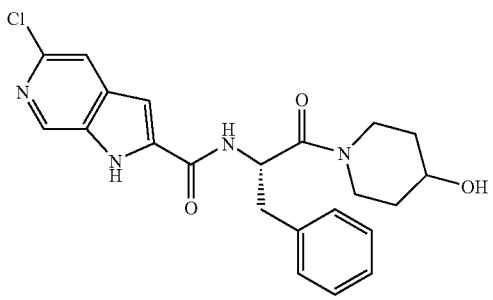

213
-continued
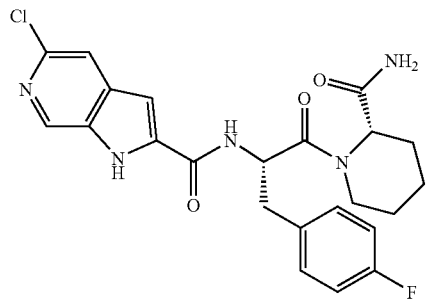
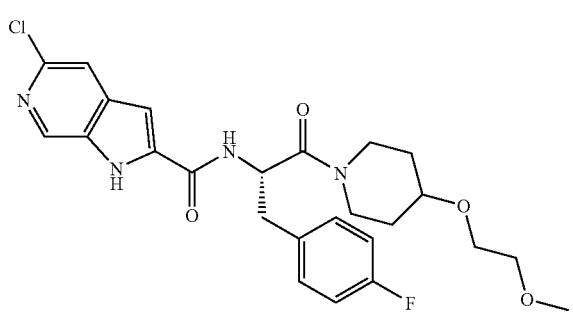
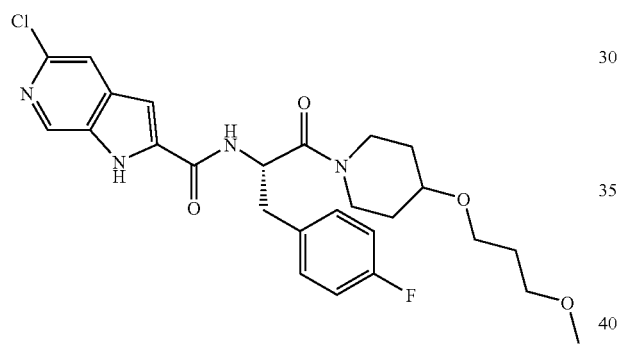
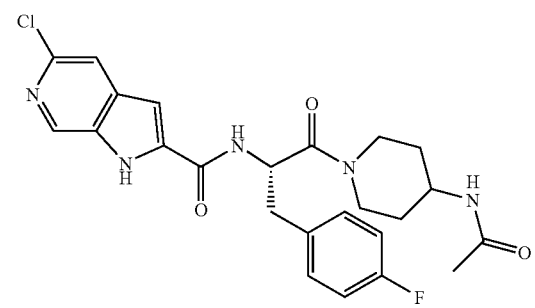
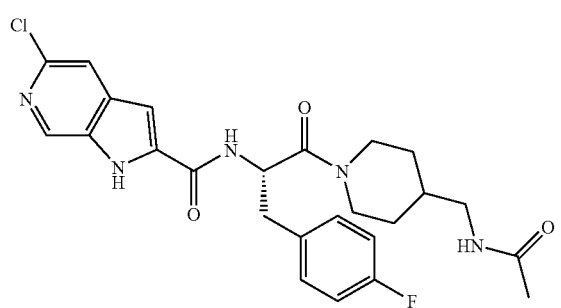
214
-continued
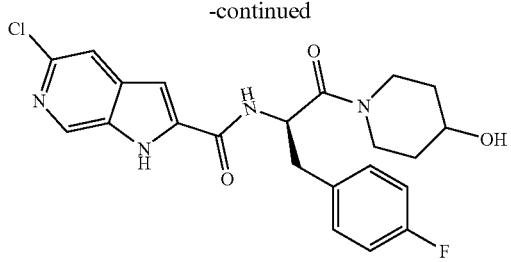
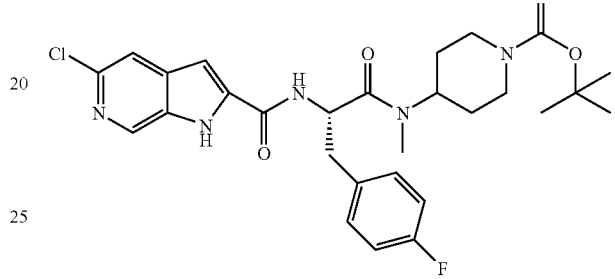
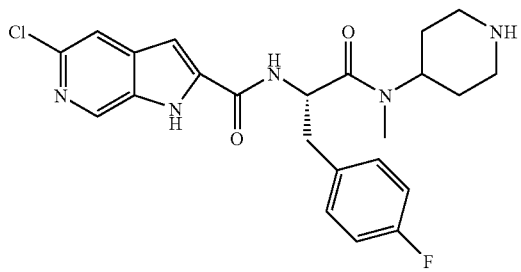
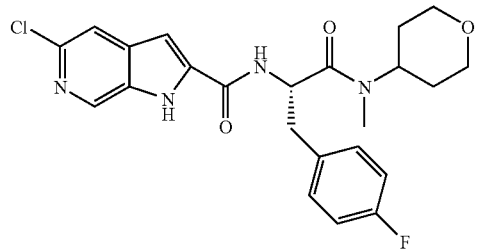
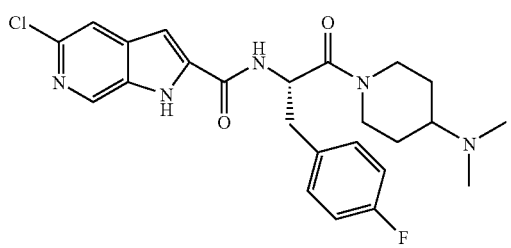

-continued
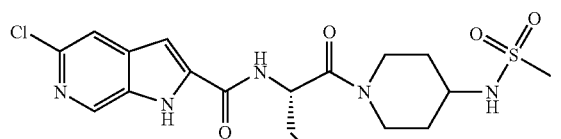
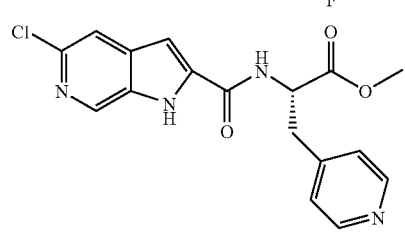
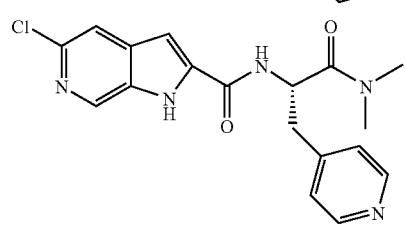
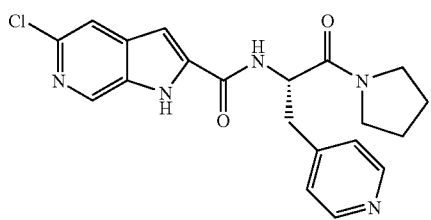
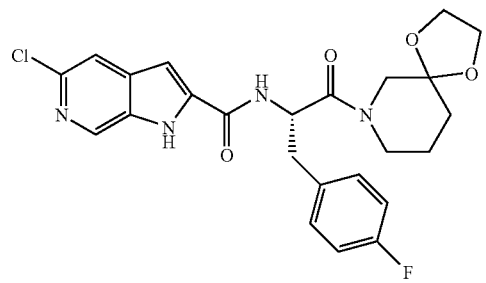
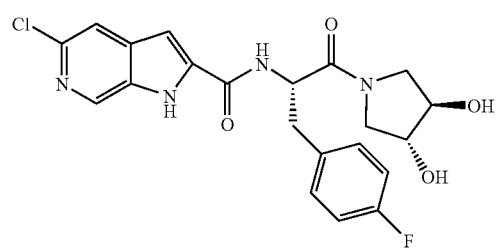
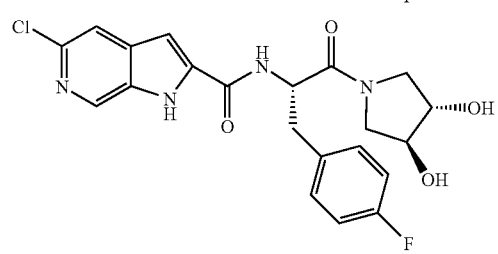
-continued
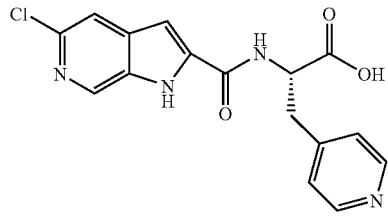
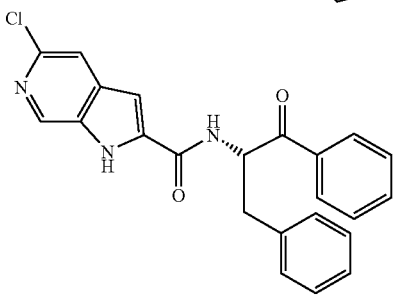
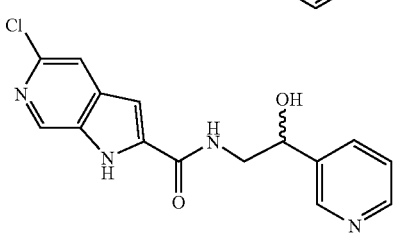
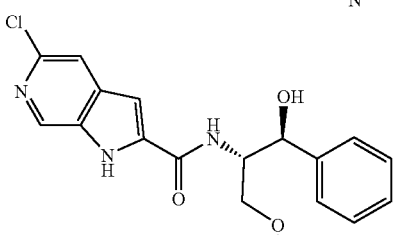
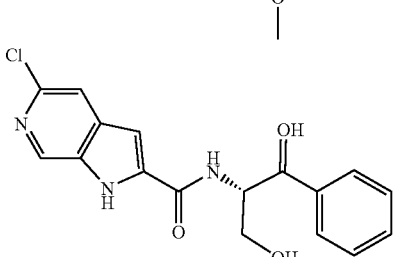
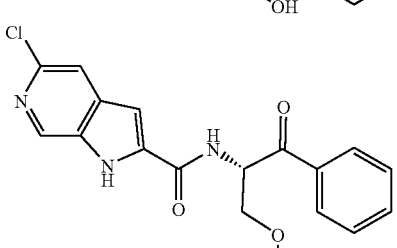
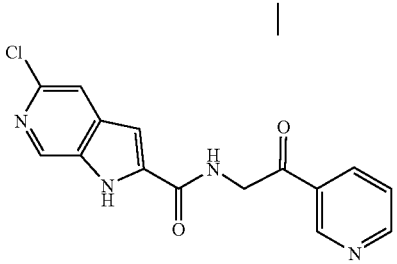

217
-continued
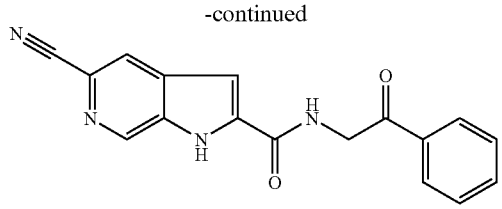
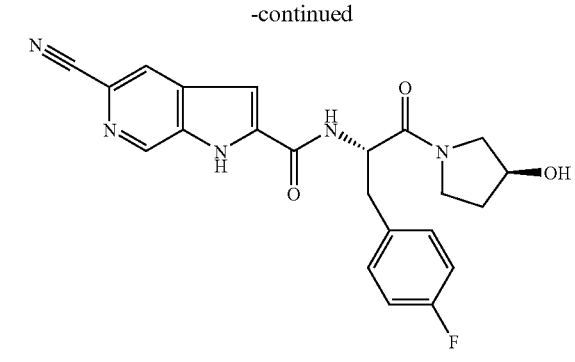
218
-continued
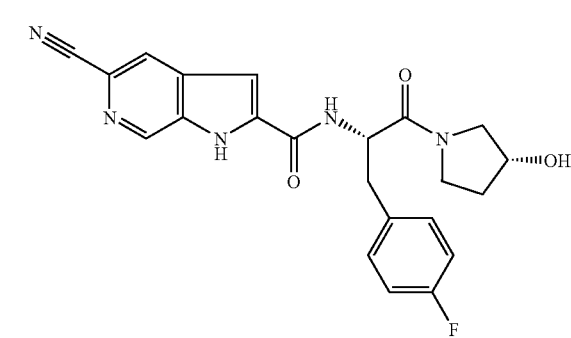
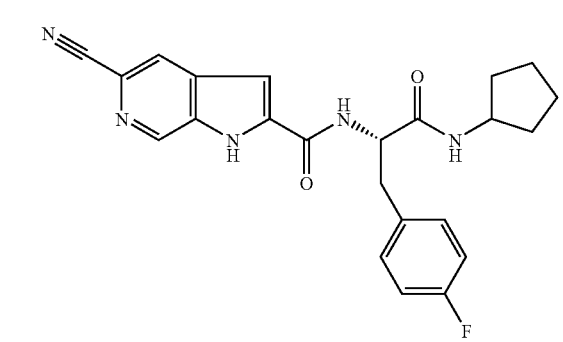
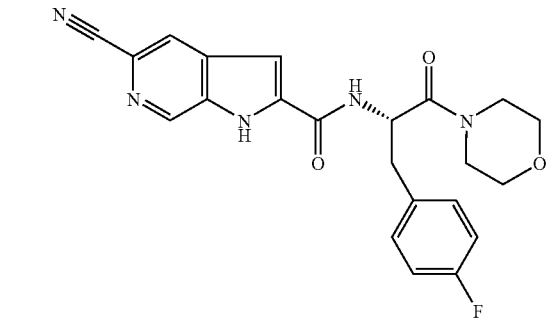

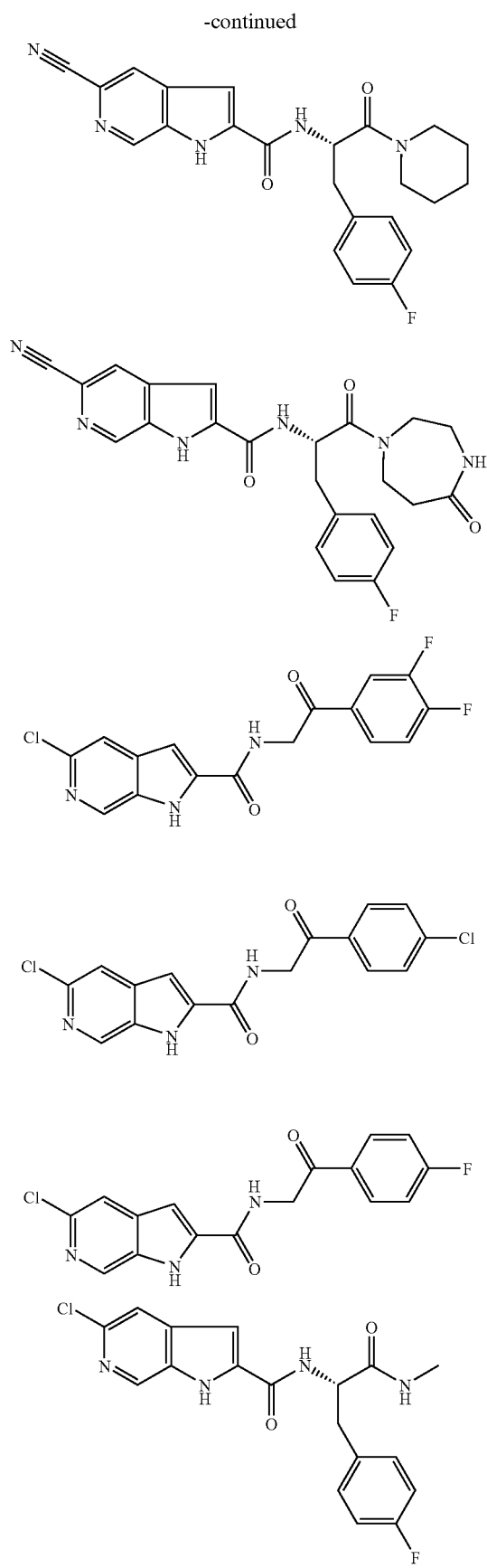
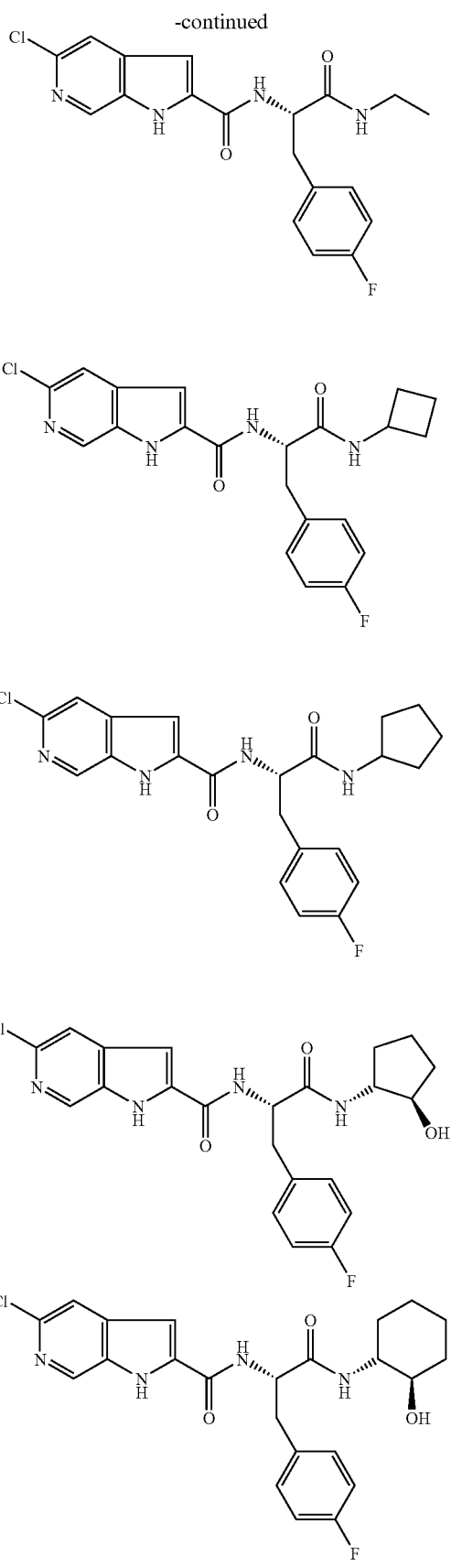

221
-continued
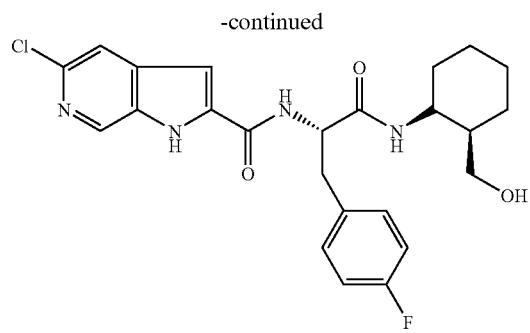
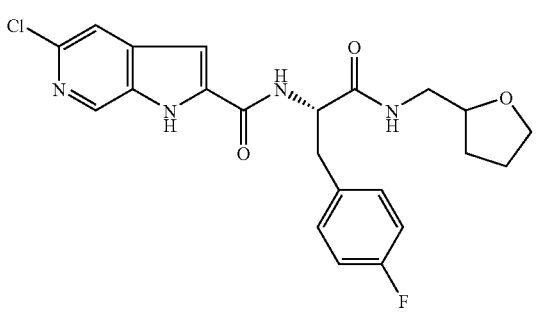
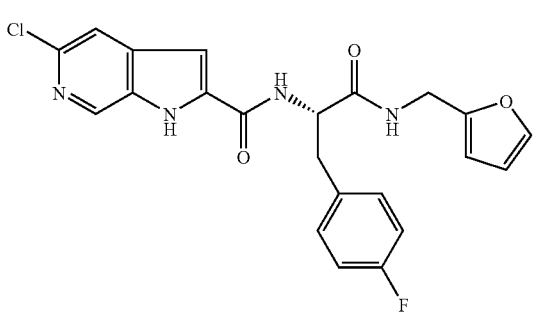
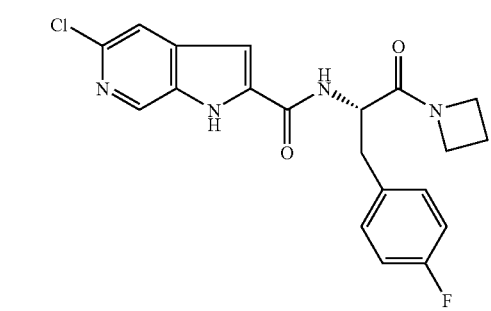
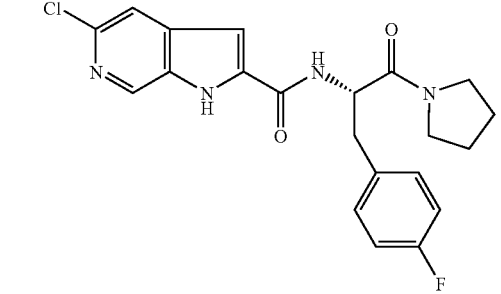
222
-continued
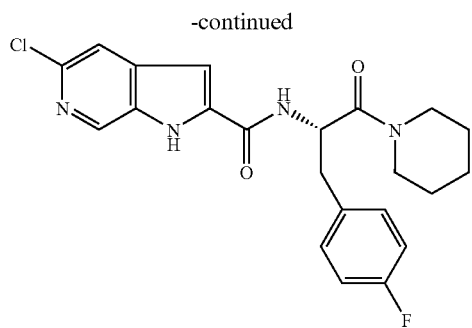
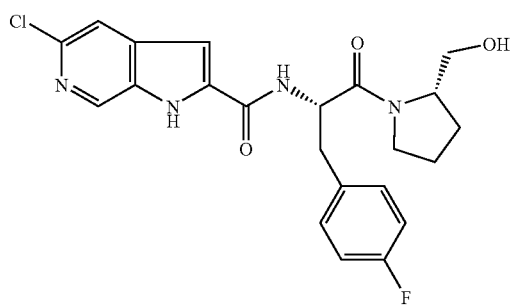
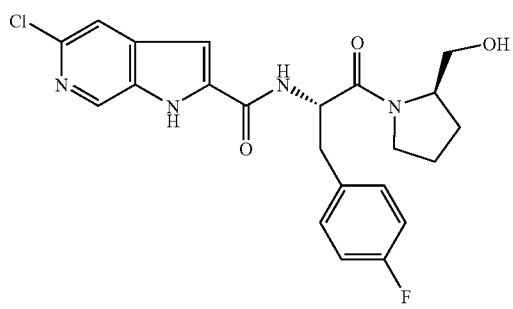
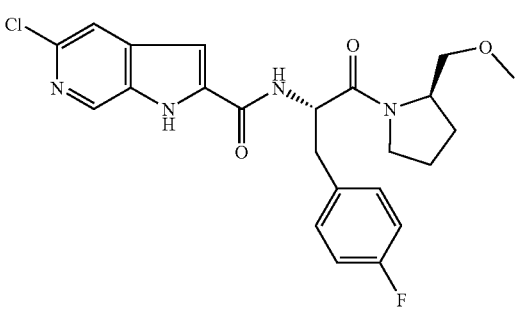
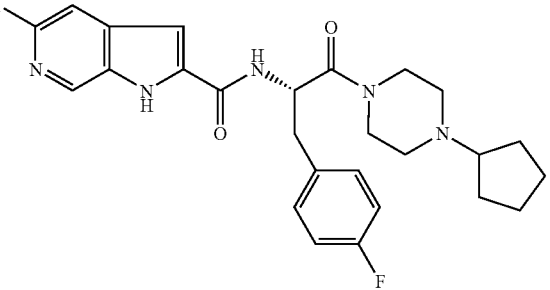

223
-continued
224
-continued
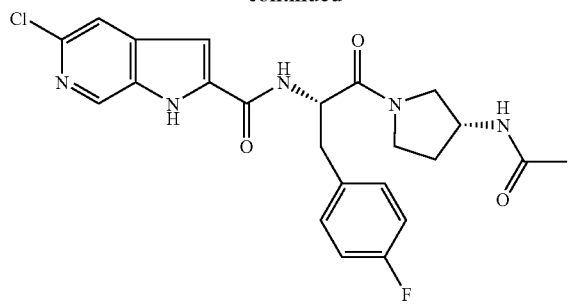
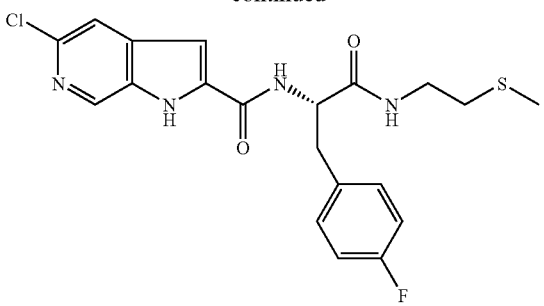

225
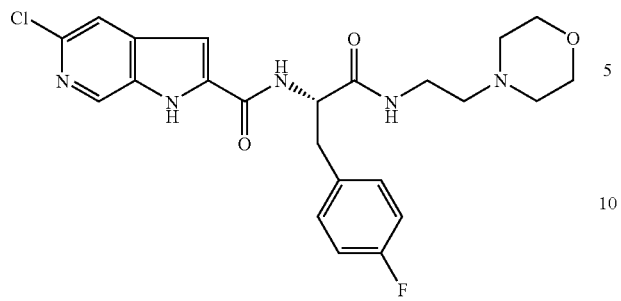
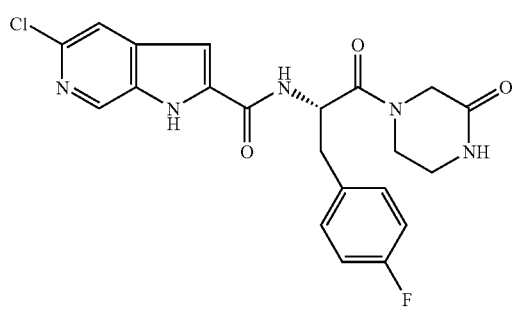
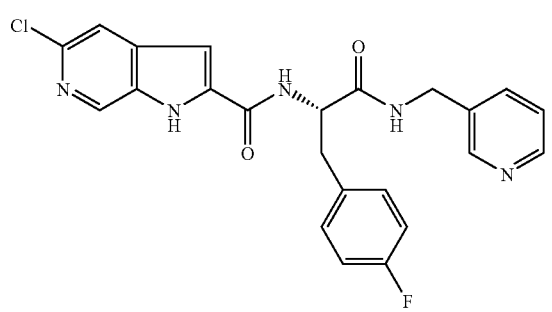
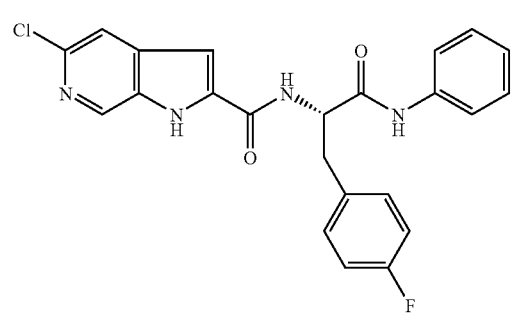
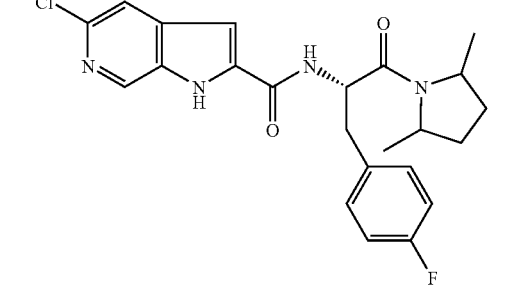
226
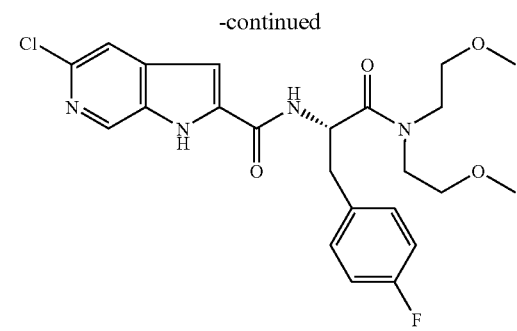
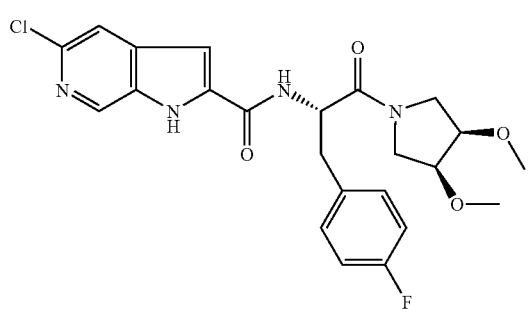
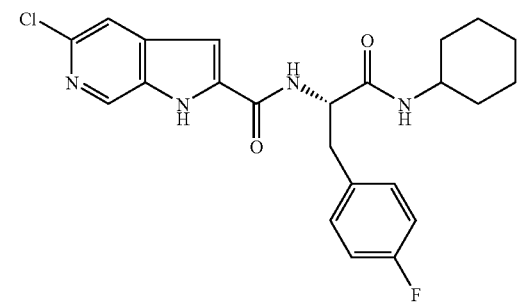
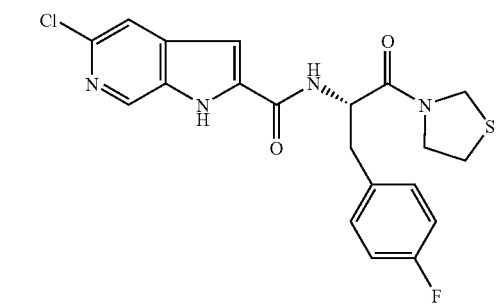

227 228
-continued -continued
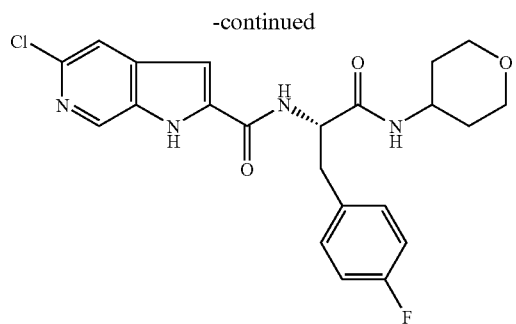
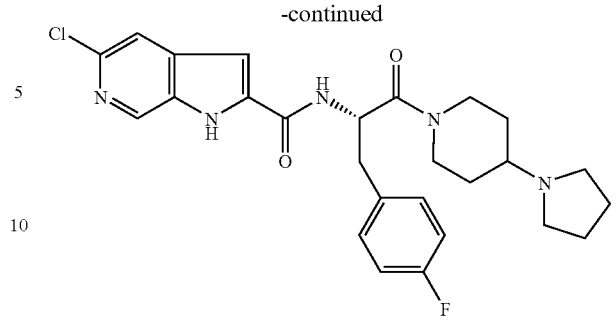
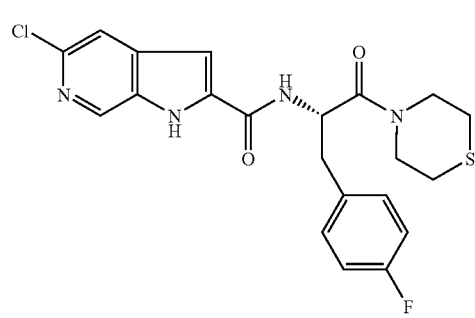
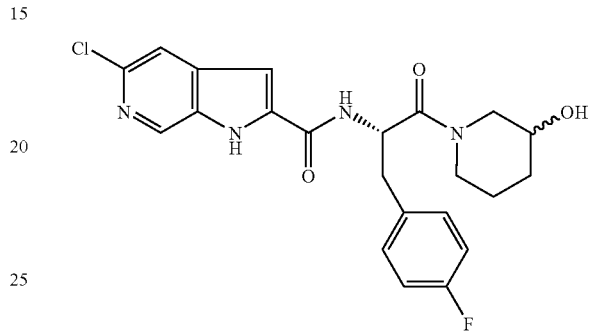
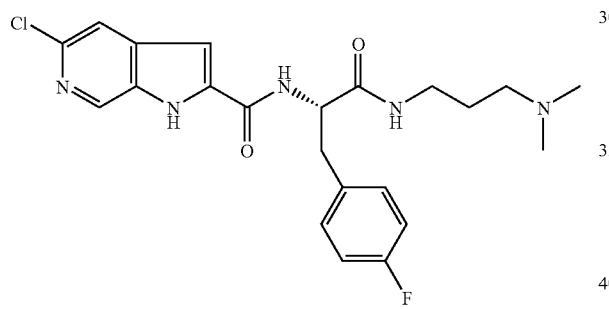
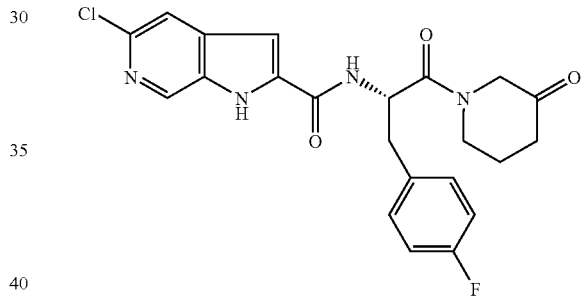
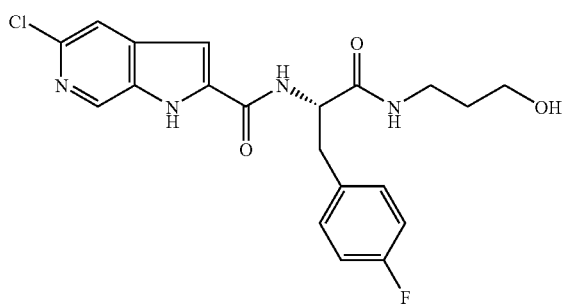
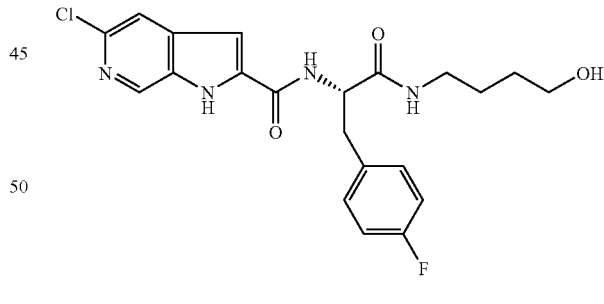
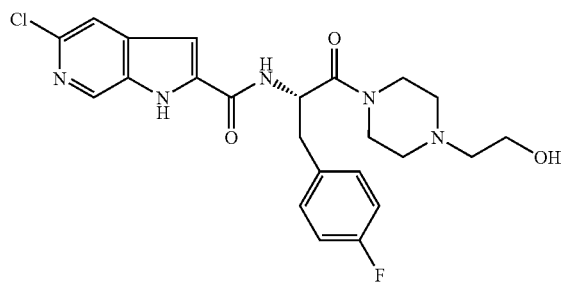
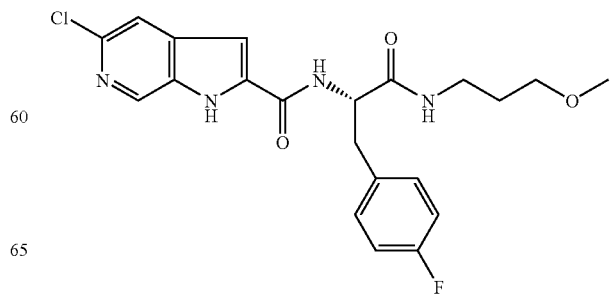

-continued

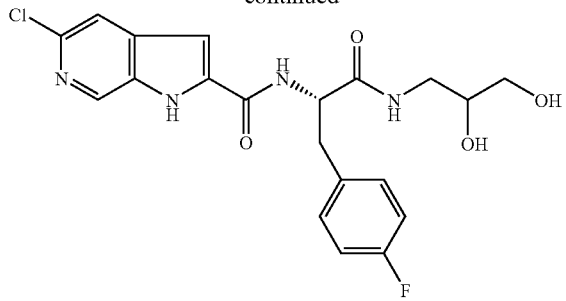

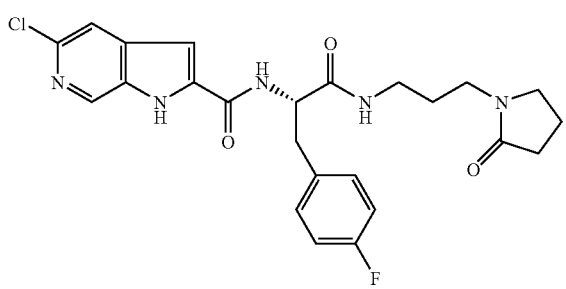

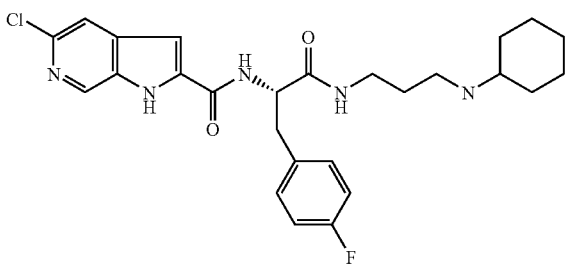

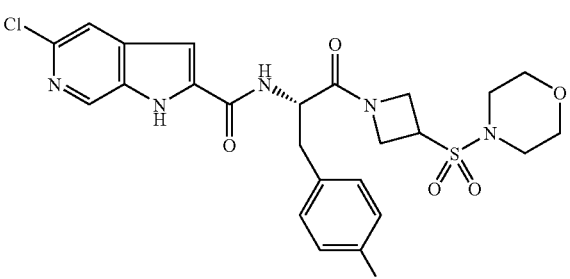

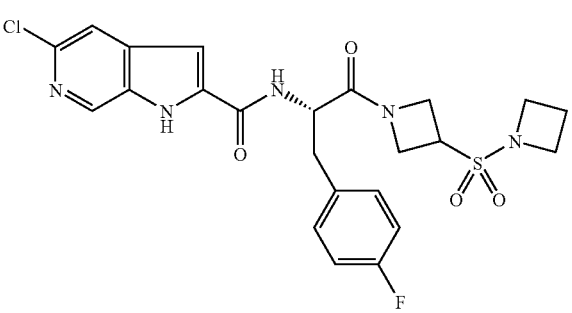

or a pharmaceutically acceptable salt thereof.

15. A pharmaceutical composition comprising a compound of Formula (I):

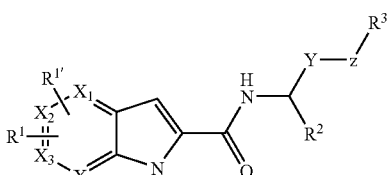

or a stereoisomer, or a pharmaceutically acceptable salt thereof, wherein:

$X_3$ is N; and $X_1$, $X_2$, and $X_4$ are each C;

$R^1$ and $R^{1'}$ are each independently, halogen, hydroxy, cyano, $C_{0-4}$alkyl, $C_{1-4}$alkoxy, fluoromethyl, difluoromethyl, trifluoromethyl, ethenyl, or ethynyl;

$R^2$ is $C_{0-4}$alkyl, $COOR^6$, $COR^6$, $C_{1-4}$alkoxy$C_{1-4}$alkyl-, hydroxy$C_{1-4}$alkyl-, aryl$C_{0-4}$alkyl-, hetaryl$C_{0-4}$alkyl-, wherein any of the aryl or hetaryl rings are optionally substituted with 1-2 independent halogen, cyano, $C_{1-4}$alkyl, $C_{1-4}$alkoxy, —N($C_{0-4}$alkyl)($C_{0-4}$alkyl), —$SO_2C_{1-4}$alkyl, —$SO_2$N($C_{0-4}$alkyl)($C_{0-4}$alkyl), hydroxy, fluoromethyl, difluoromethyl, or trifluoromethyl substituents;

Y is $C_{0-2}$alkyl or —CH(OH)—;

Z is $CH_2$, —C(O)—, —O—, >N($C_{0-4}$alkyl), >N($C_{3-6}$cycloalkyl), or absent; but when Y is —CH(OH)—, Z or $R^3$ must be bonded to Y through a carbon-carbon bond;

$R^3$ is hydrogen, —COO$C_{0-4}$alkyl, $C_{1-4}$alkoxy, $C_{1-4}$alkyl, aryl$C_{1-4}$alkylthio-, —$C_{0-4}$alkylaryl, —$C_{0-4}$alkylhetaryl, —$C_{0-4}$alkylcycloalkyl or —$C_{0-4}$alkylheterocyclyl, wherein any of the rings is optionally substituted with 1-3 independent halogen, cyano, $C_{1-4}$alkyl, fluoromethyl, difluoromethyl, trifluoromethyl, —$C_{0-4}$alkylNHC(O)O($C_{1-4}$alkyl), —$C_{0-4}$alkylNR$^7$R$^8$, —C(O)R$^9$, $C_{1-4}$alkoxy$C_{0-4}$alkyl-, —COO$C_{0-4}$alkyl, —$C_{0-4}$alkyl-NHC(O)R$^9$, —$C_{0-4}$alkylC(O)N(R$^{10}$)$_2$, —$C_{1-4}$alkoxy$C_{1-4}$alkoxy, hydroxy$C_{0-4}$alkyl-, —NHSO$_2$R$^{10}$, —SO$_2$($C_{1-4}$alkyl), —SO$_2$NR$^{11}$R$^{12}$, 5- to 6-membered heterocyclyl, phenyl$C_{0-2}$alkoxy, or phenyl$C_{0-2}$alkyl substituents, wherein phenyl is optionally substituted with 1-2 independent halogen, cyano, $C_{1-4}$alkyl, $C_{1-4}$alkoxy, —N($C_{0-4}$alkyl)($C_{0-4}$alkyl), —SO$_2$$C_{1-4}$alkyl, —SO$_2$N($C_{0-4}$alkyl)($C_{0-4}$alkyl), hydroxy, fluoromethyl, difluoromethyl or trifluoromethyl substituents, or two bonds on a ring carbon of the heterocyclyl group optionally can form an oxo (=O) substituent;

or $R^3$ is —NR$^4$(—$C_{0-4}$alkylR$^5$);

$R^4$ is $C_{0-3}$alkyl, —$C_{2-3}$alkyl-NR$^7$R$^8$, $C_{3-6}$cycloalkyl optionally substituted by hydroxy$C_{0-4}$alkyl- further optionally substituted by hydroxy, $C_{1-2}$alkoxy$C_{2-4}$alkyl-, or $C_{1-2}$alkyl-S(O)$_n$—$C_{2-3}$alkyl-;

n is 0, 1, or 2;

$R^5$ is hydrogen, hydroxy$C_{2-3}$alkyl-, $C_{1-2}$alkoxy$C_{0-4}$alkyl-, or aryl, hetaryl, or heterocyclyl;

wherein a heterocyclic nitrogen-containing $R^5$ ring optionally is mono-substituted on the ring nitrogen with $C_{1-4}$alkyl, benzyl, benzoyl, $C_{1-4}$alkyl-C(O)—, —SO$_2$$C_{1-4}$alkyl, —SO$_2$N($C_{0-4}$alkyl)($C_{0-4}$alkyl), $C_{1-4}$alkoxycarbonyl or aryl($C_{1-4}$alkoxy) carbonyl; and wherein the $R^5$ rings are optionally mono-substituted on a ring carbon with halogen, cyano, $C_{1-4}$alkyl-C(O)—, $C_{1-4}$alkyl-SO$_2$—, $C_{1-4}$alkyl, $C_{1-4}$alkoxy, hydroxy, —N($C_{0-4}$alkyl)($C_{0-4}$alkyl), hydroxy$C_{0-4}$alkyl-, or $C_{0-4}$alkylcarbamoyl-, provided that no quatemised nitrogen is included; or two bonds on a ring carbon of the heterocyclyl group optionally can form an oxo (=O) substituent;

$R^6$ is $C_{1-4}$alkyl, aryl, or hetaryl;

$R^7$ and $R^8$ are independently $C_{0-4}$alkyl, $C_{3-6}$cycloalkyl, or CO($C_{1-4}$alkyl);

$R^9$ is $C_{1-4}$alkyl, or $C_{3-6}$cycloalkyl;

$R^{10}$ is $C_{0-4}$alkyl, or $C_{3-6}$cycloalkyl;

$R^{11}$ and $R^{12}$ are independently $C_{0-4}$alkyl or together with the nitrogen to which they are attached may form a 4- to 6-membered heterocycle; and wherein there are no nitrogen-oxygen, nitrogen-nitrogen or nitrogen-halogen bonds in linking the three components —Y—Z—$R^3$ to each other;

and a pharmaceutically acceptable carrier.

16. A pharmaceutical composition according to claim 15 wherein $R^2$ is $C_{0-4}$alkyl, COOR$^6$, COR$^6$, $C_{1-4}$alkoxy$C_{1-4}$alkyl, hydroxy$C_{1-4}$alkyl-, aryl$C_{0-4}$alkyl-, hetaryl$C_{0-4}$alkyl-, wherein any of the aryl or hetaryl rings are optionally substituted with 1-2 independent halogen, cyano, C1-4alkyl, C1-4alkoxy, —N($C_{0-4}$alkyl)($C_{0-4}$alkyl), —SO$_2$C$_{1-4}$alkyl, —SO$_2$N($C_{0-4}$alkyl)($C_{0-4}$alkyl), hydroxy, fluoromethyl, difluoromethyl, or trifluoromethyl substituents.

17. A method of therapeutic treatment of hyperglycemia or diabetes comprising a step of administering an effective amount of a compound of Formula (I):

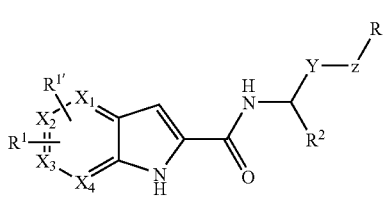

or a stereoisomer, or a pharmaceutically acceptable salt thereof, wherein:

$X_3$ is N; and $X_1$, $X_2$, and $X_4$ are each C;

$R^1$ and $R^{1'}$ are each independently, halogen, hydroxy, cyano, $C_{0-4}$alkyl, $C_{1-4}$alkoxy, fluoromethyl, difluoromethyl, trifluoromethyl, ethenyl, or ethynyl;

$R^2$ is $C_{0-4}$alkyl, COOR$^6$, COR$^6$, $C_{1-4}$alkoxy$C_{1-4}$alkyl-, hydroxy$C_{1-4}$alkyl-, aryl$C_{0-4}$alkyl-, hetaryl$C_{0-4}$alkyl-, wherein any of the aryl or hetaryl rings are optionally substituted with 1-2 independent halogen, cyano, $C_{1-4}$alkyl, $C_{1-4}$alkoxy, —N($C_{0-4}$alkyl)($C_{0-4}$alkyl), —SO$_2$C$_{1-4}$alkyl, —SO$_2$N($C_{0-4}$alkyl)($C_{0-4}$alkyl), hydroxy, fluoromethyl, difluoromethyl, or trifluoromethyl substituents;

Y is $C_{0-2}$alkyl or —CH(OH)—;

Z is CH$_2$, —C(O)—, —O—, >N($C_{0-4}$alkyl), >N($C_{3-6}$cycloalkyl), or absent; but when Y is —CH(OH)—, Z or $R^3$ must be bonded to Y through a carbon-carbon bond;

$R^3$ is hydrogen, —COOC$_{0-4}$alkyl, $C_{1-4}$alkoxy, $C_{1-4}$alkyl, aryl$C_{1-4}$alkylthio-, —$C_{0-4}$alkylaryl, —$C_{0-4}$alkylhetaryl, —$C_{0-4}$alkylcycloalkyl or —$C_{0-4}$alkylheterocyclyl, wherein any of the rings is optionally substituted with 1-3 independent halogen, cyano, $C_{1-4}$alkyl, fluoromethyl, difluoromethyl, trifluoromethyl, —$C_{0-4}$alkylNHC(O)O($C_{1-4}$alkyl), —$C_{0-4}$alkylNR$^7$R$^8$, —C(O)R$^9$, $C_{1-4}$alkoxy$C_{0-4}$alkyl-, —COOC$_{0-4}$alkyl, —$C_{0-4}$alkyl-NHC(O)R$^9$, —$C_{0-4}$alkylC(O)N(R$^{10}$)$_2$, —$C_{1-4}$alkoxy$C_{1-4}$alkoxy, hydroxy$C_{0-4}$alkyl-, —NHSO$_2$R$^{10}$, —SO$_2$($C_{1-4}$alkyl), —SO$_2$NR$^{11}$R$^{12}$, 5- to 6-membered heterocyclyl, phenyl$C_{0-2}$alkoxy, or phenyl$C_{0-2}$alkyl substituents, wherein phenyl is optionally substituted with 1-2 independent halogen, cyano, $C_{1-4}$alkyl, $C_{1-4}$alkoxy, —N($C_{0-4}$alkyl)($C_{0-4}$alkyl), —SO$_2$C$_{1-4}$alkyl, —SO$_2$N($C_{0-4}$alkyl)($C_{0-4}$alkyl), hydroxy, fluoromethyl, difluoromethyl or trifluoromethyl substituents, or two bonds on a ring carbon of the heterocyclyl group optionally can form an oxo (=O) substituent;

or $R^3$ is —NR$^4$(—$C_{0-4}$alkylR$^5$);

$R^4$ is $C_{0-3}$alkyl, —$C_{2-3}$alkyl-NR$^7$R$^8$, $C_{3-6}$cycloalkyl optionally substituted by hydroxy$C_{0-4}$alkyl— further optionally substituted by hydroxy, $C_{1-2}$alkoxy$C_{2-4}$alkyl—, or $C_{1-2}$alkyl-S(O)$_n$—$C_{2-3}$alkyl-;

n is 0, 1, or 2;

$R^5$ is hydrogen, hydroxy$C_{2-3}$alkyl-, $C_{1-2}$alkoxy$C_{0-4}$alkyl-, or aryl, hetaryl, or heterocyclyl;

wherein a heterocyclic nitrogen-containing $R^5$ ring optionally is mono-substituted on the ring nitrogen with $C_{1-4}$alkyl, benzyl, benzoyl, $C_{1-4}$alkyl-C(O)—, —SO$_2$C$_{1-4}$alkyl, —SO$_2$N($C_{0-4}$alkyl)($C_{0-4}$alkyl), $C_{1-4}$alkoxycarbonyl or aryl($C_{1-4}$alkoxy) carbonyl; and wherein the $R^5$ rings are optionally mono-substituted on a ring carbon with halogen, cyano, $C_{1-4}$alkyl-C(O)—, $C_{1-4}$alkyl-SO$_2$—, $C_{1-4}$alkyl, $C_{1-4}$alkoxy, hydroxy, —N($C_{0-4}$alkyl)($C_{0-4}$alkyl), hydroxy$C_{0-4}$alkyl-, or $C_{0-4}$alkylcarbamoyl-, provided that no quatemised nitrogen is included; or two bonds on a ring carbon of the heterocyclyl group optionally can form an oxo (=O) substituent;

$R^6$ is $C_{1-4}$alkyl, aryl, or hetaryl;

$R^7$ and $R^8$ are independently $C_{0-4}$alkyl, $C_{3-6}$cycloalkyl, or CO($C_{1-4}$alkyl);

$R^9$ is $C_{1-4}$alkyl, or $C_{3-6}$cycloalkyl;

$R^{10}$ is $C_{0-4}$alkyl, or $C_{3-6}$cycloalkyl;

$R^{11}$ and $R^{12}$ are independently $C_{0-4}$alkyl or together with the nitrogen to which they are attached may form a 4- to 6-membered heterocycle; and wherein there are no nitrogen-oxygen, nitrogen-nitrogen or nitrogen-halogen bonds in linking the three components —Y—Z—$R^3$ to each other.

18. A method of treating diabetes in a human demonstrating pre-diabetic hyperglycemia or impaired glucose tolerance comprising a step of administering an effective amount of a compound of Formula (I):

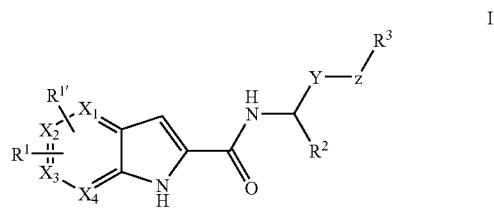

or a stereoisomer, or a pharmaceutically acceptable salt thereof, wherein:

$X_3$ is N; and $X_1$, $X_2$, and $X_4$ are each C;

$R^1$ and $R^{1'}$ are each independently, halogen, hydroxy, cyano, $C_{0-4}$alkyl, $C_{1-4}$alkoxy, fluoromethyl, difluoromethyl, trifluoromethyl, ethenyl, or ethynyl;

$R^2$ is $C_{0-4}$alkyl, $COOR^6$, $COR^6$, $C_{1-4}$alkoxy$C_{1-4}$alkyl-, hydroxy$C_{1-4}$alkyl-, aryl$C_{0-4}$alkyl-, hetaryl$C_{0-4}$alkyl-, wherein any of the aryl or hetaryl rings are optionally substituted with 1-2 independent halogen, cyano, $C_{1-4}$alkyl, $C_{1-4}$alkoxy, —$N(C_{0-4}$alkyl$)(C_{0-4}$alkyl$)$, —$SO_2C_{1-4}$alkyl, —$SO_2N(C_{0-4}$alkyl$)(C_{0-4}$alkyl$)$, hydroxy, fluoromethyl, difluoromethyl, or trifluoromethyl substituents;

Y is $C_{0-2}$alkyl or —CH(OH)—;

Z is $CH_2$, —C(O)—, —O—, >$N(C_{0-4}$alkyl$)$, >$N(C_{3-6}$cycloalkyl$)$, or absent; but when Y is —CH(OH)—, Z or $R^3$ must be bonded to Y through a carbon-carbon bond;

$R^3$ is hydrogen, —$COOC_{0-4}$alkyl, $C_{1-4}$alkoxy, $C_{1-4}$alkyl, aryl$C_{1-4}$alkylthio-, —$C_{0-4}$alkylaryl, —$C_{0-4}$alkylhetaryl, —$C_{0-4}$alkylcycloalkyl or —$C_{0-4}$alkylheterocyclyl, wherein any of the rings is optionally substituted with 1-3 independent halogen, cyano, $C_{1-4}$alkyl, fluoromethyl, difluoromethyl, trifluoromethyl, —$C_{0-4}$alkylNHC(O)O($C_{1-4}$alkyl), —$C_{0-4}$alkylNR$^7$R$^8$, —C(O)R$^9$, $C_{1-4}$alkoxy$C_{0-4}$alkyl-, —$COOC_{0-4}$alkyl, —$C_{0-4}$alkyl-NHC(O)R$^9$, —$C_{0-4}$alkylC(O)N(R$^{10}$)$_2$, —$C_{1-4}$alkoxy$C_{1-4}$alkoxy, hydroxy$C_{0-4}$alkyl-, —NHSO$_2$R$^{10}$, —SO$_2$($C_{1-4}$alkyl), —SO$_2$NR$^{11}$R$^{12}$, 5- to 6-membered heterocyclyl, phenyl$C_{0-2}$alkoxy, or phenyl$C_{0-2}$alkyl substituents, wherein phenyl is optionally substituted with 1-2 independent halogen, cyano, $C_{1-4}$alkyl, $C_{1-4}$alkoxy, —$N(C_{0-4}$alkyl$)(C_{0-4}$alkyl$)$, —$SO_2C_{1-4}$alkyl, —$SO_2N(C_{0-4}$alkyl$)(C_{0-4}$alkyl$)$, hydroxy, fluoromethyl, difluoromethyl or trifluoromethyl substituents, or two bonds on a ring carbon of the heterocyclyl group optionally can form an oxo (=O) substituent;

or $R^3$ is —NR$^4$(—$C_{0-4}$alkylR$^5$);

$R^4$ is $C_{0-3}$alkyl, —$C_{2-3}$alkyl-NR$^7$R$^8$, $C_{3-6}$cycloalkyl optionally substituted by hydroxy$C_{0-4}$alkyl- further optionally substituted by hydroxy, $C_{1-2}$alkoxy$C_{2-4}$alkyl-, or $C_{1-2}$alkyl-S(O)$_n$—$C_{2-3}$alkyl-;

n is 0, 1, or 2;

$R^5$ is hydrogen, hydroxy$C_{2-3}$alkyl-, $C_{1-2}$alkoxy$C_{0-4}$alkyl-, or aryl, hetaryl, or heterocyclyl;

wherein a heterocyclic nitrogen-containing $R^5$ ring optionally is mono-substituted on the ring nitrogen with $C_{1-4}$alkyl, benzyl, benzoyl, $C_{1-4}$alkyl-C(O)—, —SO$_2$C$_{1-4}$alkyl, —SO$_2$N(C$_{0-4}$alkyl)(C$_{0-4}$alkyl), $C_{1-4}$alkoxycarbonyl or aryl($C_{1-4}$alkoxy)carbonyl; and wherein the $R^5$ rings are optionally mono-substituted on a ring carbon with halogen, cyano, $C_{1-4}$alkyl-C(O)—, $C_{1-4}$alkyl-SO$_2$—, $C_{1-4}$alkyl, $C_{1-4}$alkoxy, hydroxy, —N(C$_{0-4}$alkyl)(C$_{0-4}$alkyl), hydroxy$C_{0-4}$alkyl-, or $C_{0-4}$alkylcarbamoyl-, provided that no quaternised nitrogen is included; or two bonds on a ring carbon of the heterocyclyl group optionally can form an oxo (=O) substituent;

$R^6$ is $C_{1-4}$alkyl, aryl, or hetaryl;

$R^7$ and $R^8$ are independently $C_{0-4}$alkyl, $C_{3-6}$cycloalkyl, or CO($C_{1-4}$alkyl);

$R^9$ is $C_{1-4}$alkyl, or $C_{3-6}$cycloalkyl;

$R^{10}$ is $C_{0-4}$alkyl, or $C_{3-6}$cycloalkyl;

$R^{11}$ and $R^{12}$ are independently $C_{0-4}$alkyl or together with the nitrogen to which they are attached may form a 4- to 6-membered heterocycle; and wherein there are no nitrogen-oxygen, nitrogen-nitrogen or nitrogen-halogen bonds in linking the three components —Y—Z—$R^3$ to each other.

19. A method of therapeutic treatment of hypercholesterolemia, hyperinsulinemia, hyperlipidemia, atherosclerosis or myocardial ischemia comprising a step of administering an effective amount of a compound of Formula (I):

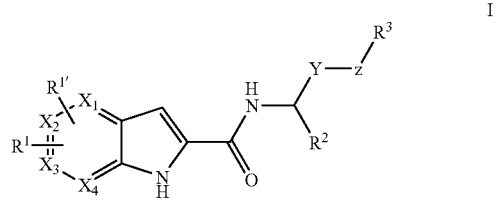

or a stereoisomer, or a pharmaceutically acceptable salt thereof, wherein:

$X_3$ is N; and $X_1$, $X_2$, and $X_4$ are each C;

$R^1$ and $R^{1'}$ are each independently, halogen, hydroxy, cyano, $C_{0-4}$alkyl, $C_{1-4}$alkoxy, fluoromethyl, difluoromethyl, trifluoromethyl, ethenyl, or ethynyl;

$R^2$ is $C_{0-4}$alkyl, $COOR^6$, $COR^6$, $C_{1-4}$alkoxy$C_{1-4}$alkyl-, hydroxy$C_{1-4}$alkyl-, aryl$C_{0-4}$alkyl-, hetaryl$C_{0-4}$alkyl-, wherein any of the aryl or hetaryl rings are optionally substituted with 1-2 independent halogen, cyano, $C_{1-4}$alkyl, $C_{1-4}$alkoxy, —$N(C_{0-4}$alkyl$)(C_{0-4}$alkyl$)$, —$SO_2C_{1-4}$alkyl, —$SO_2N(C_{0-4}$alkyl$)(C_{0-4}$alkyl$)$, hydroxy, fluoromethyl, difluoromethyl, or trifluoromethyl substituents;

Y is $C_{0-2}$alkyl or —CH(OH)—;

Z is $CH_2$, —C(O)—, —O—, >$N(C_{0-4}$alkyl$)$, >$N(C_{3-6}$cycloalkyl$)$, or absent; but when Y is —CH(OH)—, Z or $R^3$ must be bonded to Y through a carbon-carbon bond;

$R^3$ is hydrogen, —$COOC_{0-4}$alkyl, $C_{1-4}$alkoxy, $C_{1-4}$alkyl, aryl$C_{1-4}$alkylthio-, —$C_{0-4}$alkylaryl, —$C_{0-4}$alkylhetaryl, —$C_{0-4}$alkylcycloalkyl or —$C_{0-4}$alkylheterocyclyl, wherein any of the rings is optionally substituted with 1-3 independent halogen, cyano, $C_{1-4}$alkyl, fluoromethyl, difluoromethyl, trifluoromethyl, —$C_{0-4}$alkylNHC(O)O($C_{1-4}$alkyl), —$C_{0-4}$alkylNR$^7$R$^8$, —C(O)R$^9$, $C_{1-4}$alkoxy$C_{0-4}$alkyl-, —$COOC_{0-4}$alkyl, —$C_{0-4}$alkyl-NHC(O)R$^9$, —$C_{0-4}$alkylC(O)N(R$^{10}$)$_2$, —$C_{1-4}$alkoxy$C_{1-4}$alkoxy, hydroxy$C_{0-4}$alkyl-, —NHSO$_2$R$^{10}$, —SO$_2$($C_{1-4}$alkyl), —SO$_2$NR$^{11}$R$^{12}$, 5- to 6-membered heterocyclyl, phenyl$C_{0-2}$alkoxy, or phenyl$C_{0-2}$alkyl substituents, wherein phenyl is optionally substituted with 1-2 independent halogen, cyano, $C_{1-4}$alkyl, $C_{1-4}$alkoxy, —$N(C_{0-4}$alkyl$)(C_{0-4}$alkyl$)$, —$SO_2C_{1-4}$alkyl, —$SO_2N(C_{0-4}$alkyl$)(C_{0-4}$alkyl$)$, hydroxy, fluoromethyl, difluoromethyl or trifluoromethyl substituents, or two bonds on a ring carbon of the heterocyclyl group optionally can form an oxo (=O) substituent;

or $R^3$ is —NR$^4$(—$C_{0-4}$alkylR$^5$);

$R^4$ is $C_{0-3}$alkyl, —$C_{2-3}$alkyl-NR$^7$R$^8$, $C_{3-6}$cycloalkyl optionally substituted by hydroxy$C_{0-4}$alkyl- further optionally substituted by hydroxy, $C_{1-2}$alkoxy$C_{2-4}$alkyl-, or $C_{1-2}$alkyl-S(O)$_n$—$C_{2-3}$alkyl-;

n is 0, 1, or 2;

$R^5$ is hydrogen, hydroxy$C_{2-3}$alkyl-, $C_{1-2}$alkoxy$C_{0-4}$alkyl-, or aryl, hetaryl, or heterocyclyl;

wherein a heterocyclic nitrogen-containing $R^5$ ring optionally is mono-substituted on the ring nitrogen with $C_{1-4}$alkyl, benzyl, benzoyl, $C_{1-4}$alkyl-C(O)—, —SO$_2$C$_{1-4}$alkyl, —SO$_2$N(C$_{0-4}$alkyl)(C$_{0-4}$alkyl), $C_{1-4}$alkoxycarbonyl or aryl($C_{1-4}$alkoxy)carbonyl; and wherein the $R^5$ rings are optionally mono-substituted on a ring carbon with halogen, cyano, $C_{1-4}$alkyl-C(O)—, $C_{1-4}$alkyl-$SO_2$—, $C_{1-4}$alkyl, $C_{1-4}$alkoxy, hydroxy, —N($C_{0-4}$alkyl)($C_{0-4}$alkyl), hydroxy$C_{0-4}$alkyl-, or $C_{0-4}$alkylcarbamoyl-, provided that no quatemised nitrogen is included; or two bonds on a ring carbon of the heterocyclyl group optionally can form an oxo (=O) substituent;

$R^6$ is $C_{1-4}$alkyl, aryl, or hetaryl;

$R^7$ and $R^8$ are independently $C_{0-4}$alkyl, $C_{3-6}$cycloalkyl, or CO($C_{1-4}$alkyl);

$R^9$ is $C_{1-4}$alkyl, or $C_{3-6}$cycloalkyl;

$R^{10}$ is $C_{0-4}$alkyl, or $C_{3-6}$cycloalkyl;

$R^{11}$ and $R^{12}$ are independently $C_{0-4}$alkyl or together with the nitrogen to which they are attached may form a 4- to 6-membered heterocycle; and wherein there are no nitrogen-oxygen, nitrogen-nitrogen or nitrogen-halogen bonds in linking the three components —Y—Z—$R^3$ to each other.

20. A process for the production of a compound of Formula (I) according to claim 1, comprising:

a)

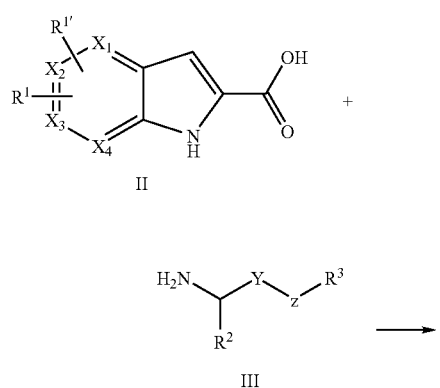

coupling a pyrrolopyridine-2-carboxylic acid of Formula (II), or a protected or activated derivative thereof, with an amine of Formula (III); or b)

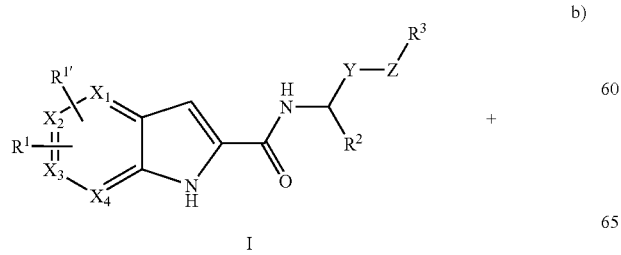

for compounds of Formula (I) wherein Z is C=O and $R^3$ is —$NR^4$(—$C_{0-4}$alkyl$R^5$), coupling a carboxylic acid of Formula (I), or a protected or activated derivative thereof, wherein Z is absent and $R^3$ is —$CO_2H$, with an amine of Formula (IV); or (c)

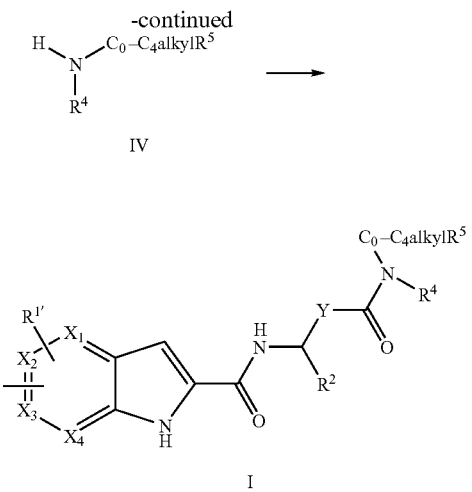

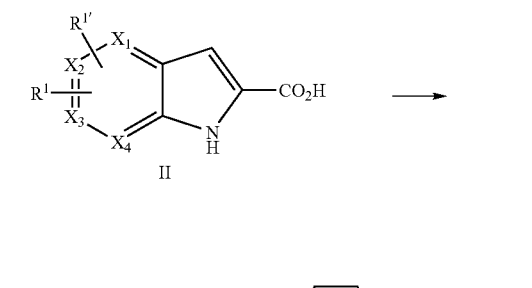

for compounds of Formula (III) wherein $R^2$ is H, Y is $C_0$ alkyl, Z is —C(O)— and $R^3$ is —$C_0$alkylaryl or —$C_0$alkylhetaryl coupling of a compound of Formula (XX) with a compound of Formula (II) under standard coupling conditions to give a compound of Formula (XIX), followed by removal of the ketal group in the presence of acid; or d)
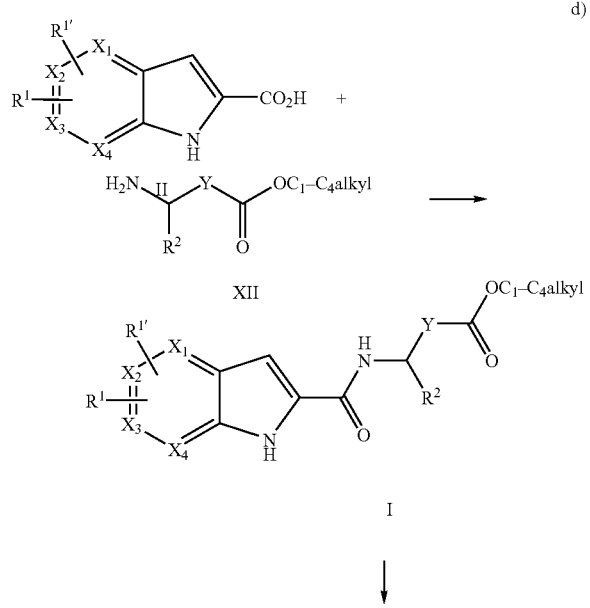
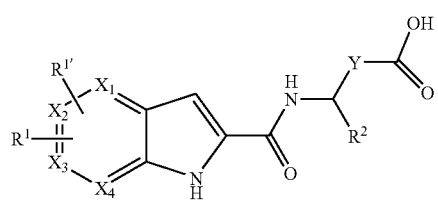
for compounds of Formula (I) wherein Z is C=O and $R^3$ is $C_{1-4}$alkoxy, coupling a compound of Formula (II), or a protected or activated derivative thereof, and a compound of Formula (XII); or
e) for compounds of Formula (I) wherein Z is absent and R3 is —$CO_2H$, ester hydrolysis of compounds of Formula (I) where Z is C=O and $R^3$ is a $C_{1-4}$alkoxy group.
* * * * *